United States Patent
Shankar et al.

(10) Patent No.: US 8,802,692 B2
(45) Date of Patent: Aug. 12, 2014

(54) SYNERGISTIC EFFECTS BETWEEN SPHINGOSINE-1-PHOSPHATE RECEPTOR ANTAGONISTS AND ANTIMICROTUBULE AGENTS

(75) Inventors: Geetha Shankar, Palo Alto, CA (US); Frauke Bentzien, San Francisco, CA (US); Peter Lamb, Oakland, CA (US); David Matthews, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 523 days.

(21) Appl. No.: 13/124,586

(22) PCT Filed: Oct. 16, 2009

(86) PCT No.: PCT/US2009/061071
§ 371 (c)(1),
(2), (4) Date: Aug. 3, 2011

(87) PCT Pub. No.: WO2010/045601
PCT Pub. Date: Apr. 22, 2010

(65) Prior Publication Data
US 2011/0301188 A1    Dec. 8, 2011

Related U.S. Application Data

(60) Provisional application No. 61/196,410, filed on Oct. 17, 2008.

(51) Int. Cl.
*A61K 31/44* (2006.01)
*A01N 43/36* (2006.01)
*A61K 31/40* (2006.01)

(52) U.S. Cl.
USPC .......................................... 514/283; 514/422

(58) Field of Classification Search
USPC .................................................. 514/283, 422
See application file for complete search history.

(56) References Cited

FOREIGN PATENT DOCUMENTS

| JP | 2002-212070 A | 7/2002 |
|---|---|---|
| WO | 03/014299 A2 | 2/2003 |
| WO | 03/051876 A1 | 6/2003 |
| WO | 2010/019646 A1 | 2/2010 |

OTHER PUBLICATIONS

Database WPI Week 200281 Thomson Scientific, London, XP002575872.
Shankar, G. et al., "335 Poster Identification of potent, selective sphingosine-1-phosphate 1 receptor (S1P1R) antagonists with anti-tumor activity", European Journal of Cancer, 2008, 6(12), 106-107.
Davis, M. D. et al., "Sphingosine 1-phosphate analogs as receptor antagonists", Journal of Biological Chemistry 20050318 American Society for Biochemistry and Molecular Biology Inc., 2005, 280(11), 9833-9841.
Sanchez, T. et al., "Targeting sphingosine-1-phosphate receptors as anti-tumor and anti-angiogenic therapy in renal cell carcinoma", Journal of Urology, 2009, p. 156.
Nowak, A. et al., "Systematic review of taxane-containing versus non-taxane-containing regimens for adjuvant and neoadjuvant treatment of early breast cancer", Lancet Oncology, 2004, 5(6), 372-380.
Colomer et al., "Review of gemcitabine plus taxane combination therapy in the first-line treatment of metastatic breast cancer", European Journal of Cancer, 2008, 6(8), 9-12.
Clemons, M. et al., "Review of recent trials of chemotherapy for advanced breast cancer: the taxanes", European Journal of Cancer, 1997, 33(13), 2183-2193.
Chu, Q. et al., "Taxanes as first-line therapy for advanced non-small cell lung cancer: A systematic review and practice guideline", Lung Cancer, 2005, 50(3), 355-374.
Sugimori, H. et al., "Treatmetn of advanced cervical cancer by a combination of peplomycin, vincristine, mitomycin-C, and cisplatin", International Journal of Gynecology and Obstetrics, 1990, 31(3), p. 298.
Sorensen, J. B. et al., "Vinca alkaloids in the treatment of non-small cell lung cancer", Cancer Treatment Reviews, 1987, 14(1), 29-51.
Shankar et al., "Identification of potent, selective sphingosine-1-phosphate 1 receptor (S1P1R) antagonists with antitumor activity", 2008, XP002575874.

*Primary Examiner* — Samira Jean-Louis
(74) *Attorney, Agent, or Firm* — Honigman Miller Schwartz and Cohn LLP; Heidi M. Berven; Jonathan P. O'Brien

(57) ABSTRACT

This invention is based on the discovery that the administration of a sphingosine-1-phosphate receptor antagonist (S1P) and at least one chemotherapeutic agent selected from the the group of antimicrotubule agents provides an unexpectedly superior treatment for cancer. Antimicrobial agents such as the taxane compounds are known in the art, for example, paclitaxel (available as TAXOL® from Bristol-Myers Squibb, Princeton, N.J.), docetaxel (available as TAXOTERE® from Sanofi-aventis, Bridgewater, N.J.) and the like and other compounds that act as antimicrotubule agents, such as Vincristine (ONCOVIN®, VINCASAR PFS®, VCR), Vinblastin (VELBAN®, VELSAR®) and Vinorelbine, and similar compounds. The present invention also provides methods of modulating the growth of selected cell populations, such as cancer cells, by administering a therapeutically effective amount of at least one sphingosine-1-phosphate 1 (S1P1R) receptor antagonists, and at least one antimicrotubule agent.

51 Claims, 4 Drawing Sheets

SYNERGISTIC EFFECTS BETWEEN SPHINGOSINE-1-PHOSPHATE RECEPTOR ANTAGONISTS AND ANTIMICROTUBULE AGENTS

This application is a U.S. national phase of International Application No. PCT/US2009/061071 filed on Oct. 16, 2009, which claims the benefit of U.S. Provisional Application No. 61/196,410 filed on Oct. 17, 2008, the disclosures of which are incorporated herein by reference in their entirety.

CROSS REFERENCE TO RELATED APPLICATIONS

This disclosure relates to the S1P receptor antagonists, compositions comprising the S1P receptor antagonists and methods for using and processes for making the S1P receptor antagonists described in a patent application entitled "Sphingosine-1-Phosphate Receptor Antagonists" co-owned by Exelixis, Inc, filed concurrently and whose U.S. Provisional Application No. is 61/196,495, the disclosure of which is incorporated by reference herein in its entirety.

FIELD OF THE INVENTION

This invention is based on the discovery that the administration of a sphingosine-1-phosphate receptor antagonist (S1P) and at least one chemotherapeutic agent selected from the the group of antimicrotubule agents provides an unexpectedly superior treatment for cancer. Antimicrobial agents such as the taxane compounds are known in the art, for example, paclitaxel (available as TAXOL® from Bristol-Myers Squibb, Princeton, N.J.), docetaxel (available as TAXOTERE® from Sanofi-aventis, Bridgewater, N.J.) and the like. Other compounds that act as antimicrotubule agents, are the vinca alkaloids, such as Vincristine (available as ONCOVIN® from Eli Lilly and Company, Indianapolis, Ind., VINCASAR PFS®, VCR), Vinblastin (available as VELBAN® from Eli Lilly and Company, Indianapolis, Ind., VELSAR®) and Vinorelbine, and similar compounds are also known in the art. The present invention also provides methods of modulating the growth of selected cell populations, such as cancer cells, by administering a therapeutically effective amount of at least one sphingosine-1-phosphate 1 (S1P1R) receptor antagonists, and at least one antimicrotubule agent such as a taxane or a vinca alkaloid.

BACKGROUND OF THE INVENTION

Sphingosine 1-phosphate (S1P) is derived from sphingosine, which provides the backbone to all sphingolipids. Phosphorylation of sphingosine, a metabolite of the pro-apoptotic lipid ceramide, to S1P, is mediated by lipid kinases called sphingosine kinases (SphK). There are two SphK isoenzymes: SphK1 or SphK2. SIP may be reversibly deactivated through dephosphorylation by several phosphatases or irreversibly deactivated by S1P lyase. S1P is produced intracellularly in organelles and the plasma membrane and then secreted. The newly generated S1P is then secreted and is bound extensively by albumin and other plasma proteins. This provides a stable reservoir in extracellular fluids, presumably at higher total concentrations than in tissues, and rapid delivery to cell surface receptors. S1P, via its five cognate G-protein coupled receptors (GPCRs), S1P1-5 Rs, regulates diverse biological functions, including inflammatory responses, cell proliferation, apoptosis, cell migration, lymphocyte trafficking and cell senescence. Thus, coordinated activities of biosynthetic and biodegradative enzymes help maintain and regulate concentrations of S1P in the range required for physiological activities.

S1P has been shown to be an important mediator of angiogenesis and tumorigenesis. One way to modulate S1P levels is to target SphK, and thereby affect biosynthesis of S1P. SphK1 has been shown to stimulate proliferation in vitro, and is tumorigenic in vivo. It also imparts resistance to radiotherapy and chemotherapy and is elevated in some solid tumors. SphK1 inhibitors have been shown to have anti-cancer effects in vivo. These effects have been attributed to the inhibition of formation of S1P. Further, a monoclonal antibody against S1P reduces progression of or eliminates tumors in murine xenograft and allograft models. Thus, lowering levels of S1P by inhibiting SphK or by an S1P-specific antibody has anti-tumorigenic effects.

Since many, if not all effects of S1P are mediated by five GPCRs, an alternative approach to cancer therapy may be inhibition of S1P receptors. Of the five known S1P receptors, S1P1R has been shown to play an important role in vascular permeability and S1P1R knock-out mice have an embryonic lethal phenotype. Furthermore, there is increasing evidence for cross-talk between S1P1R and other growth factor receptors such as PDGFR. Thus, S1P1R receptor antagonists have the potential to offer clinical benefit as anti-cancer therapeutics.

Antimicrotubule drugs such as taxanes, vinca alkaloids and epothilones are a major category of anticancer agents (Rowinsky, E. K., and Tolcher, A. W., *Antimicrotubule agents*. In: V. T. Devita, Jr., and S. Hellman, and S. A. Rosenberg (eds.) *Cancer Principles and Practice*, Ed. 6, pp 431-452. Philadelphia: Lippincott Williams and Wilkins, 2001). Antimicrotubule drugs work by interfering with the function of cellular microtubules, particularly the mitotic spindle. The disruption of normal spindle function leads to apoptotic cell death.

Taxanes are antimicrotubule agents and are part of a class of compounds called diterpenes. Compounds of this type are produced by and originally isolated from plants of the genus *Taxus*. For example, paclitaxel was originally isolated from the bark of the Pacific yew tree *Taxus brevivolia*. Recently, taxanes and their intermediates were isolated from other plant species as well, (Ottaggio et al., *J. Nat. Prod.* 2008, 71:58-60). Presently, most of the drug used for clinical use is produced by a semisynthesis (Holton et al., in *Taxol Science and applications*; Suffness, M., Ed.; CRC Press: Boca Raton, 1995; pp 97-121), starting from a natural precursor, 10-deadetylbaddatin III, that is more redily available from the needles of yew species as a renewable source (Hook, I. et al., *Phytochemistry* 1999, 52:1041-1045, van Rocendaal, E. L. M., et al., *Phytochemistry* 2000, 53:383-389).

The taxanes are a group of drugs that are used in the treatment of cancer. Taxanes have a unique way of preventing the growth of cancer cells, they are anti-mitotic and anti-microtubule agents. Taxanes are microtubule stabilizing agents and interfere with microtubule breakdown which results in cessation of cancer cell growth and division. Taxanes have been used in the treatment of a wide variety of cancers.

Vinca alkaloids are antimicrotubule agents and are part of a class of compounds called plant alkaloids. Vinca compounds of this type are produced and were originally isolated from plants of the genus *Vinca* and specifically from *Vinca rosea*. Unlike the taxanes which are microtubule stabilizing agents, vinca alkaloids are microtubule destabilizing agents that cause microtubule depolymerization and inhibit mitotic progression and ultimately result in apoptotic cell death (Perez, E. A., *Molecular Cancer Therapeutics* 2009, 8:2086-2095). Vinca alkaloids have also been used in the treatment of a wide variety of cancers.

SUMMARY OF THE INVENTION

The present invention is based on the discovery that the use of at least one S1P1R receptor antagonist and at least one antimicrotubule agent produces unexpectedly superior results in the treatment of cancer.

The present invention describes methods of treating cancer in a patient in need thereof by administering to the patient a therapeutically effective amoung of at least one S1P1R receptor antagonist and at least one antimicrotubule agent, preferably a taxane compound or a vinca alkaloid compound. The S1P1R receptor antagonists of the invention are described in the Patent Application entitled "Sphingosine-1-Phosphate Receptor Antagonists" co-owned by Exelixis, Inc, filed concurrently and whose U.S. Provisional Application No. is 61/196,495. The taxanes of the invention are compounds well known in the art and are part of a class of compounds called diterpenes. Compounds of this type are produced by and originally isolated from plants of the genus *Taxus*. Compounds of this type interfere with microtubule breakdown which results in cessation of cancer cell growth and division. The vinca alkaloids of the invention are also well known in the art and are part of the class of compounds called plant alkaloids. Compounds of this type are produced by and originally isolated from the plant *Vinca rosea*. Compounds of this type destabilize the microtubule resulting in the cessation of cancer cell growth and division. The S1P1R receptor antagonist and the antimicrotubule agent, preferably a taxane compound or a vinca alkaloid compound can be administered separately or as components of the same composition.

The present invention describes methods of modulating the growth of selected cell populations, such as cancer cells, by administering a therapeutically effective amoung of at least one S1P1R receptor antagonist and at least one antimicrotubule agent, preferably a taxane compound or a vinca alkaloid compound. The S1P1R receptor antagonists of the invention are described in the Patent Application entitled "Sphingosine-1-Phosphate Receptor Antagonists" co-owned by Exelixis, Inc, filed concurrently and whose Provisional Application No. is 61/196,495. The taxanes of the invention are compounds well known in the art and are part of a class of compounds called diterpenes. Compounds of this type are produced by and originally isolated from plants of the genus *Taxus*. Compounds of this type interfere with microtubule breakdown which results in cessation of cancer cell growth and division. The vinca alkaloids of the invention are also well known in the art and are part of the class of compounds called plant alkaloids. Compounds of this type are produced by and originally isolated from the plant *Vinca rosea*. Compounds of this type destabilize the microtubule resulting in the cessation of cancer cell growth and division. The S1P1R receptor antagonist and the antimicrotubule agent, preferably a taxane compound or a vinca alkaloid compound, can be administered separately or as components of the same composition.

The present invention also describes compositions comprising at least one S1P1R receptor antagonist and at least one antimicrotubule agent, preferably a taxane compound or a vinca alkaloid compound. The S1P1R receptor antagonists of the invention are described in the Patent Application entitled "Sphingosine-1-Phosphate Receptor Antagonists" co-owned by Exelixis, Inc, filed concurrently and whose Provisional Application No. is 61/196,495. The taxanes of the invention are compounds well known in the art and are part of a class of compounds called diterpenes. Compounds of this type are produced by and originally isolated from plants of the genus *Taxus*. Compounds of this type interfere with microtubule breakdown which results in cessation of cancer cell growth and division. The vinca alkaloids of the invention are also well known in the art and are part of the class of compounds called plant alkaloids. Compounds of this type are produced by and originally isolated from the plant *Vinca rosea*. Compounds of this type destabilize the microtubule resulting in the cessation of cancer cell growth and division. The composition can comprise a pharmaceutically acceptable carrier, excipient or diluent. These and other aspects of the invention are described in detail herein.

DETAILED DESCRIPTION OF THE INVENTION

Figure 1A:
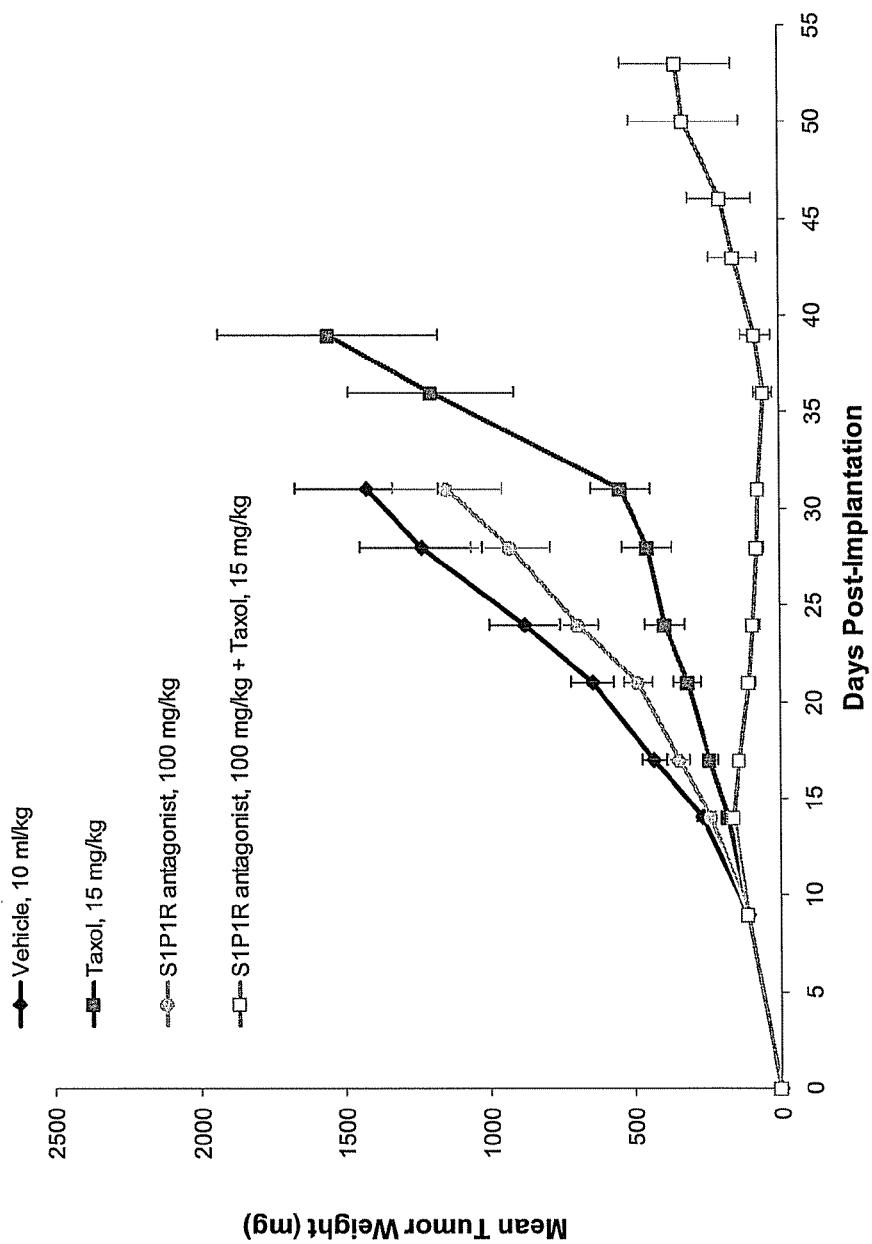
FIG. 1*a* is a graph comparing the anti-tumor activity of a control, an S1P1R receptor antagonist, paclitaxel, and the combination of the S1P1R receptor antagonist and paclitaxel, against human non-small cell lung carcinoma xenographs in NUDE mice (S1P1R antagonist+taxol in Calu-6 XN Model).

The present invention is based on the unexpected discovery that the administration of at least on S1P1R receptor antagonist and at least one antimicrotubule agent preferable a taxane compound or a vinca alkaloid compound, produces superior results in the treatment of cancer. Appropriate S1P1R receptor antagonists, taxanes and vinca alkaloids are described herein.

Definitions:

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, chemotherapy, and the like), "administration" and its variants are each understood to include concurrent and sequential introduction of the compound or prodrug thereof and other agents such as taxanes.

"Cancer" refers to cellular-proliferative disease states, including but not limited to (a) cardiac cancer, such as sarcoma (angiosarcoma, fibrosarcoma, rhabdomyosarcoma, liposarcoma), myxoma, rhabdomyoma, fibroma, lipoma and teratoma; (b) lung cancer, such as bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma and inesothelioma; (c) gastrointestinal cancer, such as esophagial (squamous cell carcinoma, adenocarcinoma, leiomyosarcoma, lymphoma), stomach (carcinoma, lymphoma, leiomyosarcoma), pancreatic (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma) and large bowel (adenocarcinoma, tubular adenoma, villous adenoma, hamartoma, leiomyoma) cancers; (d) genitourinary tract cancer, such as kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma) and testis (seminoma, teratoma, embryonal carcinoma, teratocarcinoma, choriocarcinoma, sarcoma, interstitial cell carcinoma, fibroma, fibroadenoma, adenomatoid tumors, lipoma) cancers; (e) liver cancers, such as hepatoma (hepatocellular carcinoma), cholangiocarcinoma, hepatoblastoma, angiosarcoma, hepatocellular adenoma and hemangioma cancers; (f) bone cancers, such as osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (g) nervous system cancers, such as skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors) and spinal cord (neurofibroma, meningioma, glioma, sarcoma) cancers; (h) gynecological cancers, such as uterus (endometrial carcinoma), cervix (cervical carcinoma, pre-tumor cervical dysplasia), ovarian (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma) cancers; (i) hematologic cancers, such as blood (acute and chronic myeloid leukemia, acute lymphoblastic leukemia, chronic lymphocytic leukemia, myeloproliferative diseases, multiple myeloma, myelodysplastic syndrome), Hodgkin's disease and non-Hodgkin's lymphoma [malignant lymphoma]; (j) skin cancer, such as malignant melanoma, basal cell carcinoma, squamous cell carcinoma, Karposi's sarcoma, moles dysplastic nevi, lipoma, angioma, dermatofibroma, keloids and psoriasis; (k) adrenal glands cancer, such as neuroblastoma; and breast cancer. Thus, the term "cancerous cell" as provided herein, includes a cell afflicted by any one of the above-identified conditions.

Preferably, cancer refers to AIDS related Kaposi's Sarcoma, angiosarcoma, breast cancer, carcinoma of the bladder, carcinoma of the esophagus, carcinoma of the fallopian tube, carcinoma of the pancreas, carcinoma of the prostate, cervical cancer, colorectal cancer, gastric cancer, head and neck cancer, Hodgkin's disease, leukemia, malignant glioma, malignant lymphoma, malignant melanoma, malignant neoplasm of endometrium of corpus uteri, malignant neoplasm of liver, malignant tumor of nasopharynx, malignant tumor of peritoneum, multiple myeloma, non-small cell lung carcinoma, oligodendroglioma of the brain, osteosarcoma, ovarian cancer, small cell lung carcinoma, soft tissue sarcoma and testicular cancer.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see goodman and gilman, "The Pharmacological Basis of Therapeutics" 8.sup.th Ed., Pergamon Press, gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, $17^{th}$ ed., Mack Publishing Company, Easton, Pa., 1985, which is incorporated herein by reference or S. M. Berge, et al., "Pharmaceutical Salts," J. Pharm. Sci., 1977;66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium and magnesium salts. Salts derived from pharmaceutically acceptable organic non-toxic bases include, but are not limited to, salts of primary, secondary and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, effectively treats the disease. The amount of a compound of the invention which constitutes a "therapeutically effective amount" will vary depending upon a sundry of factors including the activity, metabolic stability, rate of excretion and duration of action of the compound, the age, weight, general health, sex, diet and species of the patient, the mode and time of administration of the compound, the concurrent administration of adjuvants or additional therapies and the severity of the disease for which the therapeutic effect is sought. The therapeutically effective amount for a given circumstance can be determined without undue experimentation.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, the age, weight, general health, sex, diet and species of the patient, the mode and time of administration of the compound, the concurrent administration of adjuvants or additional therapeutically active ingredients and the severity of the disease for which the therapeutic effect is sought may be necessary, and will be ascertainable with routine experimentation.

Representative S1P1R Receptor antagonist compounds of the inventions are set forth in the following Table 1.

TABLE 1

1

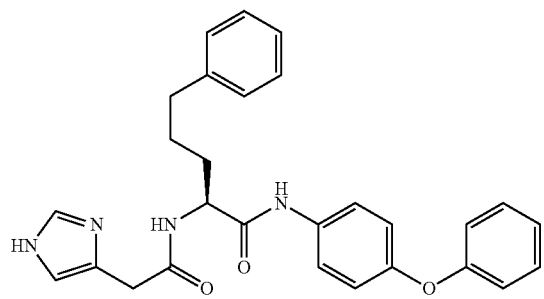 [SMILES: O=C(Cc1c[nH]cn1)N[C@@H](CCCc1ccccc1)C(=O)Nc1ccc(Oc2ccccc2)cc1]

2

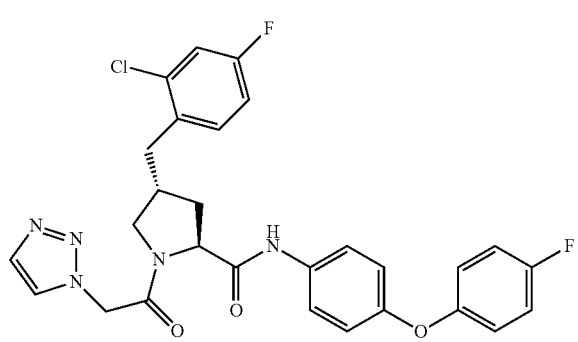 [SMILES: O=C(Nc1ccc(Oc2ccc(F)cc2)cc1)[C@@H]1C[C@@H](Cc2ccc(F)cc2Cl)CN1C(=O)Cn1ccnn1]

3

TABLE 1-continued
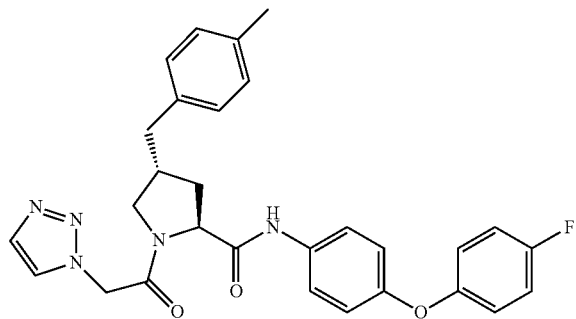 [SMILES: Cc1ccc(C[C@@H]2C[C@@H](C(=O)Nc3ccc(Oc4ccc(F)cc4)cc3)N(C(=O)Cn3ccnn3)C2)cc1]
4
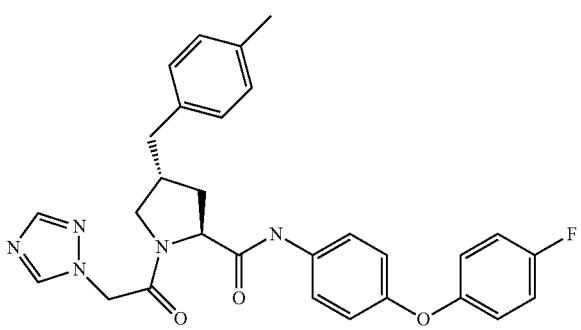 [SMILES: Cc1ccc(C[C@@H]2C[C@@H](C(=O)Nc3ccc(Oc4ccc(F)cc4)cc3)N(C(=O)Cn3cncn3)C2)cc1]
5
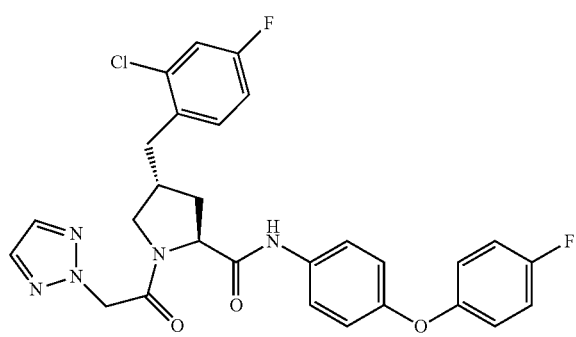 [SMILES: O=C(Nc1ccc(Oc2ccc(F)cc2)cc1)[C@@H]1C[C@@H](Cc2ccc(F)cc2Cl)CN1C(=O)Cn1nccn1]
6
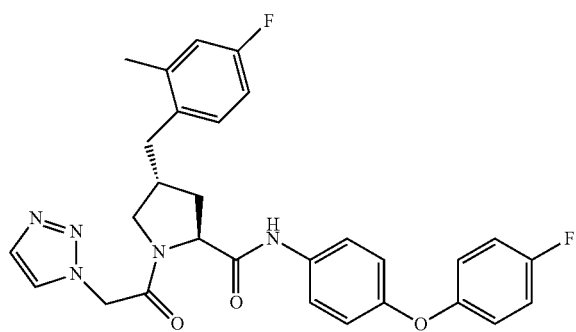 [SMILES: Cc1cc(F)ccc1C[C@@H]1C[C@@H](C(=O)Nc2ccc(Oc3ccc(F)cc3)cc2)N(C(=O)Cn2ccnn2)C1]
7

TABLE 1-continued
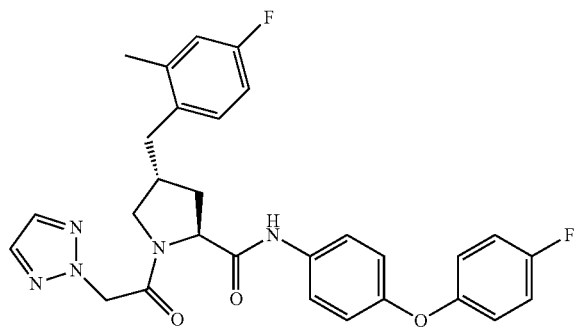 [SMILES: Cc1cc(F)ccc1C[C@@H]1C[C@@H](C(=O)Nc2ccc(Oc3ccc(F)cc3)cc2)N(C(=O)Cn2nccn2)C1]
8
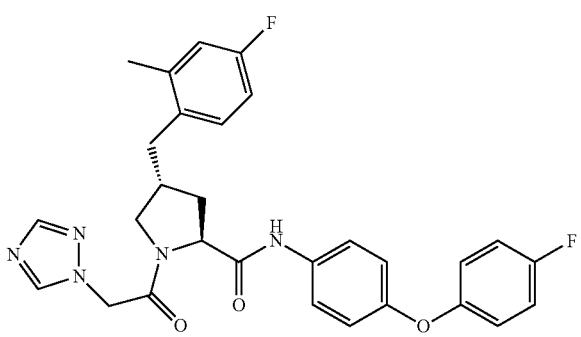 [SMILES: Cc1cc(F)ccc1C[C@@H]1C[C@@H](C(=O)Nc2ccc(Oc3ccc(F)cc3)cc2)N(C(=O)Cn2cncn2)C1]
9
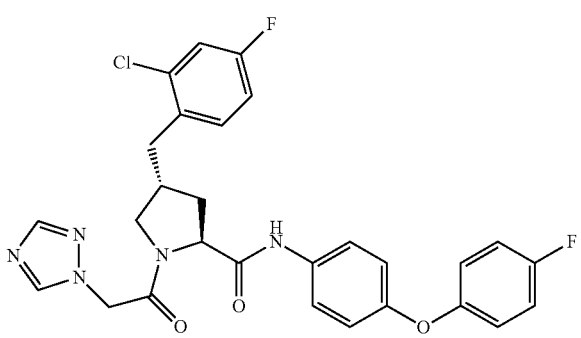 [SMILES: O=C(Nc1ccc(Oc2ccc(F)cc2)cc1)[C@@H]1C[C@@H](Cc2ccc(F)cc2Cl)CN1C(=O)Cn1cncn1]
10
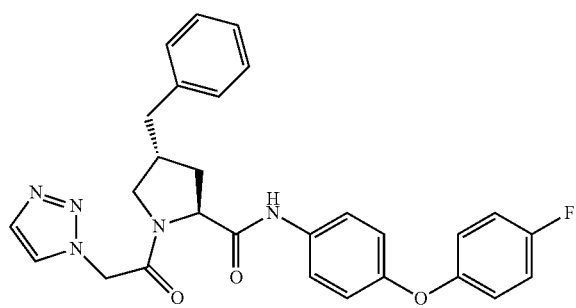 [SMILES: O=C(Nc1ccc(Oc2ccc(F)cc2)cc1)[C@@H]1C[C@@H](Cc2ccccc2)CN1C(=O)Cn1ccnn1]
11

TABLE 1-continued
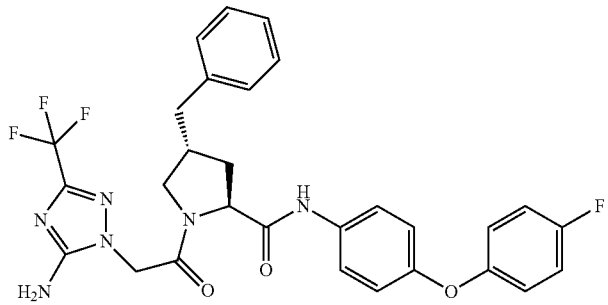 [SMILES: Nc1nc(C(F)(F)F)nn1CC(=O)N1C[C@H](Cc2ccccc2)C[C@H]1C(=O)Nc1ccc(Oc2ccc(F)cc2)cc1]
12
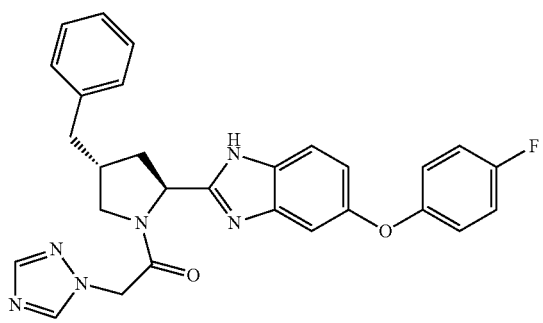 [SMILES: O=C(Cn1cncn1)N1C[C@H](Cc2ccccc2)C[C@H]1c1nc2cc(Oc3ccc(F)cc3)ccc2[nH]1]
13
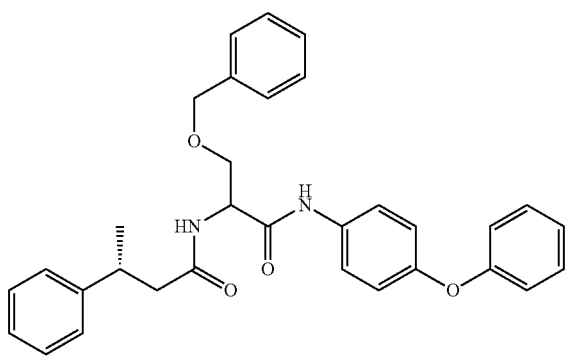 [SMILES: C[C@H](CC(=O)NC(COCc1ccccc1)C(=O)Nc1ccc(Oc2ccccc2)cc1)c1ccccc1]
14
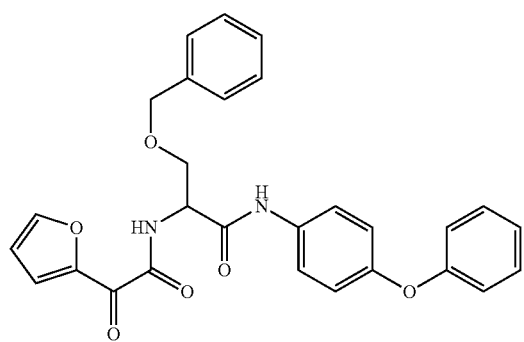 [SMILES: O=C(NC(COCc1ccccc1)C(=O)Nc1ccc(Oc2ccccc2)cc1)C(=O)c1ccco1]
15

TABLE 1-continued
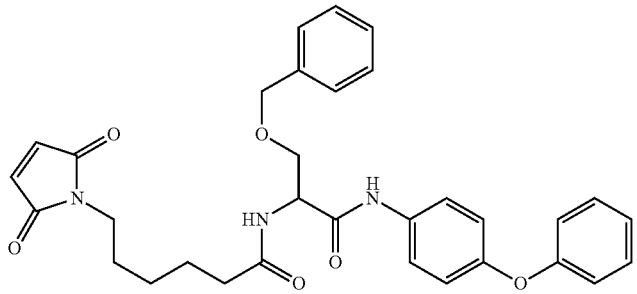 [SMILES: O=C(CCCCCN1C(=O)C=CC1=O)NC(COCc1ccccc1)C(=O)Nc1ccc(Oc2ccccc2)cc1]
16
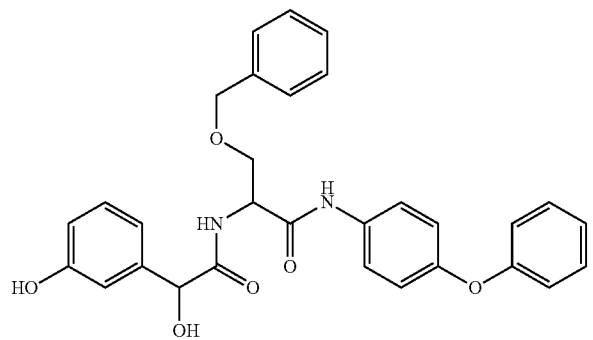 [SMILES: O=C(Nc1ccc(Oc2ccccc2)cc1)C(COCc1ccccc1)NC(=O)C(O)c1cccc(O)c1]
17
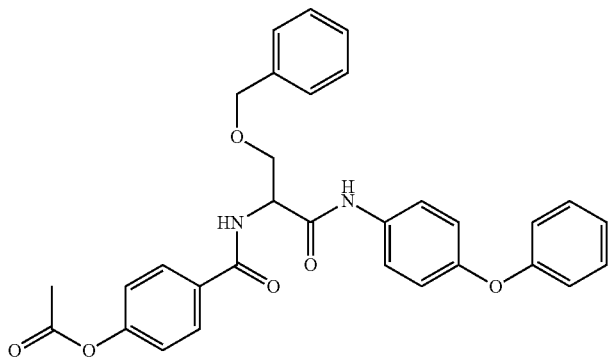 [SMILES: CC(=O)Oc1ccc(C(=O)NC(COCc2ccccc2)C(=O)Nc2ccc(Oc3ccccc3)cc2)cc1]
18
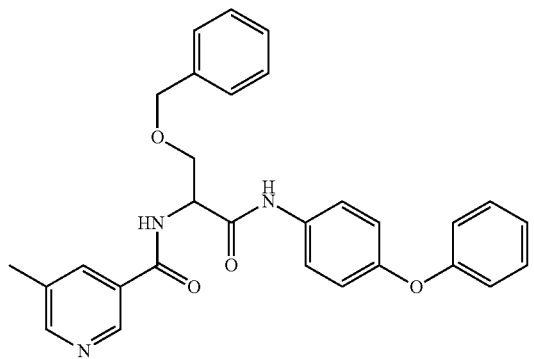 [SMILES: Cc1cncc(C(=O)NC(COCc2ccccc2)C(=O)Nc2ccc(Oc3ccccc3)cc2)c1]
19

TABLE 1-continued
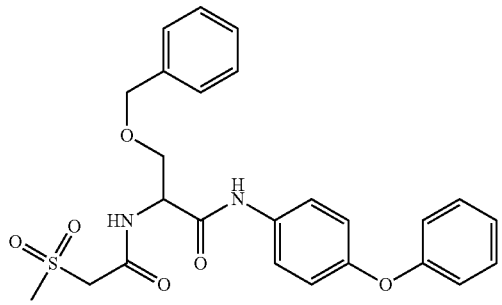 [SMILES: CS(=O)(=O)CC(=O)NC(COCc1ccccc1)C(=O)Nc1ccc(Oc2ccccc2)cc1]
20
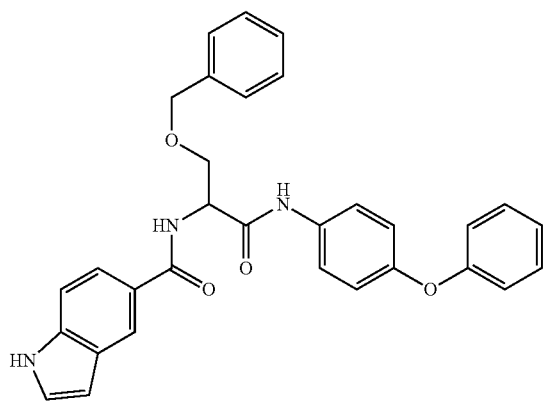 [SMILES: O=C(NC(COCc1ccccc1)C(=O)Nc1ccc(Oc2ccccc2)cc1)c1ccc2[nH]ccc2c1]
21
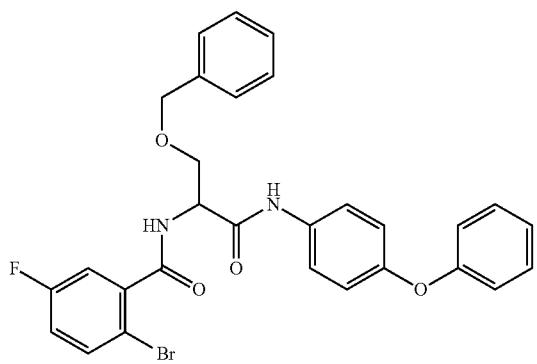 [SMILES: O=C(NC(COCc1ccccc1)C(=O)Nc1ccc(Oc2ccccc2)cc1)c1cc(F)ccc1Br]
22
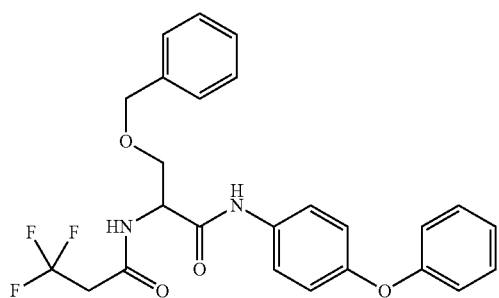 [SMILES: O=C(CC(F)(F)F)NC(COCc1ccccc1)C(=O)Nc1ccc(Oc2ccccc2)cc1]
23

TABLE 1-continued
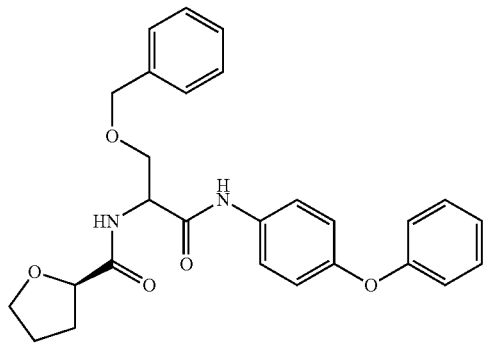 [SMILES: O=C(Nc1ccc(Oc2ccccc2)cc1)C(COCc1ccccc1)NC(=O)[C@H]1CCCO1]
24
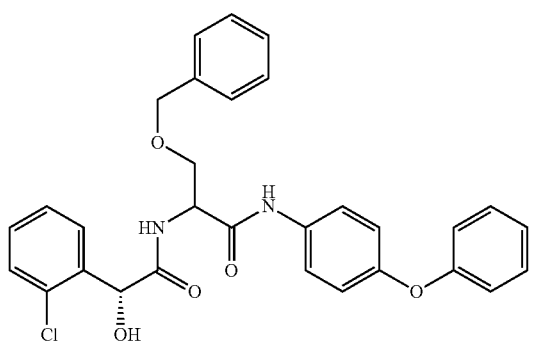 [SMILES: O=C(Nc1ccc(Oc2ccccc2)cc1)C(COCc1ccccc1)NC(=O)[C@H](O)c1ccccc1Cl]
25
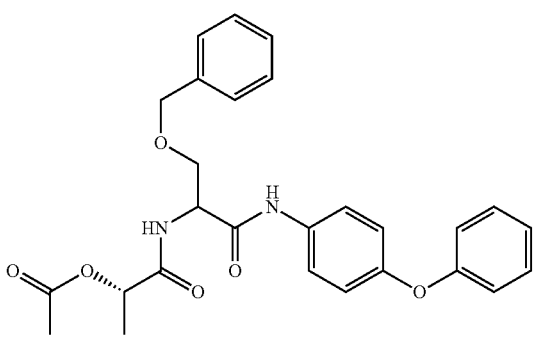 [SMILES: CC(=O)O[C@@H](C)C(=O)NC(COCc1ccccc1)C(=O)Nc1ccc(Oc2ccccc2)cc1]
26
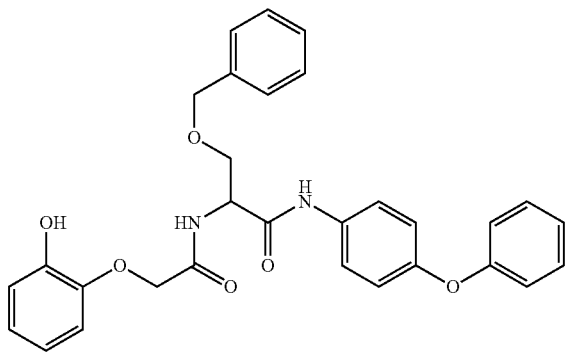 [SMILES: O=C(COc1ccccc1O)NC(COCc1ccccc1)C(=O)Nc1ccc(Oc2ccccc2)cc1]
27

TABLE 1-continued
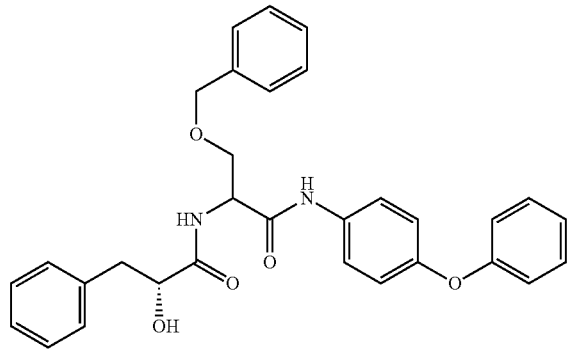 [SMILES: O=C(Nc1ccc(Oc2ccccc2)cc1)C(COCc1ccccc1)NC(=O)[C@H](O)Cc1ccccc1]
28
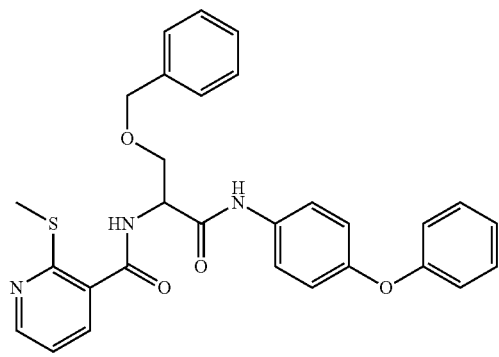 [SMILES: CSc1ncccc1C(=O)NC(COCc1ccccc1)C(=O)Nc1ccc(Oc2ccccc2)cc1]
29
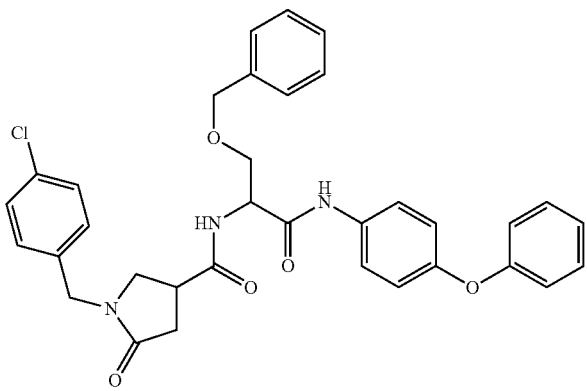 [SMILES: O=C(NC(COCc1ccccc1)C(=O)Nc1ccc(Oc2ccccc2)cc1)C1CC(=O)N(Cc2ccc(Cl)cc2)C1]
30
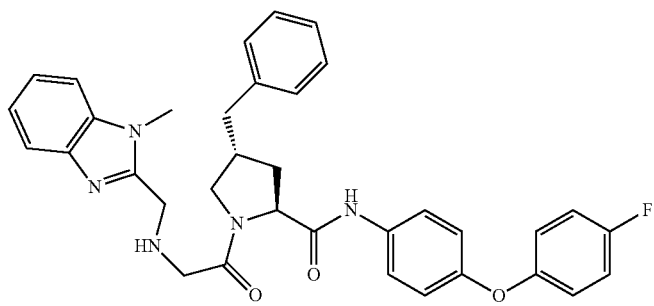 [SMILES: Cn1c(CNCC(=O)N2C[C@H](Cc3ccccc3)C[C@H]2C(=O)Nc2ccc(Oc3ccc(F)cc3)cc2)nc2ccccc21]
31

TABLE 1-continued
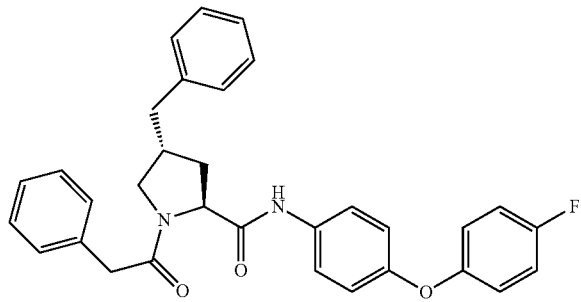 [SMILES: O=C(Nc1ccc(Oc2ccc(F)cc2)cc1)[C@@H]1C[C@@H](Cc2ccccc2)CN1C(=O)Cc1ccccc1]
32
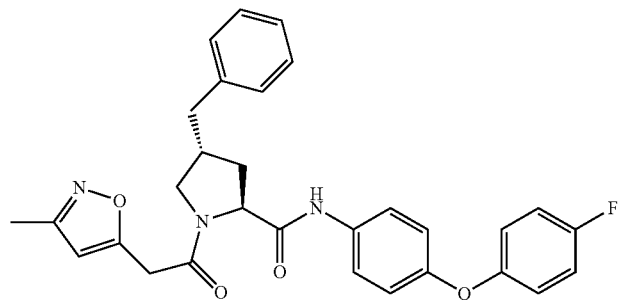 [SMILES: Cc1cc(CC(=O)N2C[C@H](Cc3ccccc3)C[C@H]2C(=O)Nc2ccc(Oc3ccc(F)cc3)cc2)on1]
33
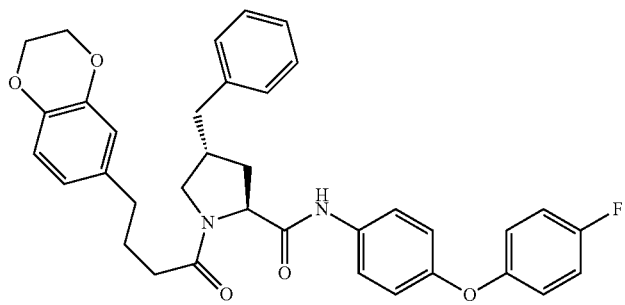 [SMILES: O=C(Nc1ccc(Oc2ccc(F)cc2)cc1)[C@@H]1C[C@@H](Cc2ccccc2)CN1C(=O)CCCc1ccc2c(c1)OCCO2]
34
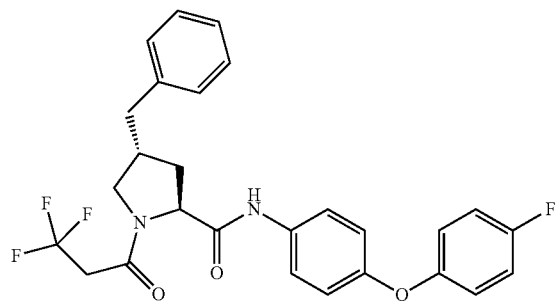 [SMILES: O=C(Nc1ccc(Oc2ccc(F)cc2)cc1)[C@@H]1C[C@@H](Cc2ccccc2)CN1C(=O)CC(F)(F)F]
35
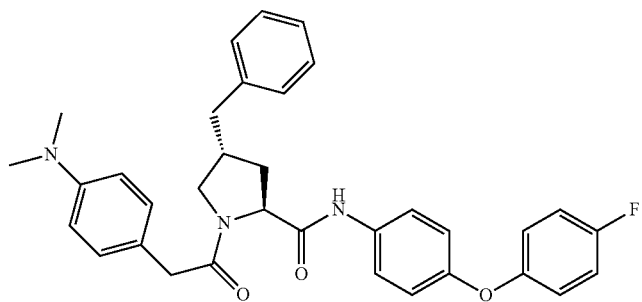 [SMILES: CN(C)c1ccc(CC(=O)N2C[C@H](Cc3ccccc3)C[C@H]2C(=O)Nc2ccc(Oc3ccc(F)cc3)cc2)cc1]

TABLE 1-continued
36
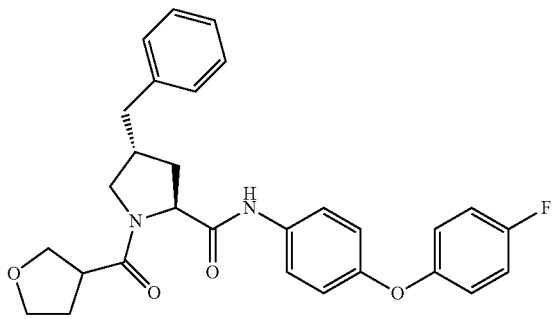 [SMILES: O=C(Nc1ccc(Oc2ccc(F)cc2)cc1)[C@@H]1C[C@@H](Cc2ccccc2)CN1C(=O)C1CCOC1]
37
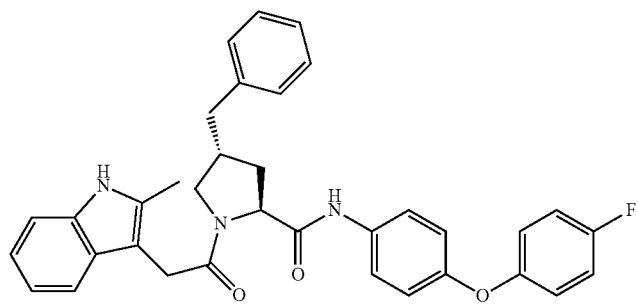 [SMILES: Cc1[nH]c2ccccc2c1CC(=O)N1C[C@H](Cc2ccccc2)C[C@H]1C(=O)Nc1ccc(Oc2ccc(F)cc2)cc1]
38
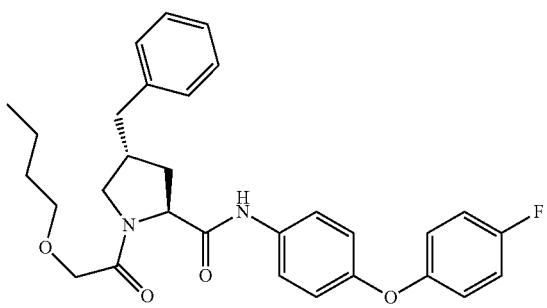 [SMILES: CCCCOCC(=O)N1C[C@H](Cc2ccccc2)C[C@H]1C(=O)Nc1ccc(Oc2ccc(F)cc2)cc1]
39
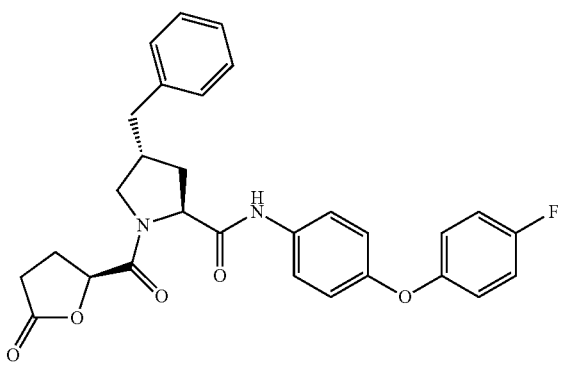 [SMILES: O=C1CC[C@@H](C(=O)N2C[C@H](Cc3ccccc3)C[C@H]2C(=O)Nc2ccc(Oc3ccc(F)cc3)cc2)O1]
40

TABLE 1-continued
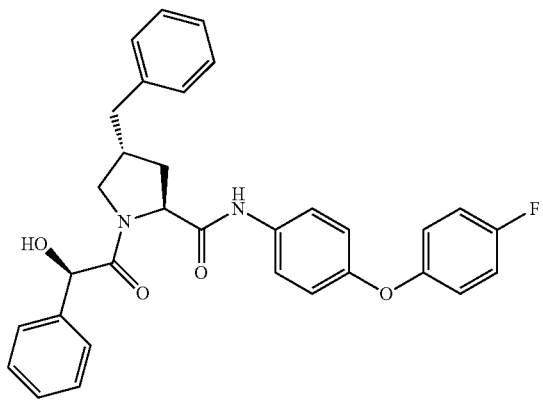 [SMILES: O=C(Nc1ccc(Oc2ccc(F)cc2)cc1)[C@@H]1C[C@@H](Cc2ccccc2)CN1C(=O)[C@H](O)c1ccccc1]
41
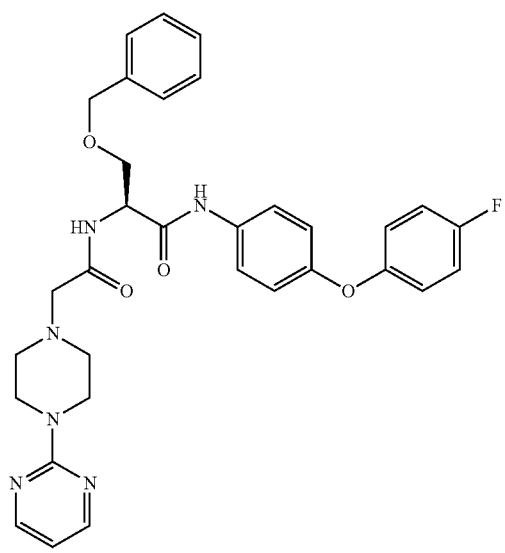 [SMILES: O=C(CN1CCN(c2ncccn2)CC1)N[C@@H](COCc1ccccc1)C(=O)Nc1ccc(Oc2ccc(F)cc2)cc1]
42
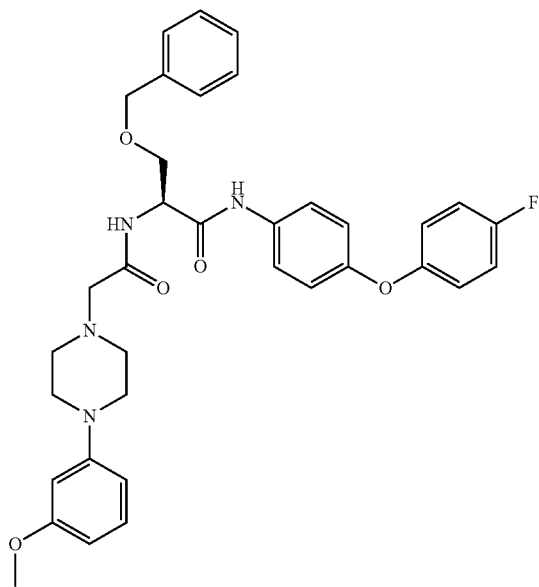 [SMILES: COc1cccc(N2CCN(CC(=O)N[C@@H](COCc3ccccc3)C(=O)Nc3ccc(Oc4ccc(F)cc4)cc3)CC2)c1]
43

TABLE 1-continued
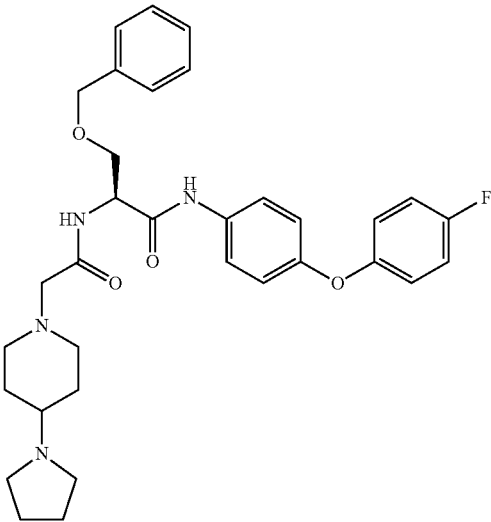 [SMILES: O=C(CN1CCC(N2CCCC2)CC1)N[C@@H](COCc1ccccc1)C(=O)Nc1ccc(Oc2ccc(F)cc2)cc1]
44
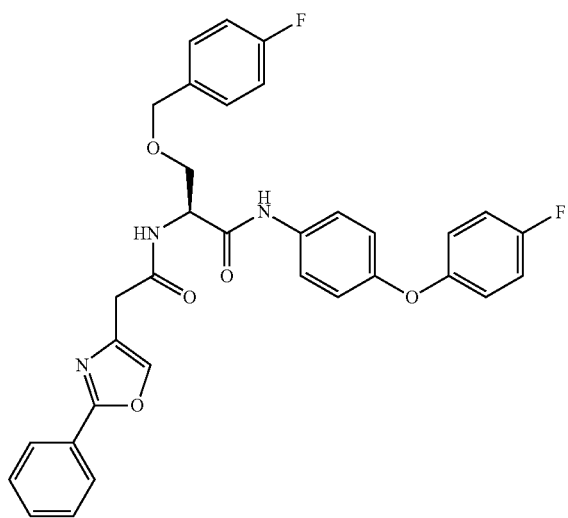 [SMILES: O=C(Cc1coc(-c2ccccc2)n1)N[C@@H](COCc1ccc(F)cc1)C(=O)Nc1ccc(Oc2ccc(F)cc2)cc1]
45
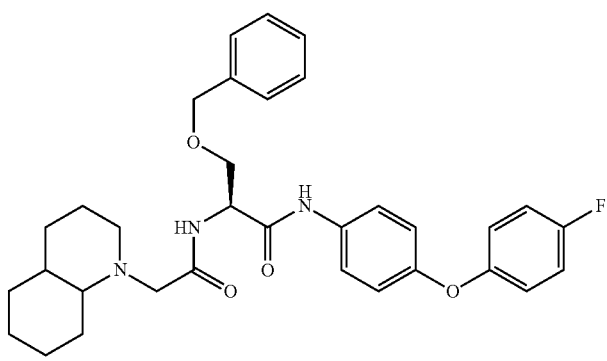 [SMILES: O=C(CN1CCCC2CCCCC21)N[C@@H](COCc1ccccc1)C(=O)Nc1ccc(Oc2ccc(F)cc2)cc1]
46

TABLE 1-continued
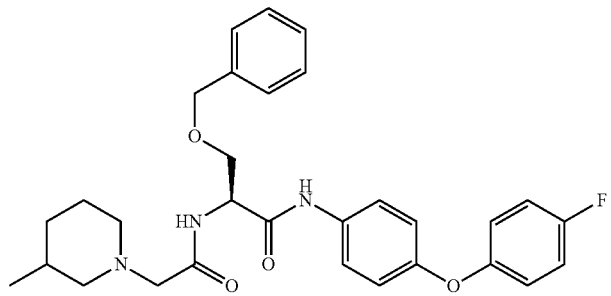 [SMILES: CC1CCCN(CC(=O)N[C@@H](COCc2ccccc2)C(=O)Nc2ccc(Oc3ccc(F)cc3)cc2)C1]
47
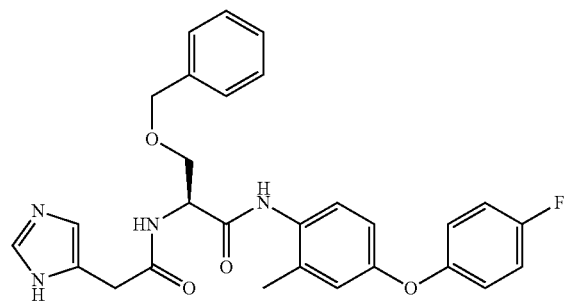 [SMILES: Cc1cc(Oc2ccc(F)cc2)ccc1NC(=O)[C@H](COCc1ccccc1)NC(=O)Cc1cnc[nH]1]
48
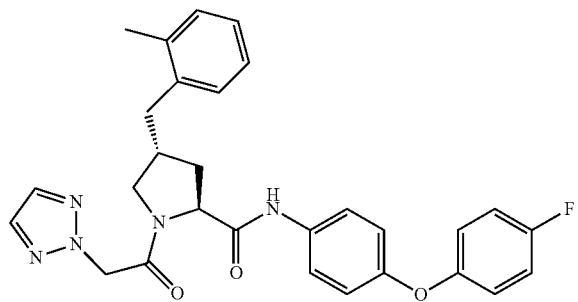 [SMILES: Cc1ccccc1C[C@@H]1C[C@@H](C(=O)Nc2ccc(Oc3ccc(F)cc3)cc2)N(C(=O)Cn2nccn2)C1]
49
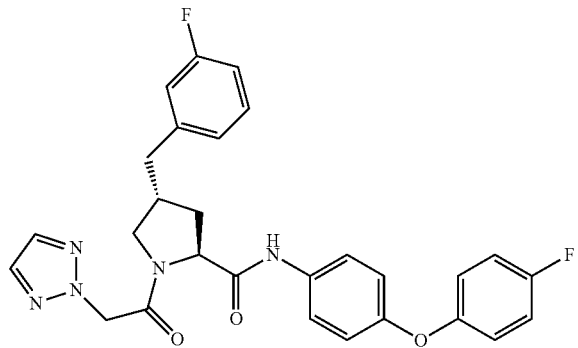 [SMILES: O=C(Nc1ccc(Oc2ccc(F)cc2)cc1)[C@@H]1C[C@@H](Cc2cccc(F)c2)CN1C(=O)Cn1nccn1]
50

TABLE 1-continued
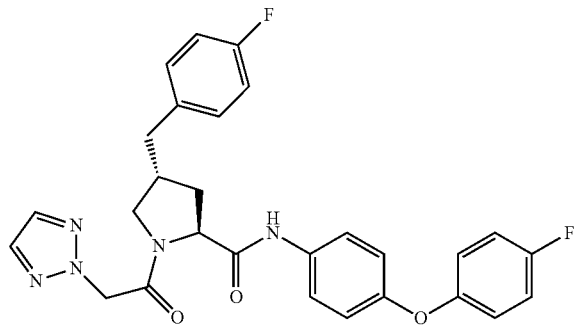
51
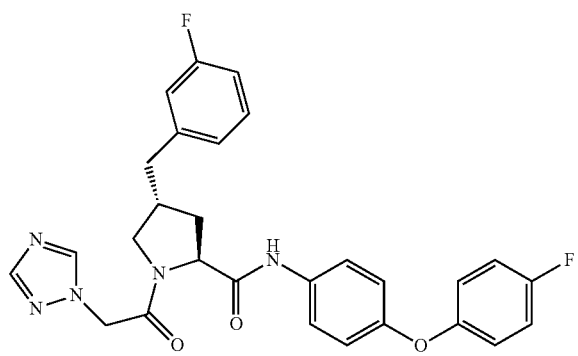 [SMILES: O=C(Nc1ccc(Oc2ccc(F)cc2)cc1)[C@@H]1C[C@@H](Cc2cccc(F)c2)CN1C(=O)Cn1cncn1]
52
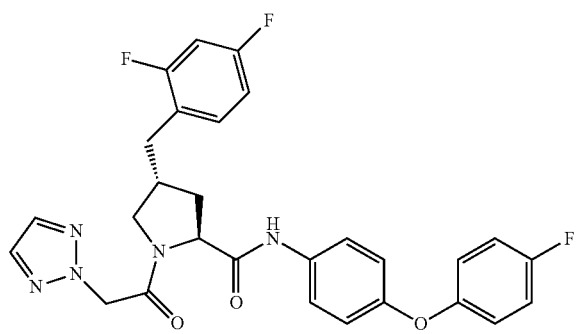 [SMILES: O=C(Nc1ccc(Oc2ccc(F)cc2)cc1)[C@@H]1C[C@@H](Cc2ccc(F)cc2F)CN1C(=O)Cn1nccn1]
53
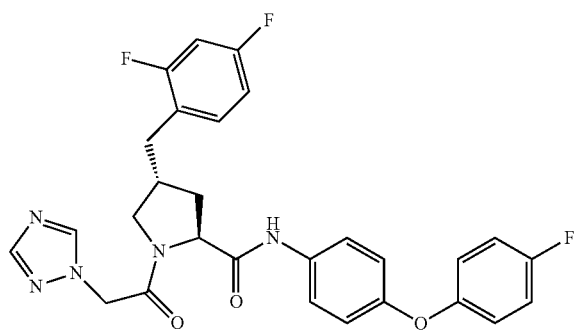 [SMILES: O=C(Nc1ccc(Oc2ccc(F)cc2)cc1)[C@@H]1C[C@@H](Cc2ccc(F)cc2F)CN1C(=O)Cn1cncn1]
54

TABLE 1-continued
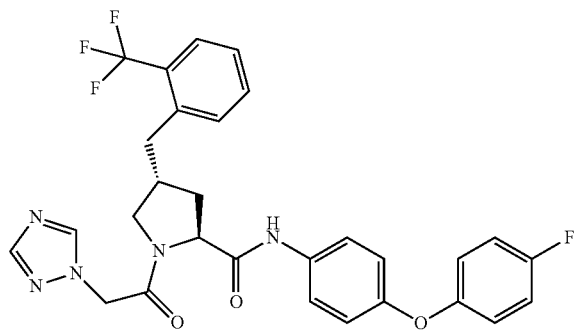 [SMILES: O=C(Nc1ccc(Oc2ccc(F)cc2)cc1)[C@@H]1C[C@@H](Cc2ccccc2C(F)(F)F)CN1C(=O)Cn1cncn1]
54
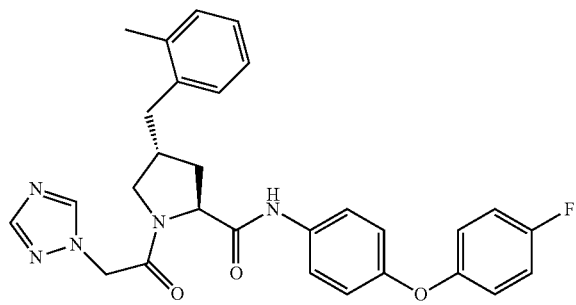 [SMILES: Cc1ccccc1C[C@@H]1C[C@@H](C(=O)Nc2ccc(Oc3ccc(F)cc3)cc2)N(C(=O)Cn2cncn2)C1]
55
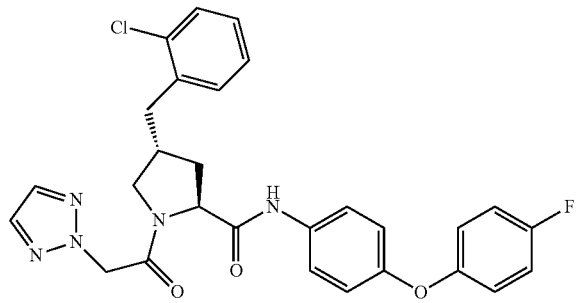 [SMILES: O=C(Nc1ccc(Oc2ccc(F)cc2)cc1)[C@@H]1C[C@@H](Cc2ccccc2Cl)CN1C(=O)Cn1nccn1]
56
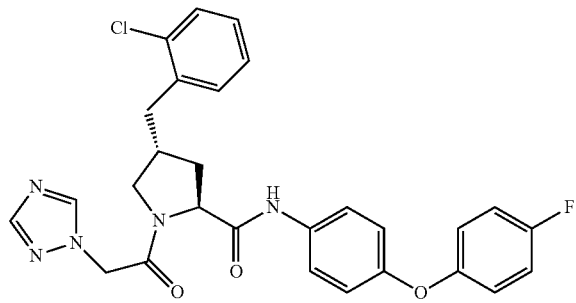 [SMILES: O=C(Nc1ccc(Oc2ccc(F)cc2)cc1)[C@@H]1C[C@@H](Cc2ccccc2Cl)CN1C(=O)Cn1cncn1]
57
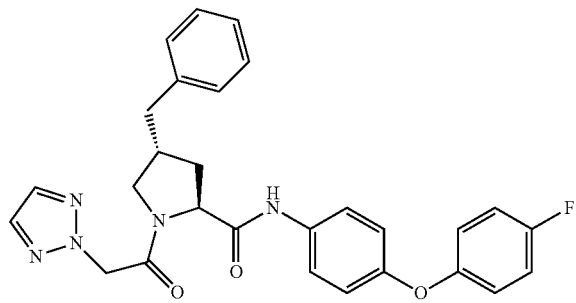 [SMILES: O=C(Nc1ccc(Oc2ccc(F)cc2)cc1)[C@@H]1C[C@@H](Cc2ccccc2)CN1C(=O)Cn1nccn1]
58

TABLE 1-continued
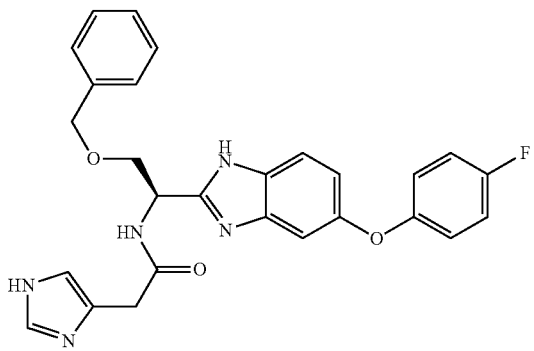 [SMILES: O=C(Cc1c[nH]cn1)N[C@@H](COCc1ccccc1)c1nc2cc(Oc3ccc(F)cc3)ccc2[nH]1]
59
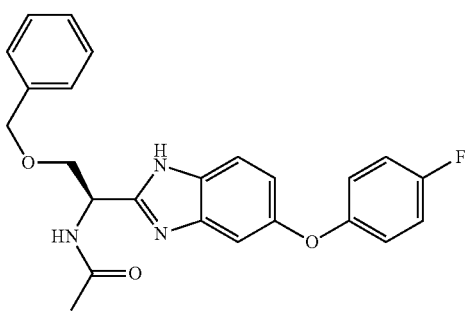 [SMILES: CC(=O)N[C@@H](COCc1ccccc1)c1nc2cc(Oc3ccc(F)cc3)ccc2[nH]1]
60
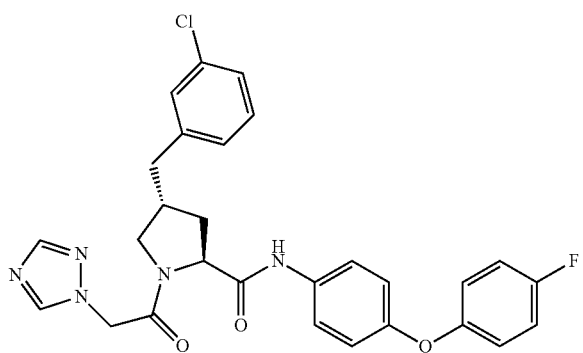 [SMILES: O=C(Nc1ccc(Oc2ccc(F)cc2)cc1)[C@@H]1C[C@@H](Cc2cccc(Cl)c2)CN1C(=O)Cn1cncn1]
61
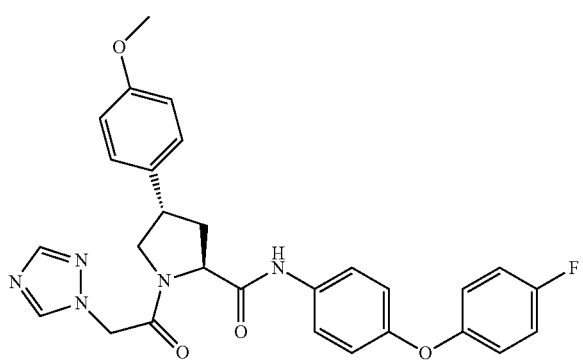 [SMILES: COc1ccc([C@@H]2C[C@@H](C(=O)Nc3ccc(Oc4ccc(F)cc4)cc3)N(C(=O)Cn3cncn3)C2)cc1]
62
63

TABLE 1-continued
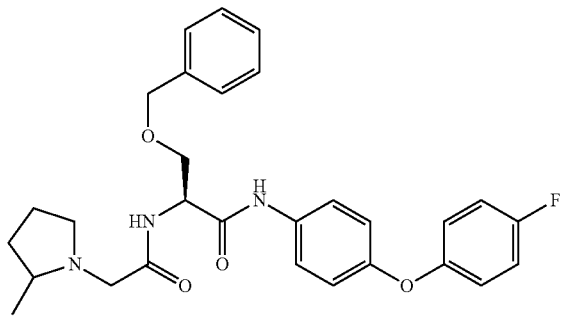 [SMILES: CC1CCCN1CC(=O)N[C@@H](COCc1ccccc1)C(=O)Nc1ccc(Oc2ccc(F)cc2)cc1]
64
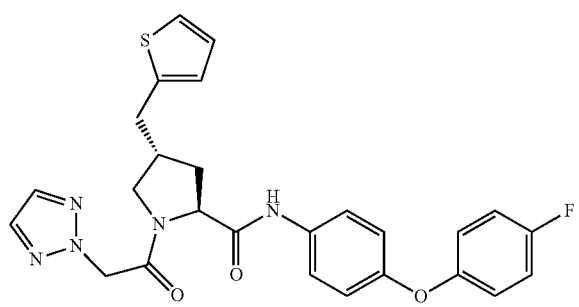 [SMILES: O=C(Nc1ccc(Oc2ccc(F)cc2)cc1)[C@@H]1C[C@@H](Cc2cccs2)CN1C(=O)Cn1nccn1]
65
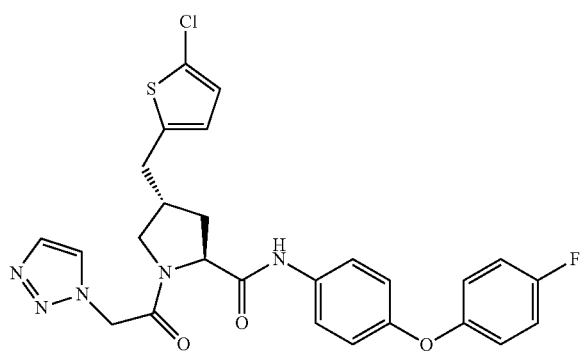 [SMILES: O=C(Nc1ccc(Oc2ccc(F)cc2)cc1)[C@@H]1C[C@@H](Cc2ccc(Cl)s2)CN1C(=O)Cn1ccnn1]
66
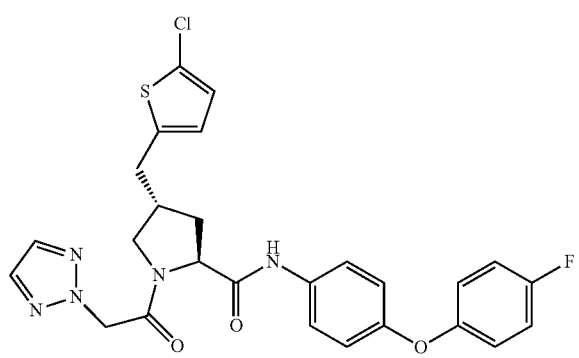 [SMILES: O=C(Nc1ccc(Oc2ccc(F)cc2)cc1)[C@@H]1C[C@@H](Cc2ccc(Cl)s2)CN1C(=O)Cn1nccn1]
67

TABLE 1-continued
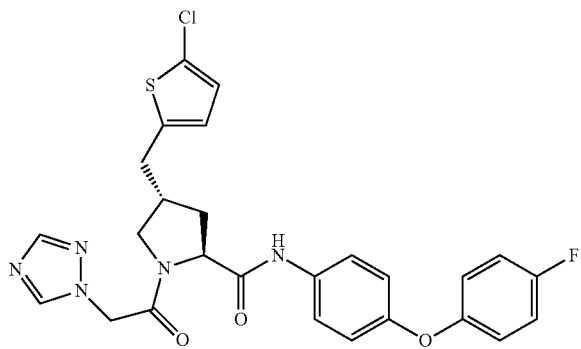 [SMILES: O=C(Nc1ccc(Oc2ccc(F)cc2)cc1)[C@@H]1C[C@@H](Cc2ccc(Cl)s2)CN1C(=O)Cn1cncn1]
68
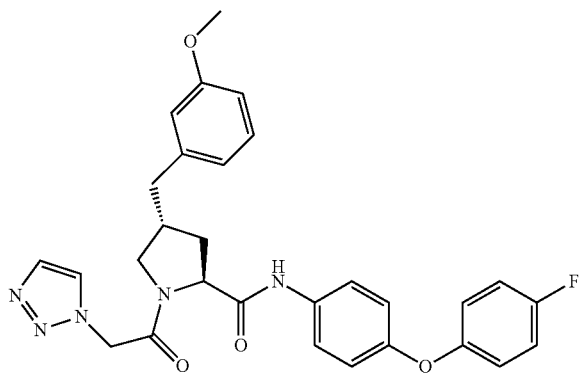 [SMILES: COc1cccc(C[C@@H]2C[C@@H](C(=O)Nc3ccc(Oc4ccc(F)cc4)cc3)N(C(=O)Cn3ccnn3)C2)c1]
69
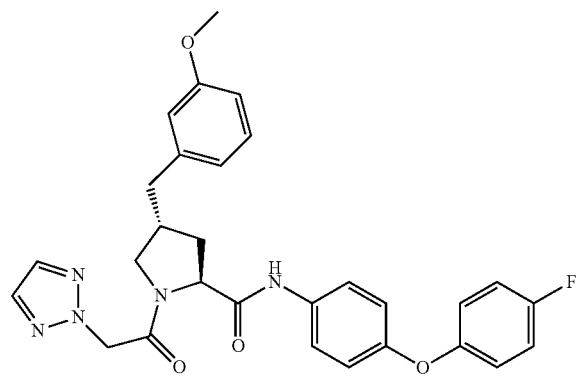 [SMILES: COc1cccc(C[C@@H]2C[C@@H](C(=O)Nc3ccc(Oc4ccc(F)cc4)cc3)N(C(=O)Cn3nccn3)C2)c1]
70
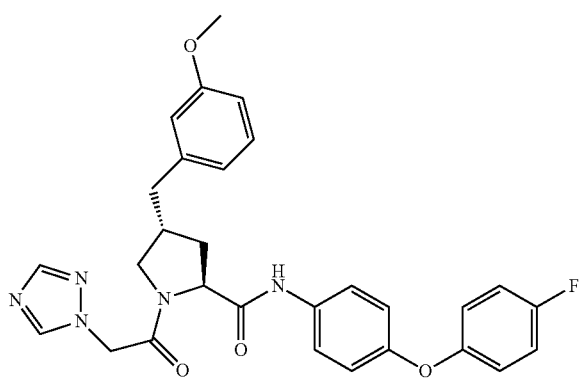 [SMILES: COc1cccc(C[C@@H]2C[C@@H](C(=O)Nc3ccc(Oc4ccc(F)cc4)cc3)N(C(=O)Cn3cncn3)C2)c1]
71

TABLE 1-continued
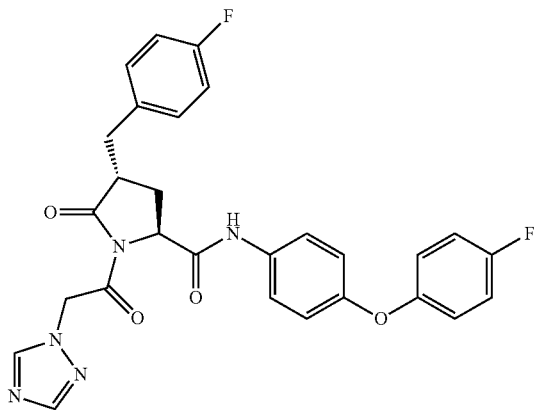 [SMILES: O=C(Nc1ccc(Oc2ccc(F)cc2)cc1)[C@@H]1C[C@@H](Cc2ccc(F)cc2)C(=O)N1C(=O)Cn1cncn1]
72
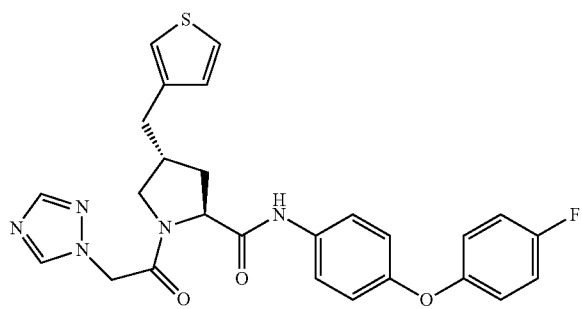 [SMILES: O=C(Nc1ccc(Oc2ccc(F)cc2)cc1)[C@@H]1C[C@@H](Cc2ccsc2)CN1C(=O)Cn1cncn1]
73
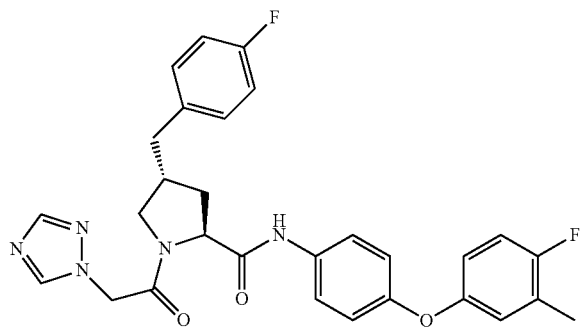 [SMILES: Cc1cc(Oc2ccc(NC(=O)[C@@H]3C[C@@H](Cc4ccc(F)cc4)CN3C(=O)Cn3cncn3)cc2)ccc1F]
74
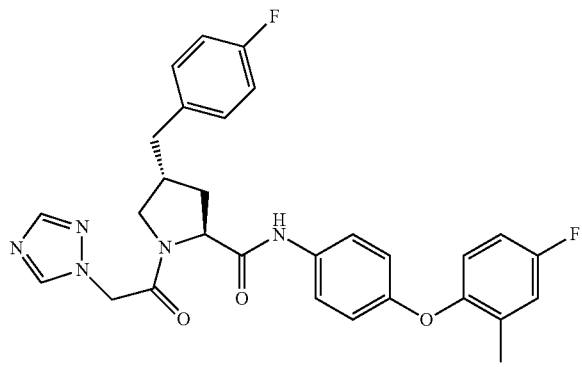 [SMILES: Cc1cc(F)ccc1Oc1ccc(NC(=O)[C@@H]2C[C@@H](Cc3ccc(F)cc3)CN2C(=O)Cn2cncn2)cc1]
75

TABLE 1-continued
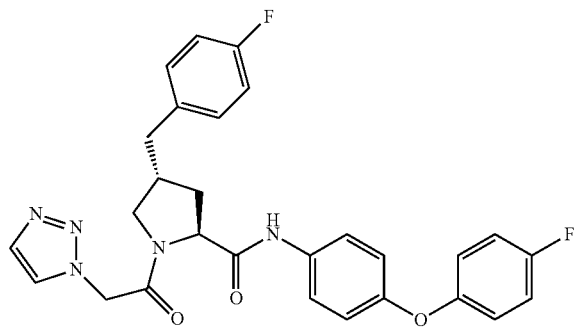 [SMILES: O=C(Nc1ccc(Oc2ccc(F)cc2)cc1)[C@@H]1C[C@@H](Cc2ccc(F)cc2)CN1C(=O)Cn1ccnn1]
76
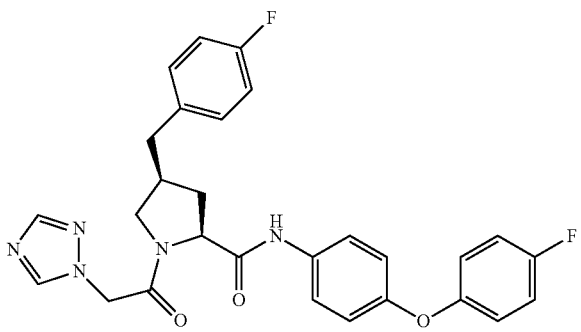 [SMILES: O=C(Nc1ccc(Oc2ccc(F)cc2)cc1)[C@@H]1C[C@H](Cc2ccc(F)cc2)CN1C(=O)Cn1cncn1]
77
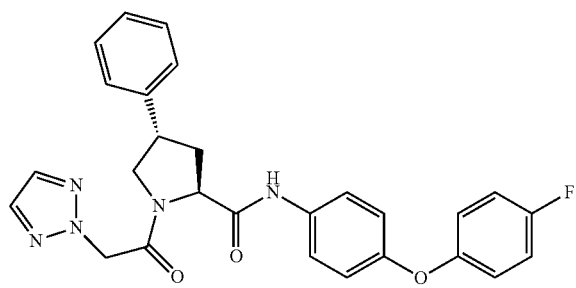 [SMILES: O=C(Nc1ccc(Oc2ccc(F)cc2)cc1)[C@@H]1C[C@@H](c2ccccc2)CN1C(=O)Cn1nccn1]
78
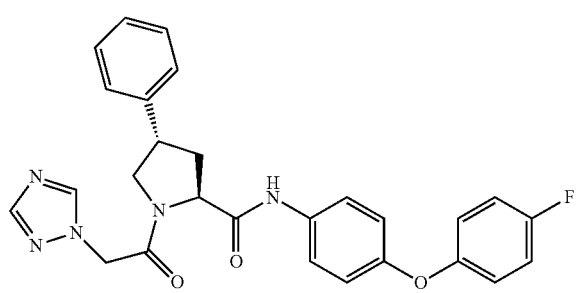 [SMILES: O=C(Nc1ccc(Oc2ccc(F)cc2)cc1)[C@@H]1C[C@@H](c2ccccc2)CN1C(=O)Cn1cncn1]
79
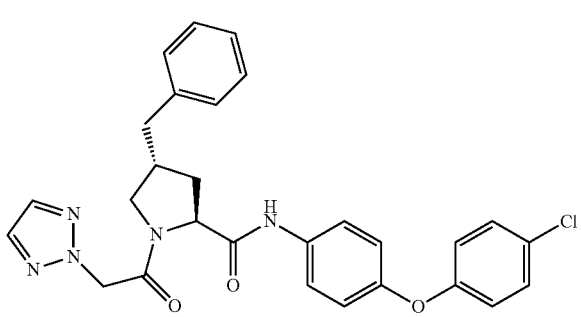 [SMILES: O=C(Nc1ccc(Oc2ccc(Cl)cc2)cc1)[C@@H]1C[C@@H](Cc2ccccc2)CN1C(=O)Cn1nccn1]

TABLE 1-continued
80
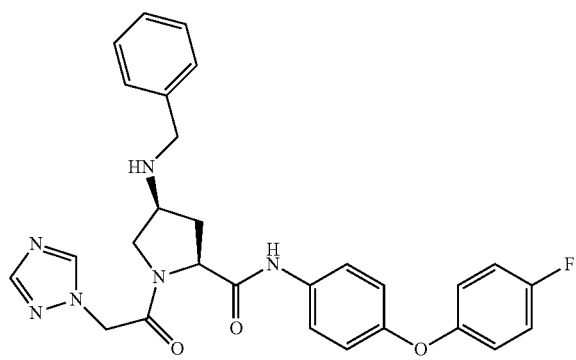 [SMILES: O=C(Nc1ccc(Oc2ccc(F)cc2)cc1)[C@@H]1C[C@H](NCc2ccccc2)CN1C(=O)Cn1cncn1]
81
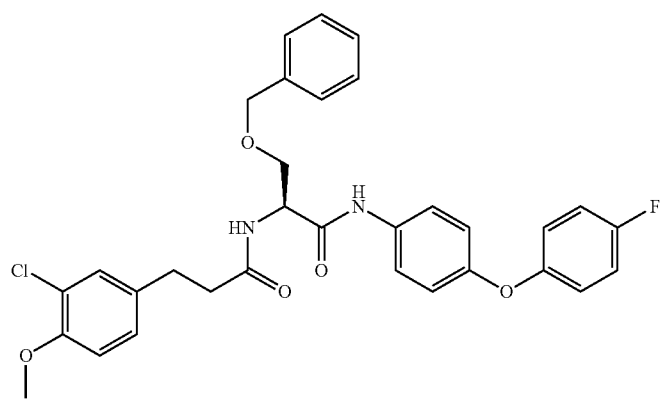 [SMILES: COc1ccc(CCC(=O)N[C@@H](COCc2ccccc2)C(=O)Nc2ccc(Oc3ccc(F)cc3)cc2)cc1Cl]
82
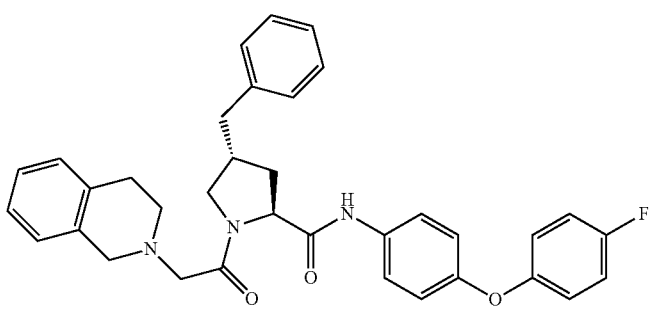 [SMILES: O=C(Nc1ccc(Oc2ccc(F)cc2)cc1)[C@@H]1C[C@@H](Cc2ccccc2)CN1C(=O)CN1CCc2ccccc2C1]
83
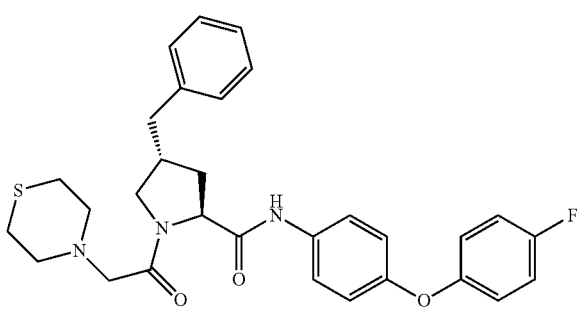 [SMILES: O=C(Nc1ccc(Oc2ccc(F)cc2)cc1)[C@@H]1C[C@@H](Cc2ccccc2)CN1C(=O)CN1CCSCC1]
84

TABLE 1-continued
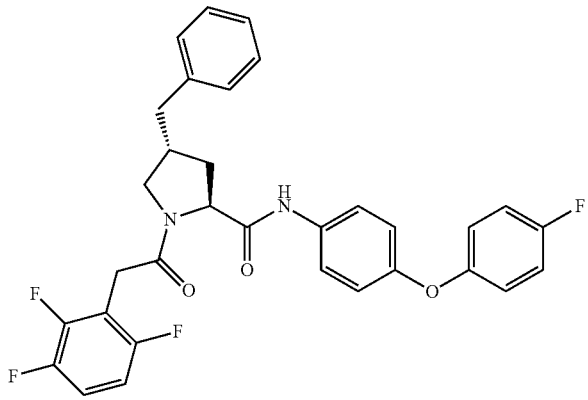 [SMILES: O=C(Nc1ccc(Oc2ccc(F)cc2)cc1)[C@@H]1C[C@@H](Cc2ccccc2)CN1C(=O)Cc1c(F)ccc(F)c1F]
85
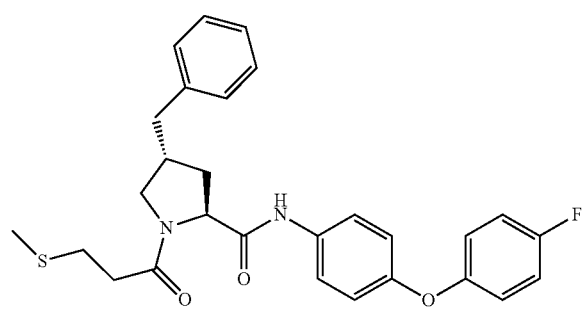
86
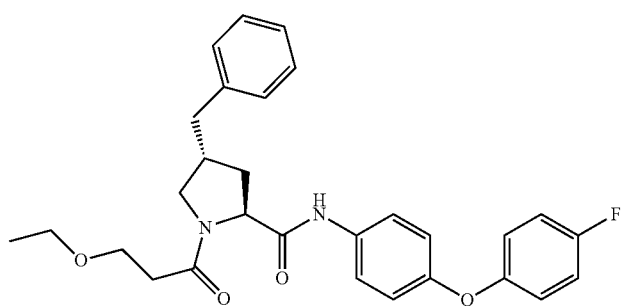 [SMILES: CCOCCC(=O)N1C[C@H](Cc2ccccc2)C[C@H]1C(=O)Nc1ccc(Oc2ccc(F)cc2)cc1]
87
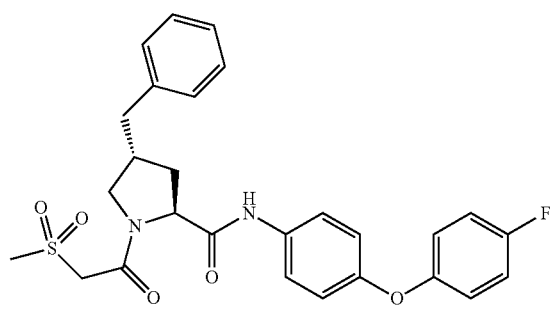 [SMILES: CS(=O)(=O)CC(=O)N1C[C@H](Cc2ccccc2)C[C@H]1C(=O)Nc1ccc(Oc2ccc(F)cc2)cc1]
88

TABLE 1-continued
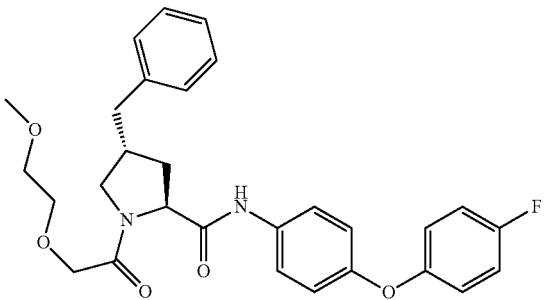 [SMILES: COCCOCC(=O)N1C[C@H](Cc2ccccc2)C[C@H]1C(=O)Nc1ccc(Oc2ccc(F)cc2)cc1]
89
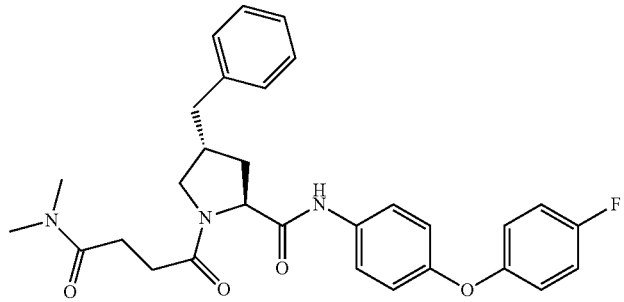 [SMILES: CN(C)C(=O)CCC(=O)N1C[C@H](Cc2ccccc2)C[C@H]1C(=O)Nc1ccc(Oc2ccc(F)cc2)cc1]
90
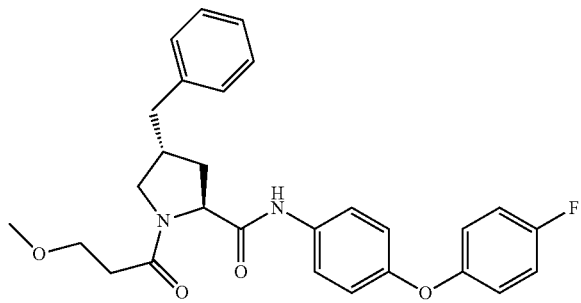
91
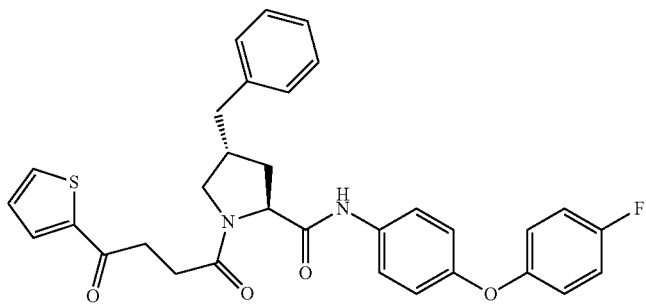 [SMILES: O=C(CCC(=O)N1C[C@H](Cc2ccccc2)C[C@H]1C(=O)Nc1ccc(Oc2ccc(F)cc2)cc1)c1cccs1]
92

TABLE 1-continued
| 93 |
|---|
| 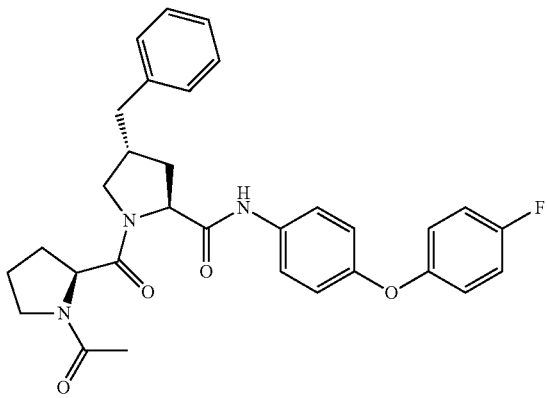 [SMILES: CC(=O)N1CCC[C@H]1C(=O)N1C[C@H](Cc2ccccc2)C[C@H]1C(=O)Nc1ccc(Oc2ccc(F)cc2)cc1] |
| 94 |
|---|
| 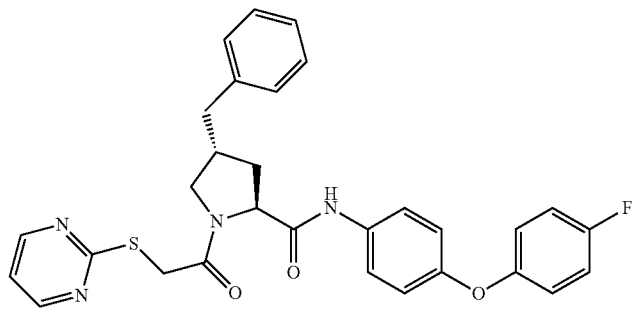 [SMILES: O=C(Nc1ccc(Oc2ccc(F)cc2)cc1)[C@@H]1C[C@@H](Cc2ccccc2)CN1C(=O)CSc1ncccn1] |
| 95 |
|---|
| 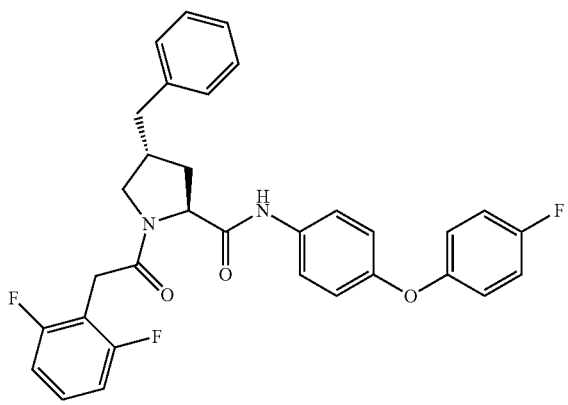 [SMILES: O=C(Nc1ccc(Oc2ccc(F)cc2)cc1)[C@@H]1C[C@@H](Cc2ccccc2)CN1C(=O)Cc1c(F)cccc1F] |
| 96 |
|---|
| 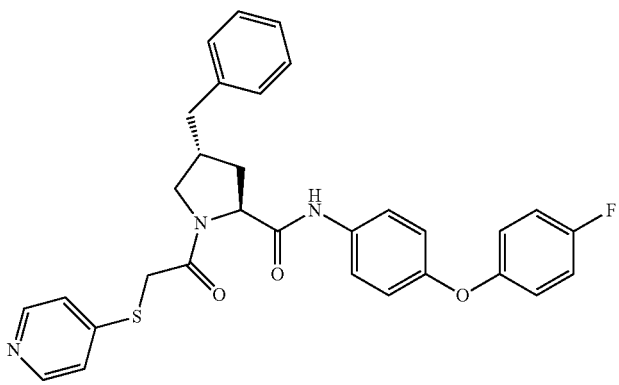 [SMILES: O=C(Nc1ccc(Oc2ccc(F)cc2)cc1)[C@@H]1C[C@@H](Cc2ccccc2)CN1C(=O)CSc1ccncc1] |
97

TABLE 1-continued
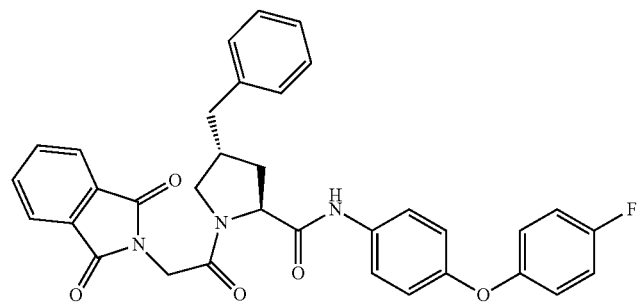 [SMILES: O=C(Nc1ccc(Oc2ccc(F)cc2)cc1)[C@@H]1C[C@@H](Cc2ccccc2)CN1C(=O)CN1C(=O)c2ccccc2C1=O]
98
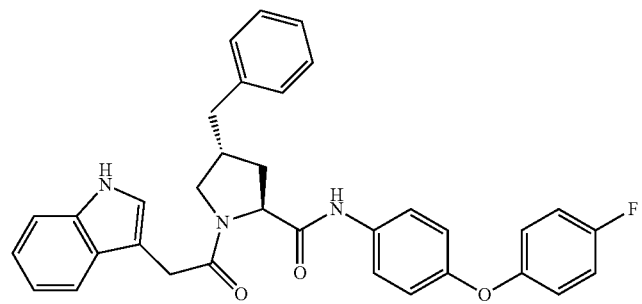 [SMILES: O=C(Nc1ccc(Oc2ccc(F)cc2)cc1)[C@@H]1C[C@@H](Cc2ccccc2)CN1C(=O)Cc1c[nH]c2ccccc12]
99
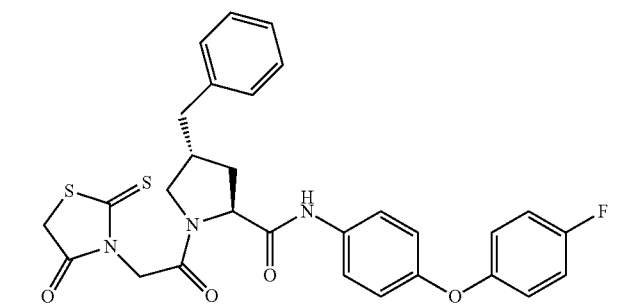 [SMILES: O=C(Nc1ccc(Oc2ccc(F)cc2)cc1)[C@@H]1C[C@@H](Cc2ccccc2)CN1C(=O)CN1C(=O)CSC1=S]
100
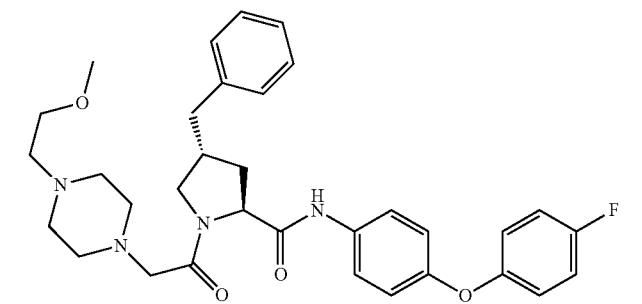 [SMILES: COCCN1CCN(CC(=O)N2C[C@H](Cc3ccccc3)C[C@H]2C(=O)Nc2ccc(Oc3ccc(F)cc3)cc2)CC1]
101
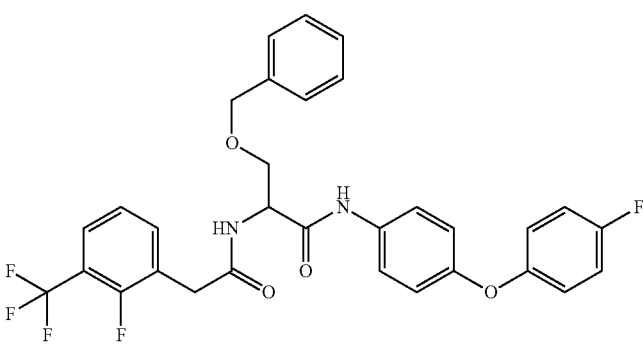 [SMILES: O=C(Cc1cccc(C(F)(F)F)c1F)NC(COCc1ccccc1)C(=O)Nc1ccc(Oc2ccc(F)cc2)cc1]

TABLE 1-continued
102
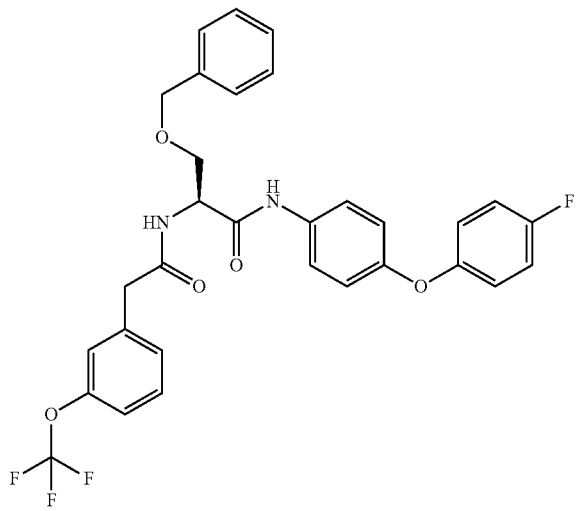 [SMILES: O=C(Cc1cccc(OC(F)(F)F)c1)N[C@@H](COCc1ccccc1)C(=O)Nc1ccc(Oc2ccc(F)cc2)cc1]
103
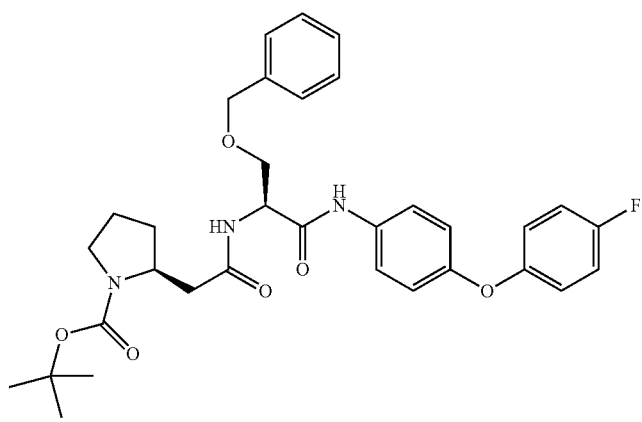 [SMILES: CC(C)(C)OC(=O)N1CCC[C@H]1CC(=O)N[C@@H](COCc1ccccc1)C(=O)Nc1ccc(Oc2ccc(F)cc2)cc1]
104
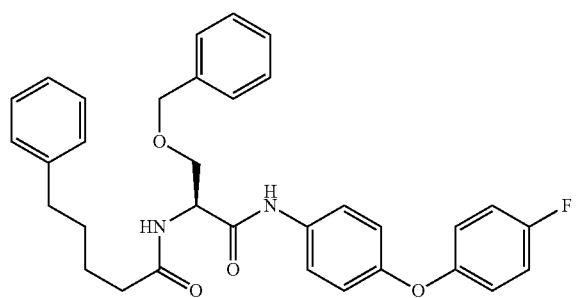 [SMILES: O=C(CCCCc1ccccc1)N[C@@H](COCc1ccccc1)C(=O)Nc1ccc(Oc2ccc(F)cc2)cc1]
105

TABLE 1-continued
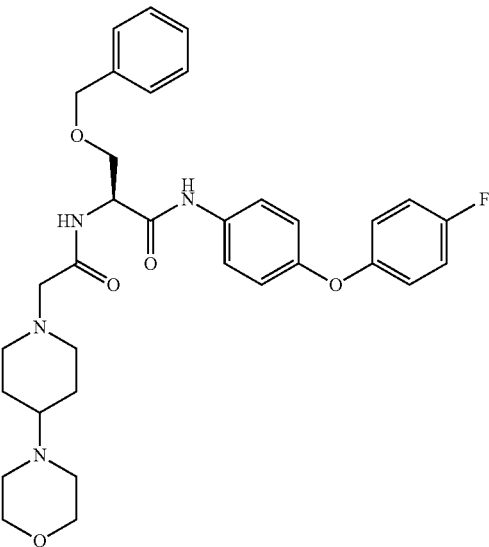 [SMILES: O=C(CN1CCC(N2CCOCC2)CC1)N[C@@H](COCc1ccccc1)C(=O)Nc1ccc(Oc2ccc(F)cc2)cc1]
106
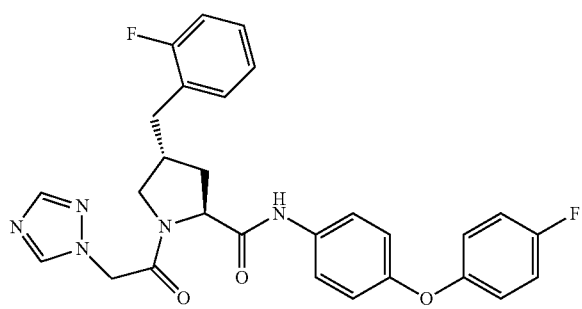 [SMILES: O=C(Nc1ccc(Oc2ccc(F)cc2)cc1)[C@@H]1C[C@@H](Cc2ccccc2F)CN1C(=O)Cn1cncn1]
107
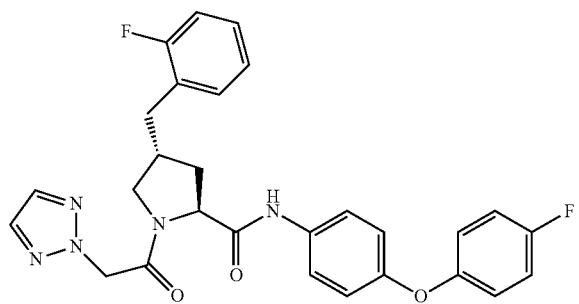
108
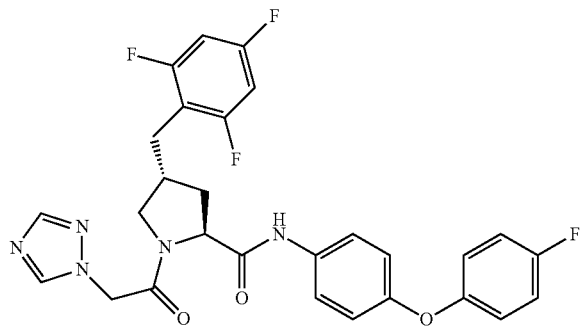 [SMILES: O=C(Nc1ccc(Oc2ccc(F)cc2)cc1)[C@@H]1C[C@@H](Cc2c(F)cc(F)cc2F)CN1C(=O)Cn1cncn1]
109

TABLE 1-continued
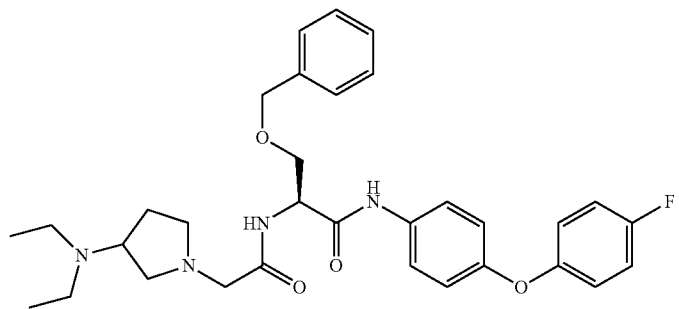 [SMILES: CCN(CC)C1CCN(CC(=O)N[C@@H](COCc2ccccc2)C(=O)Nc2ccc(Oc3ccc(F)cc3)cc2)C1]
110
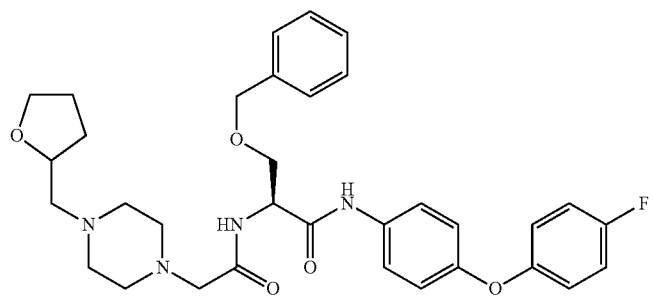 [SMILES: O=C(CN1CCN(CC2CCCO2)CC1)N[C@@H](COCc1ccccc1)C(=O)Nc1ccc(Oc2ccc(F)cc2)cc1]
111
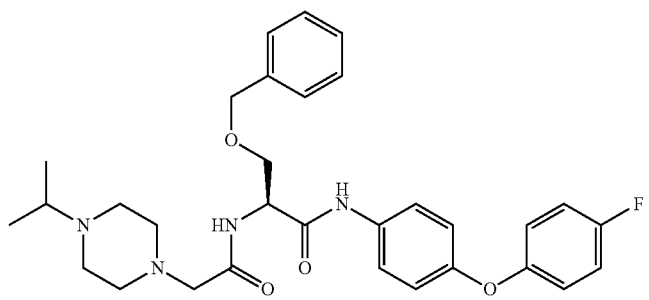 [SMILES: CC(C)N1CCN(CC(=O)N[C@@H](COCc2ccccc2)C(=O)Nc2ccc(Oc3ccc(F)cc3)cc2)CC1]
112
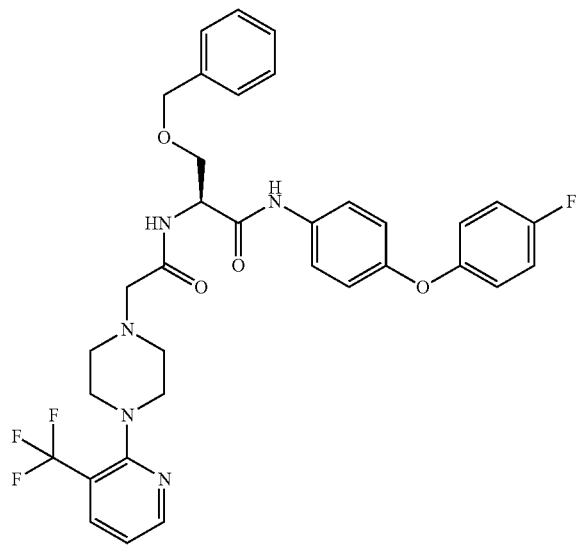 [SMILES: O=C(CN1CCN(c2ncccc2C(F)(F)F)CC1)N[C@@H](COCc1ccccc1)C(=O)Nc1ccc(Oc2ccc(F)cc2)cc1]
113

TABLE 1-continued
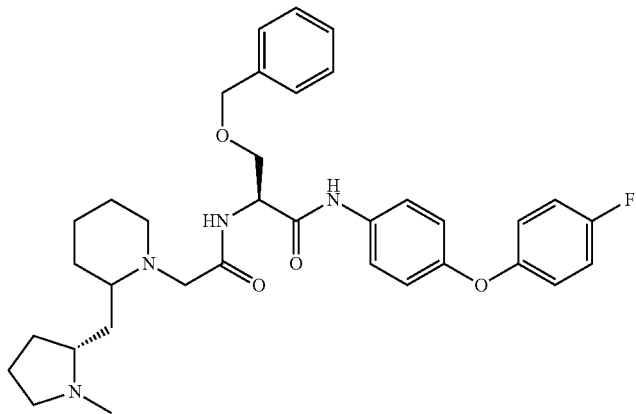 [SMILES: CN1CCC[C@@H]1CC1CCCCN1CC(=O)N[C@@H](COCc1ccccc1)C(=O)Nc1ccc(Oc2ccc(F)cc2)cc1]
114
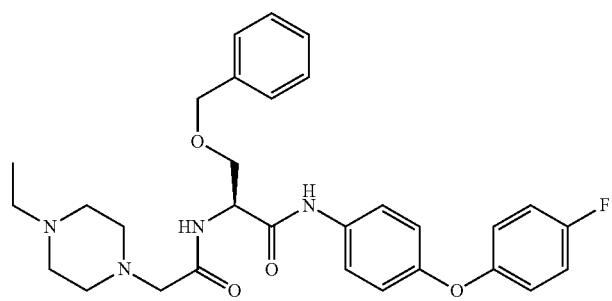 [SMILES: CCN1CCN(CC(=O)N[C@@H](COCc2ccccc2)C(=O)Nc2ccc(Oc3ccc(F)cc3)cc2)CC1]
115
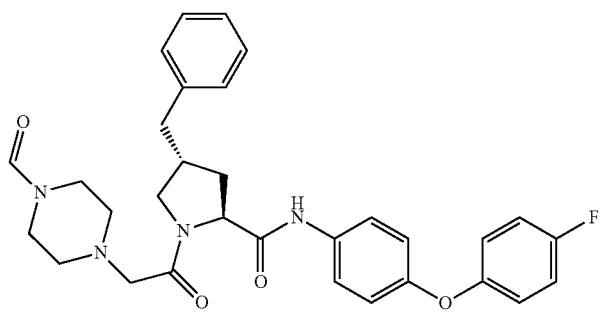 [SMILES: O=CN1CCN(CC(=O)N2C[C@H](Cc3ccccc3)C[C@H]2C(=O)Nc2ccc(Oc3ccc(F)cc3)cc2)CC1]
116
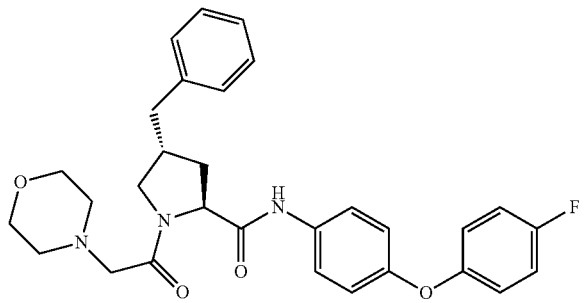
117

TABLE 1-continued
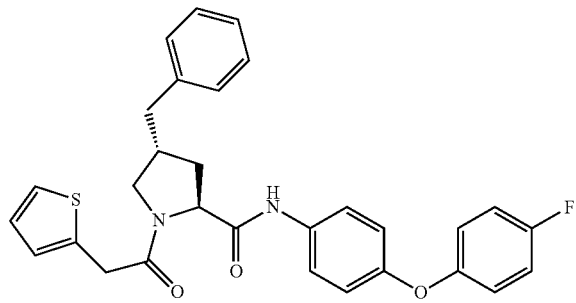 [SMILES: O=C(Nc1ccc(Oc2ccc(F)cc2)cc1)[C@@H]1C[C@@H](Cc2ccccc2)CN1C(=O)Cc1cccs1]
118
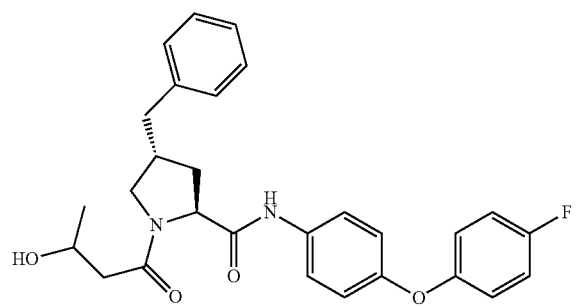 [SMILES: CC(O)CC(=O)N1C[C@H](Cc2ccccc2)C[C@H]1C(=O)Nc1ccc(Oc2ccc(F)cc2)cc1]
119
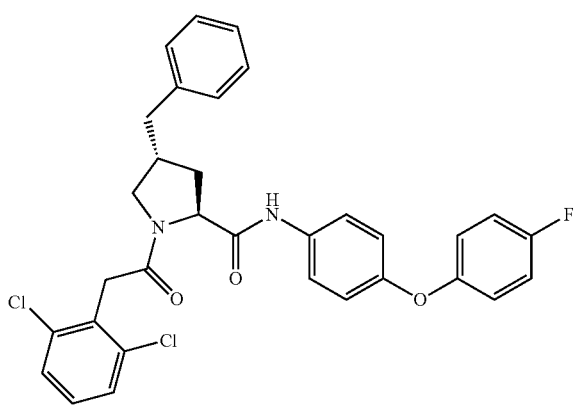 [SMILES: O=C(Nc1ccc(Oc2ccc(F)cc2)cc1)[C@@H]1C[C@@H](Cc2ccccc2)CN1C(=O)Cc1c(Cl)cccc1Cl]
120
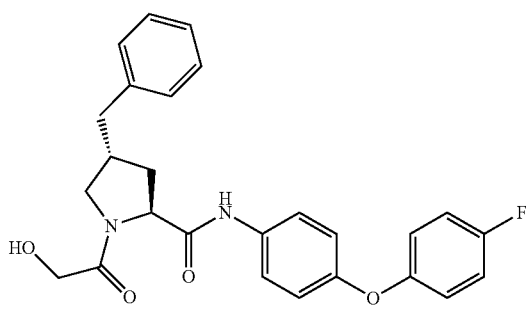 [SMILES: O=C(Nc1ccc(Oc2ccc(F)cc2)cc1)[C@@H]1C[C@@H](Cc2ccccc2)CN1C(=O)CO]
121

TABLE 1-continued
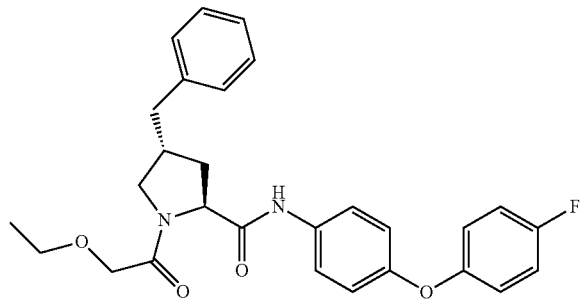 [SMILES: CCOCC(=O)N1C[C@H](Cc2ccccc2)C[C@H]1C(=O)Nc1ccc(Oc2ccc(F)cc2)cc1]
122
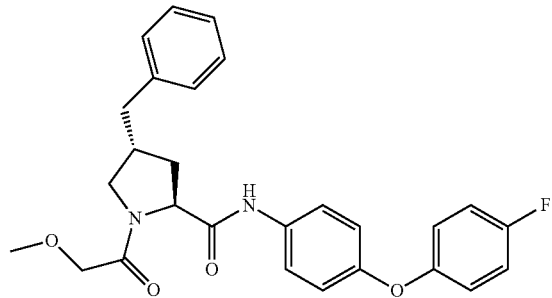 [SMILES: COCC(=O)N1C[C@H](Cc2ccccc2)C[C@H]1C(=O)Nc1ccc(Oc2ccc(F)cc2)cc1]
123
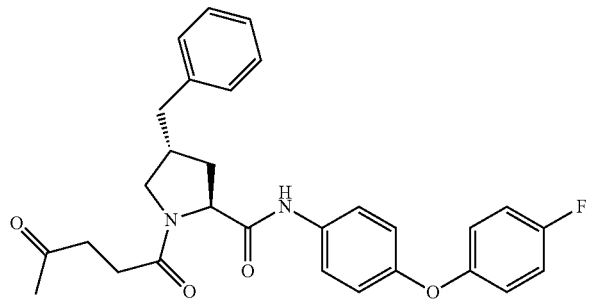 [SMILES: CC(=O)CCC(=O)N1C[C@H](Cc2ccccc2)C[C@H]1C(=O)Nc1ccc(Oc2ccc(F)cc2)cc1]
124
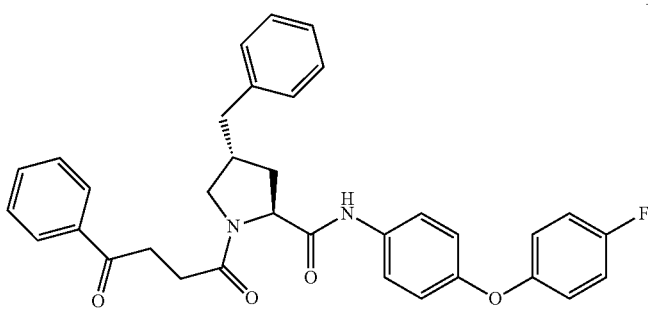
125
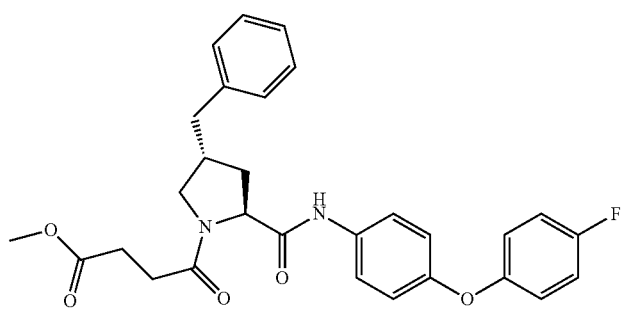 [SMILES: COC(=O)CCC(=O)N1C[C@H](Cc2ccccc2)C[C@H]1C(=O)Nc1ccc(Oc2ccc(F)cc2)cc1]

TABLE 1-continued
126
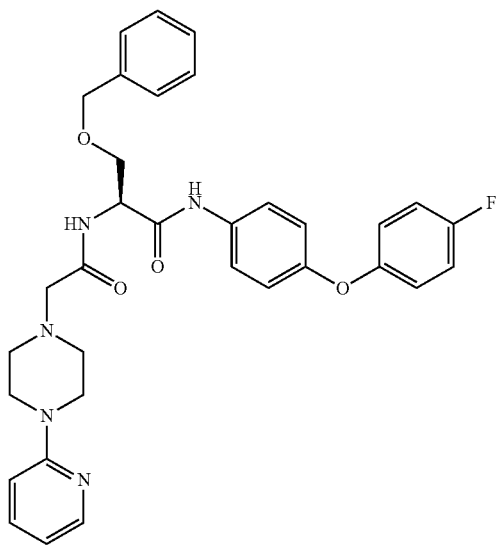 [SMILES: O=C(CN1CCN(c2ccccn2)CC1)N[C@@H](COCc1ccccc1)C(=O)Nc1ccc(Oc2ccc(F)cc2)cc1]
127
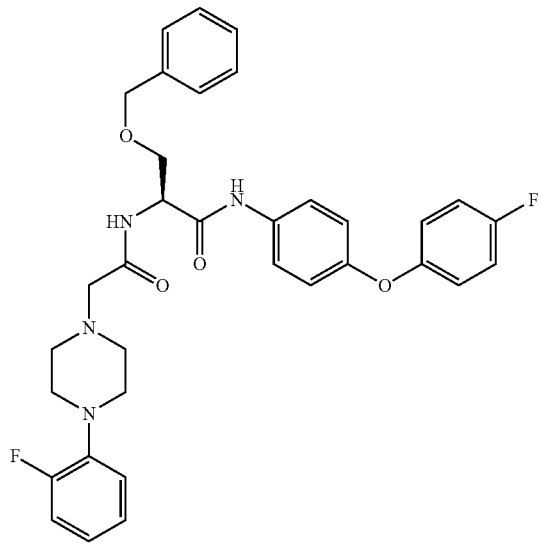 [SMILES: O=C(CN1CCN(c2ccccc2F)CC1)N[C@@H](COCc1ccccc1)C(=O)Nc1ccc(Oc2ccc(F)cc2)cc1]
128
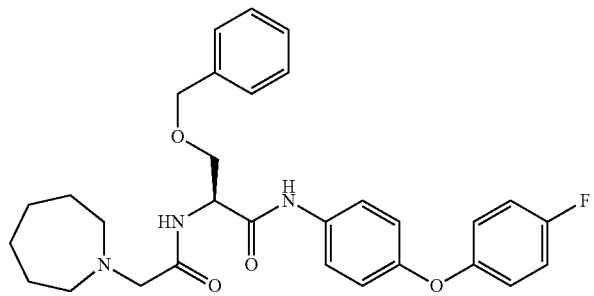 [SMILES: O=C(CN1CCCCCC1)N[C@@H](COCc1ccccc1)C(=O)Nc1ccc(Oc2ccc(F)cc2)cc1]
129

TABLE 1-continued
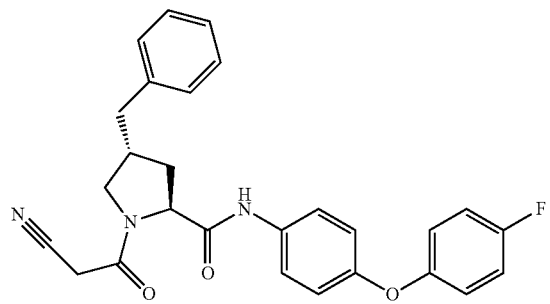 [SMILES: N#CCC(=O)N1C[C@H](Cc2ccccc2)C[C@H]1C(=O)Nc1ccc(Oc2ccc(F)cc2)cc1]
130
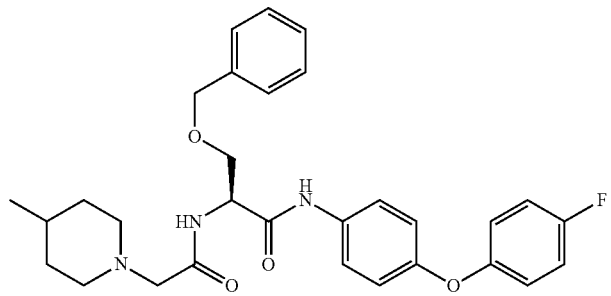
131
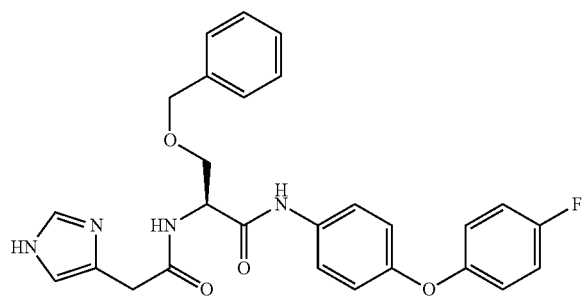 [SMILES: O=C(Cc1c[nH]cn1)N[C@@H](COCc1ccccc1)C(=O)Nc1ccc(Oc2ccc(F)cc2)cc1]
132
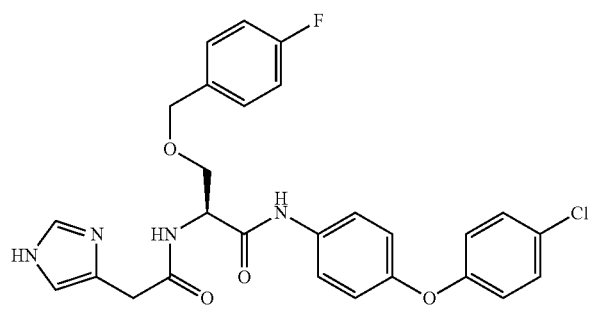 [SMILES: O=C(Cc1c[nH]cn1)N[C@@H](COCc1ccc(F)cc1)C(=O)Nc1ccc(Oc2ccc(Cl)cc2)cc1]
133
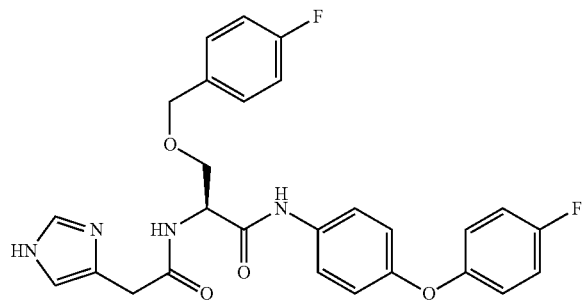 [SMILES: O=C(Cc1c[nH]cn1)N[C@@H](COCc1ccc(F)cc1)C(=O)Nc1ccc(Oc2ccc(F)cc2)cc1]
134

TABLE 1-continued
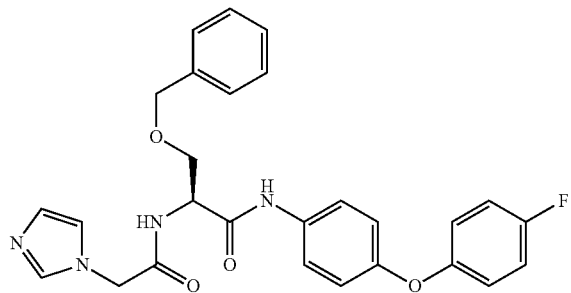 [SMILES: O=C(Cn1ccnc1)N[C@@H](COCc1ccccc1)C(=O)Nc1ccc(Oc2ccc(F)cc2)cc1]
135
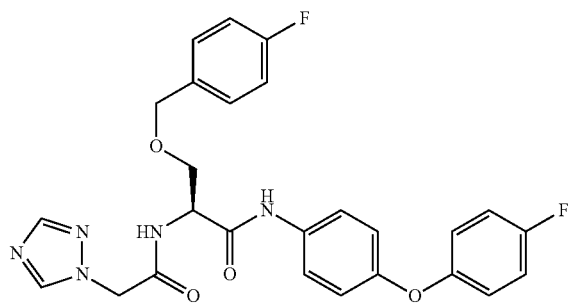 [SMILES: O=C(Cn1cncn1)N[C@@H](COCc1ccc(F)cc1)C(=O)Nc1ccc(Oc2ccc(F)cc2)cc1]
136
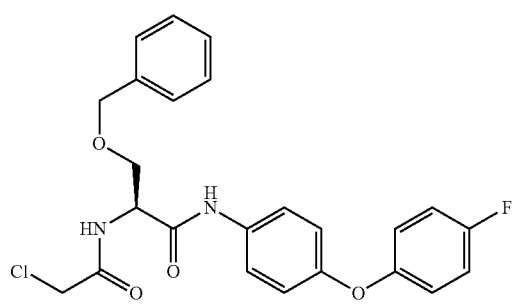 [SMILES: O=C(CCl)N[C@@H](COCc1ccccc1)C(=O)Nc1ccc(Oc2ccc(F)cc2)cc1]
137
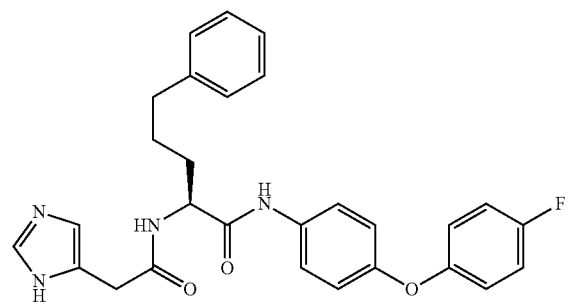 [SMILES: O=C(Cc1cnc[nH]1)N[C@@H](CCCc1ccccc1)C(=O)Nc1ccc(Oc2ccc(F)cc2)cc1]
138
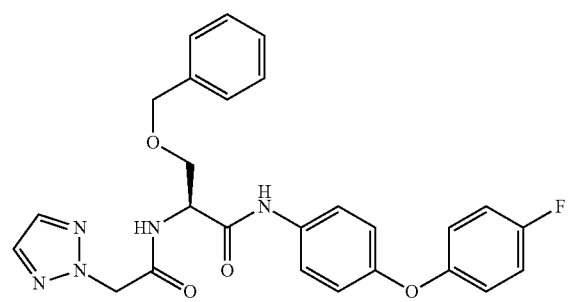 [SMILES: O=C(Cn1nccn1)N[C@@H](COCc1ccccc1)C(=O)Nc1ccc(Oc2ccc(F)cc2)cc1]
139

TABLE 1-continued
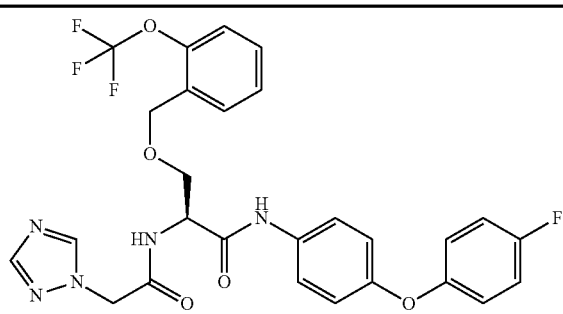
140
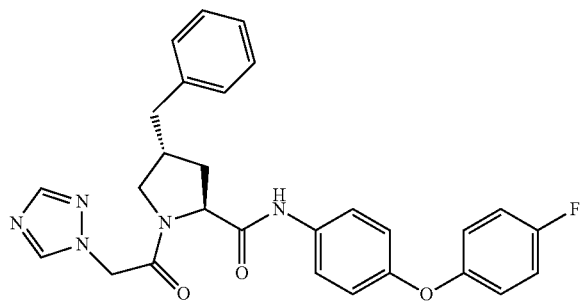 [SMILES: O=C(Nc1ccc(Oc2ccc(F)cc2)cc1)[C@@H]1C[C@@H](Cc2ccccc2)CN1C(=O)Cn1cncn1]
141
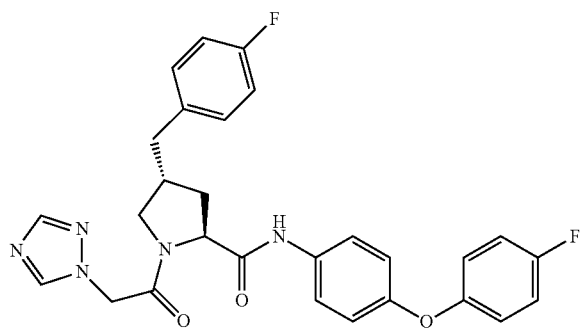 [SMILES: O=C(Nc1ccc(Oc2ccc(F)cc2)cc1)[C@@H]1C[C@@H](Cc2ccc(F)cc2)CN1C(=O)Cn1cncn1]
142
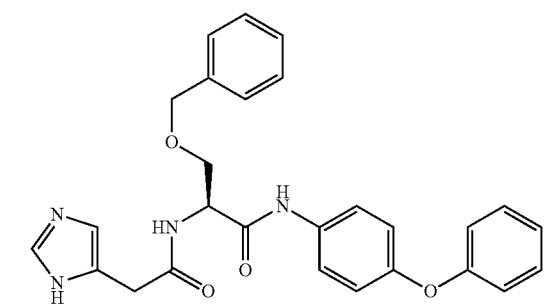 [SMILES: O=C(Cc1cnc[nH]1)N[C@@H](COCc1ccccc1)C(=O)Nc1ccc(Oc2ccccc2)cc1]
143
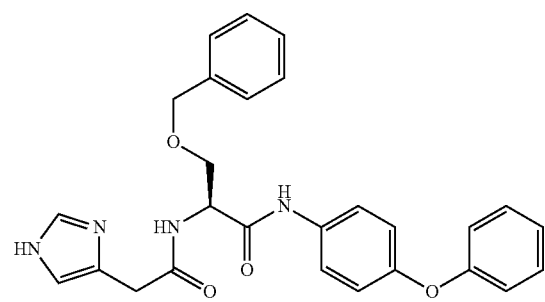

TABLE 1-continued
144
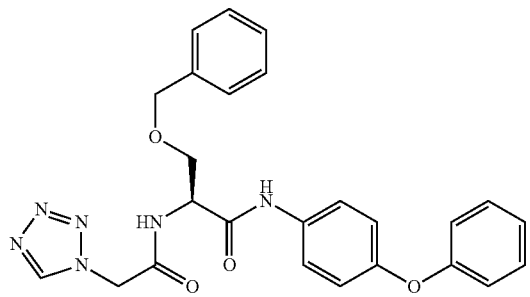 [SMILES: O=C(Cn1cnnn1)N[C@@H](COCc1ccccc1)C(=O)Nc1ccc(Oc2ccccc2)cc1]
145
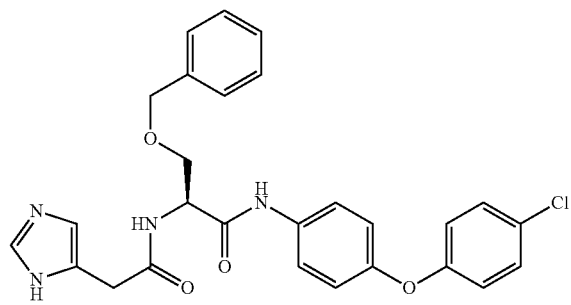 [SMILES: O=C(Cc1cnc[nH]1)N[C@@H](COCc1ccccc1)C(=O)Nc1ccc(Oc2ccc(Cl)cc2)cc1]
146
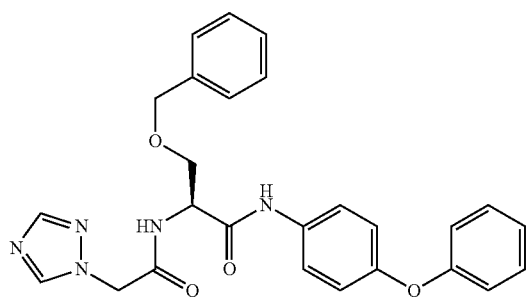 [SMILES: O=C(Cn1cncn1)N[C@@H](COCc1ccccc1)C(=O)Nc1ccc(Oc2ccccc2)cc1]
147
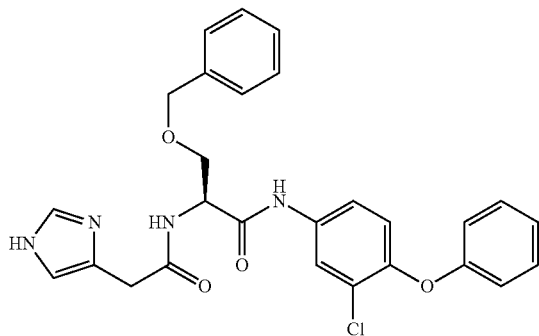 [SMILES: O=C(Cc1c[nH]cn1)N[C@@H](COCc1ccccc1)C(=O)Nc1ccc(Oc2ccccc2)c(Cl)c1]
148
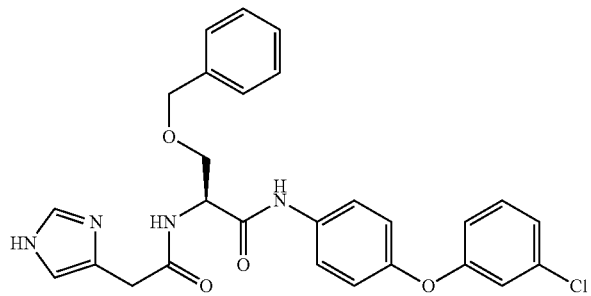 [SMILES: O=C(Cc1c[nH]cn1)N[C@@H](COCc1ccccc1)C(=O)Nc1ccc(Oc2cccc(Cl)c2)cc1]

TABLE 1-continued
149
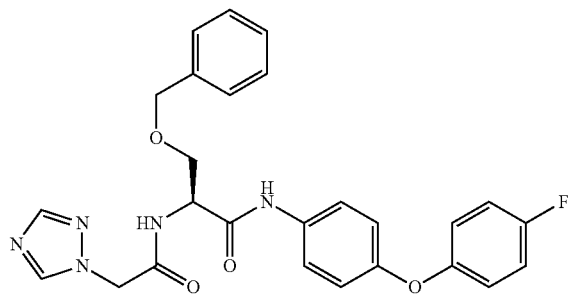 [SMILES: O=C(Cn1cncn1)N[C@@H](COCc1ccccc1)C(=O)Nc1ccc(Oc2ccc(F)cc2)cc1]
150
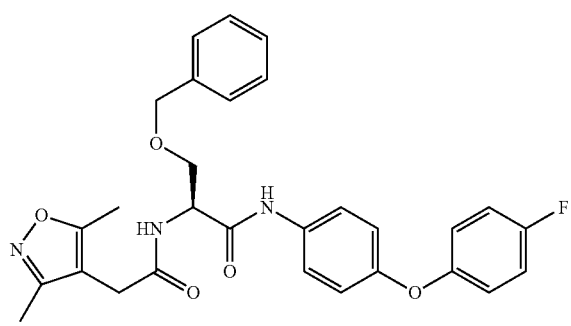 [SMILES: Cc1noc(C)c1CC(=O)N[C@@H](COCc1ccccc1)C(=O)Nc1ccc(Oc2ccc(F)cc2)cc1]
151
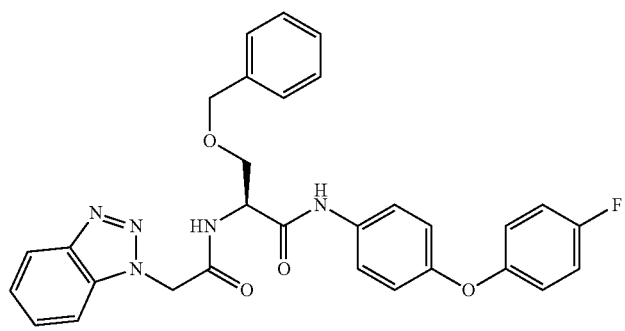 [SMILES: O=C(Cn1nnc2ccccc21)N[C@@H](COCc1ccccc1)C(=O)Nc1ccc(Oc2ccc(F)cc2)cc1]
152
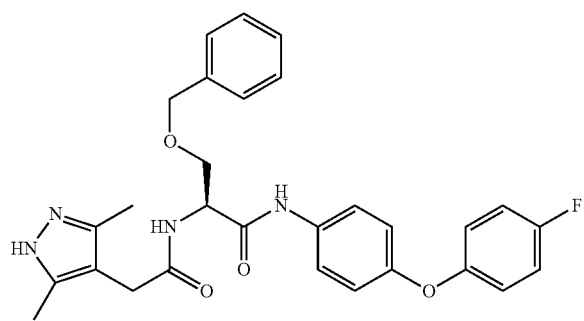 [SMILES: Cc1n[nH]c(C)c1CC(=O)N[C@@H](COCc1ccccc1)C(=O)Nc1ccc(Oc2ccc(F)cc2)cc1]
153

TABLE 1-continued
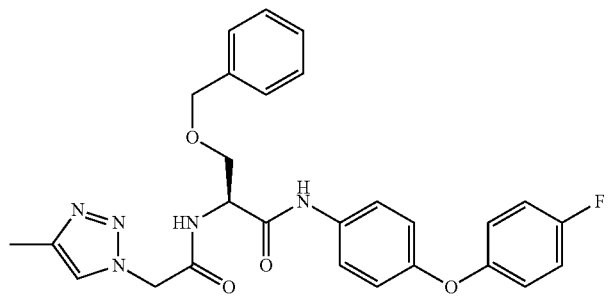 [SMILES: Cc1cn(CC(=O)N[C@@H](COCc2ccccc2)C(=O)Nc2ccc(Oc3ccc(F)cc3)cc2)nn1]
154
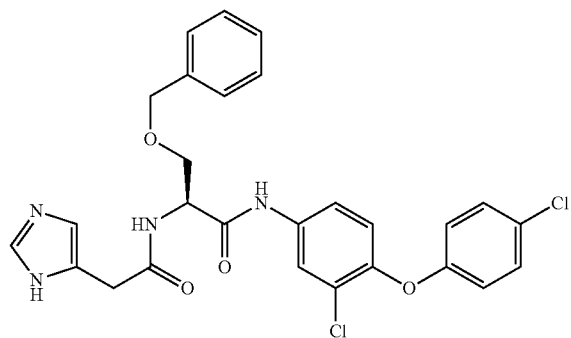 [SMILES: O=C(Cc1cnc[nH]1)N[C@@H](COCc1ccccc1)C(=O)Nc1ccc(Oc2ccc(Cl)cc2)c(Cl)c1]
155
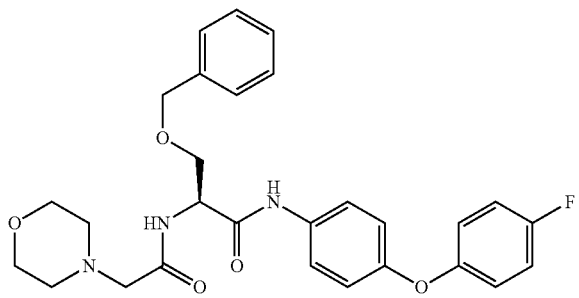 [SMILES: O=C(CN1CCOCC1)N[C@@H](COCc1ccccc1)C(=O)Nc1ccc(Oc2ccc(F)cc2)cc1]
156
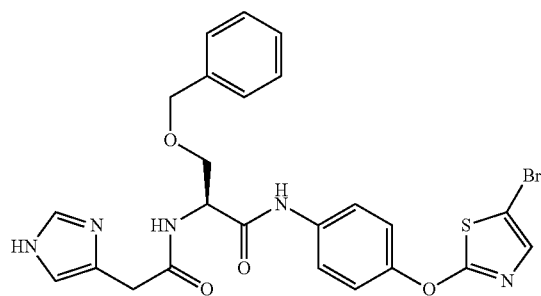 [SMILES: O=C(Cc1c[nH]cn1)N[C@@H](COCc1ccccc1)C(=O)Nc1ccc(Oc2ncc(Br)s2)cc1]
157
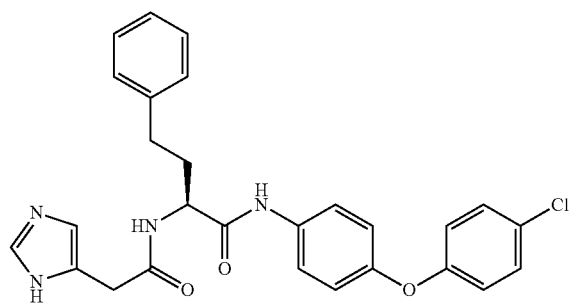 [SMILES: O=C(Cc1cnc[nH]1)N[C@@H](CCc1ccccc1)C(=O)Nc1ccc(Oc2ccc(Cl)cc2)cc1]

TABLE 1-continued
158
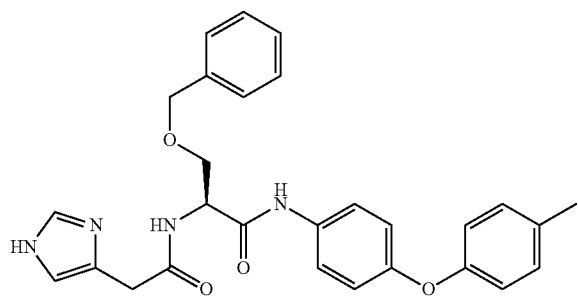 [SMILES: Cc1ccc(Oc2ccc(NC(=O)[C@H](COCc3ccccc3)NC(=O)Cc3c[nH]cn3)cc2)cc1]
159
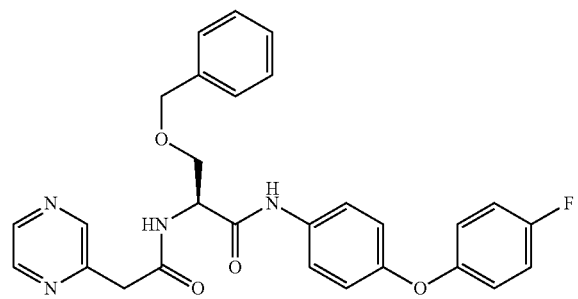 [SMILES: O=C(Cc1cnccn1)N[C@@H](COCc1ccccc1)C(=O)Nc1ccc(Oc2ccc(F)cc2)cc1]
160
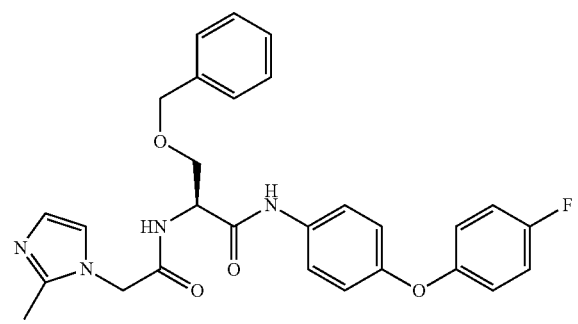 [SMILES: Cc1nccn1CC(=O)N[C@@H](COCc1ccccc1)C(=O)Nc1ccc(Oc2ccc(F)cc2)cc1]
161
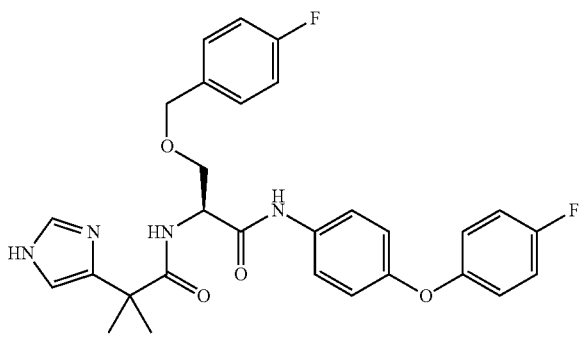 [SMILES: CC(C)(C(=O)N[C@@H](COCc1ccc(F)cc1)C(=O)Nc1ccc(Oc2ccc(F)cc2)cc1)c1c[nH]cn1]
162

TABLE 1-continued
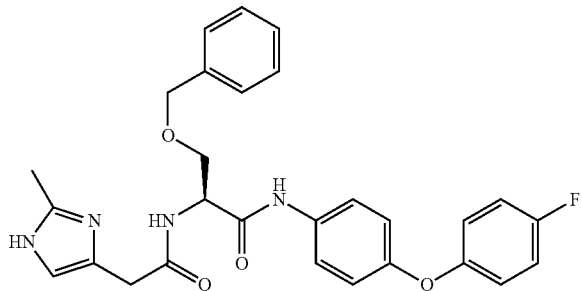 [SMILES: Cc1nc(CC(=O)N[C@@H](COCc2ccccc2)C(=O)Nc2ccc(Oc3ccc(F)cc3)cc2)c[nH]1]
163
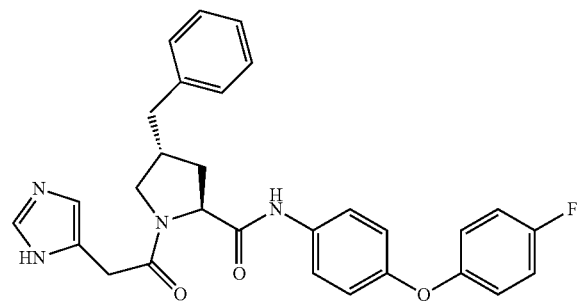 [SMILES: O=C(Nc1ccc(Oc2ccc(F)cc2)cc1)[C@@H]1C[C@@H](Cc2ccccc2)CN1C(=O)Cc1cnc[nH]1]
164
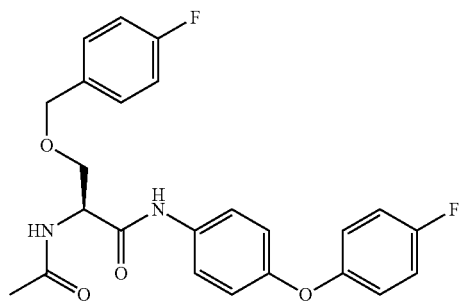 [SMILES: CC(=O)N[C@@H](COCc1ccc(F)cc1)C(=O)Nc1ccc(Oc2ccc(F)cc2)cc1]
165
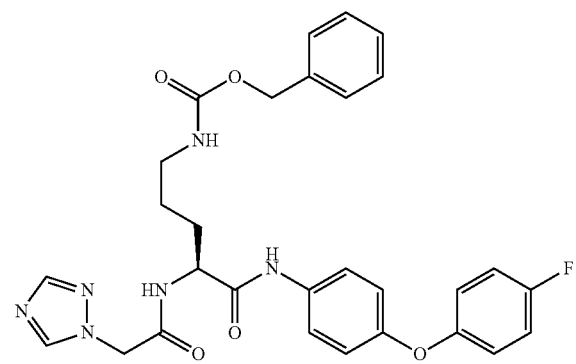 [SMILES: O=C(Cn1cncn1)N[C@@H](CCCNC(=O)OCc1ccccc1)C(=O)Nc1ccc(Oc2ccc(F)cc2)cc1]
166

TABLE 1-continued
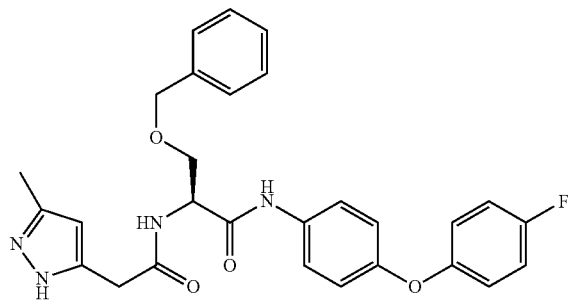 [SMILES: Cc1cc(CC(=O)N[C@@H](COCc2ccccc2)C(=O)Nc2ccc(Oc3ccc(F)cc3)cc2)[nH]n1]
167
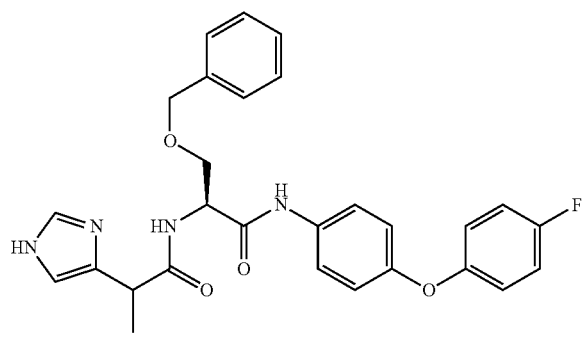 [SMILES: CC(C(=O)N[C@@H](COCc1ccccc1)C(=O)Nc1ccc(Oc2ccc(F)cc2)cc1)c1c[nH]cn1]
168
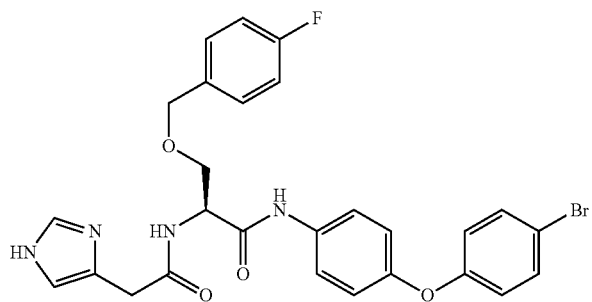 [SMILES: O=C(Cc1c[nH]cn1)N[C@@H](COCc1ccc(F)cc1)C(=O)Nc1ccc(Oc2ccc(Br)cc2)cc1]
169
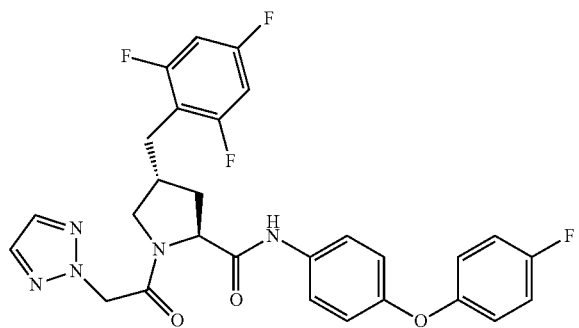 [SMILES: O=C(Nc1ccc(Oc2ccc(F)cc2)cc1)[C@@H]1C[C@@H](Cc2c(F)cc(F)cc2F)CN1C(=O)Cn1nccn1]
170

TABLE 1-continued
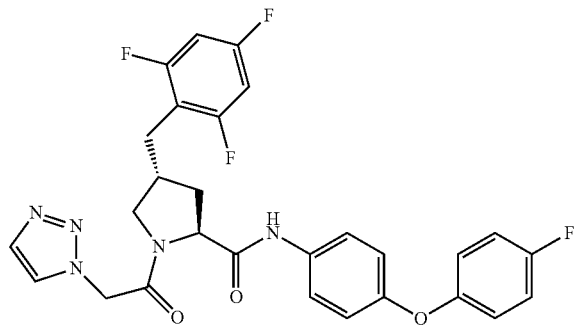 [SMILES: O=C(Nc1ccc(Oc2ccc(F)cc2)cc1)[C@@H]1C[C@@H](Cc2c(F)cc(F)cc2F)CN1C(=O)Cn1ccnn1]
171
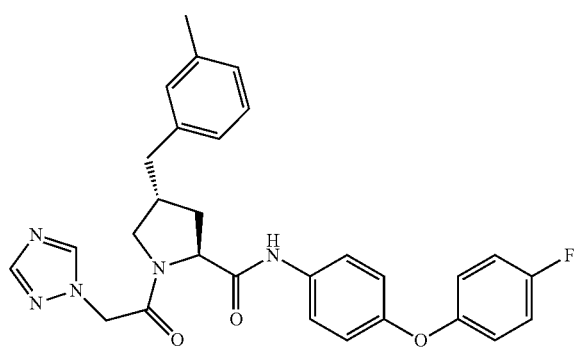 [SMILES: Cc1cccc(C[C@@H]2C[C@@H](C(=O)Nc3ccc(Oc4ccc(F)cc4)cc3)N(C(=O)Cn3cncn3)C2)c1]
172
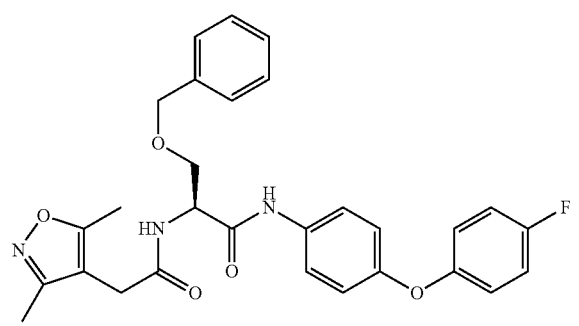 [SMILES: Cc1noc(C)c1CC(=O)N[C@@H](COCc1ccccc1)C(=O)Nc1ccc(Oc2ccc(F)cc2)cc1]
173
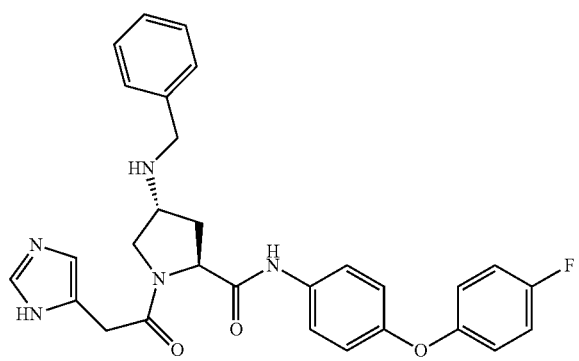 [SMILES: O=C(Nc1ccc(Oc2ccc(F)cc2)cc1)[C@@H]1C[C@@H](NCc2ccccc2)CN1C(=O)Cc1cnc[nH]1]
174

TABLE 1-continued
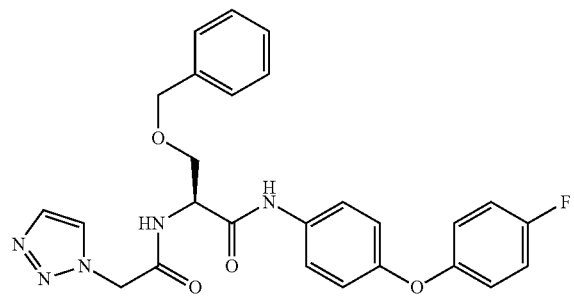
175
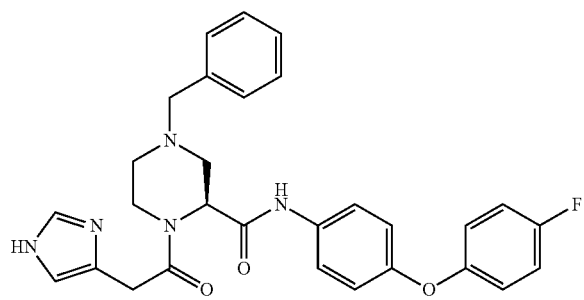 [SMILES: O=C(Nc1ccc(Oc2ccc(F)cc2)cc1)[C@@H]1CN(Cc2ccccc2)CCN1C(=O)Cc1c[nH]cn1]
176
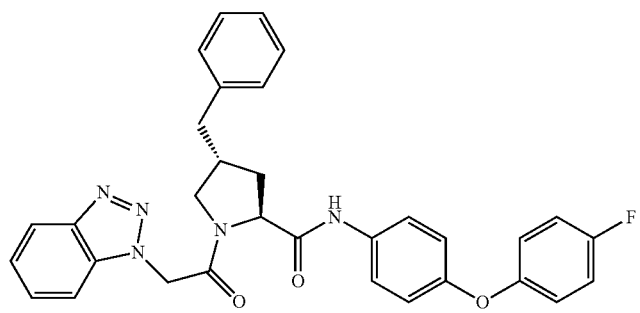 [SMILES: O=C(Nc1ccc(Oc2ccc(F)cc2)cc1)[C@@H]1C[C@@H](Cc2ccccc2)CN1C(=O)Cn1nnc2ccccc21]
177
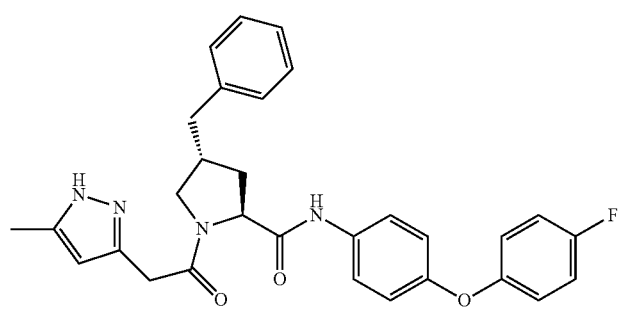 [SMILES: Cc1cc(CC(=O)N2C[C@H](Cc3ccccc3)C[C@H]2C(=O)Nc2ccc(Oc3ccc(F)cc3)cc2)n[nH]1]
178
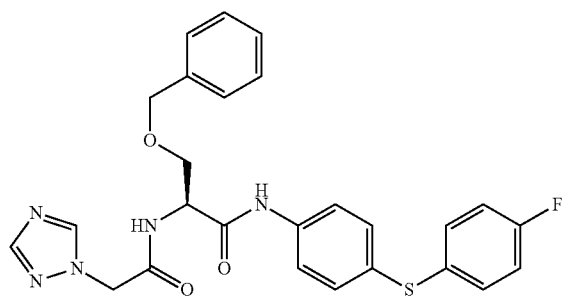 [SMILES: O=C(Cn1cncn1)N[C@@H](COCc1ccccc1)C(=O)Nc1ccc(Sc2ccc(F)cc2)cc1]
179

TABLE 1-continued
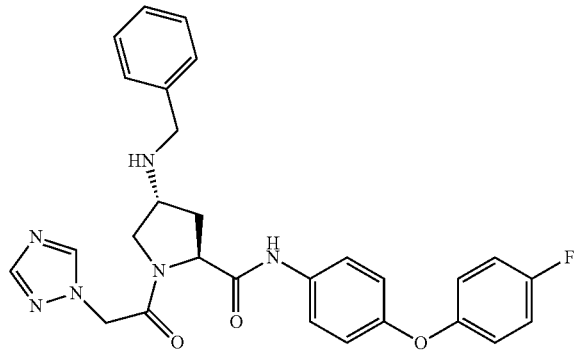 [SMILES: O=C(Nc1ccc(Oc2ccc(F)cc2)cc1)[C@@H]1C[C@@H](NCc2ccccc2)CN1C(=O)Cn1cncn1]
180
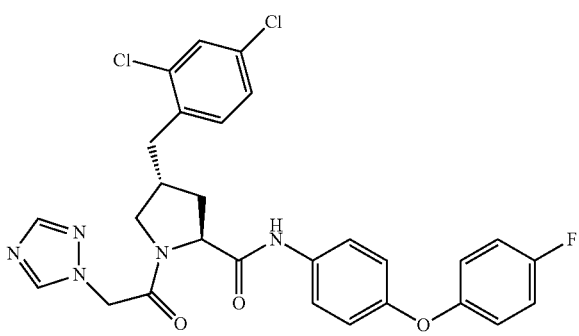 [SMILES: O=C(Nc1ccc(Oc2ccc(F)cc2)cc1)[C@@H]1C[C@@H](Cc2ccc(Cl)cc2Cl)CN1C(=O)Cn1cncn1]
181
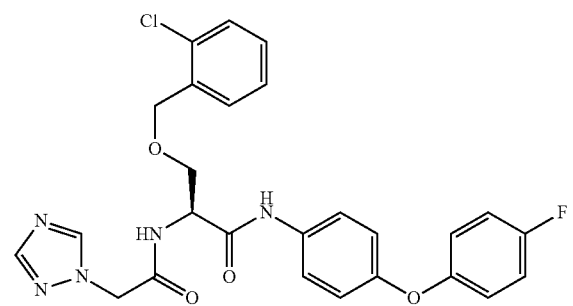 [SMILES: O=C(Cn1cncn1)N[C@@H](COCc1ccccc1Cl)C(=O)Nc1ccc(Oc2ccc(F)cc2)cc1]
182
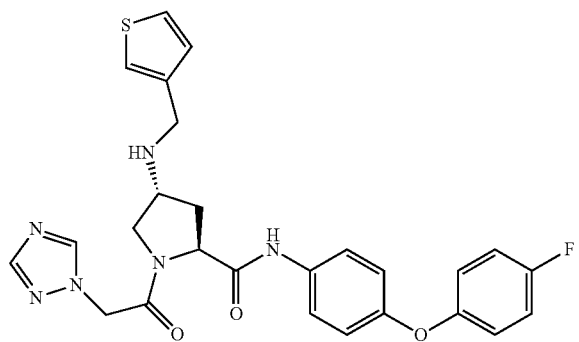 [SMILES: O=C(Nc1ccc(Oc2ccc(F)cc2)cc1)[C@@H]1C[C@@H](NCc2ccsc2)CN1C(=O)Cn1cncn1]
183

TABLE 1-continued
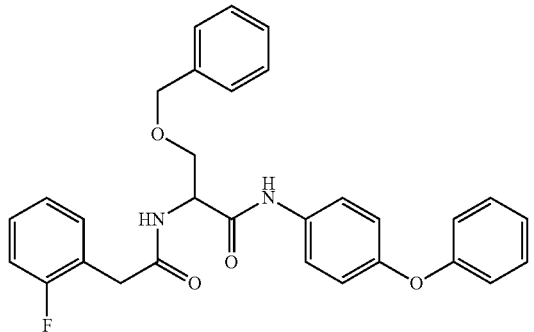 [SMILES: O=C(Cc1ccccc1F)NC(COCc1ccccc1)C(=O)Nc1ccc(Oc2ccccc2)cc1]
184
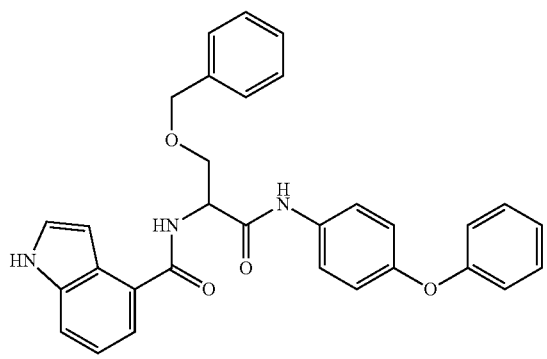 [SMILES: O=C(NC(COCc1ccccc1)C(=O)Nc1ccc(Oc2ccccc2)cc1)c1cccc2[nH]ccc12]
185
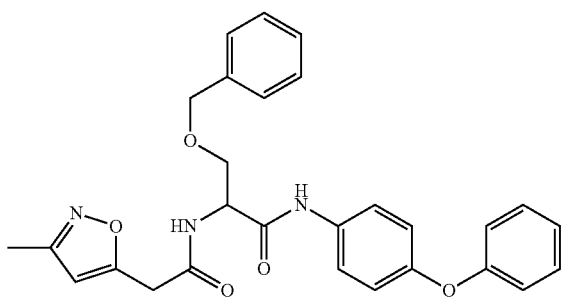 [SMILES: Cc1cc(CC(=O)NC(COCc2ccccc2)C(=O)Nc2ccc(Oc3ccccc3)cc2)on1]
186
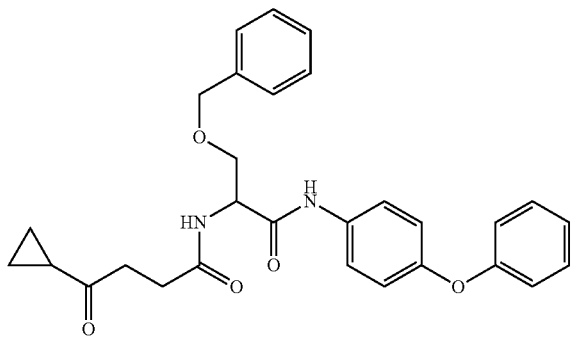 [SMILES: O=C(CCC(=O)C1CC1)NC(COCc1ccccc1)C(=O)Nc1ccc(Oc2ccccc2)cc1]
187

TABLE 1-continued
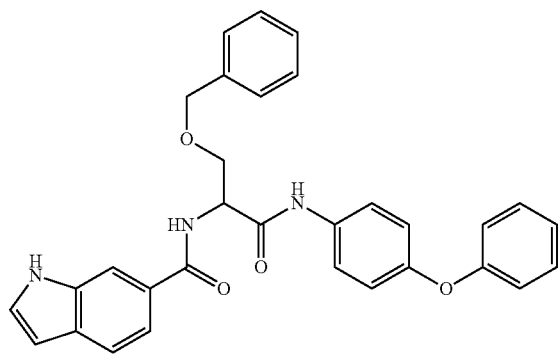 [SMILES: O=C(NC(COCc1ccccc1)C(=O)Nc1ccc(Oc2ccccc2)cc1)c1ccc2cc[nH]c2c1]
188
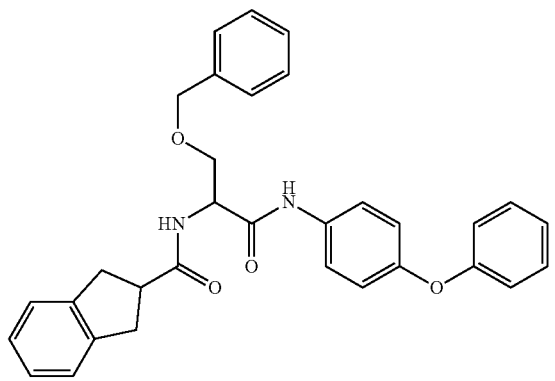 [SMILES: O=C(NC(COCc1ccccc1)C(=O)Nc1ccc(Oc2ccccc2)cc1)C1Cc2ccccc2C1]
189
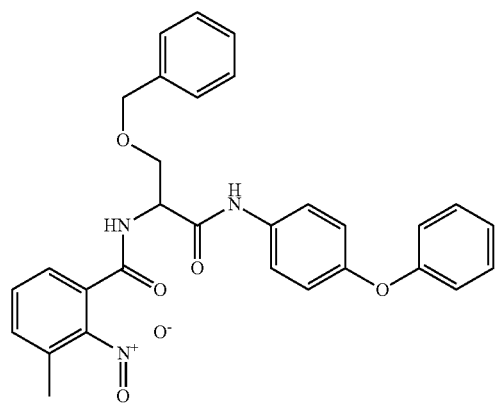
190
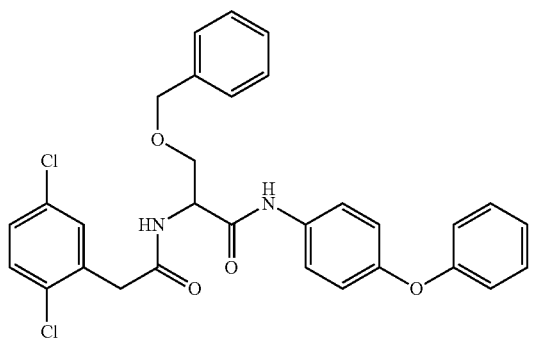 [SMILES: O=C(Cc1cc(Cl)ccc1Cl)NC(COCc1ccccc1)C(=O)Nc1ccc(Oc2ccccc2)cc1]
191

TABLE 1-continued
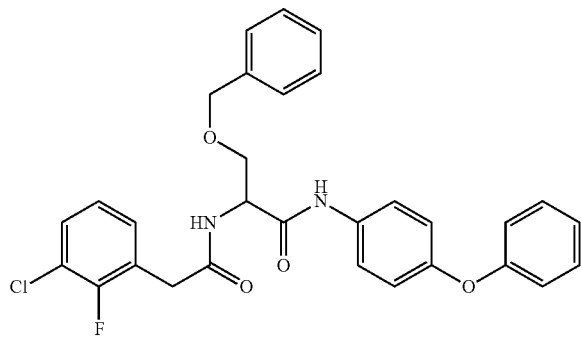 [SMILES: O=C(Cc1cccc(Cl)c1F)NC(COCc1ccccc1)C(=O)Nc1ccc(Oc2ccccc2)cc1]
192
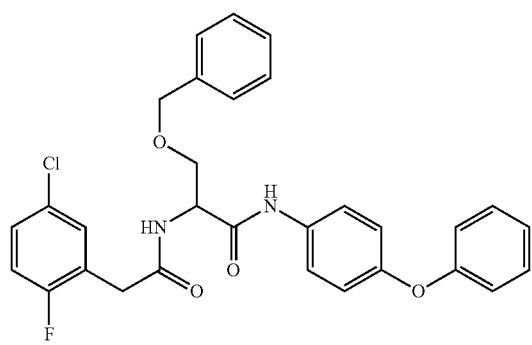 [SMILES: O=C(Cc1cc(Cl)ccc1F)NC(COCc1ccccc1)C(=O)Nc1ccc(Oc2ccccc2)cc1]
193
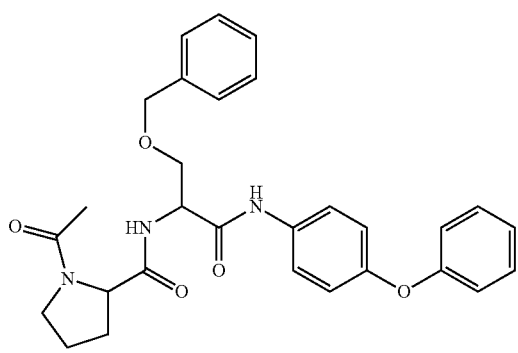 [SMILES: CC(=O)N1CCCC1C(=O)NC(COCc1ccccc1)C(=O)Nc1ccc(Oc2ccccc2)cc1]
194
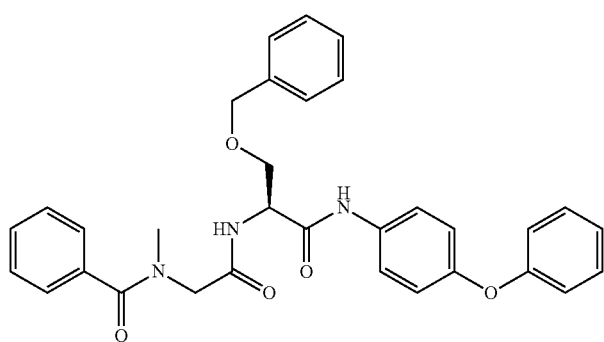 [SMILES: CN(CC(=O)N[C@@H](COCc1ccccc1)C(=O)Nc1ccc(Oc2ccccc2)cc1)C(=O)c1ccccc1]
195

TABLE 1-continued
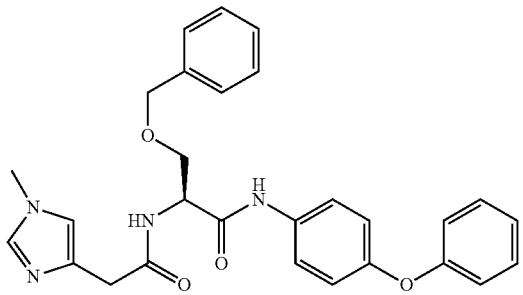 [SMILES: Cn1cnc(CC(=O)N[C@@H](COCc2ccccc2)C(=O)Nc2ccc(Oc3ccccc3)cc2)c1]
196
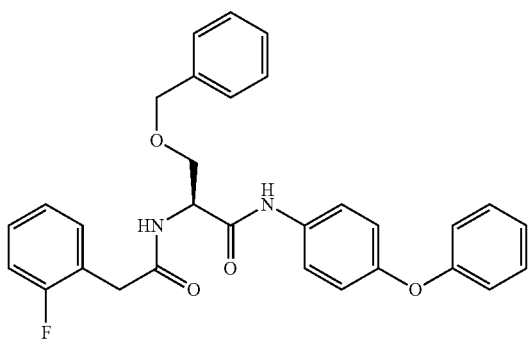 [SMILES: O=C(Cc1ccccc1F)N[C@@H](COCc1ccccc1)C(=O)Nc1ccc(Oc2ccccc2)cc1]
197
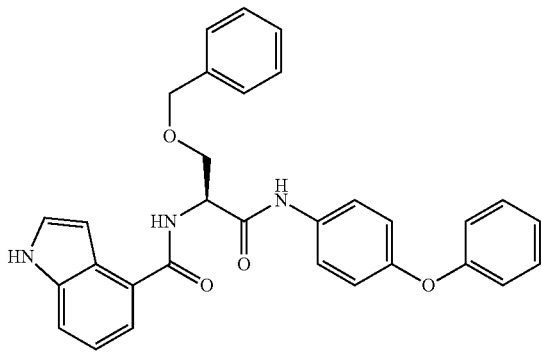 [SMILES: O=C(N[C@@H](COCc1ccccc1)C(=O)Nc1ccc(Oc2ccccc2)cc1)c1cccc2[nH]ccc12]
198
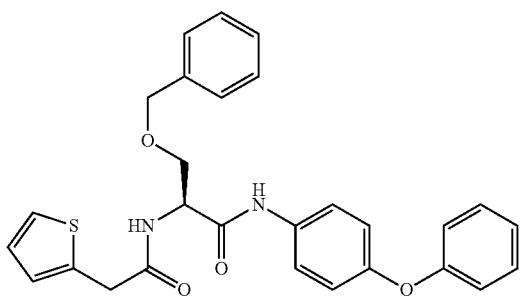 [SMILES: O=C(Cc1cccs1)N[C@@H](COCc1ccccc1)C(=O)Nc1ccc(Oc2ccccc2)cc1]
199

TABLE 1-continued
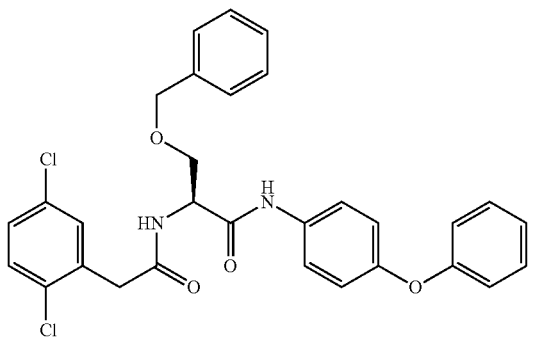 [SMILES: O=C(Cc1cc(Cl)ccc1Cl)N[C@@H](COCc1ccccc1)C(=O)Nc1ccc(Oc2ccccc2)cc1]
200
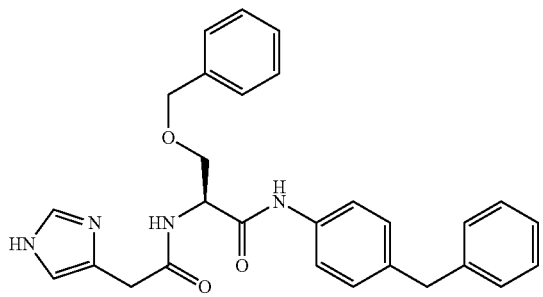 [SMILES: O=C(Cc1c[nH]cn1)N[C@@H](COCc1ccccc1)C(=O)Nc1ccc(Cc2ccccc2)cc1]
201
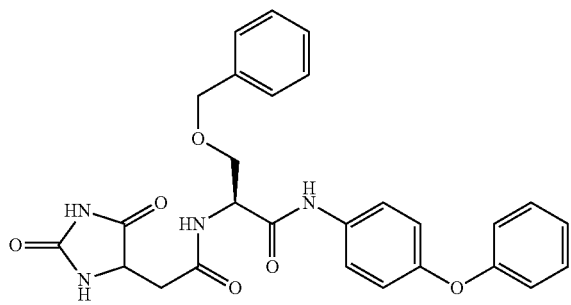 [SMILES: O=C(CC1NC(=O)NC1=O)N[C@@H](COCc1ccccc1)C(=O)Nc1ccc(Oc2ccccc2)cc1]
202
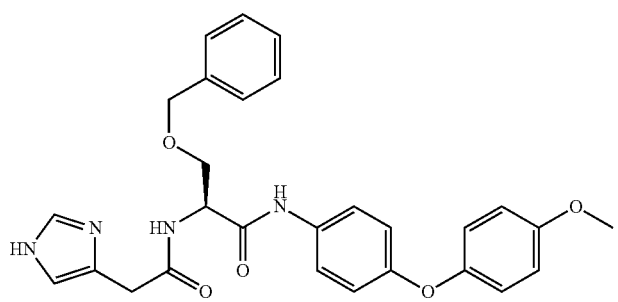 [SMILES: COc1ccc(Oc2ccc(NC(=O)[C@H](COCc3ccccc3)NC(=O)Cc3c[nH]cn3)cc2)cc1]
203
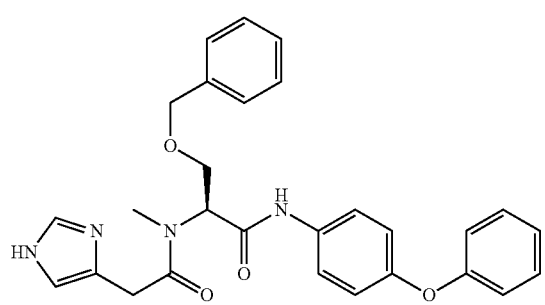 [SMILES: CN(C(=O)Cc1c[nH]cn1)[C@@H](COCc1ccccc1)C(=O)Nc1ccc(Oc2ccccc2)cc1]

TABLE 1-continued
204
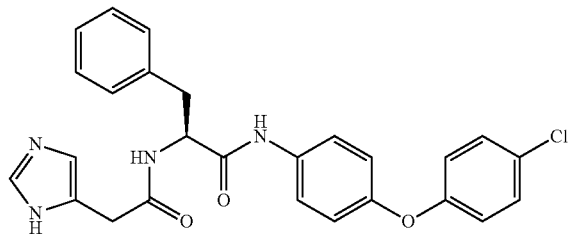 [SMILES: O=C(Cc1cnc[nH]1)N[C@@H](Cc1ccccc1)C(=O)Nc1ccc(Oc2ccc(Cl)cc2)cc1]
205
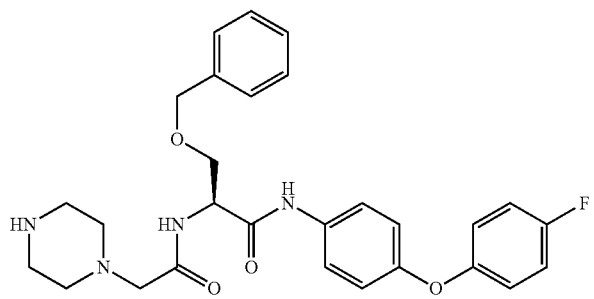 [SMILES: O=C(CN1CCNCC1)N[C@@H](COCc1ccccc1)C(=O)Nc1ccc(Oc2ccc(F)cc2)cc1]
206
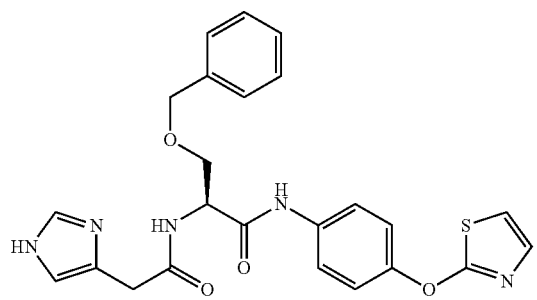 [SMILES: O=C(Cc1c[nH]cn1)N[C@@H](COCc1ccccc1)C(=O)Nc1ccc(Oc2nccs2)cc1]
207
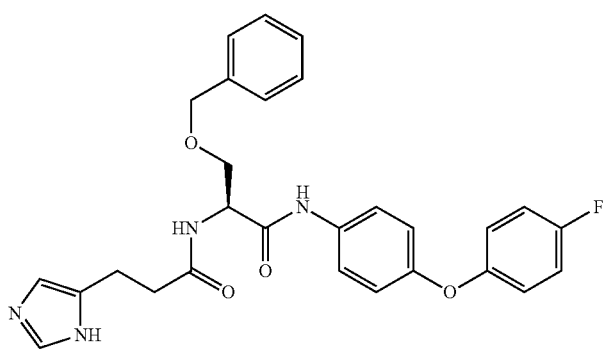 [SMILES: O=C(CCc1cnc[nH]1)N[C@@H](COCc1ccccc1)C(=O)Nc1ccc(Oc2ccc(F)cc2)cc1]
208
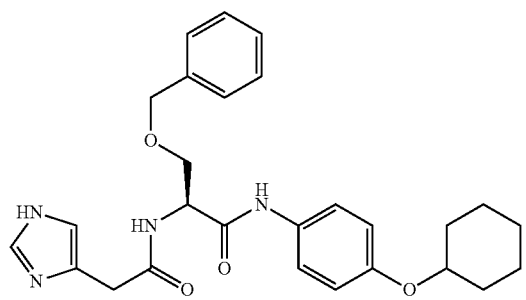 [SMILES: O=C(Cc1c[nH]cn1)N[C@@H](COCc1ccccc1)C(=O)Nc1ccc(OC2CCCCC2)cc1]
209

US 8,802,692 B2
TABLE 1-continued
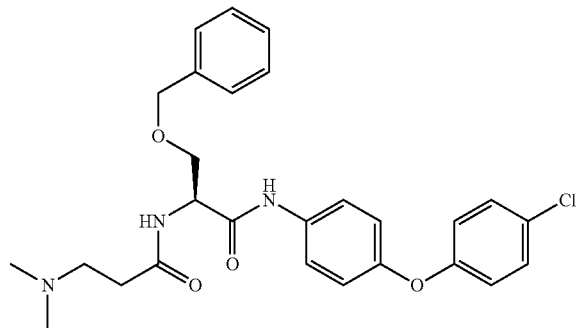 [SMILES: CN(C)CCC(=O)N[C@@H](COCc1ccccc1)C(=O)Nc1ccc(Oc2ccc(Cl)cc2)cc1]
210
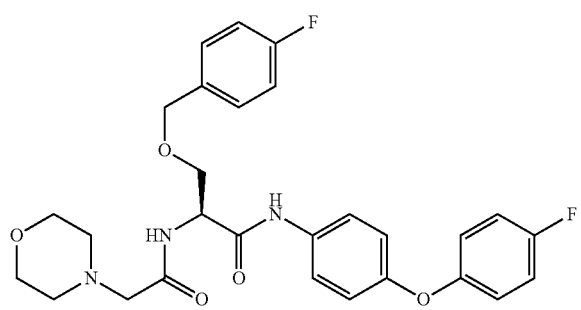 [SMILES: O=C(CN1CCOCC1)N[C@@H](COCc1ccc(F)cc1)C(=O)Nc1ccc(Oc2ccc(F)cc2)cc1]
211
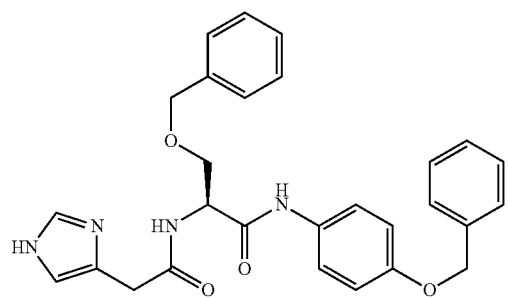 [SMILES: O=C(Cc1c[nH]cn1)N[C@@H](COCc1ccccc1)C(=O)Nc1ccc(OCc2ccccc2)cc1]
212
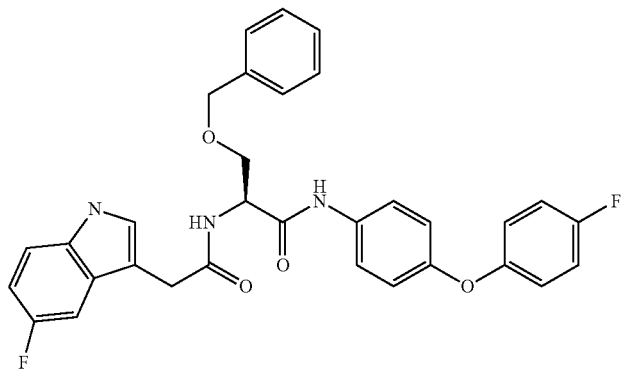 [SMILES: O=C(Cc1c[nH]c2ccc(F)cc12)N[C@@H](COCc1ccccc1)C(=O)Nc1ccc(Oc2ccc(F)cc2)cc1]
213

TABLE 1-continued
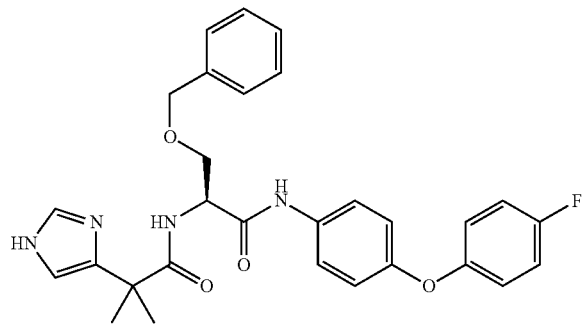 [SMILES: CC(C)(C(=O)N[C@@H](COCc1ccccc1)C(=O)Nc1ccc(Oc2ccc(F)cc2)cc1)c1c[nH]cn1]
214
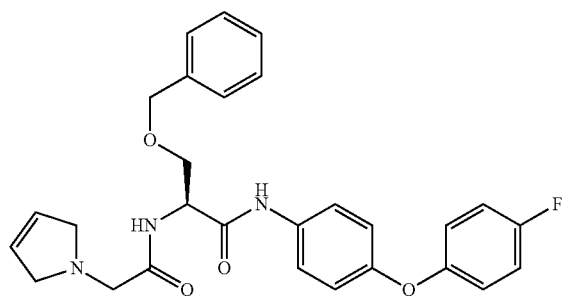 [SMILES: O=C(CN1CC=CC1)N[C@@H](COCc1ccccc1)C(=O)Nc1ccc(Oc2ccc(F)cc2)cc1]
215
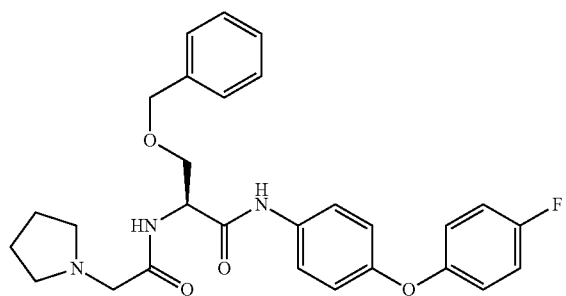 [SMILES: O=C(CN1CCCC1)N[C@@H](COCc1ccccc1)C(=O)Nc1ccc(Oc2ccc(F)cc2)cc1]
216
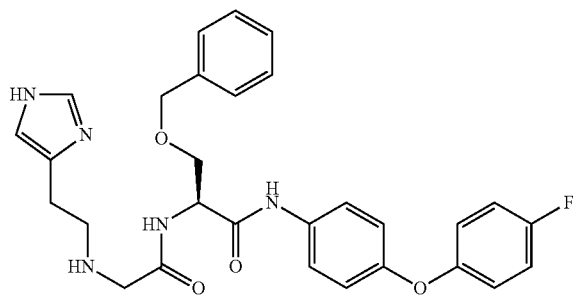 [SMILES: O=C(CNCCc1c[nH]cn1)N[C@@H](COCc1ccccc1)C(=O)Nc1ccc(Oc2ccc(F)cc2)cc1]
217

TABLE 1-continued
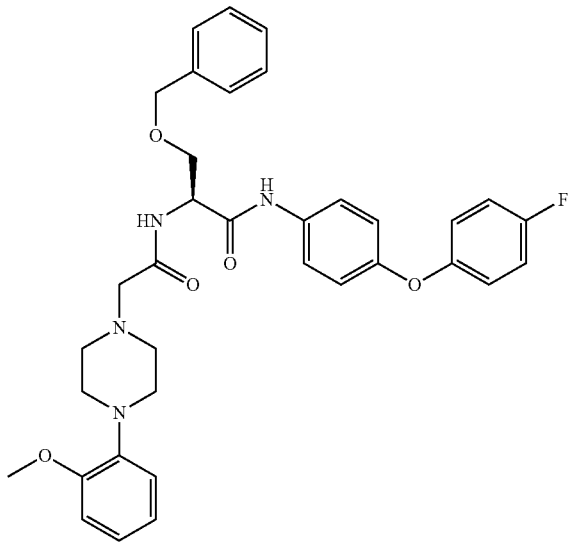 [SMILES: COc1ccccc1N1CCN(CC(=O)N[C@@H](COCc2ccccc2)C(=O)Nc2ccc(Oc3ccc(F)cc3)cc2)CC1]
218
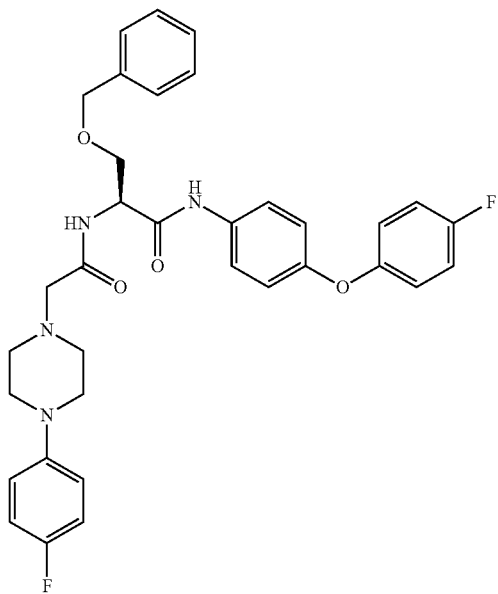 [SMILES: O=C(CN1CCN(c2ccc(F)cc2)CC1)N[C@@H](COCc1ccccc1)C(=O)Nc1ccc(Oc2ccc(F)cc2)cc1]
219
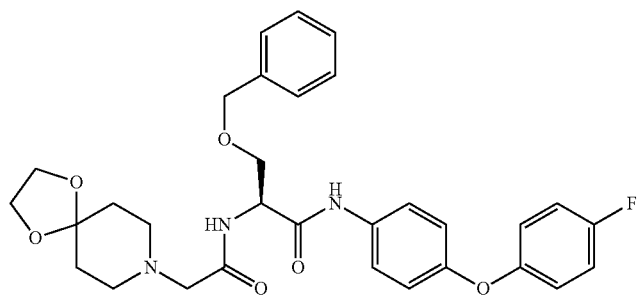 [SMILES: O=C(CN1CCC2(CC1)OCCO2)N[C@@H](COCc1ccccc1)C(=O)Nc1ccc(Oc2ccc(F)cc2)cc1]
220

TABLE 1-continued
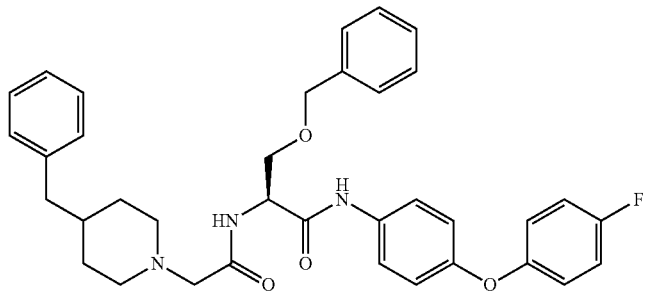 [SMILES: O=C(CN1CCC(Cc2ccccc2)CC1)N[C@@H](COCc1ccccc1)C(=O)Nc1ccc(Oc2ccc(F)cc2)cc1]
221
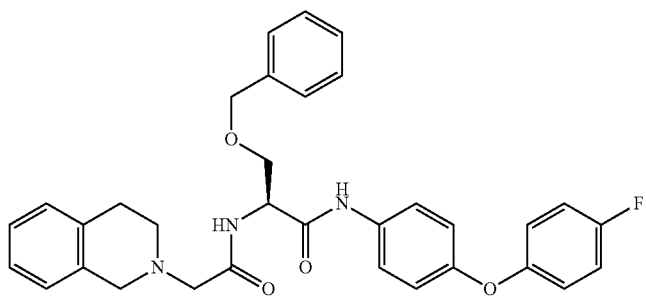 [SMILES: O=C(CN1CCc2ccccc2C1)N[C@@H](COCc1ccccc1)C(=O)Nc1ccc(Oc2ccc(F)cc2)cc1]
222
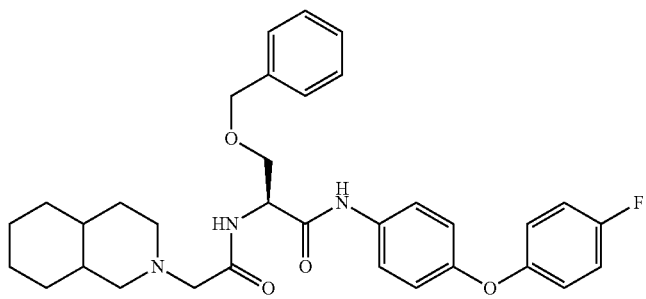 [SMILES: O=C(CN1CCC2CCCCC2C1)N[C@@H](COCc1ccccc1)C(=O)Nc1ccc(Oc2ccc(F)cc2)cc1]
223
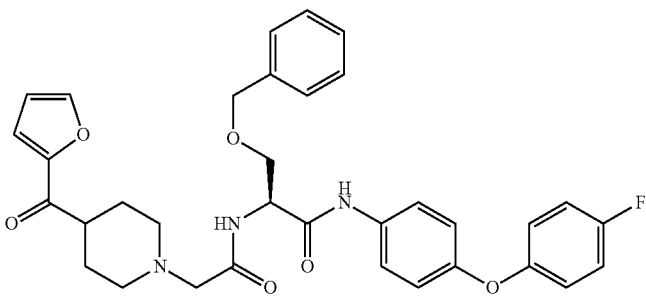 [SMILES: O=C(CN1CCC(C(=O)c2ccco2)CC1)N[C@@H](COCc1ccccc1)C(=O)Nc1ccc(Oc2ccc(F)cc2)cc1]
224

TABLE 1-continued
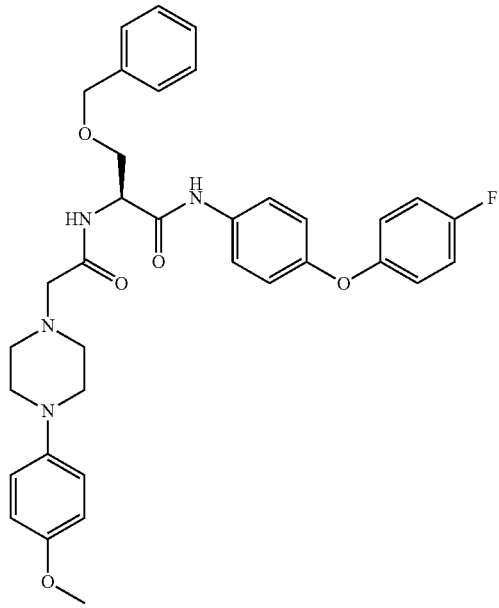 [SMILES: COc1ccc(N2CCN(CC(=O)N[C@@H](COCc3ccccc3)C(=O)Nc3ccc(Oc4ccc(F)cc4)cc3)CC2)cc1]
225
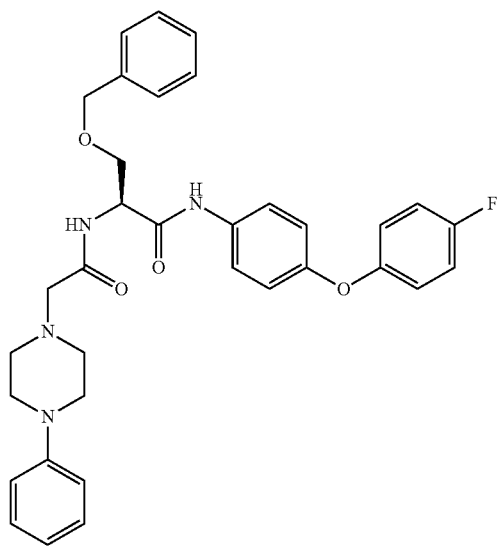 [SMILES: O=C(CN1CCN(c2ccccc2)CC1)N[C@@H](COCc1ccccc1)C(=O)Nc1ccc(Oc2ccc(F)cc2)cc1]
226
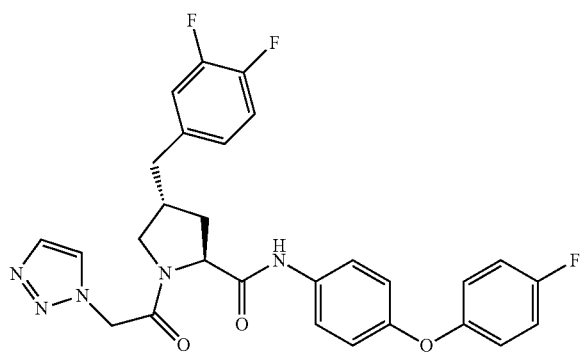 [SMILES: O=C(Nc1ccc(Oc2ccc(F)cc2)cc1)[C@@H]1C[C@@H](Cc2ccc(F)c(F)c2)CN1C(=O)Cn1ccnn1]
227

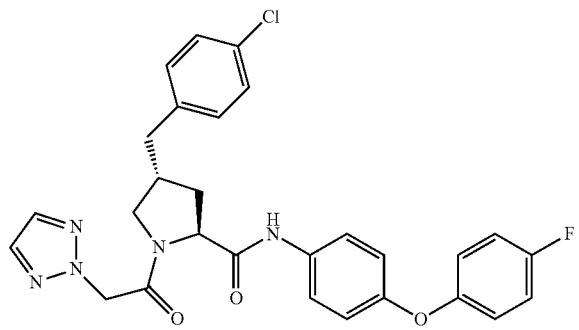
228
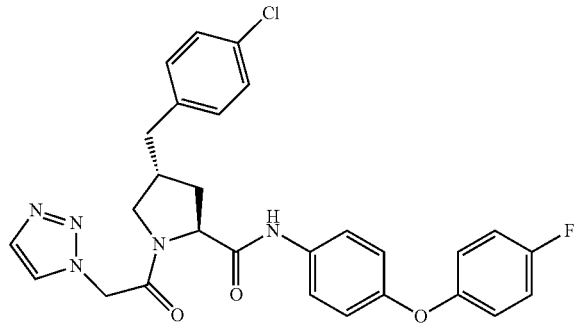 [SMILES: O=C(Nc1ccc(Oc2ccc(F)cc2)cc1)[C@@H]1C[C@@H](Cc2ccc(Cl)cc2)CN1C(=O)Cn1ccnn1]
229
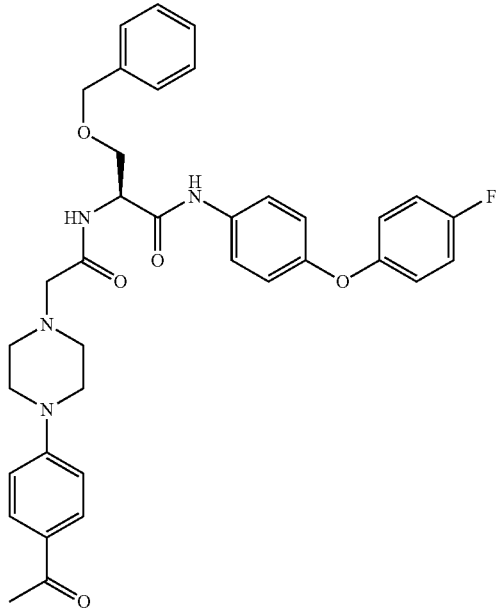 [SMILES: CC(=O)c1ccc(N2CCN(CC(=O)N[C@@H](COCc3ccccc3)C(=O)Nc3ccc(Oc4ccc(F)cc4)cc3)CC2)cc1]
230
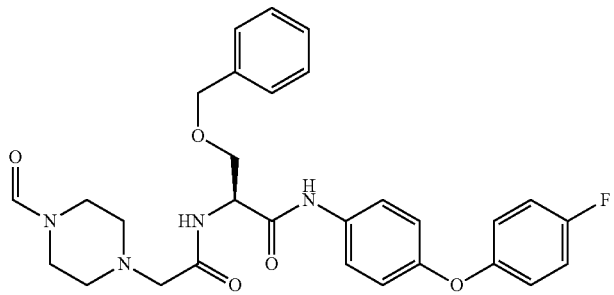 [SMILES: O=CN1CCN(CC(=O)N[C@@H](COCc2ccccc2)C(=O)Nc2ccc(Oc3ccc(F)cc3)cc2)CC1]

TABLE 1-continued
231
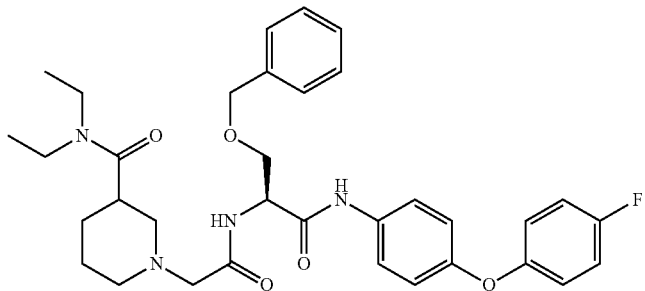 [SMILES: CCN(CC)C(=O)C1CCCN(CC(=O)N[C@@H](COCc2ccccc2)C(=O)Nc2ccc(Oc3ccc(F)cc3)cc2)C1]
232
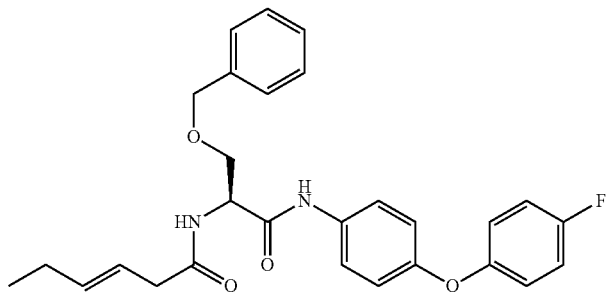 [SMILES: CC/C=C/CC(=O)N[C@@H](COCc1ccccc1)C(=O)Nc1ccc(Oc2ccc(F)cc2)cc1]
233
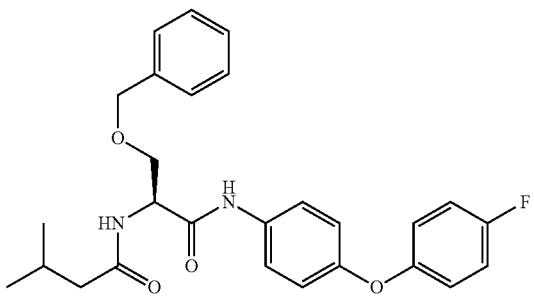 [SMILES: CC(C)CC(=O)N[C@@H](COCc1ccccc1)C(=O)Nc1ccc(Oc2ccc(F)cc2)cc1]
234
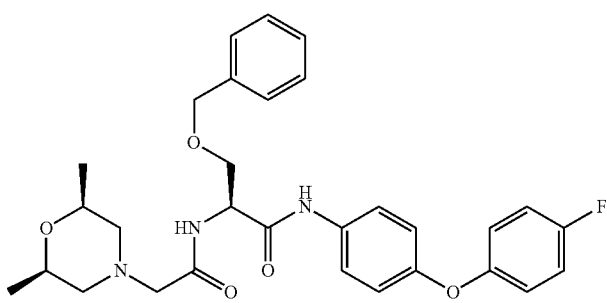 [SMILES: C[C@@H]1CN(CC(=O)N[C@@H](COCc2ccccc2)C(=O)Nc2ccc(Oc3ccc(F)cc3)cc2)C[C@H](C)O1]
235
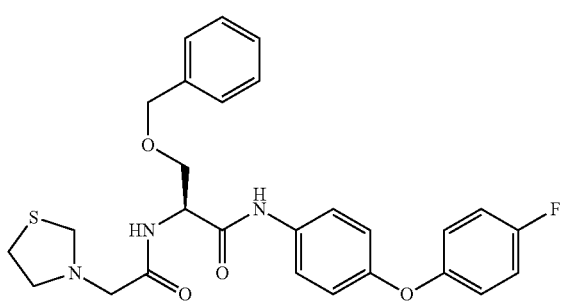
236

TABLE 1-continued
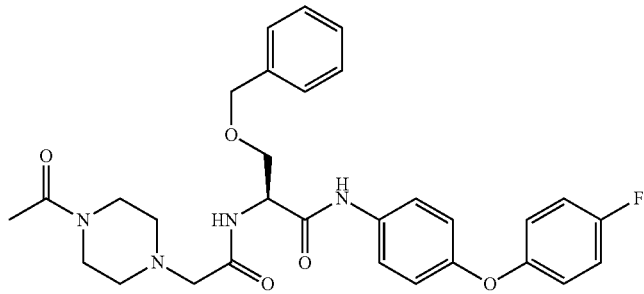
237
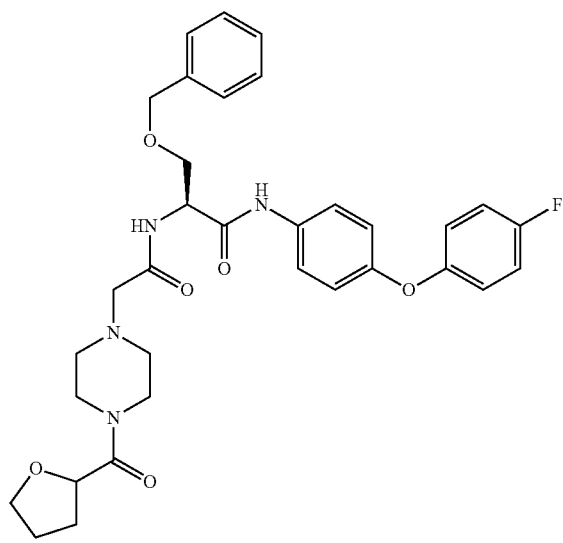 [SMILES: O=C(CN1CCN(C(=O)C2CCCO2)CC1)N[C@@H](COCc1ccccc1)C(=O)Nc1ccc(Oc2ccc(F)cc2)cc1]
238
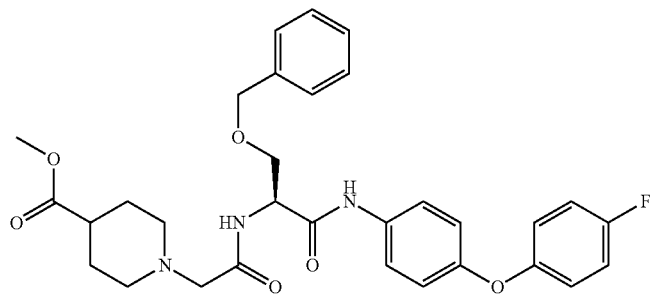 [SMILES: COC(=O)C1CCN(CC(=O)N[C@@H](COCc2ccccc2)C(=O)Nc2ccc(Oc3ccc(F)cc3)cc2)CC1]
239

TABLE 1-continued
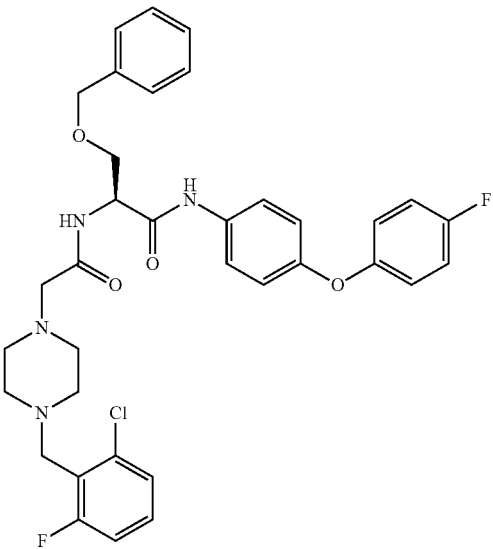 [SMILES: O=C(CN1CCN(Cc2c(F)cccc2Cl)CC1)N[C@@H](COCc1ccccc1)C(=O)Nc1ccc(Oc2ccc(F)cc2)cc1]
240
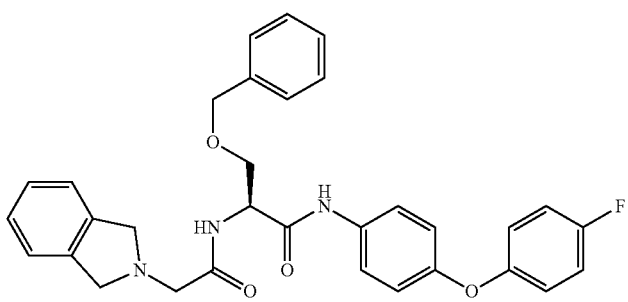 [SMILES: O=C(CN1Cc2ccccc2C1)N[C@@H](COCc1ccccc1)C(=O)Nc1ccc(Oc2ccc(F)cc2)cc1]
241
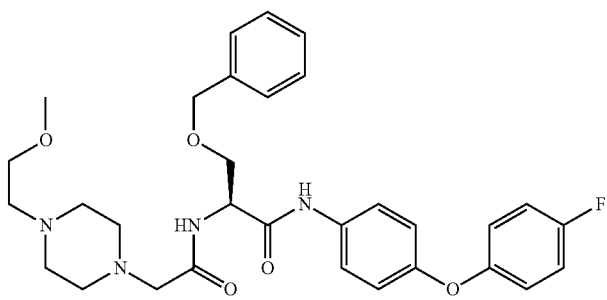 [SMILES: COCCN1CCN(CC(=O)N[C@@H](COCc2ccccc2)C(=O)Nc2ccc(Oc3ccc(F)cc3)cc2)CC1]
242
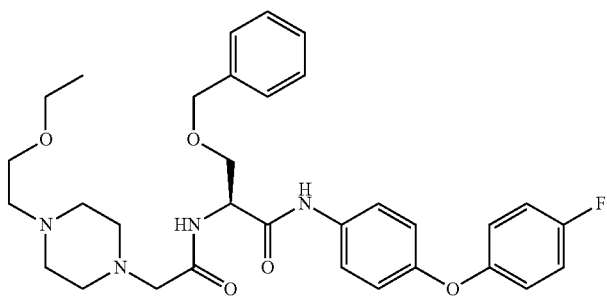 [SMILES: CCOCCN1CCN(CC(=O)N[C@@H](COCc2ccccc2)C(=O)Nc2ccc(Oc3ccc(F)cc3)cc2)CC1]
243

TABLE 1-continued
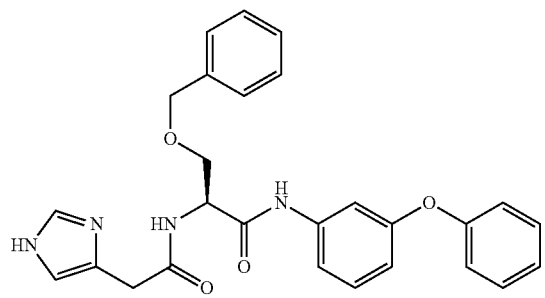 [SMILES: O=C(Cc1c[nH]cn1)N[C@@H](COCc1ccccc1)C(=O)Nc1cccc(Oc2ccccc2)c1]
244
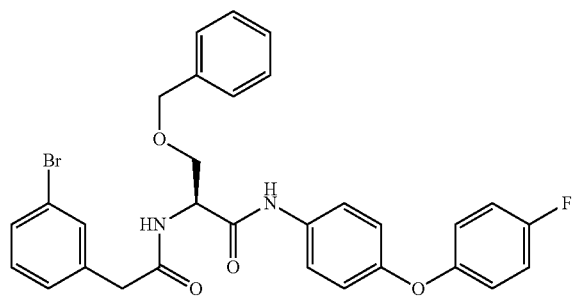 [SMILES: O=C(Cc1cccc(Br)c1)N[C@@H](COCc1ccccc1)C(=O)Nc1ccc(Oc2ccc(F)cc2)cc1]
245
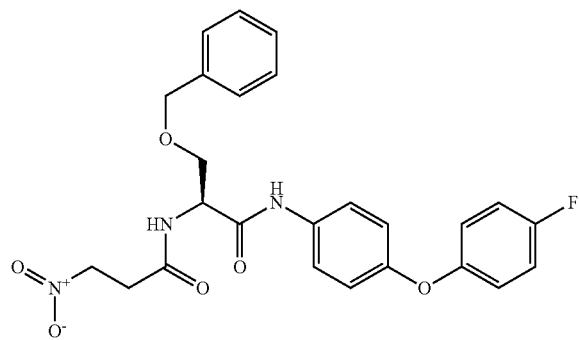 [SMILES: O=C(CC[N+](=O)[O-])N[C@@H](COCc1ccccc1)C(=O)Nc1ccc(Oc2ccc(F)cc2)cc1]
246
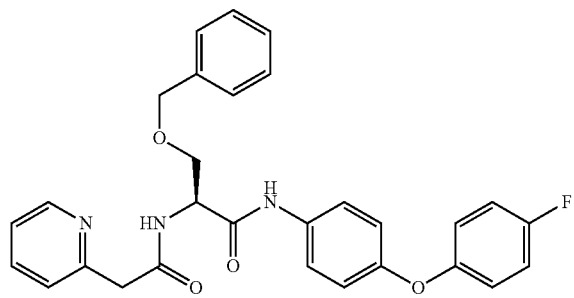 [SMILES: O=C(Cc1ccccn1)N[C@@H](COCc1ccccc1)C(=O)Nc1ccc(Oc2ccc(F)cc2)cc1]
247
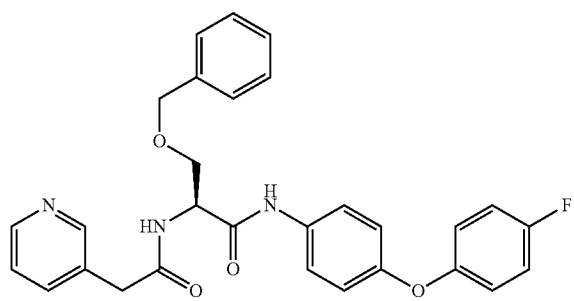 [SMILES: O=C(Cc1cccnc1)N[C@@H](COCc1ccccc1)C(=O)Nc1ccc(Oc2ccc(F)cc2)cc1]

TABLE 1-continued
248
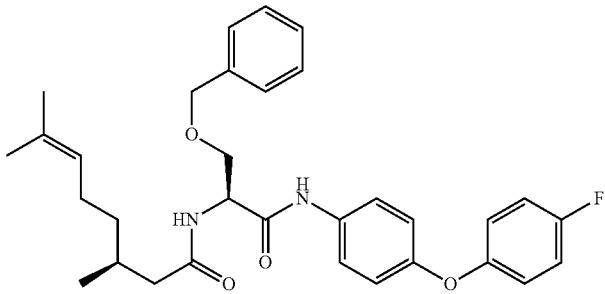 [SMILES: CC(C)=CCC[C@H](C)CC(=O)N[C@@H](COCc1ccccc1)C(=O)Nc1ccc(Oc2ccc(F)cc2)cc1]
249
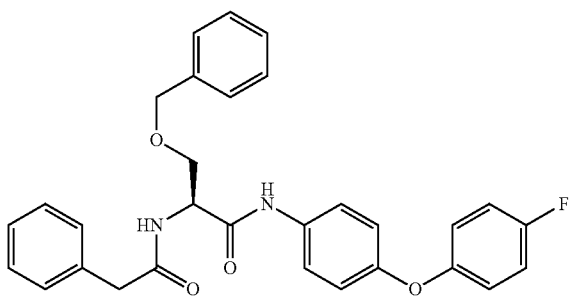 [SMILES: O=C(Cc1ccccc1)N[C@@H](COCc1ccccc1)C(=O)Nc1ccc(Oc2ccc(F)cc2)cc1]
250
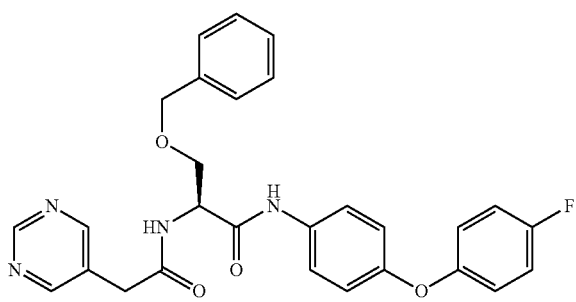 [SMILES: O=C(Cc1cncnc1)N[C@@H](COCc1ccccc1)C(=O)Nc1ccc(Oc2ccc(F)cc2)cc1]
251
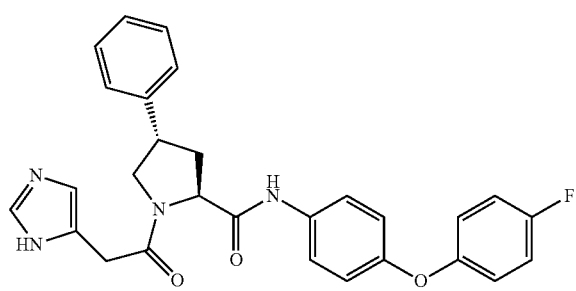 [SMILES: O=C(Nc1ccc(Oc2ccc(F)cc2)cc1)[C@@H]1C[C@@H](c2ccccc2)CN1C(=O)Cc1cnc[nH]1]
252
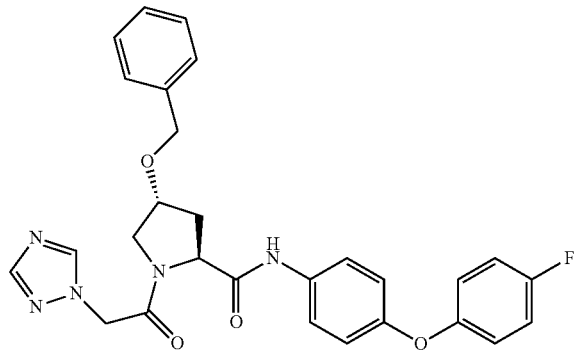 [SMILES: O=C(Nc1ccc(Oc2ccc(F)cc2)cc1)[C@@H]1C[C@@H](OCc2ccccc2)CN1C(=O)Cn1cncn1]

TABLE 1-continued
253
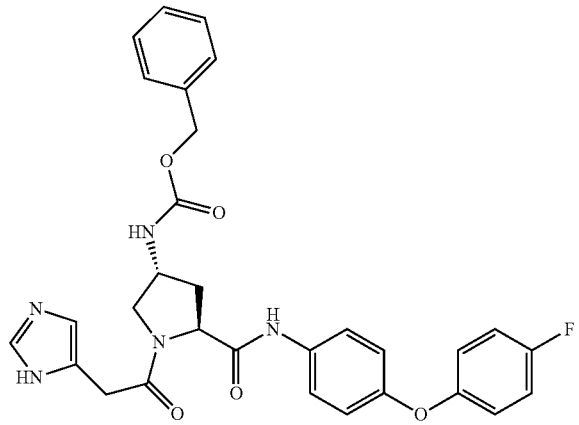 [SMILES: O=C(N[C@@H]1C[C@@H](C(=O)Nc2ccc(Oc3ccc(F)cc3)cc2)N(C(=O)Cc2cnc[nH]2)C1)OCc1ccccc1]
254
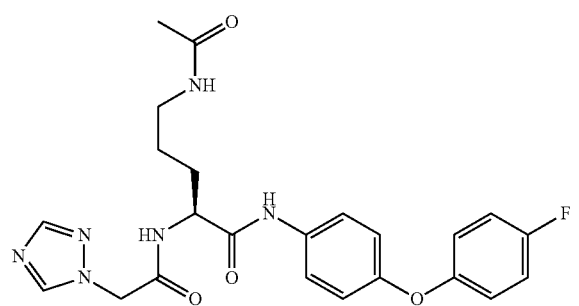 [SMILES: CC(=O)NCCC[C@H](NC(=O)Cn1cncn1)C(=O)Nc1ccc(Oc2ccc(F)cc2)cc1]
255
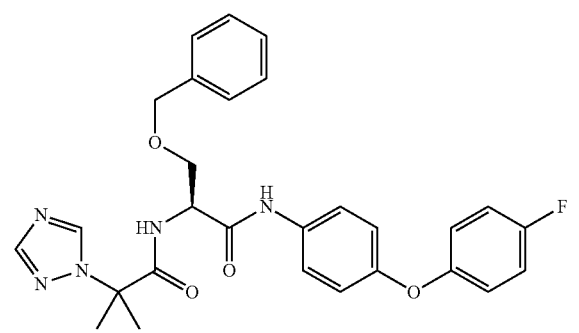 [SMILES: CC(C)(C(=O)N[C@@H](COCc1ccccc1)C(=O)Nc1ccc(Oc2ccc(F)cc2)cc1)n1cncn1]
256
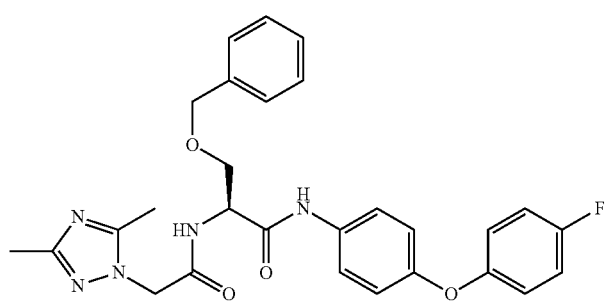 [SMILES: Cc1nc(C)n(CC(=O)N[C@@H](COCc2ccccc2)C(=O)Nc2ccc(Oc3ccc(F)cc3)cc2)n1]
257

TABLE 1-continued
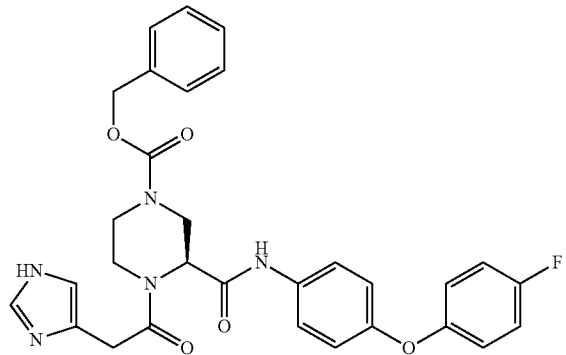 [SMILES: O=C(Nc1ccc(Oc2ccc(F)cc2)cc1)[C@@H]1CN(C(=O)OCc2ccccc2)CCN1C(=O)Cc1c[nH]cn1]
258
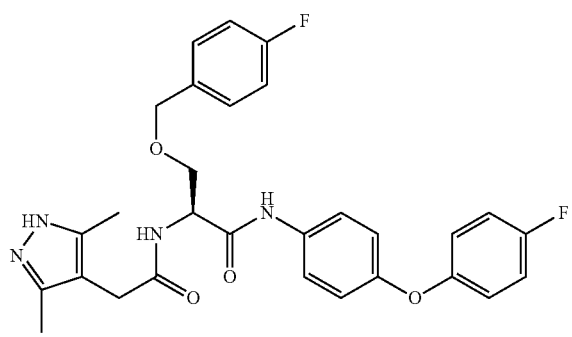 [SMILES: Cc1n[nH]c(C)c1CC(=O)N[C@@H](COCc1ccc(F)cc1)C(=O)Nc1ccc(Oc2ccc(F)cc2)cc1]
259
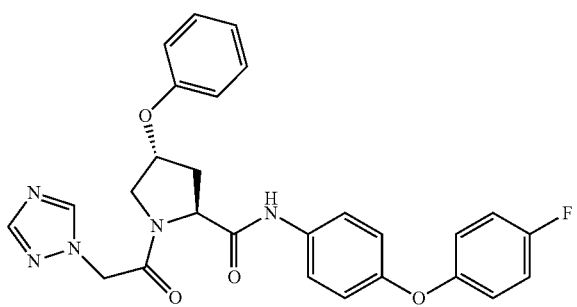 [SMILES: O=C(Nc1ccc(Oc2ccc(F)cc2)cc1)[C@@H]1C[C@@H](Oc2ccccc2)CN1C(=O)Cn1cncn1]
260
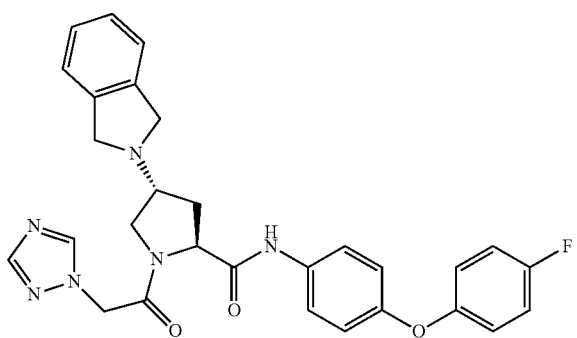 [SMILES: O=C(Nc1ccc(Oc2ccc(F)cc2)cc1)[C@@H]1C[C@@H](N2Cc3ccccc3C2)CN1C(=O)Cn1cncn1]
261

TABLE 1-continued
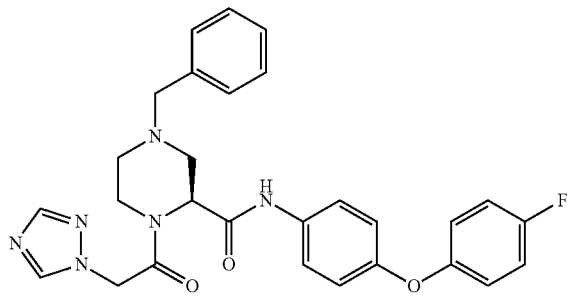 [SMILES: O=C(Nc1ccc(Oc2ccc(F)cc2)cc1)[C@@H]1CN(Cc2ccccc2)CCN1C(=O)Cn1cncn1]
262
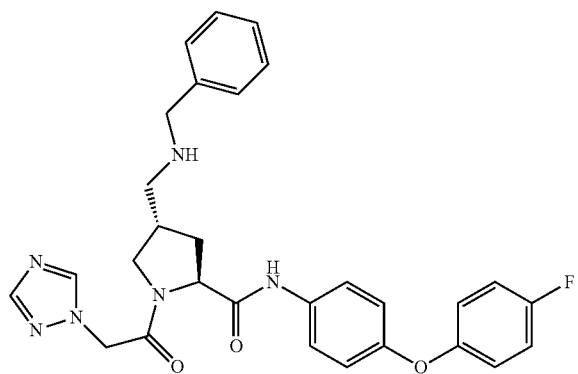 [SMILES: O=C(Nc1ccc(Oc2ccc(F)cc2)cc1)[C@@H]1C[C@@H](CNCc2ccccc2)CN1C(=O)Cn1cncn1]
263
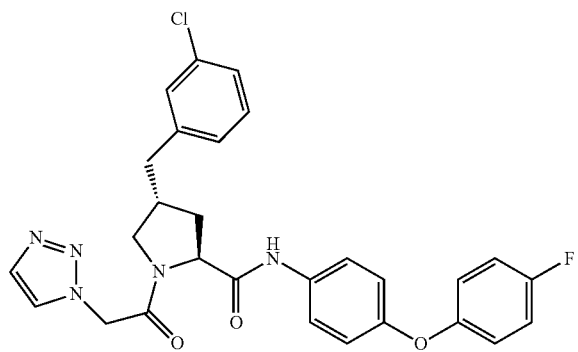 [SMILES: O=C(Nc1ccc(Oc2ccc(F)cc2)cc1)[C@@H]1C[C@@H](Cc2cccc(Cl)c2)CN1C(=O)Cn1ccnn1]
264
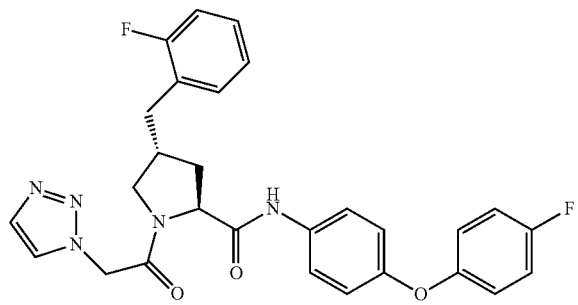 [SMILES: O=C(Nc1ccc(Oc2ccc(F)cc2)cc1)[C@@H]1C[C@@H](Cc2ccccc2F)CN1C(=O)Cn1ccnn1]
265

TABLE 1-continued
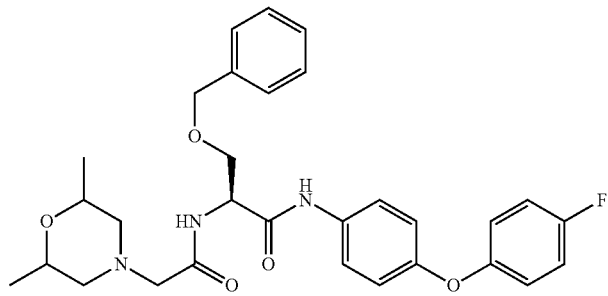
266
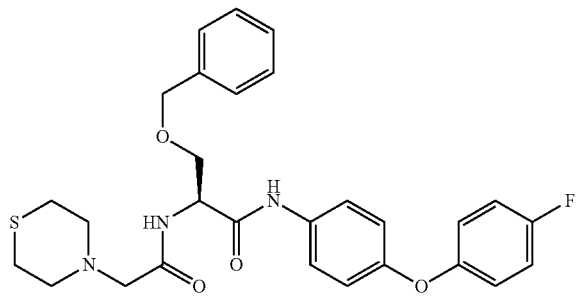 [SMILES: O=C(CN1CCSCC1)N[C@@H](COCc1ccccc1)C(=O)Nc1ccc(Oc2ccc(F)cc2)cc1]
267
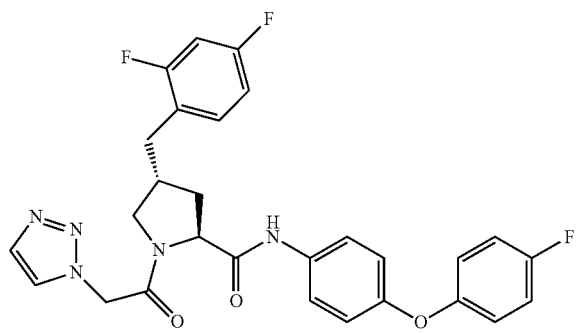 [SMILES: O=C(Nc1ccc(Oc2ccc(F)cc2)cc1)[C@@H]1C[C@@H](Cc2ccc(F)cc2F)CN1C(=O)Cn1ccnn1]
268
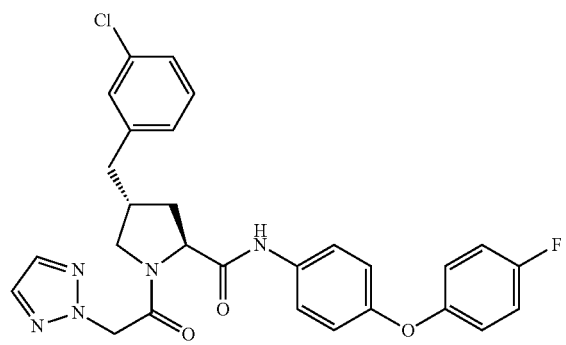 [SMILES: O=C(Nc1ccc(Oc2ccc(F)cc2)cc1)[C@@H]1C[C@@H](Cc2cccc(Cl)c2)CN1C(=O)Cn1nccn1]
269

TABLE 1-continued
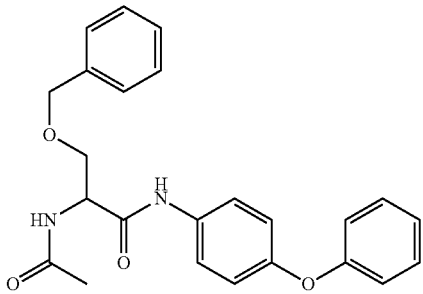 [SMILES: CC(=O)NC(COCc1ccccc1)C(=O)Nc1ccc(Oc2ccccc2)cc1]
270
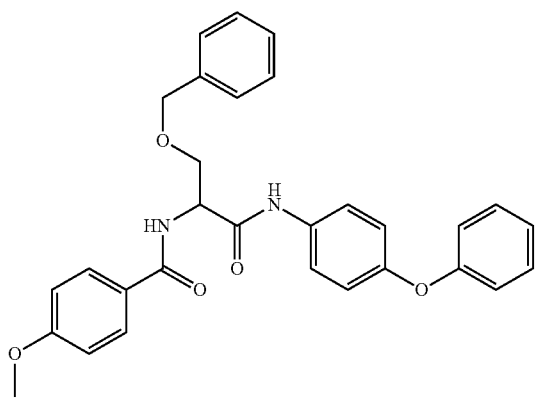 [SMILES: COc1ccc(C(=O)NC(COCc2ccccc2)C(=O)Nc2ccc(Oc3ccccc3)cc2)cc1]
271
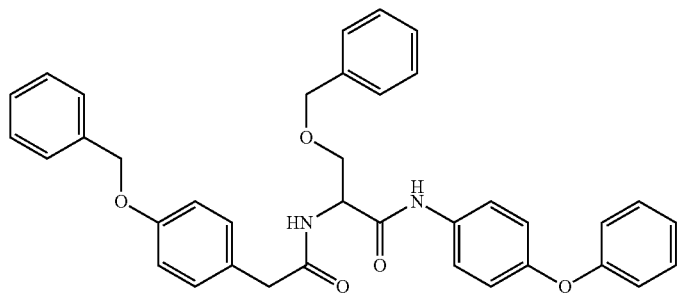 [SMILES: O=C(Cc1ccc(OCc2ccccc2)cc1)NC(COCc1ccccc1)C(=O)Nc1ccc(Oc2ccccc2)cc1]
272
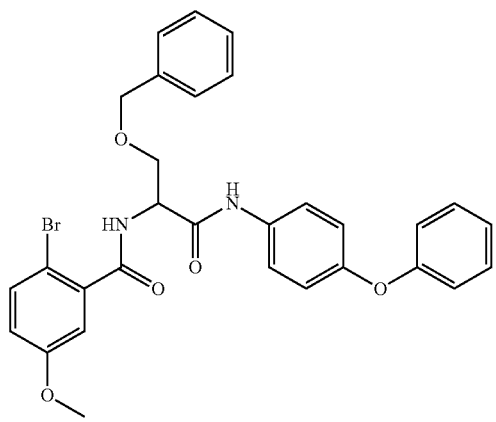 [SMILES: COc1ccc(Br)c(C(=O)NC(COCc2ccccc2)C(=O)Nc2ccc(Oc3ccccc3)cc2)c1]
273

TABLE 1-continued
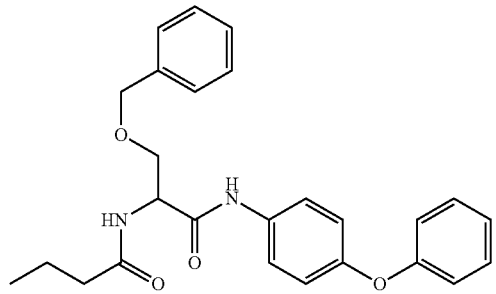 [SMILES: CCCC(=O)NC(COCc1ccccc1)C(=O)Nc1ccc(Oc2ccccc2)cc1]
274
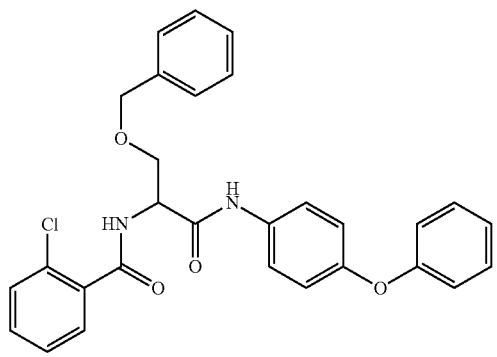 [SMILES: O=C(NC(COCc1ccccc1)C(=O)Nc1ccc(Oc2ccccc2)cc1)c1ccccc1Cl]
275
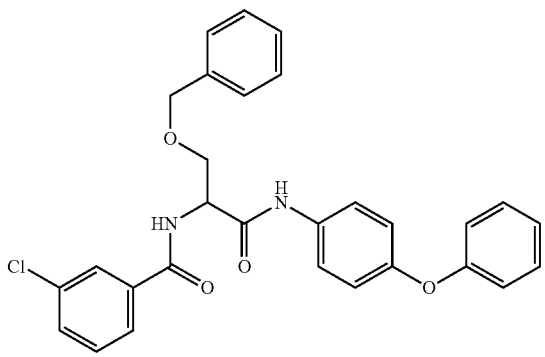 [SMILES: O=C(NC(COCc1ccccc1)C(=O)Nc1ccc(Oc2ccccc2)cc1)c1cccc(Cl)c1]
276
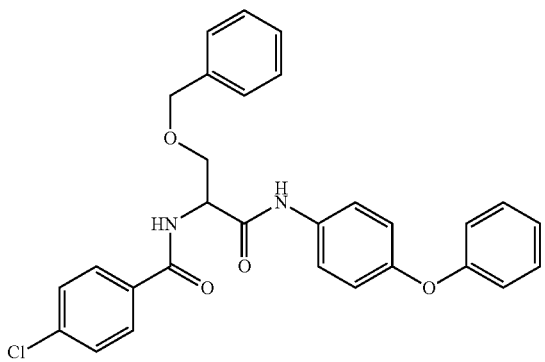 [SMILES: O=C(NC(COCc1ccccc1)C(=O)Nc1ccc(Oc2ccccc2)cc1)c1ccc(Cl)cc1]
277

TABLE 1-continued
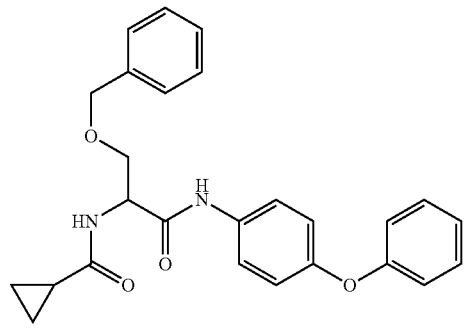 [SMILES: O=C(NC(COCc1ccccc1)C(=O)Nc1ccc(Oc2ccccc2)cc1)C1CC1]
278
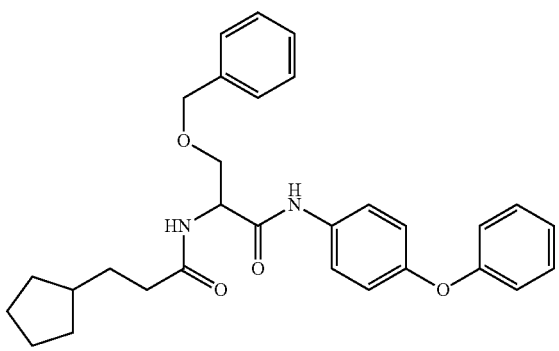 [SMILES: O=C(CCC1CCCC1)NC(COCc1ccccc1)C(=O)Nc1ccc(Oc2ccccc2)cc1]
279
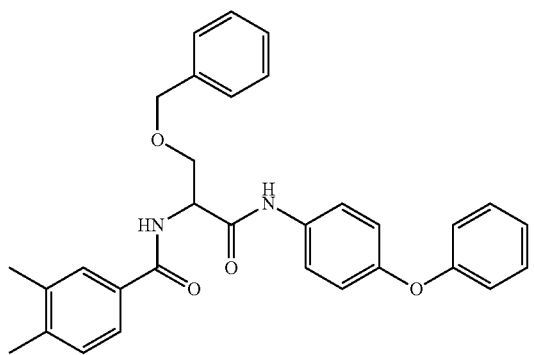 [SMILES: Cc1ccc(C(=O)NC(COCc2ccccc2)C(=O)Nc2ccc(Oc3ccccc3)cc2)cc1C]
280
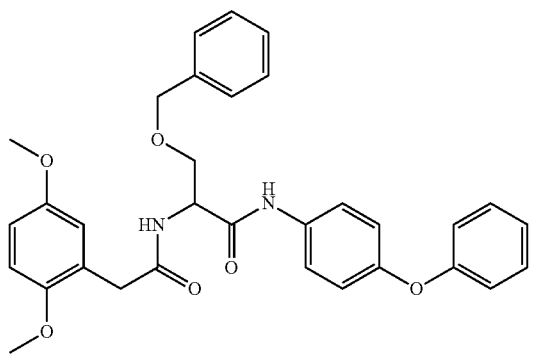 [SMILES: COc1ccc(OC)c(CC(=O)NC(COCc2ccccc2)C(=O)Nc2ccc(Oc3ccccc3)cc2)c1]
281

TABLE 1-continued
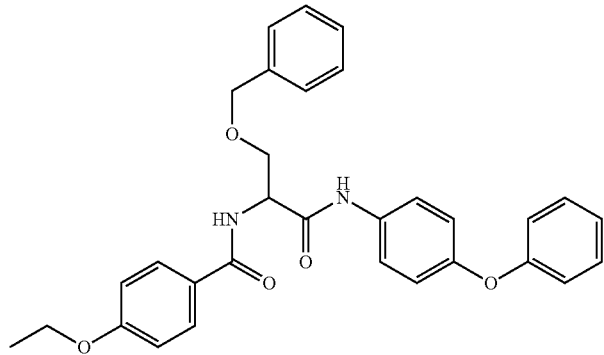 [SMILES: CCOc1ccc(C(=O)NC(COCc2ccccc2)C(=O)Nc2ccc(Oc3ccccc3)cc2)cc1]
282
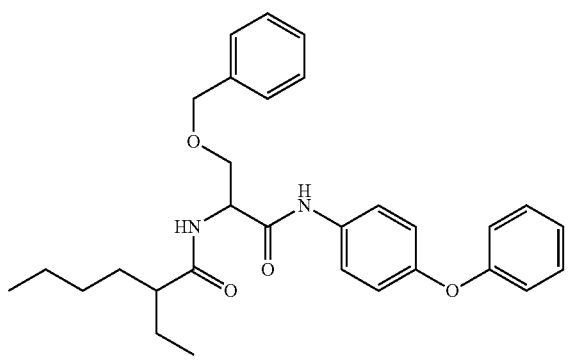 [SMILES: CCCCC(CC)C(=O)NC(COCc1ccccc1)C(=O)Nc1ccc(Oc2ccccc2)cc1]
283
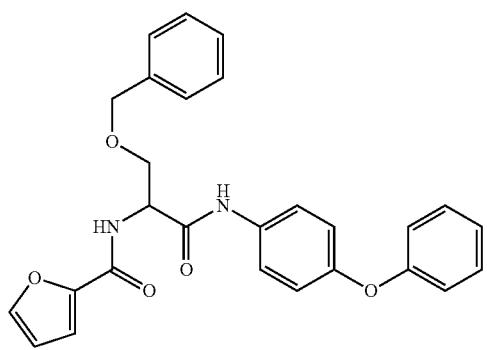 [SMILES: O=C(NC(COCc1ccccc1)C(=O)Nc1ccc(Oc2ccccc2)cc1)c1ccco1]
284
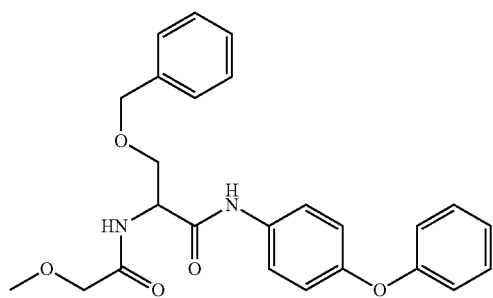 [SMILES: COCC(=O)NC(COCc1ccccc1)C(=O)Nc1ccc(Oc2ccccc2)cc1]
285

TABLE 1-continued
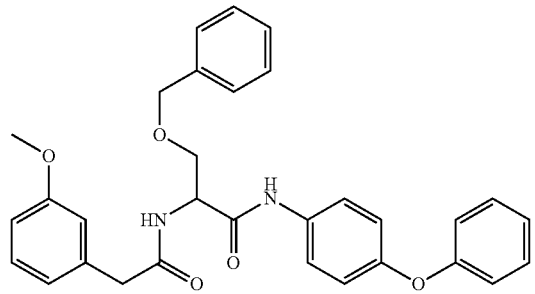 [SMILES: COc1cccc(CC(=O)NC(COCc2ccccc2)C(=O)Nc2ccc(Oc3ccccc3)cc2)c1]
286
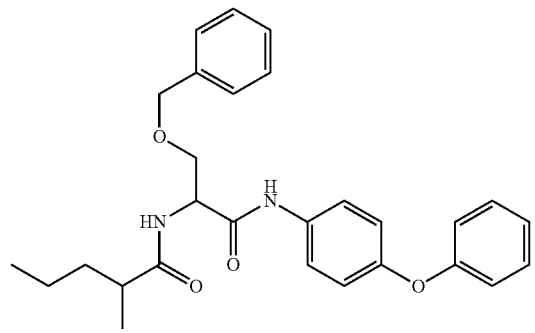 [SMILES: CCCC(C)C(=O)NC(COCc1ccccc1)C(=O)Nc1ccc(Oc2ccccc2)cc1]
287
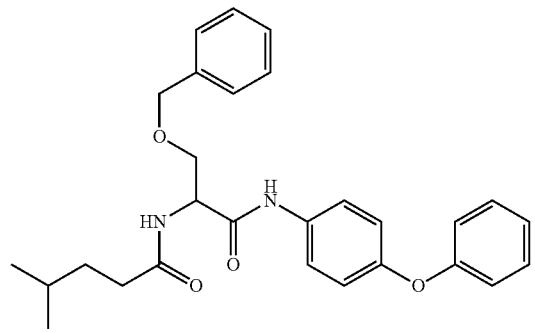 [SMILES: CC(C)CCC(=O)NC(COCc1ccccc1)C(=O)Nc1ccc(Oc2ccccc2)cc1]
288
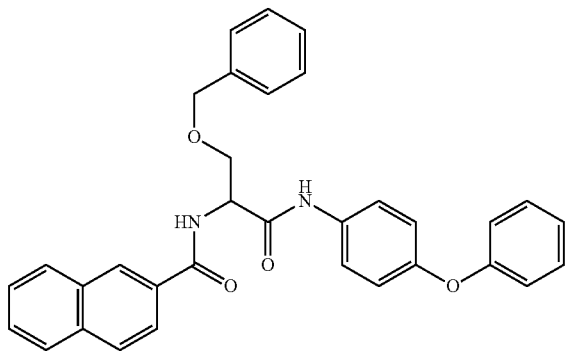 [SMILES: O=C(NC(COCc1ccccc1)C(=O)Nc1ccc(Oc2ccccc2)cc1)c1ccc2ccccc2c1]
289

TABLE 1-continued
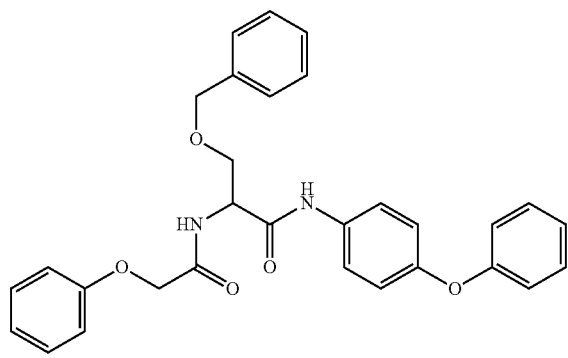
290
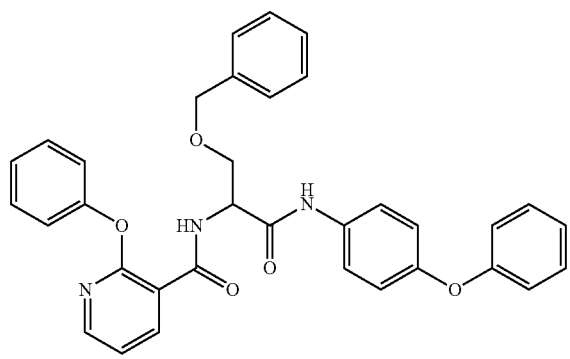 [SMILES: O=C(NC(COCc1ccccc1)C(=O)Nc1ccc(Oc2ccccc2)cc1)c1cccnc1Oc1ccccc1]
291
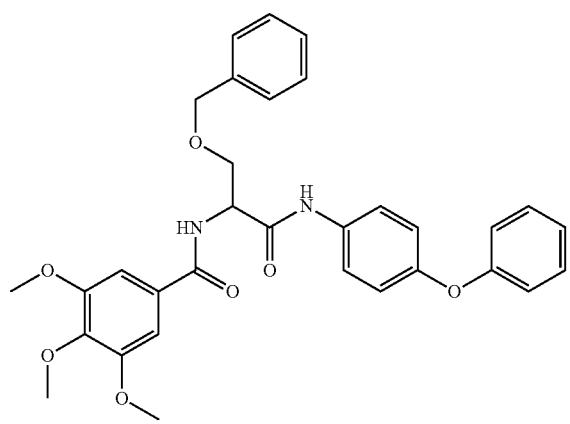 [SMILES: COc1cc(C(=O)NC(COCc2ccccc2)C(=O)Nc2ccc(Oc3ccccc3)cc2)cc(OC)c1OC]
292
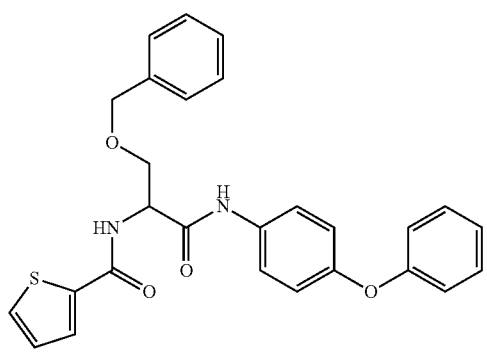 [SMILES: O=C(NC(COCc1ccccc1)C(=O)Nc1ccc(Oc2ccccc2)cc1)c1cccs1]
293

TABLE 1-continued
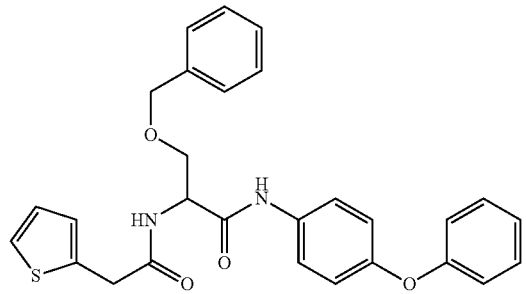 [SMILES: O=C(Cc1cccs1)NC(COCc1ccccc1)C(=O)Nc1ccc(Oc2ccccc2)cc1]
294
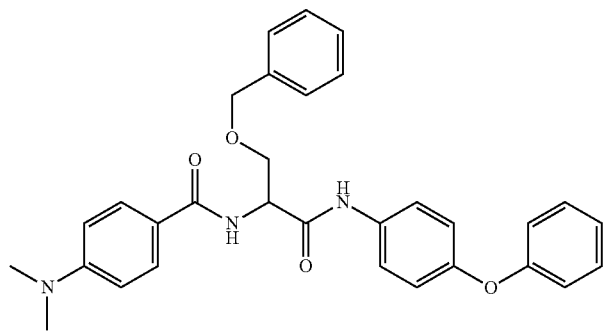 [SMILES: CN(C)c1ccc(C(=O)NC(COCc2ccccc2)C(=O)Nc2ccc(Oc3ccccc3)cc2)cc1]
295
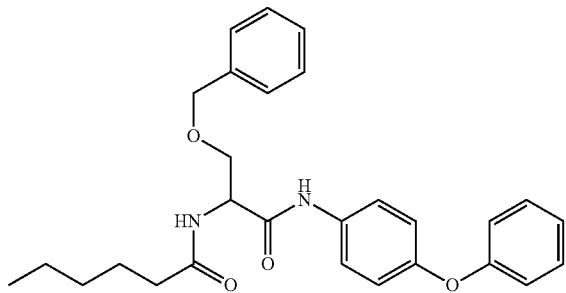 [SMILES: CCCCCC(=O)NC(COCc1ccccc1)C(=O)Nc1ccc(Oc2ccccc2)cc1]
296
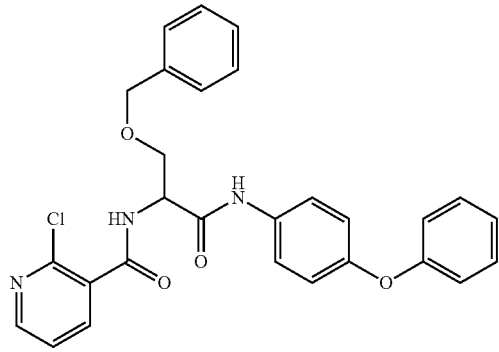 [SMILES: O=C(NC(COCc1ccccc1)C(=O)Nc1ccc(Oc2ccccc2)cc1)c1cccnc1Cl]
297

TABLE 1-continued
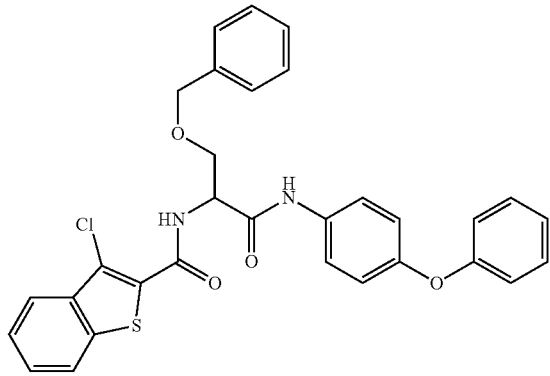 [SMILES: O=C(NC(COCc1ccccc1)C(=O)Nc1ccc(Oc2ccccc2)cc1)c1sc2ccccc2c1Cl]
298
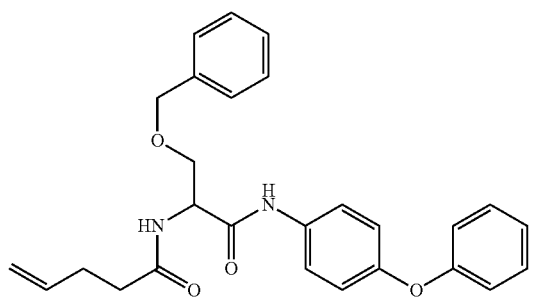 [SMILES: C=CCCC(=O)NC(COCc1ccccc1)C(=O)Nc1ccc(Oc2ccccc2)cc1]
299
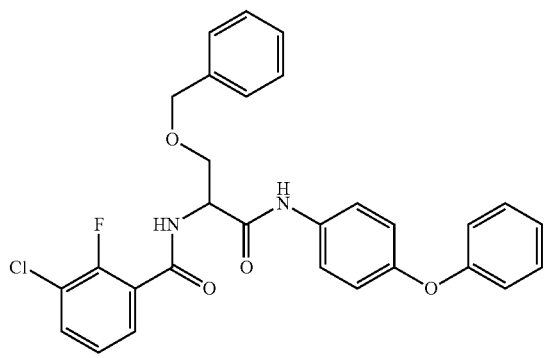 [SMILES: O=C(NC(COCc1ccccc1)C(=O)Nc1ccc(Oc2ccccc2)cc1)c1cccc(Cl)c1F]
300
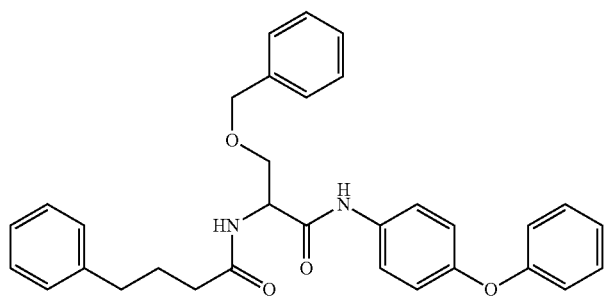 [SMILES: O=C(CCCc1ccccc1)NC(COCc1ccccc1)C(=O)Nc1ccc(Oc2ccccc2)cc1]
301

TABLE 1-continued
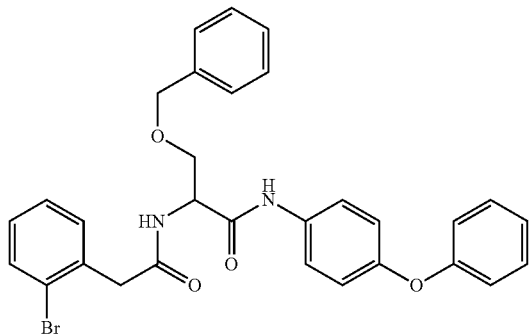 [SMILES: O=C(Cc1ccccc1Br)NC(COCc1ccccc1)C(=O)Nc1ccc(Oc2ccccc2)cc1]
302
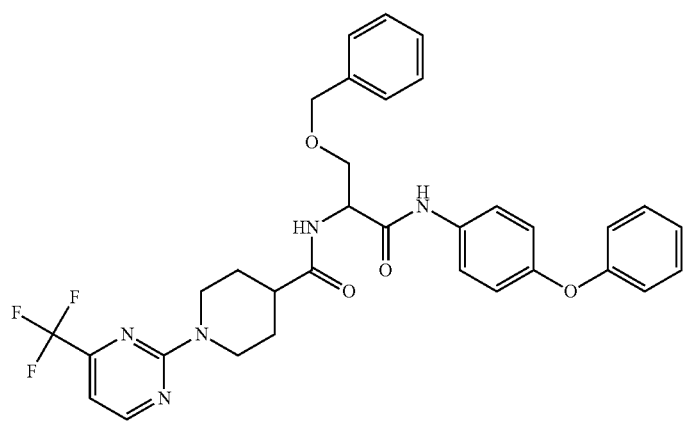 [SMILES: O=C(NC(COCc1ccccc1)C(=O)Nc1ccc(Oc2ccccc2)cc1)C1CCN(c2nccc(C(F)(F)F)n2)CC1]
303
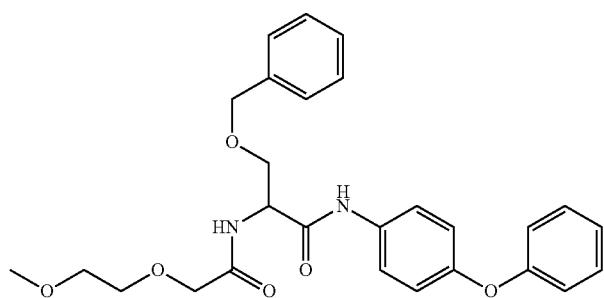 [SMILES: COCCOCC(=O)NC(COCc1ccccc1)C(=O)Nc1ccc(Oc2ccccc2)cc1]
304
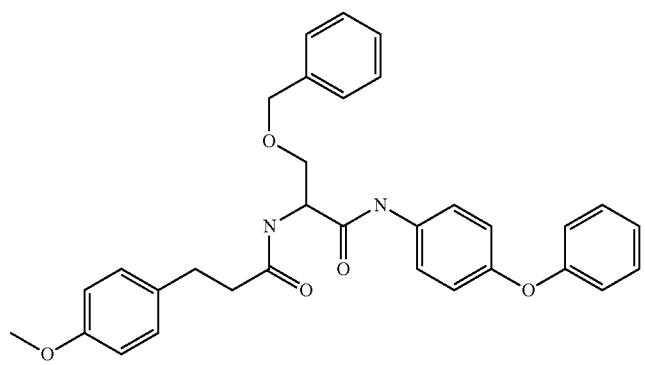 [SMILES: COc1ccc(CCC(=O)NC(COCc2ccccc2)C(=O)Nc2ccc(Oc3ccccc3)cc2)cc1]
305

TABLE 1-continued
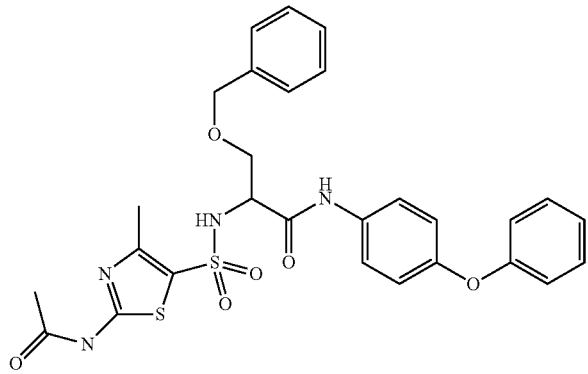 [SMILES: CC(=O)Nc1nc(C)c(S(=O)(=O)NC(COCc2ccccc2)C(=O)Nc2ccc(Oc3ccccc3)cc2)s1]
306
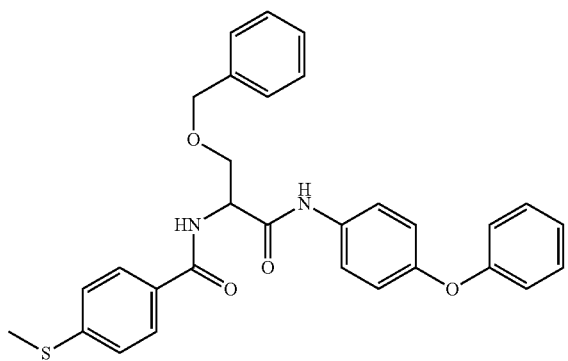 [SMILES: CSc1ccc(C(=O)NC(COCc2ccccc2)C(=O)Nc2ccc(Oc3ccccc3)cc2)cc1]
307
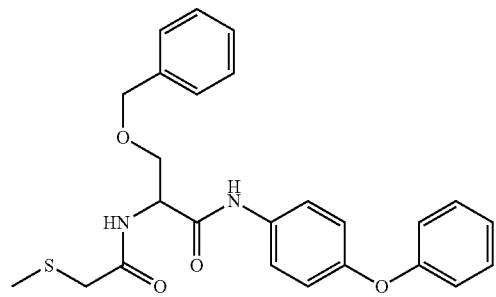
308
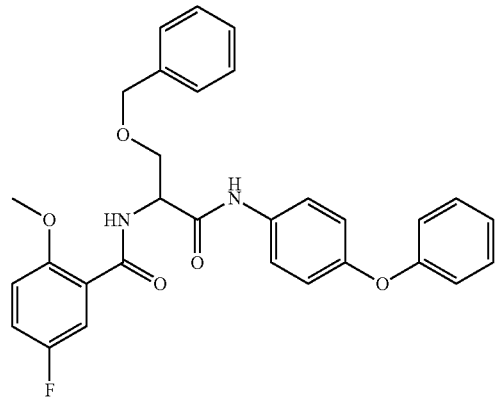 [SMILES: COc1ccc(F)cc1C(=O)NC(COCc1ccccc1)C(=O)Nc1ccc(Oc2ccccc2)cc1]
309

TABLE 1-continued
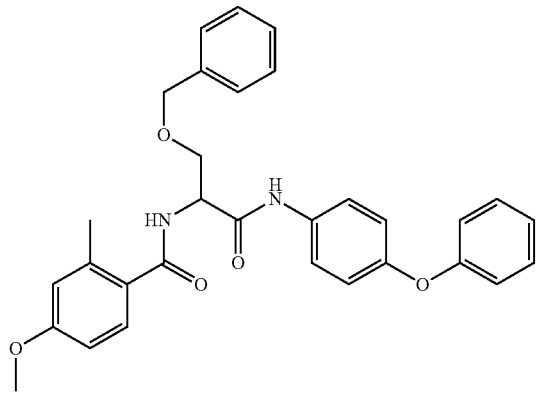 [SMILES: COc1ccc(C(=O)NC(COCc2ccccc2)C(=O)Nc2ccc(Oc3ccccc3)cc2)c(C)c1]
310
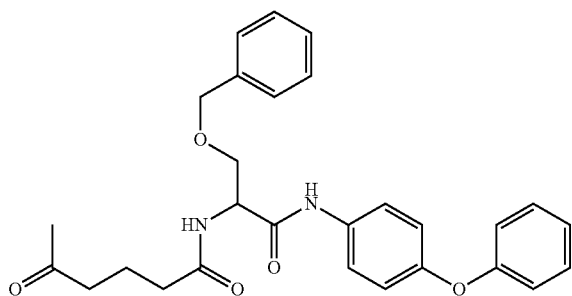 [SMILES: CC(=O)CCCC(=O)NC(COCc1ccccc1)C(=O)Nc1ccc(Oc2ccccc2)cc1]
311
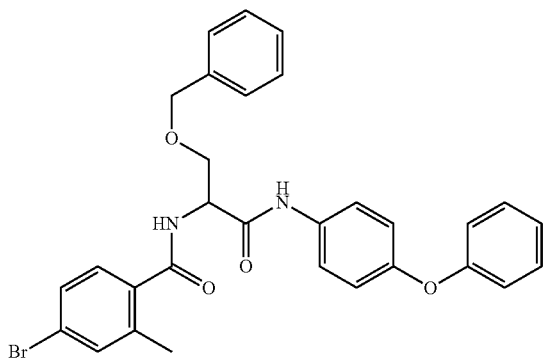 [SMILES: Cc1cc(Br)ccc1C(=O)NC(COCc1ccccc1)C(=O)Nc1ccc(Oc2ccccc2)cc1]
312
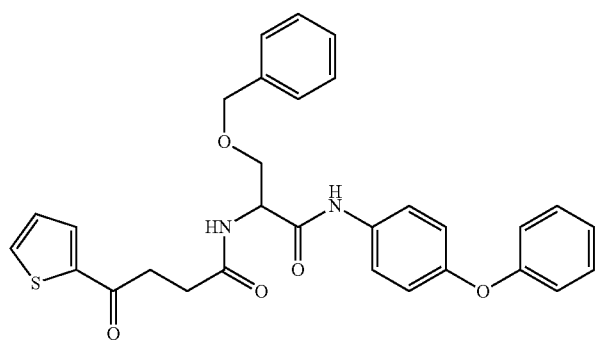 [SMILES: O=C(CCC(=O)c1cccs1)NC(COCc1ccccc1)C(=O)Nc1ccc(Oc2ccccc2)cc1]
313

TABLE 1-continued
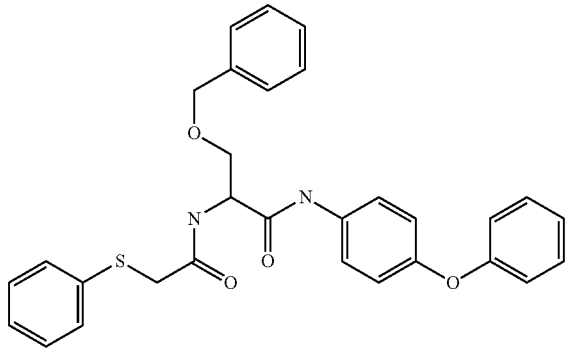 [SMILES: O=C(CSc1ccccc1)NC(COCc1ccccc1)C(=O)Nc1ccc(Oc2ccccc2)cc1]
314
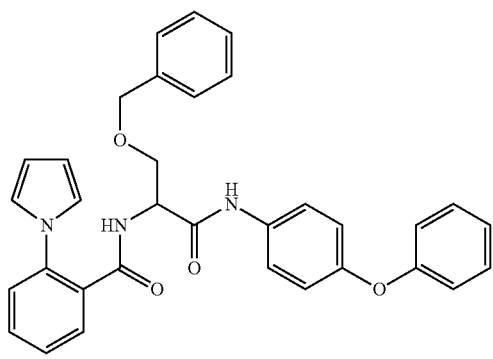 [SMILES: O=C(NC(COCc1ccccc1)C(=O)Nc1ccc(Oc2ccccc2)cc1)c1ccccc1-n1cccc1]
315
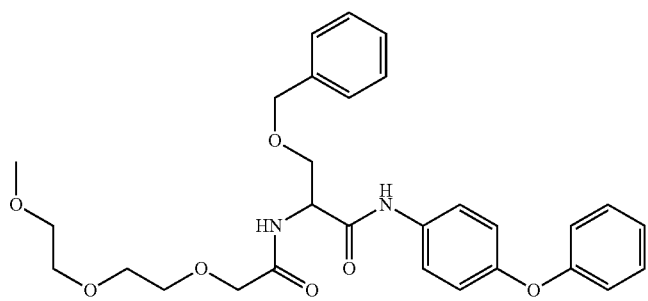 [SMILES: COCCOCCOCC(=O)NC(COCc1ccccc1)C(=O)Nc1ccc(Oc2ccccc2)cc1]
316
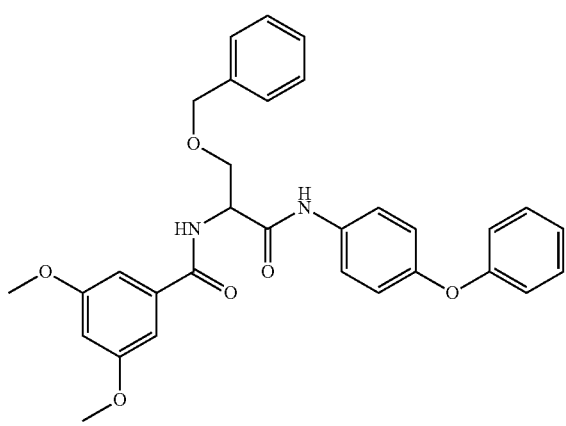 [SMILES: COc1cc(OC)cc(C(=O)NC(COCc2ccccc2)C(=O)Nc2ccc(Oc3ccccc3)cc2)c1]
317

TABLE 1-continued
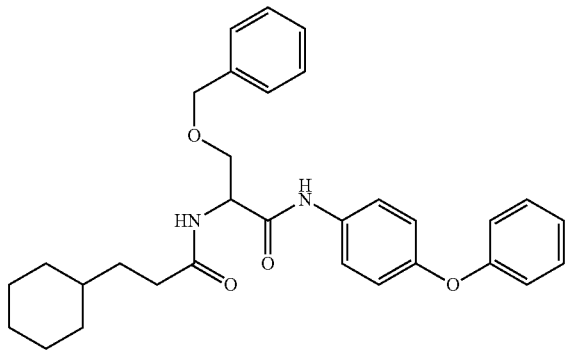 [SMILES: O=C(CCC1CCCCC1)NC(COCc1ccccc1)C(=O)Nc1ccc(Oc2ccccc2)cc1]
318
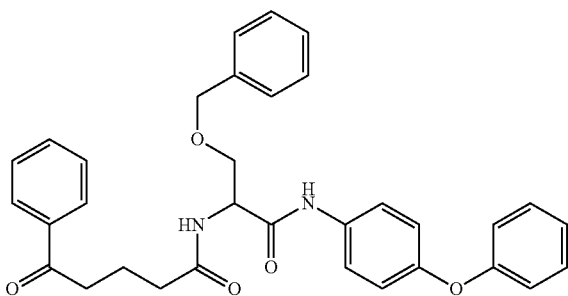 [SMILES: O=C(CCCC(=O)c1ccccc1)NC(COCc1ccccc1)C(=O)Nc1ccc(Oc2ccccc2)cc1]
319
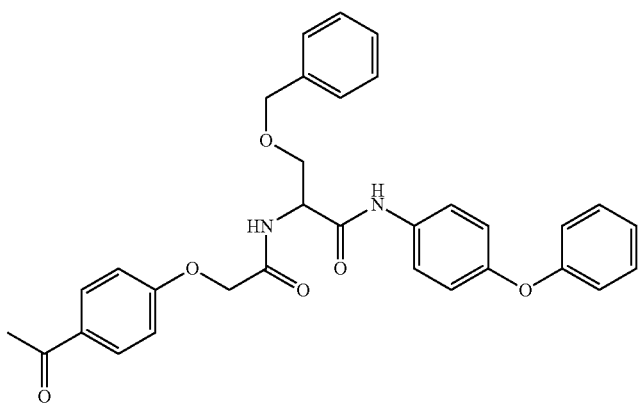 [SMILES: CC(=O)c1ccc(OCC(=O)NC(COCc2ccccc2)C(=O)Nc2ccc(Oc3ccccc3)cc2)cc1]
320
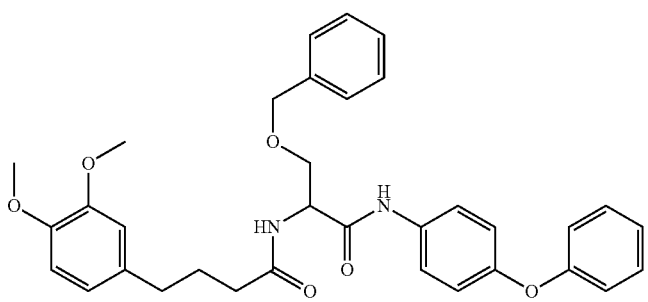 [SMILES: COc1ccc(CCCC(=O)NC(COCc2ccccc2)C(=O)Nc2ccc(Oc3ccccc3)cc2)cc1OC]
321

TABLE 1-continued
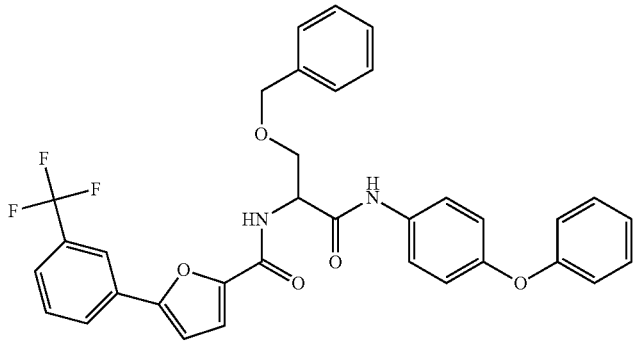 [SMILES: O=C(NC(COCc1ccccc1)C(=O)Nc1ccc(Oc2ccccc2)cc1)c1ccc(-c2cccc(C(F)(F)F)c2)o1]
322
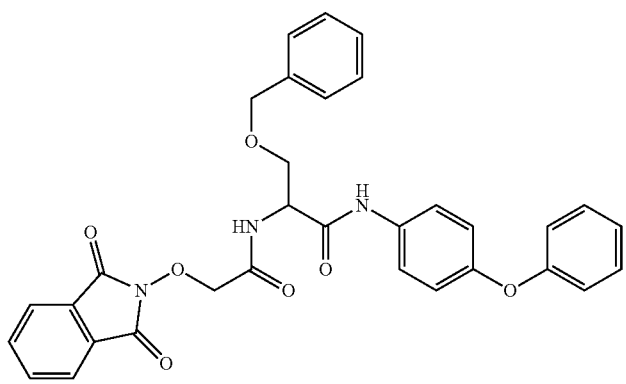 [SMILES: O=C(CON1C(=O)c2ccccc2C1=O)NC(COCc1ccccc1)C(=O)Nc1ccc(Oc2ccccc2)cc1]
323
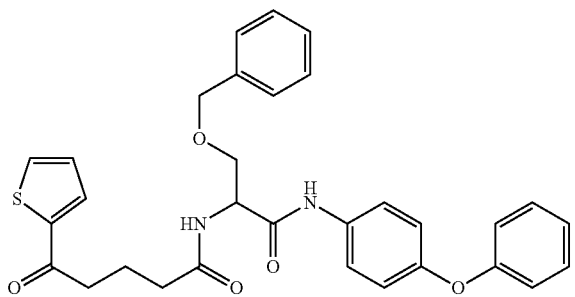 [SMILES: O=C(CCCC(=O)c1cccs1)NC(COCc1ccccc1)C(=O)Nc1ccc(Oc2ccccc2)cc1]
324
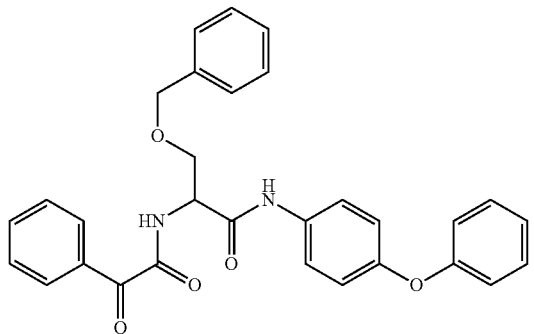 [SMILES: O=C(NC(COCc1ccccc1)C(=O)Nc1ccc(Oc2ccccc2)cc1)C(=O)c1ccccc1]
325

TABLE 1-continued
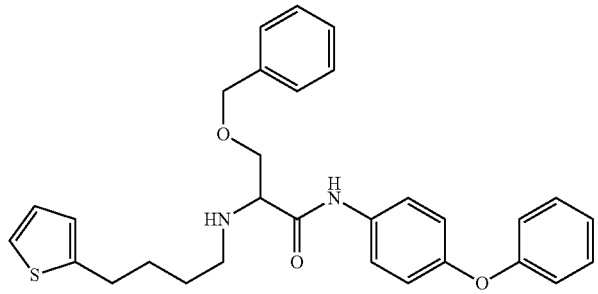 [SMILES: O=C(Nc1ccc(Oc2ccccc2)cc1)C(COCc1ccccc1)NCCCCc1cccs1]
326
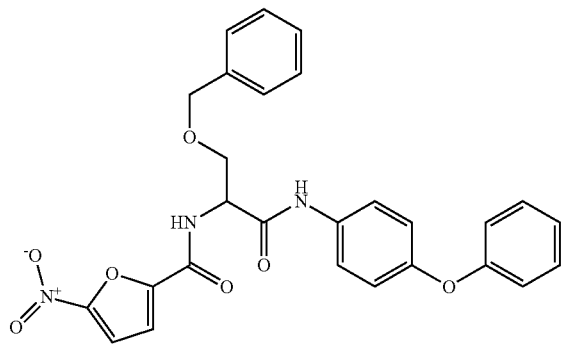
327
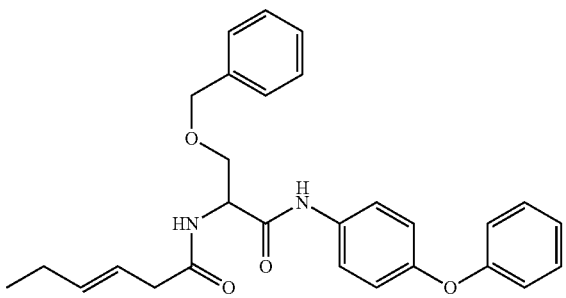 [SMILES: CC/C=C/CC(=O)NC(COCc1ccccc1)C(=O)Nc1ccc(Oc2ccccc2)cc1]
328
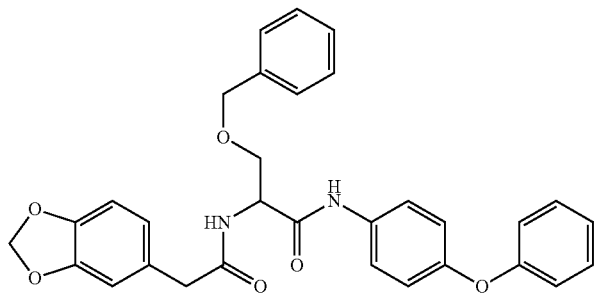 [SMILES: O=C(Cc1ccc2c(c1)OCO2)NC(COCc1ccccc1)C(=O)Nc1ccc(Oc2ccccc2)cc1]
329

TABLE 1-continued
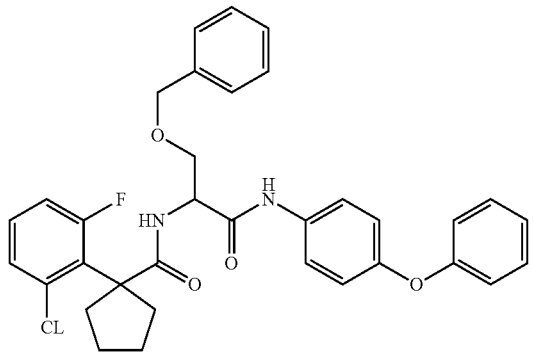
330
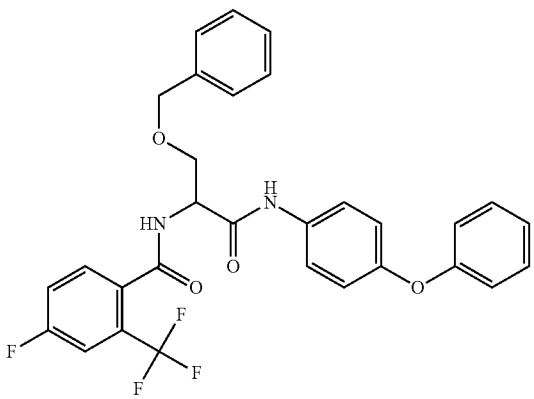 [SMILES: O=C(NC(COCc1ccccc1)C(=O)Nc1ccc(Oc2ccccc2)cc1)c1ccc(F)cc1C(F)(F)F]
331
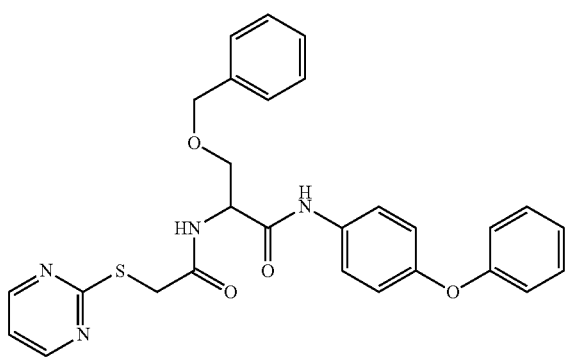 [SMILES: O=C(CSc1ncccn1)NC(COCc1ccccc1)C(=O)Nc1ccc(Oc2ccccc2)cc1]
332
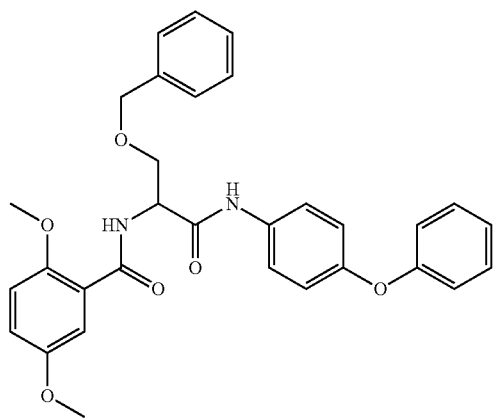 [SMILES: COc1ccc(OC)c(C(=O)NC(COCc2ccccc2)C(=O)Nc2ccc(Oc3ccccc3)cc2)c1]
333

TABLE 1-continued
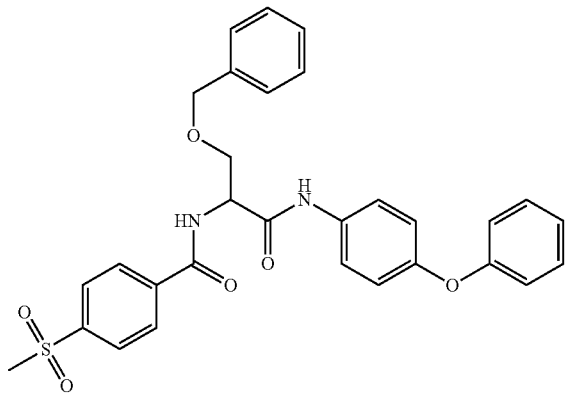 [SMILES: CS(=O)(=O)c1ccc(C(=O)NC(COCc2ccccc2)C(=O)Nc2ccc(Oc3ccccc3)cc2)cc1]
334
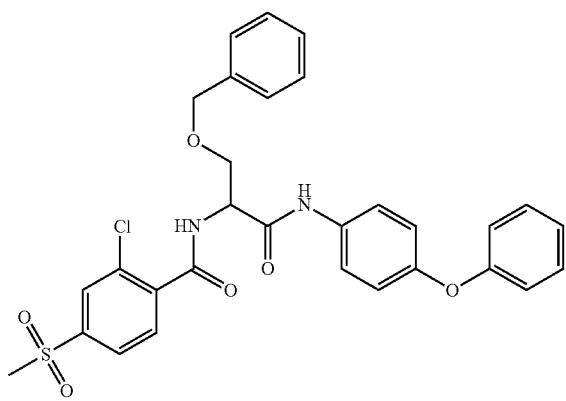 [SMILES: CS(=O)(=O)c1ccc(C(=O)NC(COCc2ccccc2)C(=O)Nc2ccc(Oc3ccccc3)cc2)c(Cl)c1]
335
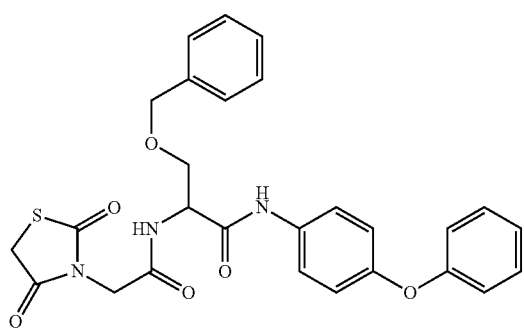 [SMILES: O=C(CN1C(=O)CSC1=O)NC(COCc1ccccc1)C(=O)Nc1ccc(Oc2ccccc2)cc1]
336
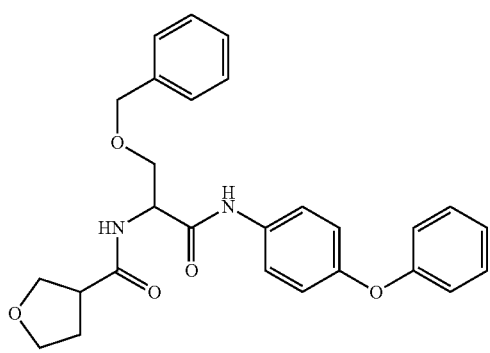 [SMILES: O=C(NC(COCc1ccccc1)C(=O)Nc1ccc(Oc2ccccc2)cc1)C1CCOC1]
337

TABLE 1-continued
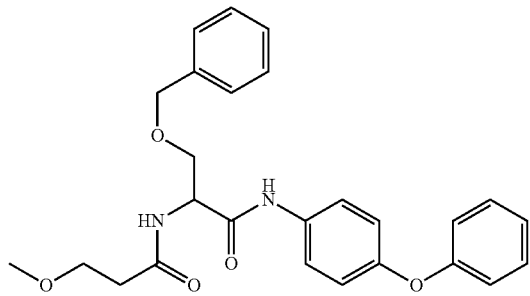 [SMILES: COCCC(=O)NC(COCc1ccccc1)C(=O)Nc1ccc(Oc2ccccc2)cc1]
338
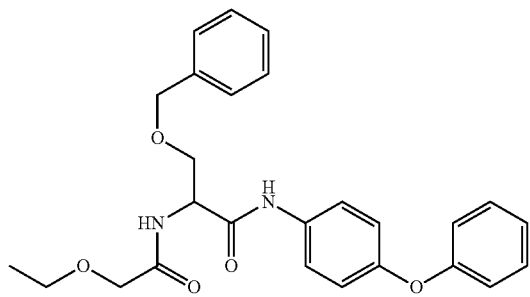 [SMILES: CCOCC(=O)NC(COCc1ccccc1)C(=O)Nc1ccc(Oc2ccccc2)cc1]
339
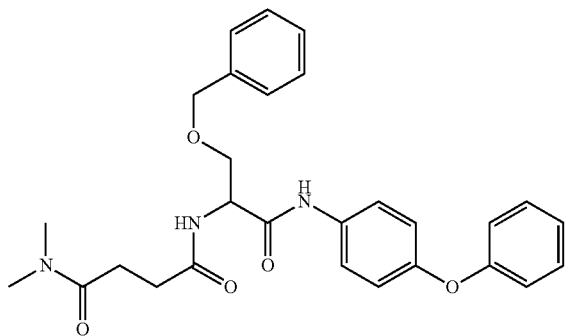 [SMILES: CN(C)C(=O)CCC(=O)NC(COCc1ccccc1)C(=O)Nc1ccc(Oc2ccccc2)cc1]
340
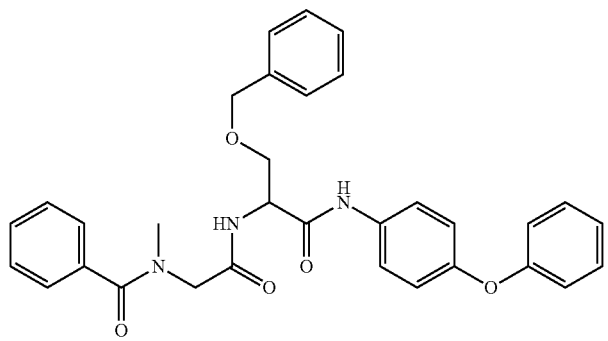 [SMILES: CN(CC(=O)NC(COCc1ccccc1)C(=O)Nc1ccc(Oc2ccccc2)cc1)C(=O)c1ccccc1]
341

TABLE 1-continued
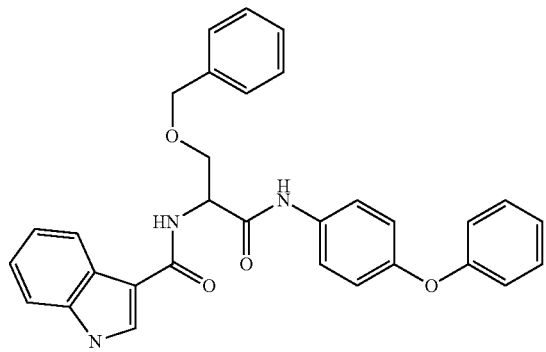 [SMILES: O=C(NC(COCc1ccccc1)C(=O)Nc1ccc(Oc2ccccc2)cc1)c1c[nH]c2ccccc12]
342
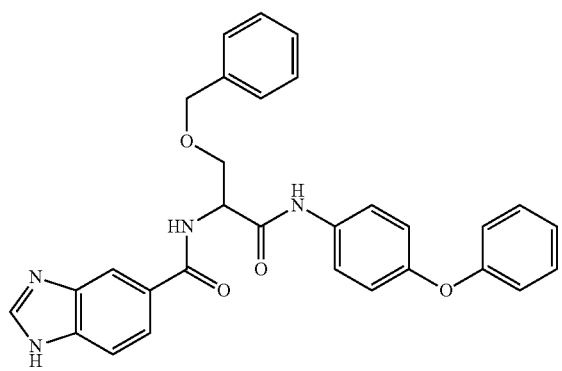 [SMILES: O=C(NC(COCc1ccccc1)C(=O)Nc1ccc(Oc2ccccc2)cc1)c1ccc2[nH]cnc2c1]
343
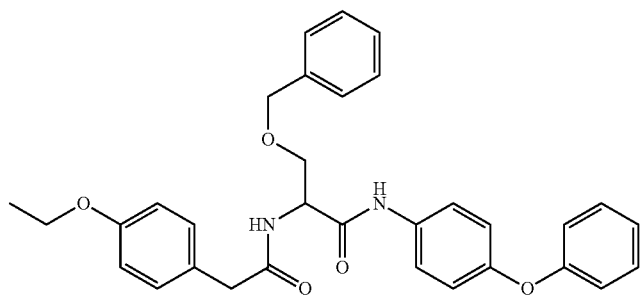 [SMILES: CCOc1ccc(CC(=O)NC(COCc2ccccc2)C(=O)Nc2ccc(Oc3ccccc3)cc2)cc1]
344
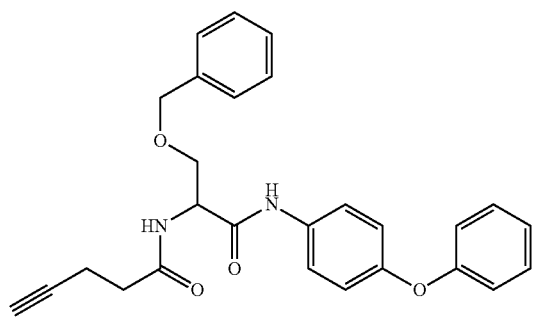 [SMILES: C#CCCC(=O)NC(COCc1ccccc1)C(=O)Nc1ccc(Oc2ccccc2)cc1]
345

TABLE 1-continued
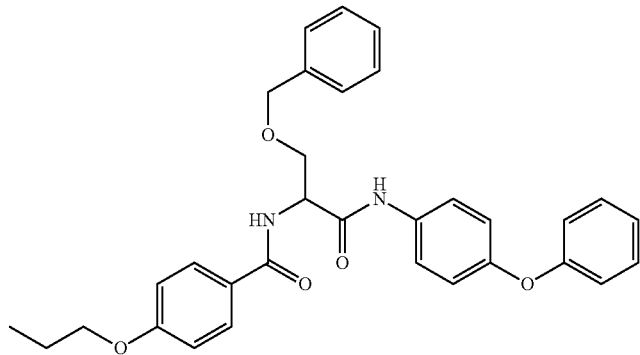 [SMILES: CCCOc1ccc(C(=O)NC(COCc2ccccc2)C(=O)Nc2ccc(Oc3ccccc3)cc2)cc1]
346
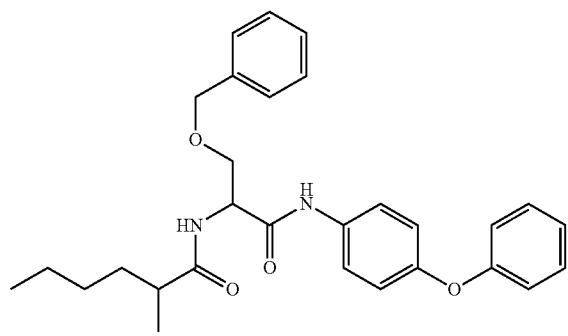 [SMILES: CCCCC(C)C(=O)NC(COCc1ccccc1)C(=O)Nc1ccc(Oc2ccccc2)cc1]
347
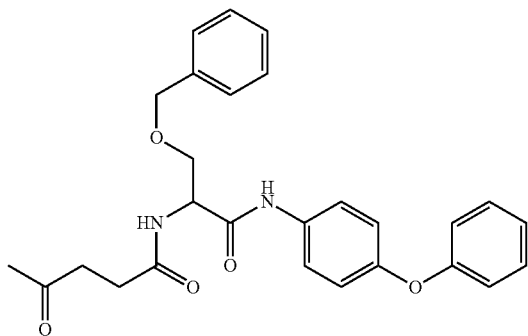 [SMILES: CC(=O)CCC(=O)NC(COCc1ccccc1)C(=O)Nc1ccc(Oc2ccccc2)cc1]
348
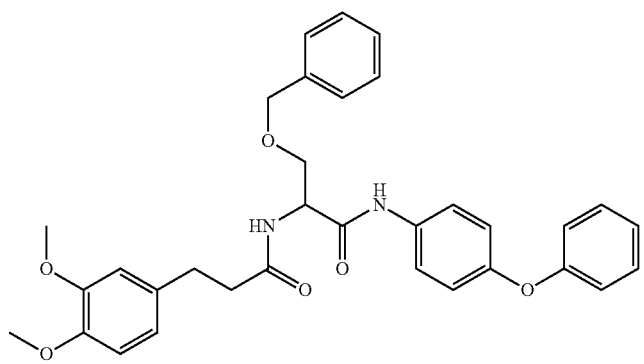 [SMILES: COc1ccc(CCC(=O)NC(COCc2ccccc2)C(=O)Nc2ccc(Oc3ccccc3)cc2)cc1OC]
349

TABLE 1-continued
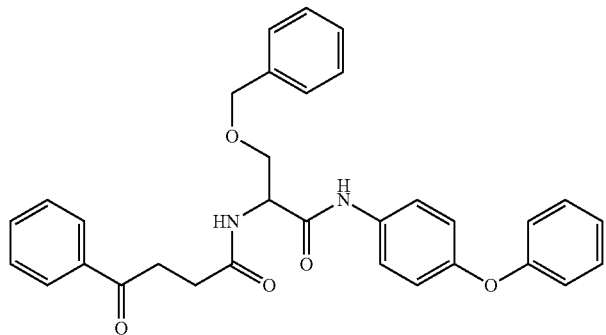
350
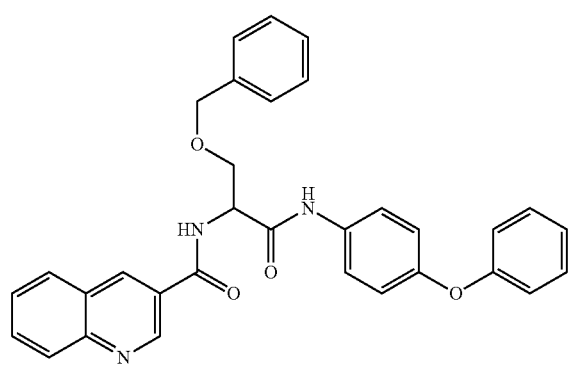 [SMILES: O=C(NC(COCc1ccccc1)C(=O)Nc1ccc(Oc2ccccc2)cc1)c1cnc2ccccc2c1]
351
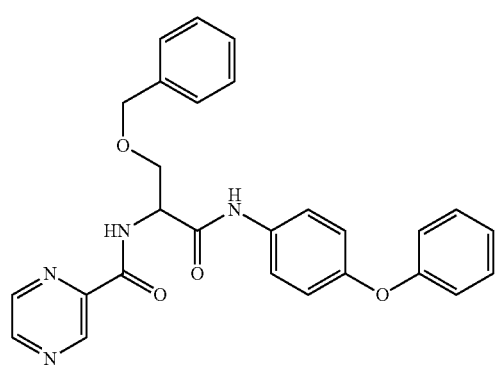 [SMILES: O=C(NC(COCc1ccccc1)C(=O)Nc1ccc(Oc2ccccc2)cc1)c1cnccn1]
352
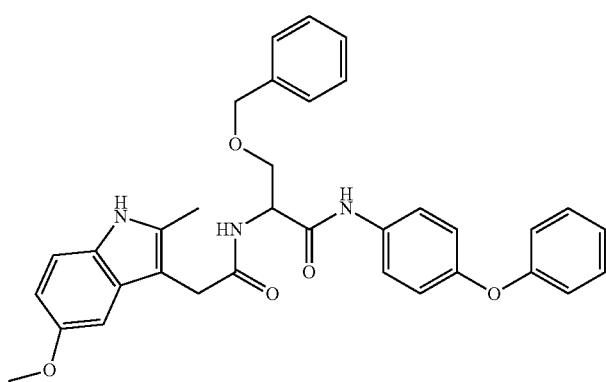 [SMILES: COc1ccc2[nH]c(C)c(CC(=O)NC(COCc3ccccc3)C(=O)Nc3ccc(Oc4ccccc4)cc3)c2c1]
353

TABLE 1-continued
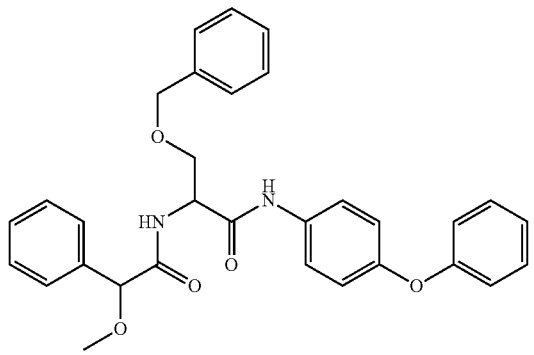 [SMILES: COC(C(=O)NC(COCc1ccccc1)C(=O)Nc1ccc(Oc2ccccc2)cc1)c1ccccc1]
354
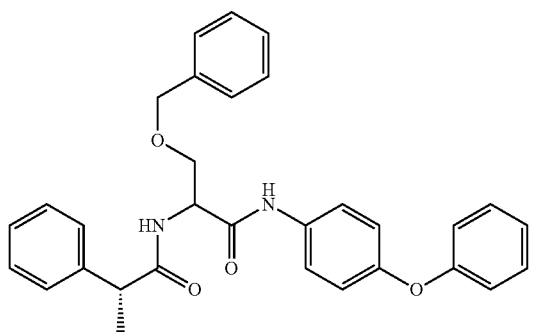 [SMILES: C[C@@H](C(=O)NC(COCc1ccccc1)C(=O)Nc1ccc(Oc2ccccc2)cc1)c1ccccc1]
355
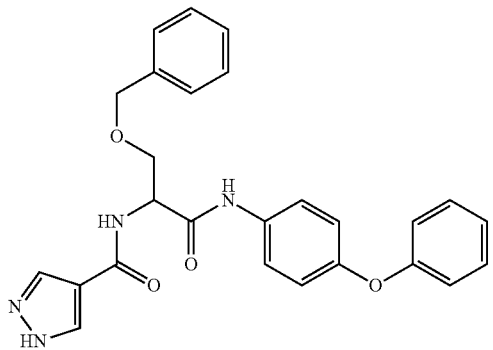 [SMILES: O=C(NC(COCc1ccccc1)C(=O)Nc1ccc(Oc2ccccc2)cc1)c1cn[nH]c1]
356
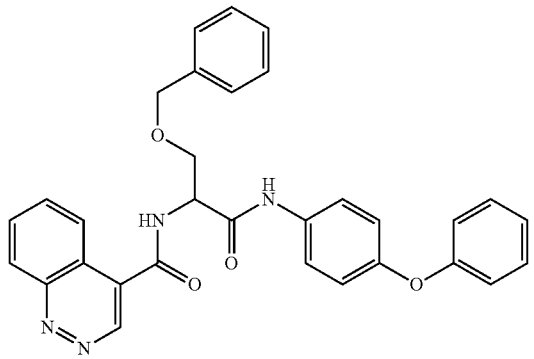 [SMILES: O=C(NC(COCc1ccccc1)C(=O)Nc1ccc(Oc2ccccc2)cc1)c1cnnc2ccccc12]
357

TABLE 1-continued
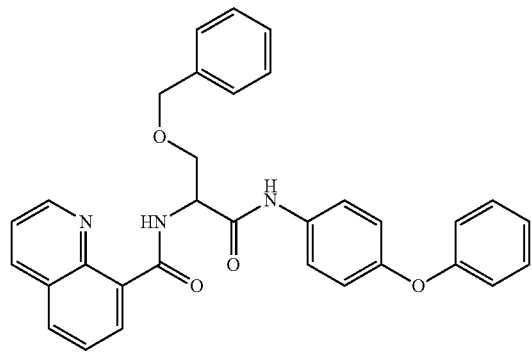 [SMILES: O=C(NC(COCc1ccccc1)C(=O)Nc1ccc(Oc2ccccc2)cc1)c1cccc2cccnc12]
358
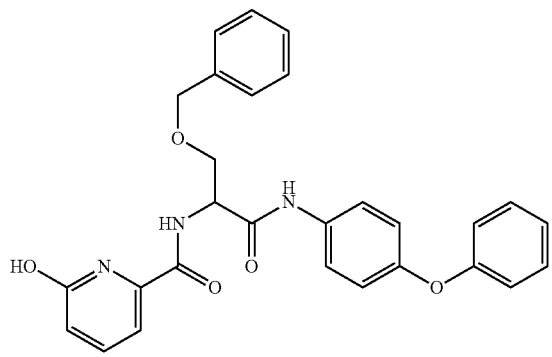 [SMILES: O=C(NC(COCc1ccccc1)C(=O)Nc1ccc(Oc2ccccc2)cc1)c1cccc(O)n1]
359
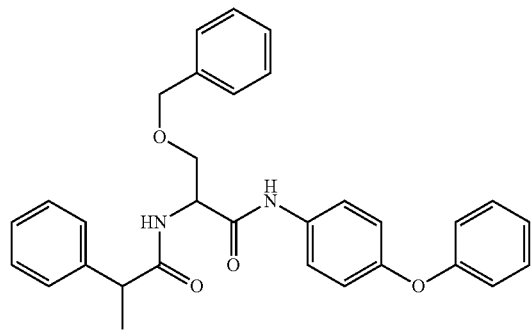 [SMILES: CC(C(=O)NC(COCc1ccccc1)C(=O)Nc1ccc(Oc2ccccc2)cc1)c1ccccc1]
360
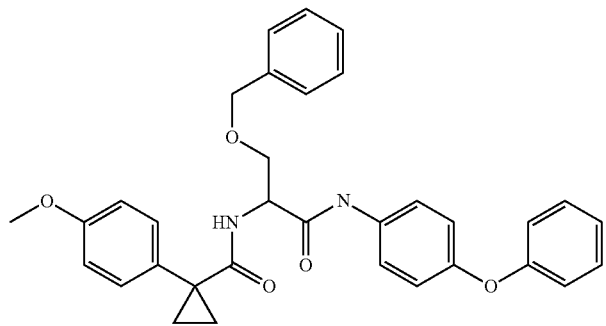 [SMILES: COc1ccc(C2(C(=O)NC(COCc3ccccc3)C(=O)Nc3ccc(Oc4ccccc4)cc3)CC2)cc1]
361

TABLE 1-continued
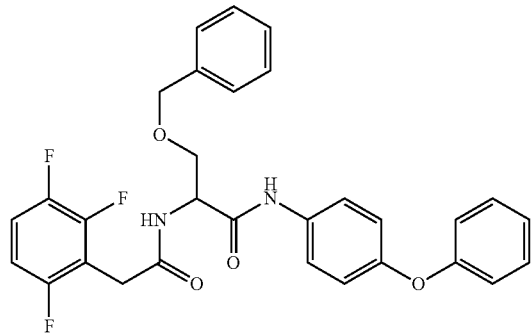 [SMILES: O=C(Cc1c(F)ccc(F)c1F)NC(COCc1ccccc1)C(=O)Nc1ccc(Oc2ccccc2)cc1]
362
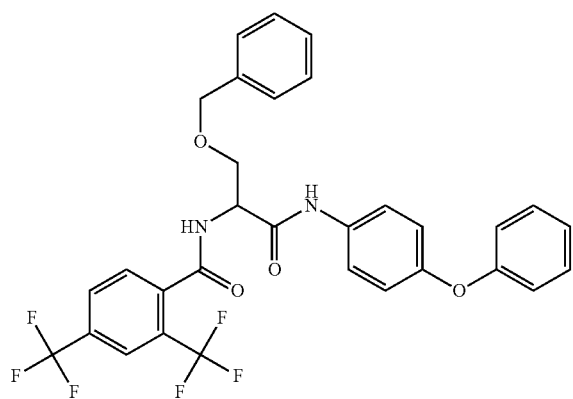 [SMILES: O=C(NC(COCc1ccccc1)C(=O)Nc1ccc(Oc2ccccc2)cc1)c1ccc(C(F)(F)F)cc1C(F)(F)F]
363
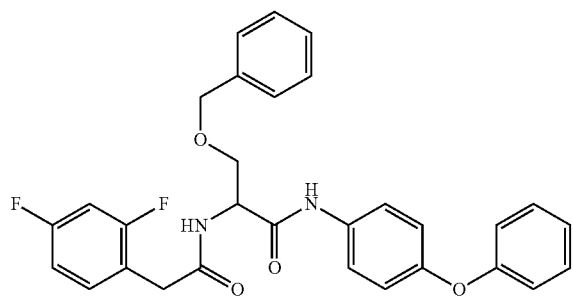 [SMILES: O=C(Cc1ccc(F)cc1F)NC(COCc1ccccc1)C(=O)Nc1ccc(Oc2ccccc2)cc1]
364
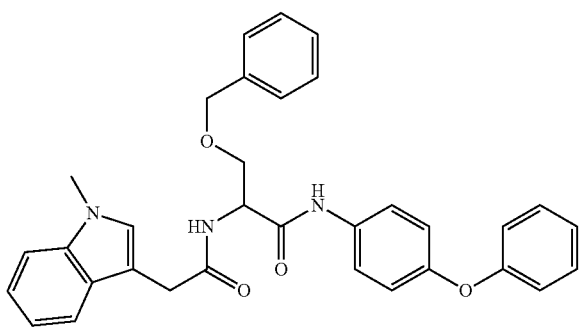 [SMILES: Cn1cc(CC(=O)NC(COCc2ccccc2)C(=O)Nc2ccc(Oc3ccccc3)cc2)c2ccccc21]
365

TABLE 1-continued
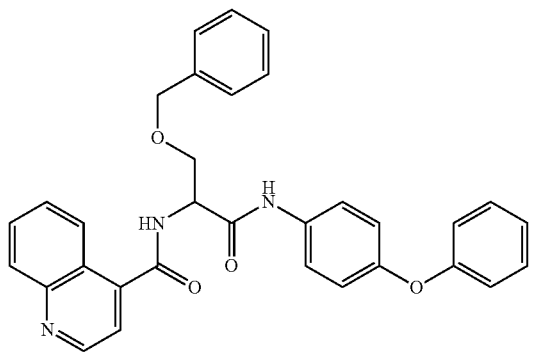 [SMILES: O=C(NC(COCc1ccccc1)C(=O)Nc1ccc(Oc2ccccc2)cc1)c1ccnc2ccccc12]
366
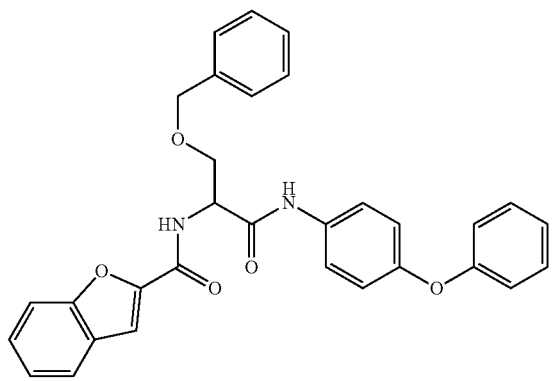 [SMILES: O=C(NC(COCc1ccccc1)C(=O)Nc1ccc(Oc2ccccc2)cc1)c1cc2ccccc2o1]
367
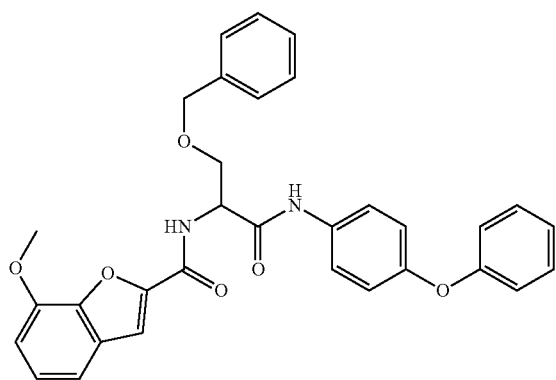 [SMILES: COc1cccc2cc(C(=O)NC(COCc3ccccc3)C(=O)Nc3ccc(Oc4ccccc4)cc3)oc12]
368
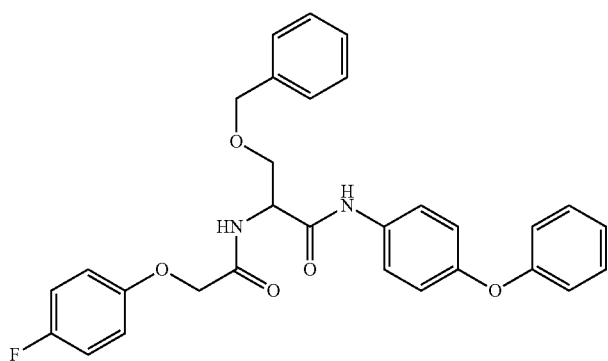 [SMILES: O=C(COc1ccc(F)cc1)NC(COCc1ccccc1)C(=O)Nc1ccc(Oc2ccccc2)cc1]
369

TABLE 1-continued
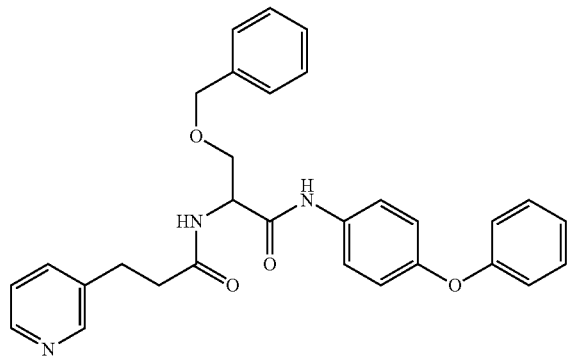 [SMILES: O=C(CCc1cccnc1)NC(COCc1ccccc1)C(=O)Nc1ccc(Oc2ccccc2)cc1]
370
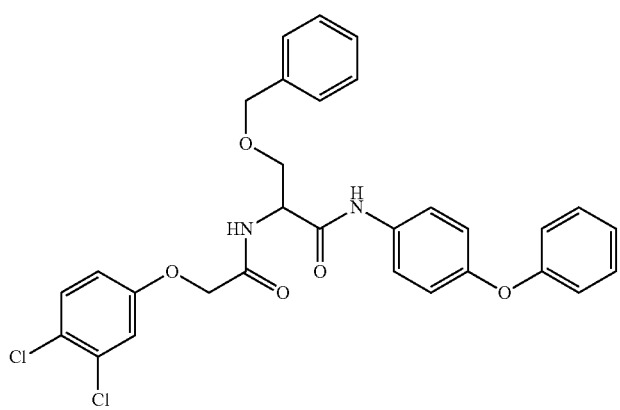 [SMILES: O=C(COc1ccc(Cl)c(Cl)c1)NC(COCc1ccccc1)C(=O)Nc1ccc(Oc2ccccc2)cc1]
371
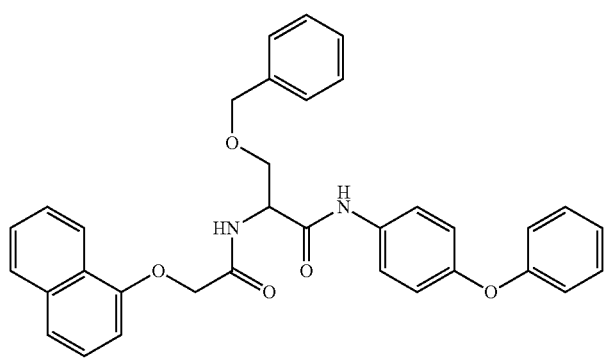 [SMILES: O=C(COc1cccc2ccccc12)NC(COCc1ccccc1)C(=O)Nc1ccc(Oc2ccccc2)cc1]
372
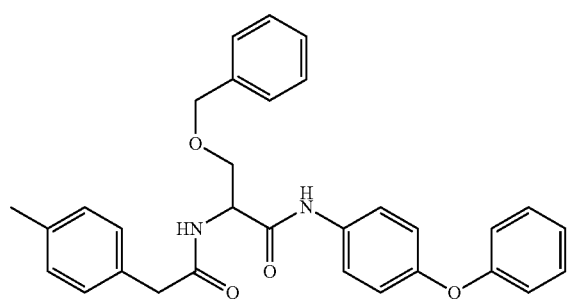 [SMILES: Cc1ccc(CC(=O)NC(COCc2ccccc2)C(=O)Nc2ccc(Oc3ccccc3)cc2)cc1]
373

TABLE 1-continued
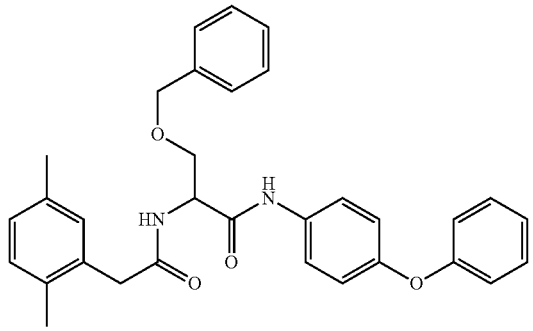 [SMILES: Cc1ccc(C)c(CC(=O)NC(COCc2ccccc2)C(=O)Nc2ccc(Oc3ccccc3)cc2)c1]
374
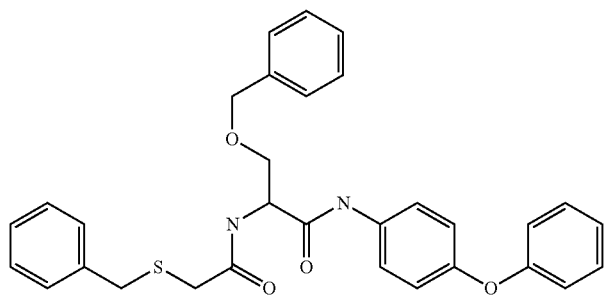 [SMILES: O=C(CSCc1ccccc1)NC(COCc1ccccc1)C(=O)Nc1ccc(Oc2ccccc2)cc1]
375
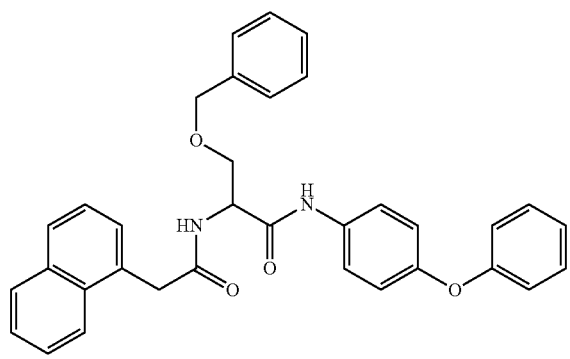 [SMILES: O=C(Cc1cccc2ccccc12)NC(COCc1ccccc1)C(=O)Nc1ccc(Oc2ccccc2)cc1]
376
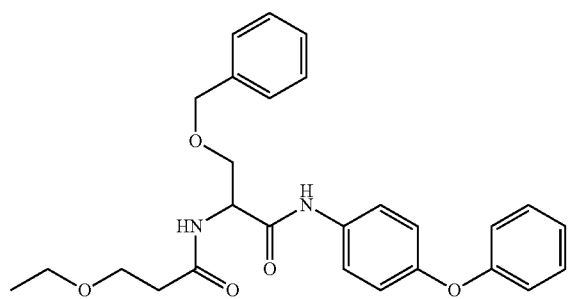 [SMILES: CCOCCC(=O)NC(COCc1ccccc1)C(=O)Nc1ccc(Oc2ccccc2)cc1]
377

TABLE 1-continued
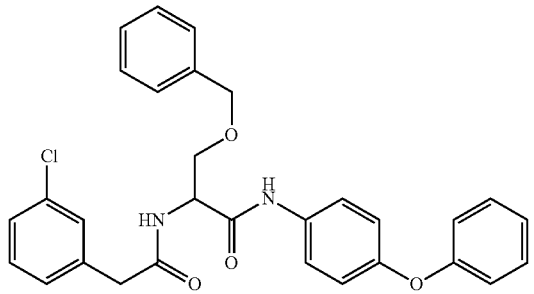 [SMILES: O=C(Cc1cccc(Cl)c1)NC(COCc1ccccc1)C(=O)Nc1ccc(Oc2ccccc2)cc1]
378
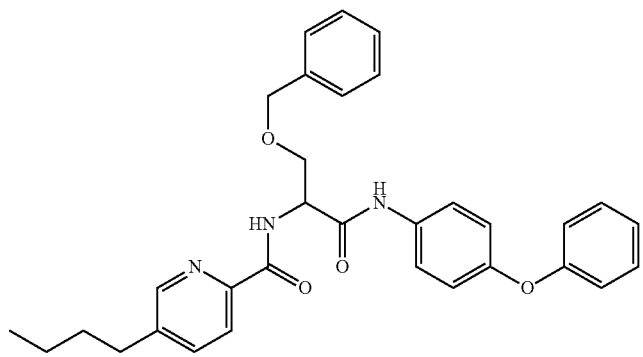 [SMILES: CCCCc1ccc(C(=O)NC(COCc2ccccc2)C(=O)Nc2ccc(Oc3ccccc3)cc2)nc1]
379
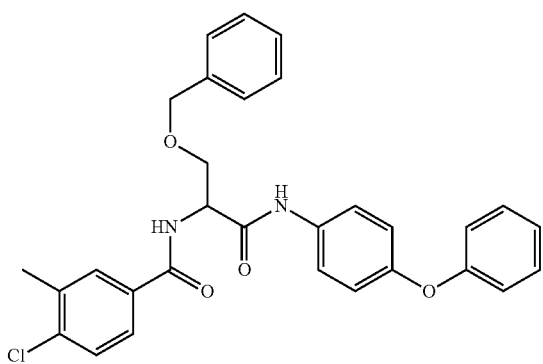 [SMILES: Cc1cc(C(=O)NC(COCc2ccccc2)C(=O)Nc2ccc(Oc3ccccc3)cc2)ccc1Cl]
380
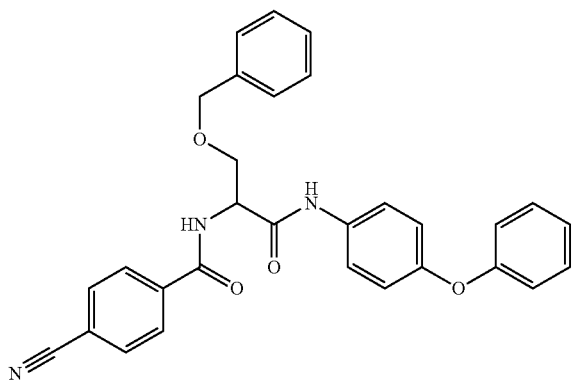 [SMILES: N#Cc1ccc(C(=O)NC(COCc2ccccc2)C(=O)Nc2ccc(Oc3ccccc3)cc2)cc1]
381

TABLE 1-continued
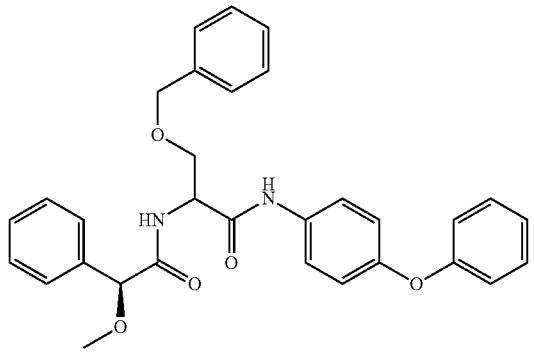
382
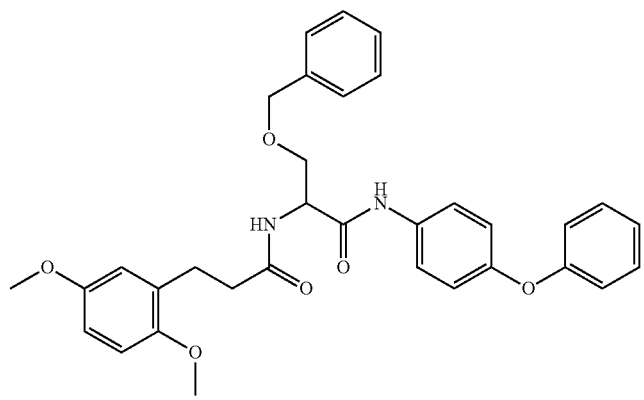 [SMILES: COc1ccc(OC)c(CCC(=O)NC(COCc2ccccc2)C(=O)Nc2ccc(Oc3ccccc3)cc2)c1]
383
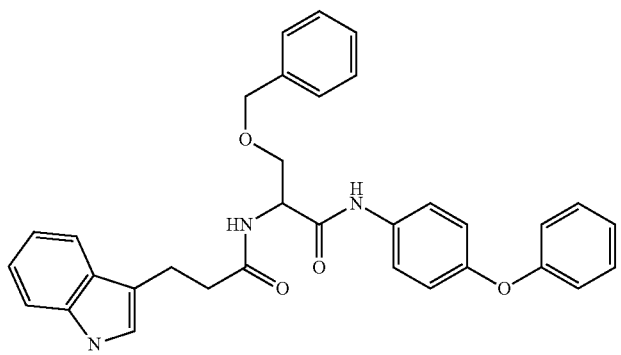 [SMILES: O=C(CCc1c[nH]c2ccccc12)NC(COCc1ccccc1)C(=O)Nc1ccc(Oc2ccccc2)cc1]
384
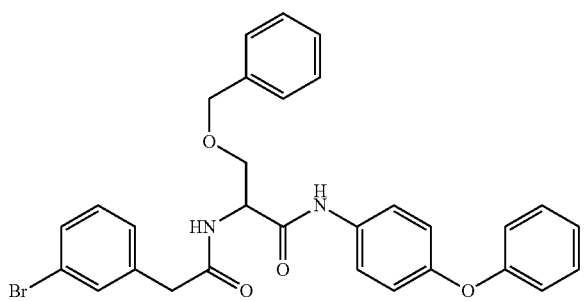 [SMILES: O=C(Cc1cccc(Br)c1)NC(COCc1ccccc1)C(=O)Nc1ccc(Oc2ccccc2)cc1]
385

TABLE 1-continued
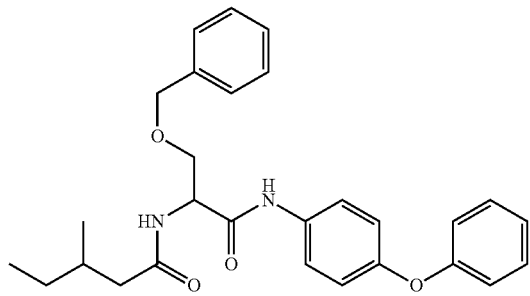 [SMILES: CCC(C)CC(=O)NC(COCc1ccccc1)C(=O)Nc1ccc(Oc2ccccc2)cc1]
386
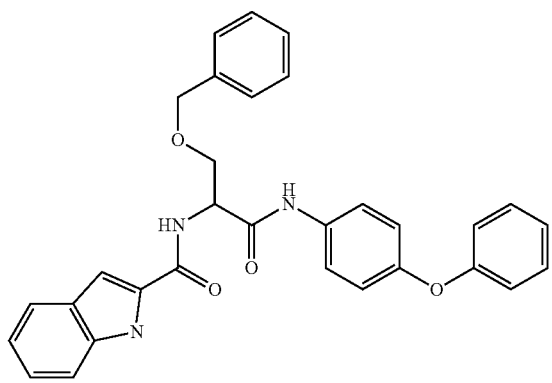 [SMILES: O=C(NC(COCc1ccccc1)C(=O)Nc1ccc(Oc2ccccc2)cc1)c1cc2ccccc2[nH]1]
387
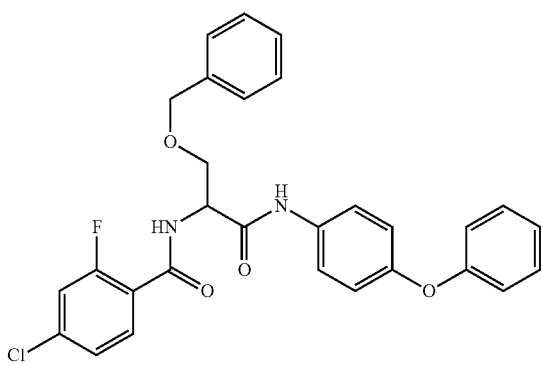 [SMILES: O=C(NC(COCc1ccccc1)C(=O)Nc1ccc(Oc2ccccc2)cc1)c1ccc(Cl)cc1F]
388
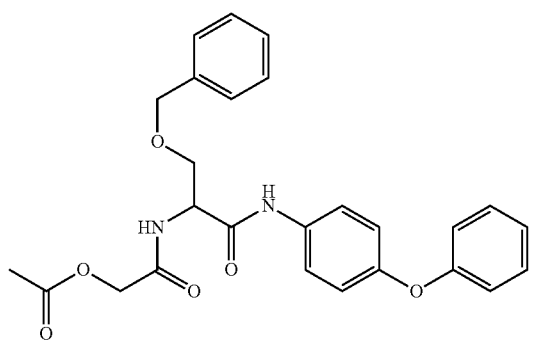 [SMILES: CC(=O)OCC(=O)NC(COCc1ccccc1)C(=O)Nc1ccc(Oc2ccccc2)cc1]
389

TABLE 1-continued
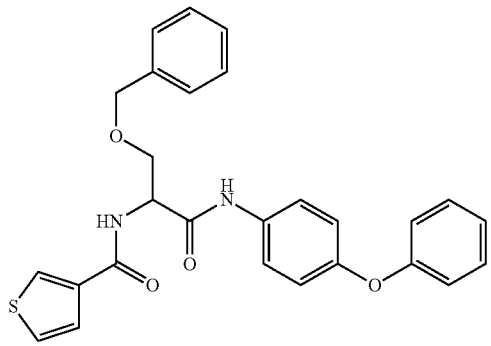 [SMILES: O=C(NC(COCc1ccccc1)C(=O)Nc1ccc(Oc2ccccc2)cc1)c1ccsc1]
390
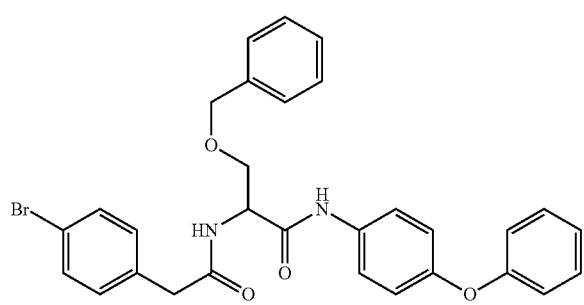 [SMILES: O=C(Cc1ccc(Br)cc1)NC(COCc1ccccc1)C(=O)Nc1ccc(Oc2ccccc2)cc1]
391
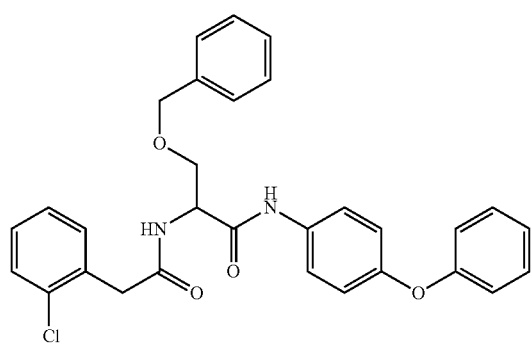 [SMILES: O=C(Cc1ccccc1Cl)NC(COCc1ccccc1)C(=O)Nc1ccc(Oc2ccccc2)cc1]
392
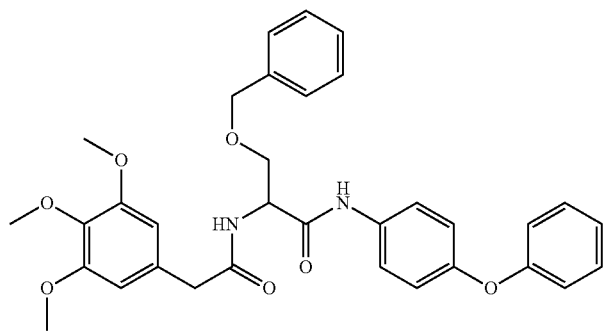 [SMILES: COc1cc(CC(=O)NC(COCc2ccccc2)C(=O)Nc2ccc(Oc3ccccc3)cc2)cc(OC)c1OC]
393

TABLE 1-continued
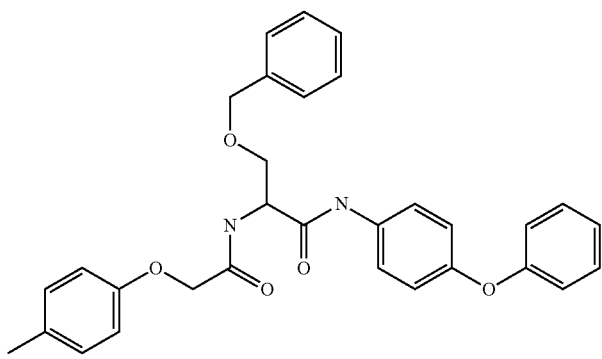 [SMILES: Cc1ccc(OCC(=O)NC(COCc2ccccc2)C(=O)Nc2ccc(Oc3ccccc3)cc2)cc1]
394
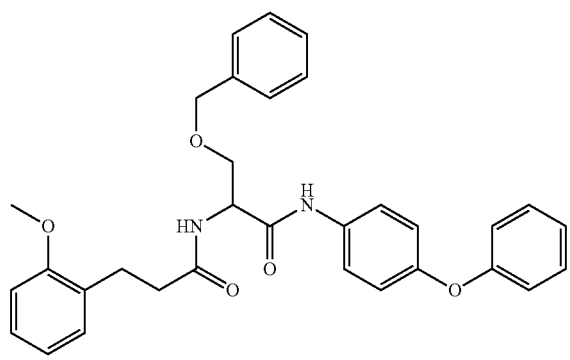 [SMILES: COc1ccccc1CCC(=O)NC(COCc1ccccc1)C(=O)Nc1ccc(Oc2ccccc2)cc1]
395
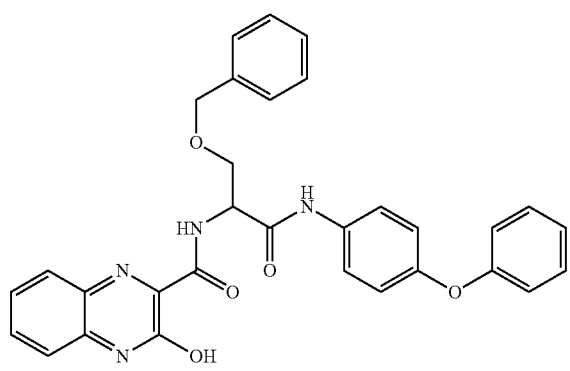 [SMILES: O=C(NC(COCc1ccccc1)C(=O)Nc1ccc(Oc2ccccc2)cc1)c1nc2ccccc2nc1O]
396
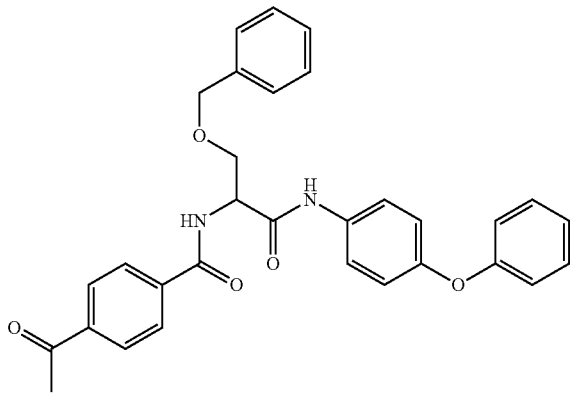 [SMILES: CC(=O)c1ccc(C(=O)NC(COCc2ccccc2)C(=O)Nc2ccc(Oc3ccccc3)cc2)cc1]
397

TABLE 1-continued
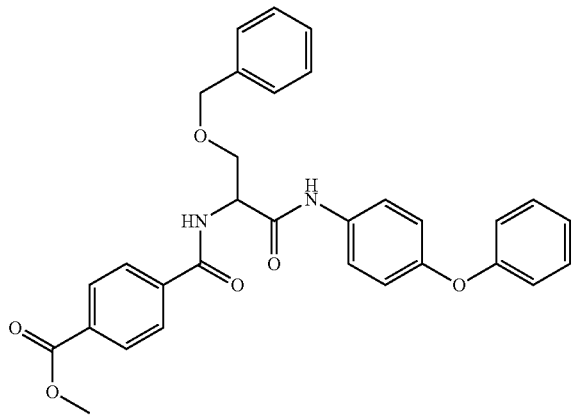 [SMILES: COC(=O)c1ccc(C(=O)NC(COCc2ccccc2)C(=O)Nc2ccc(Oc3ccccc3)cc2)cc1]
398
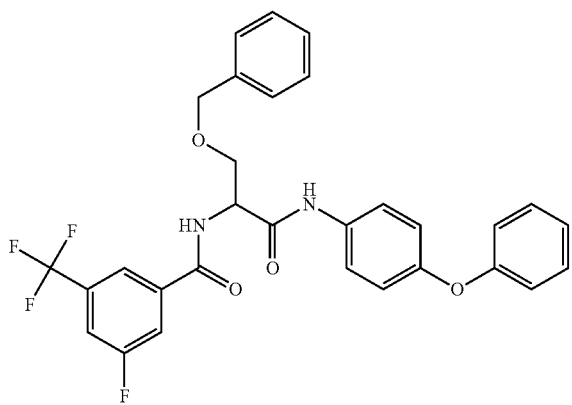 [SMILES: O=C(NC(COCc1ccccc1)C(=O)Nc1ccc(Oc2ccccc2)cc1)c1cc(F)cc(C(F)(F)F)c1]
399
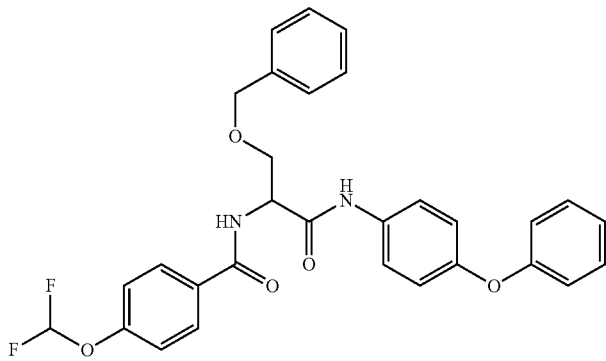 [SMILES: O=C(NC(COCc1ccccc1)C(=O)Nc1ccc(Oc2ccccc2)cc1)c1ccc(OC(F)F)cc1]
400
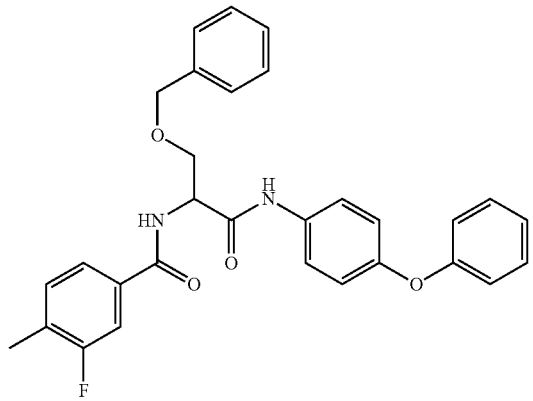 [SMILES: Cc1ccc(C(=O)NC(COCc2ccccc2)C(=O)Nc2ccc(Oc3ccccc3)cc2)cc1F]

TABLE 1-continued

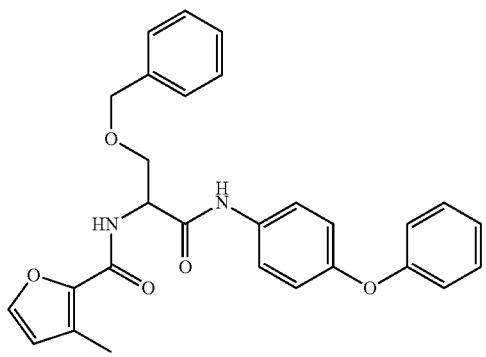 [SMILES: Cc1ccoc1C(=O)NC(COCc1ccccc1)C(=O)Nc1ccc(Oc2ccccc2)cc1]

401

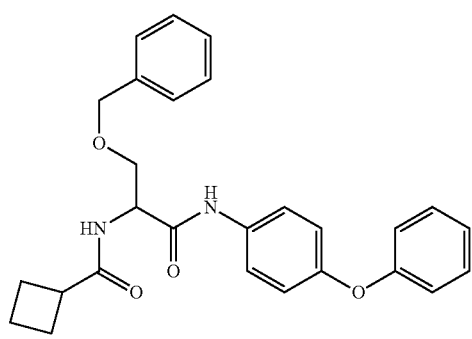 [SMILES: O=C(NC(COCc1ccccc1)C(=O)Nc1ccc(Oc2ccccc2)cc1)C1CCC1]

402

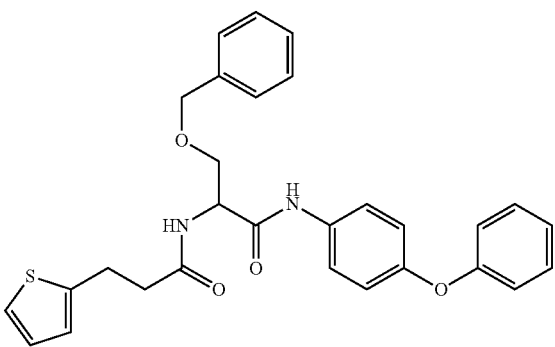 [SMILES: O=C(CCc1cccs1)NC(COCc1ccccc1)C(=O)Nc1ccc(Oc2ccccc2)cc1]

403

The S1P1R Receptor antagonist compounds of the invention depicted in Table 1 include the entire group of compounds or any consecutively or non-consecutively numbered subgroup of compounds or any individual compound in the following list: Compound 1, (S)-2-(2-(1H-imidazol-5-yl)acetamido)-5-phenyl-N-(4-phenoxyphenyl)pentanamide; Compound 2, (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide; Compound 3, (2S,4R)-5-(2-(1H-1,2,3-triazol-1-yl)acetyl)-N-(4-(4-fluorophenoxy)phenyl)-4-(4-methylbenzyl)pyrrolidine-2-carboxamide; Compound 4, (2S,4R)-5-(2-(1H-1,2,4-triazol-1-yl)acetyl)-N-(4-(4-fluorophenoxy)phenyl)-4-(4-methylbenzyl)pyrrolidine-2-carboxamide; Compound 5, (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide; Compound 6, (2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide; Compound 7, (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide; Compound 8, (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide; Compound 9, (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide; Compound 10, (2S,4R)-1-(2-(1H-1,2,3-triazol-1-yl)acetyl)-4-benzyl-N-(4-(4-fluorophenoxy)phenyl)pyrrolidine-2-carboxamide; Compound 11, (2S,4R)-1-(2-(5-amino-3-(trifluoromethyl)-1H-1,2,4-triazol-1-yl)acetyl)-4-benzyl-N-(4-(4-fluorophenoxy)phenyl)pyrrolidine-2-carboxamide; Compound 12, 1-((2S,4R)-4-benzyl-2-(5-(4-fluorophenoxy)-1H-benzo[d]imidazol-2-yl)pyrrolidin-1-yl)-2-(1H-1,2,4-triazol-1-yl)ethanone; Compound 13, 3-(benzyloxy)-2-((S)-3-hydroxy-3-phenylpropanamido)-N-(4-phenoxyphenyl)propanamide; Compound 14, 3-(benzyloxy)-2-(2-(furan-2-yl)-2-oxoacetamido)-N-(4-phenoxyphenyl)propanamide; Compound 15, N-(3-(benzyloxy)-1-oxo-1-(4-phenoxyphenylamino)propan-2-yl)-6-(2,5-dioxo-2,5-dihydro-1H-pyrrol-1-yl)hexanamide; Compound 16, 3-(benzyloxy)-2-(2-hydroxy-2-(2-hydroxyphenyl)acetamido)-N-(4-phenoxyphenyl)propanamide; Compound 17, 4-(3-(benzyloxy)-1-oxo-1-(4-phenoxyphenylamino)propan-2-ylcarbamoyl)phenyl acetate; Compound 18, N-(3-(benzyloxy)-1-oxo-1-(4-phenoxyphenylamino)propan-2-yl)-5-methylnicotinamide; Compound 19, 3-(benzyloxy)-2-(2-(methylsulfonyl)acetamido)-N-(4-phenoxyphenyl)propanamide; Compound 20, N-(3-(benzyloxy)-1-oxo-1-(4-phenoxyphenylamino)propan-2-yl)-1H-indole-5-carboxamide; Compound 21, N-(3-(benzyloxy)-1-oxo-1-(4-phenoxyphenylamino)propan-2-yl)-2-bromo-5-fluorobenzamide; Compound 22, N-(3-(benzyloxy)-1-oxo-1-(4-phenoxyphenylamino)propan-2-yl)-3,3,3-trifluoropropanamide; Compound 23, (2R)-N-(3-(benzyloxy)-1-oxo-1-(4-phenoxyphenylamino)propan-2-yl)tetrahydrofuran-2-carboxamide; Compound 24, 3-(benzyloxy)-2-((R)-2-(2-chlorophenyl)-2-hydroxyacetamido)-N-(4-phenoxyphenyl)propanamide; Compound 25, (2S)-1-(3-(benzyloxy)-1-oxo-1-(4-phenoxyphenylamino)propan-2-ylamino)-1-oxopropan-2-yl acetate; Compound 26, 3-(benzyloxy)-2-(2-(2-hydroxyphenoxy)acetamido)-N-(4-phenoxyphenyl)propanamide; Compound 27, 3-(benzyloxy)-2-((R)-2-hydroxy-3-phenylpropanamido)-N-(4-phenoxyphenyl)propanamide; Compound 28, N-(3-(benzyloxy)-1-oxo-1-(4-phenoxyphenylamino)propan-2-yl)-2-(methylthio)nicotinamide; Compound 29, N-(3-(benzyloxy)-1-oxo-1-(4-phenoxyphenylamino)propan-2-yl)-1-(4-chlorobenzyl)-5-oxopyrrolidine-3-carboxamide; Compound 30, (2S,4R)-4-benzyl-N-(4-(4-fluorophenoxy)phenyl)-1-(2-((1-methyl-1H-indol-2-yl)methylamino)acetyl)pyrrolidine-2-carboxamide; Compound 31, (2S,4R)-4-benzyl-N-(4-(4-fluorophenoxy)phenyl)-1-(2-phenylacetyl)pyrrolidine-2-carboxamide; Compound 32, (2S,4R)-4-benzyl-N-(4-(4-fluorophenoxy)phenyl)-1-(2-(3-methylisoxazol-5-yl)acetyl)pyrrolidine-2-carboxamide; Compound 33, (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide; Compound 34,(2S,4R)-4-benzyl-N-(4-(4-fluorophenoxy)phenyl)-1-(3,3,3-trifluoropropanoyl)pyrrolidine-2-carboxamide; Compound 35, (2S,4R)-4-benzyl-1-(2-(4-(dimethylamino)phenyl)acetyl)-N-(4-(4-fluorophenoxy)phenyl)pyrrolidine-2-carboxamide; Compound 36, (2S,4R)-4-benzyl-N-(4-(4-fluorophenoxy)phenyl)-1-(tetrahydrofuran-3-carbonyl)pyrrolidine-2-carboxamide; Compound 37, (2S,4R)-4-benzyl-N-(4-(4-fluorophenoxy)phenyl)-1-(2-(2-methyl-1H-indol-3-yl)acetyl)pyrrolidine-2-carboxamide; Compound 38, (2S,4R)-4-benzyl-1-(2-butoxyacetyl)-N-(4-(4-fluorophenoxy)phenyl)pyrrolidine-2-carboxamide; Compound 39, (2S,4R)-4-benzyl-N-(4-(4-fluorophenoxy)phenyl)-1-((S)-5-oxotetrahydrofuran-2-carbonyl)pyrrolidine-2-carboxamide; Compound 40, (2S,4R)-4-benzyl-N-(4-(4-fluorophenoxy)phenyl)-1-((R)-2-hydroxy-2-phenylacetyl)pyrrolidine-2-carboxamide; Compound 41, (S)-3-(benzyloxy)-N-(4-(4-fluorophenoxy)phenyl)-2-(2-(4-(pyrimidin-2-yl)piperazin-1-yl)acetamido)propanamide; Compound 42, (S)-3-(benzyloxy)-N-(4-(4-fluorophenoxy)phenyl)-2-(2-(4-(3-methoxyphenyl)piperazin-1-yl)acetamido)propanamide; Compound 43, (S)-3-(benzyloxy)-N-(4-(4-fluorophenoxy)phenyl)-2-(2-(4-(pyrrolidin-1-yl)piperidin-1-yl)acetamido)propanamide; Compound 44, (S)-3-(4-fluorobenzyloxy)-N-(4-(4-fluorophenoxy)phenyl)-2-(2-(2-phenyloxazol-4-yl)acetamido)propanamide; Compound 45, (2S)-3-(benzyloxy)-N-(4-(4-fluorophenoxy)phenyl)-2-(2-(octahydroquinolin-1(2H)-yl)acetamido)propanamide; Compound 46, (2S)-3-(benzyloxy)-N-(4-(4-fluorophenoxy)phenyl)-2-(2-(3-methylpiperidin-1-yl)acetamido)propanamide; Compound 47, (S)-2-(2-(1H-imidazol-5-yl)acetamido)-3-(benzyloxy)-N-(4-(4-fluorophenoxy)-2-methylphenyl)propanamide; Compound 48, (2S,4R)-1-(2-(2H-1,2,3-triazol-2-yl)acetyl)-N-(4-(4-fluorophenoxy)phenyl)-4-(2-methylbenzyl)pyrrolidine-2-carboxamide; Compound 49, (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide; Compound 50, (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide; Compound 51, (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide; Compound 52, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide; Compound 53, (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide; Compound 54, (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide; Compound 55, (2S,4R)-1-(2-(1H-1,2,4-triazol-1-yl)acetyl)-N-(4-(4-fluorophenoxy)phenyl)-4-(2-methylbenzyl)pyrrolidine-2-carboxamide; Compound 56, (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide; Compound 57, (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide; Compound 58, (2S,4R)-1-(2-(2H-1,2,3-triazol-2-yl)acetyl)-4-benzyl-N-(4-(4-fluorophenoxy)phenyl)pyrrolidine-2-carboxamide; Compound 59, (R)-N-(2-(benzyloxy)-1-(5-(4-fluorophenoxy)-1H-benzo[d]imidazol-2-yl)ethyl)-2-(1H-imidazol-4-yl)acetamide; Compound 60, (R)-N-(2-(benzyloxy)-1-(5-(4-fluorophenoxy)-1H-benzo[d]imidazol-2-yl)ethyl)acetamide; Compound 61, (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide; Compound 62, (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide; Compound 63, (2S)-3-(benzyloxy)-N-(4-(4-fluorophenoxy)phenyl)-2-(2-(2-methylpyrrolidin-1-yl)acetamido)propanamide; Compound 64, (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide; Compound 65, (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide; Compound 66, (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide; Compound 67, (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide; Compound 68, (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide; Compound 69, (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide; Compound 70, (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide; Compound 71, (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide; Compound 72, (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide; Compound 73, (2S,4R)-1-(2-(1H-1,2,4-triazol-1-yl)acetyl)-

N-(4-(4-fluoro-3-methylphenoxy)phenyl)-4-(4-fluorobenzyl)pyrrolidine-2-carboxamide; Compound 74, (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide; Compound 75, (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide; Compound 76, (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide; Compound 77, (2S,4S)-1-(2-(2H-1,2,3-triazol-2-yl)acetyl)-N-(4-(4-fluorophenoxy)phenyl)-4-phenylpyrrolidine-2-carboxamide; Compound 78, (2S,4S)-1-(2-(1H-1,2,4-triazol-1-yl)acetyl)-N-(4-(4-fluorophenoxy)phenyl)-4-phenylpyrrolidine-2-carboxamide; Compound 79, (2S,4R)-1-(2-(1H-1,2,4-triazol-1-yl)acetyl)-4-benzyl-N-(4-(4-chlorophenoxy)phenyl)pyrrolidine-2-carboxamide; Compound 80, (2S,4S)-1-(2-(1H-1,2,4-triazol-1-yl)acetyl)-4-(benzylamino)-N-(4-(4-fluorophenoxy)phenyl)pyrrolidine-2-carboxamide; Compound 81, (S)-3-(benzyloxy)-2-(3-(3-chloro-4-methoxyphenyl)propanamido)-N-(4-(4-fluorophenoxy)phenyl)propanamide; Compound 82, (2S,4R)-4-benzyl-1-(2-(3,4-dihydroisoquinolin-2(1H)-yl)acetyl)-N-(4-(4-fluorophenoxy)phenyl)pyrrolidine-2-carboxamide; Compound 83, (2S,4R)-4-benzyl-N-(4-(4-fluorophenoxy)phenyl)-1-(2-thiomorpholinoacetyl)pyrrolidine-2-carboxamide; Compound 84, (2S,4R)-4-benzyl-N-(4-(4-fluorophenoxy)phenyl)-1-(2-(2,3,6-trifluorophenyl)acetyl)pyrrolidine-2-carboxamide; Compound 85, (2S,4R)-4-benzyl-N-(4-(4-fluorophenoxy)phenyl)-1-(3-(methylthio)propanoyl)pyrrolidine-2-carboxamide; Compound 86, (2S,4R)-4-benzyl-1-(3-ethoxypropanoyl)-N-(4-(4-fluorophenoxy)phenyl)pyrrolidine-2-carboxamide; Compound 87, (2S,4R)-4-benzyl-N-(4-(4-fluorophenoxy)phenyl)-1-(2-(methylsulfonyl)acetyl)pyrrolidine-2-carboxamide; Compound 88, (2S,4R)-4-benzyl-N-(4-(4-fluorophenoxy)phenyl)-1-(2-(2-methoxyethoxy)acetyl)pyrrolidine-2-carboxamide; Compound 89, (2S,4R)-4-benzyl-1-(4-(dimethylamino)-4-oxobutanoyl)-N-(4-(4-fluorophenoxy)phenyl)pyrrolidine-2-carboxamide; Compound 90, (2S,4R)-4-benzyl-N-(4-(4-fluorophenoxy)phenyl)-1-(3-methoxypropanoyl)pyrrolidine-2-carboxamide; Compound 91, (2S,4R)-4-benzyl-N-(4-(4-fluorophenoxy)phenyl)-1-(4-oxo-4-(thien-2-yl)butanoyl)pyrrolidine-2-carboxamide; Compound 92, (2S,4R)-4-benzyl-N-(4-(4-fluorophenoxy)phenyl)-1-(tetrahydrofuran-2-carbonyl)pyrrolidine-2-carboxamide; Compound 93, (2S,4R)-1-((S)-1-acetylpyrrolidine-2-carbonyl)-4-benzyl-N-(4-(4-fluorophenoxy)phenyl)pyrrolidine-2-carboxamide; Compound 94, (2S,4R)-4-benzyl-N-(4-(4-fluorophenoxy)phenyl)-1-(2-(pyrimidin-2-ylthio)acetyl)pyrrolidine-2-carboxamide; Compound 95, (2S,4R)-4-benzyl-1-(2-(2,6-difluorophenyl)acetyl)-N-(4-(4-fluorophenoxy)phenyl)pyrrolidine-2-carboxamide; Compound 96, (2S,4R)-4-benzyl-N-(4-(4-fluorophenoxy)phenyl)-1-(2-(pyridin-4-ylthio)acetyl)pyrrolidine-2-carboxamide; Compound 97, (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide; Compound 98, (2S,4R)-1-(2-(1H-indol-3-yl)acetyl)-4-benzyl-N-(4-(4-fluorophenoxy)phenyl)pyrrolidine-2-carboxamide; Compound 99, (2S,4R)-4-benzyl-N-(4-(4-fluorophenoxy)phenyl)-1-(2-(4-oxo-2-thioxothiazolidin-3-yl)acetyl)pyrrolidine-2-carboxamide; Compound 100, (2S,4R)-4-benzyl-N-(4-(4-fluorophenoxy)phenyl)-1-(2-(4-(2-methoxyethyl)piperazin-1-yl)acetyl)pyrrolidine-2-carboxamide; Compound 101, (S)-3-(benzyloxy)-2-(2-(3-fluoro-4-(trifluoromethyl)phenyl)acetamido)-N-(4-(4-fluorophenoxy)phenyl)propanamide; Compound 102, (S)-3-(benzyloxy)-N-(4-(4-fluorophenoxy)phenyl)-2-(2-(3-(trifluoromethoxy)phenyl)acetamido)propanamide; Compound 103, (S)-tent-butyl 1-(2-((S)-3-(benzyloxy)-1-(4-(4-fluorophenoxy)phenylamino)-1-oxopropan-2-ylamino)-2-oxoethyl)pyrrolidine-2-carboxylate; Compound 104, (S)-N-(3-(benzyloxy)-1-(4-(4-fluorophenoxy)phenylamino)-1-oxopropan-2-yl)-5-phenylpentanamide; Compound 105, (S)-3-(benzyloxy)-N-(4-(4-fluorophenoxy)phenyl)-2-(2-(4-morpholinopiperidin-1-yl)acetamido)propanamide; Compound 106, (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide; Compound 107, (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide; Compound 108, (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide; Compound 109, (2S)-3-(benzyloxy)-2-(2-(3-(diethylamino)pyrrolidin-1-yl)acetamido)-N-(4-(4-fluorophenoxy)phenyl)propanamide; Compound 110, (2S)-3-(benzyloxy)-N-(4-(4-fluorophenoxy)phenyl)-2-(2-(4-((tetrahydrofuran-2-yl)methyl)piperazin-1-yl)acetamido)propanamide; Compound 111, (S)-3-(benzyloxy)-N-(4-(4-fluorophenoxy)phenyl)-2-(2-(4-isopropylpiperazin-1-yl)acetamido)propanamide; Compound 112, (S)-3-(benzyloxy)-N-(4-(4-fluorophenoxy)phenyl)-2-(2-(4-(3-(trifluoromethyl)pyridin-2-yl)piperazin-1-yl)acetamido)propanamide; Compound 113, (2S)-3-(benzyloxy)-N-(4-(4-fluorophenoxy)phenyl)-2-(2-(2-(((S)-1-methylpyrrolidin-2-yl)methyl)piperidin-1-yl)acetamido)propanamide, Compound 114, (S)-3-(benzyloxy)-2-(2-(4-ethylpiperazin-1-yl)acetamido)-N-(4-(4-fluorophenoxy)phenyl)propanamide; Compound 115, (2S,4R)-1-(2-(4-acetylpiperazin-1-yl)acetyl)-4-benzyl-N-(4-(4-fluorophenoxy)phenyl)pyrrolidine-2-carboxamide; Compound 116, (2S,4R)-4-benzyl-N-(4-(4-fluorophenoxy)phenyl)-1-(2-morpholinoacetyl)pyrrolidine-2-carboxamide; Compound 117, (2S,4R)-4-benzyl-N-(4-(4-fluorophenoxy)phenyl)-1-(2-(thien-2-yl)acetyl)pyrrolidine-2-carboxamide; Compound 118, (2S,4R)-4-benzyl-N-(4-(4-fluorophenoxy)phenyl)-1-(3-hydroxybutanoyl)pyrrolidine-2-carboxamide; Compound 119, (2S,4R)-4-benzyl-1-(2-(2,6-dichlorophenyl)acetyl)-N-(4-(4-fluorophenoxy)phenyl)pyrrolidine-2-carboxamide; Compound 120, (2S,4R)-4-benzyl-N-(4-(4-fluorophenoxy)phenyl)-1-(2-hydroxyacetyl)pyrrolidine-2-carboxamide; Compound 121, (2S,4R)-4-benzyl-1-(2-ethoxyacetyl)-N-(4-(4-fluorophenoxy)phenyl)pyrrolidine-2-carboxamide; Compound 122, (2S,4R)-4-benzyl-N-(4-(4-fluorophenoxy)phenyl)-1-(2-methoxyacetyl)pyrrolidine-2-carboxamide; Compound 123, (2S,4R)-4-benzyl-N-(4-(4-fluorophenoxy)phenyl)-1-(4-oxopentanoyl)pyrrolidine-2-carboxamide; Compound 124, (2S,4R)-4-benzyl-N-(4-(4-fluorophenoxy)phenyl)-1-(4-oxo-4-phenylbutanoyl)pyrrolidine-2-carboxamide; Compound 125, methyl 4-((2S,4R)-4-benzyl-2-(4-(4-fluorophenoxy)phenylcarbamoyl)pyrrolidin-1-yl)-4-oxobutanoate; Compound 126, (S)-3-(benzyloxy)-N-(4-(4-fluorophenoxy)phenyl)-2-(2-(4-(pyridin-2-yl)piperazin-1-yl)acetamido)propanamide; Compound 127, (S)-3-(benzyloxy)-N-(4-(4-fluorophenoxy)phenyl)-2-(2-(4-(2-fluorophenyl)piperazin-1-yl)acetamido)propanamide; Compound 128, (S)-2-(2-(azepan-1-yl)acetamido)-3-(benzyloxy)-N-(4-(4-fluorophenoxy)phenyl)propanamide; Compound 129, (2S,4R)-4-benzyl-1-(2-cyanoacetyl)-N-(4-(4-fluorophenoxy)phenyl)pyrrolidine-2-carboxamide; Compound 130, (S)-3-(benzyloxy)-N-(4-(4-fluorophenoxy)phenyl)-2-(2-(4-methylpiperidin-1-yl)acetamido)propanamide; Compound 131, (S)-2-(2-(1H- imidazol-5-yl)acetamido)-3-benzyloxy-N-(4-(4-fluorophenoxy)phenyl)propanamide; Compound 132, (S)-2-(2-(1H-imidazol-5-yl)acetamido)-3-(4-fluorobenzyloxy)-N-(4-(4-chlorophenoxy)phenyl)propanamide; Compound 133, (S)-2-(2-(1H-imidazol-5-yl)acetamido)-3-(4-fluorobenzyloxy)-N-(4-(4-fluorophenoxy)phenyl)propanamide; Compound 134, (S)-2-(2-(1H-imidazol-1-yl)acetamido)-3-benzyloxy-N-(4-(4-fluorophenoxy)phenyl)propanamide; Compound 135, (S)-2-(2-(1H-1,2,4-triazol-1-yl)acetamido)-3-(4-fluorobenzyloxy)-N-(4-(4-fluorophenoxy)phenyl)propanamide; Compound 136, (S)-3-(benzyloxy)-2-(2-chloroacetamido)-N-(4-(4-fluorophenoxy)phenyl)propanamide; Compound 137, (S)-2-(2-(1H-imidazol-5-yl)acetamido)-5-phenyl-N-(4-(4-fluorophenoxy)phenyl)pentanamide; Compound 138, (S)-2-(2-(2H-1,2,3-triazol-2-yl)acetamido)-3-(benzyloxy)-N-(4-(4-fluorophenoxy)phenyl)propanamide; Compound 139, (S)-2-(2-(1H-1,2,4-triazol-1-yl)acetamido)-N-(4-(4-fluorophenoxy)phenyl)-3-(2-(trifluoromethoxy)benzyloxy)propanamide; Compound 140, (2S,4R)-1-(2-(1H-1,2,4-triazol-1-yl)acetyl)-4-benzyl-N-(4-(4-fluorophenoxy)phenyl)pyrrolidine-2-carboxamide; Compound 141, (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide; Compound 142, 2-(2-(1H-imidazol-5-yl)acetamido)-3-benzyloxy-N-(4-phenoxyphenyl)propanamide; Compound 143, (S)-2-(2-(1H-imidazol-5-yl)acetamido)-3-benzyloxy-N-(4-phenoxyphenyl)propanamide; Compound 144, (S)-2-(2-(1H-tetrazol-1-yl)acetamido)-3-benzyloxy-N-(4-phenoxyphenyl)propanamide; Compound 145, (S)-2-(2-(1H-imidazol-5-yl)acetamido)-3-benzyloxy-N-(4-(4-chlorophenoxy)phenyl)propanamide; Compound 146, (S)-2-(2-(1H-1,2,4-triazol-1-yl)acetamido)-3-(benzyloxy)-N-(4-phenoxyphenyl)propanamide; Compound 147, (S)-2-(2-(1H-imidazol-4-yl)acetamido)-3-(benzyloxy)-N-(3-chloro-4-phenoxyphenyl)propanamide; Compound 148, (S)-2-(2-(1H-imidazol-4-yl)acetamido)-3-(benzyloxy)-N-(4-(3-chlorophenoxy)phenyl)propanamide; Compound 149, (S)-2-(2-(1H-1,2,4-triazol-1-yl)acetamido)-3-benzyloxy-N-(4-(4-fluorophenoxy)phenyl)propanamide; Compound 150, (S)-3-(benzyloxy)-2-(2-(3,5-dimethylisoxazol-4-yl)acetamido)-N-(4-(4-fluorophenoxy)phenyl)propanamide; Compound 151, (S)-2-(2-(1H-benzo [d][1,2,3]triazol-1-yl)acetamido)-3-(benzyloxy)-N-(4-(4-fluorophenoxy)phenyl)propanamide; Compound 152, (S)-3-(benzyloxy)-2-(2-(3,5-dimethyl-1H-pyrazol-4-yl)acetamido)-N-(4-(4-fluorophenoxy)phenyl)propanamide; Compound 153, (S)-3-(benzyloxy)-N-(4-(4-fluorophenoxy)phenyl)-2-(2-(4-methyl-1H-1,2,3-triazol-1-yl)acetamido)propanamide; Compound 154, (S)-2-(2-(1H-imidazol-4-yl)acetamido)-3-(benzyloxy)-N-(3-chloro-4-(4-chlorophenoxy)phenyl)propanamide; Compound 155, (S)-3-(benzyloxy)-N-(4-(4-fluorophenoxy)phenyl)-2-(2-morpholinoacetamido)propanamide; Compound 156, (S)-2-(2-(1H-imidazol-4-yl)acetamido)-3-(benzyloxy)-N-(4-(5-bromothiazol-2-yloxy)phenyl)propanamide; Compound 157, (S)-2-(2-(1H-imidazol-5-yl)acetamido)-N-(4-(4-chlorophenoxy)phenyl)-4-phenylbutanamide; Compound 158, (S)-2-(2-(1H-imidazol-5-yl)acetamido)-3-(benzyloxy)-N-(4-(p-tolyloxy)phenyl)propanamide; Compound 159, (S)-3-(benzyloxy)-N-(4-(4-fluorophenoxy)phenyl)-2-(2-(pyrazin-2-yl)acetamido)propanamide; Compound 160, (S)-3-(benzyloxy)-N-(4-(4-fluorophenoxy)phenyl)-2-(2-(2-methyl-1H-imidazol-1-yl)acetamido)propanamide; Compound 161, (S)-2-(2-(1H-imidazol-4-yl)-2-methylpropanamido)-3-(4-fluorobenzyloxy)-N-(4-(4-fluorophenoxy)phenyl)propanamide; Compound 162, (S)-3-(benzyloxy)-N-(4-(4-fluorophenoxy)phenyl)-2-(2-(2-methyl-1H-imidazol-4-yl)acetamido)propanamide; Compound 163, (2S,3S)-1-(2-(1H-imidazol-4-yl)acetyl)-3-benzyl-N-(4-(4-fluorophenoxy)phenyl)pyrrolidine-2-carboxamide; Compound 164, (S)-2-acetamido-3-(4-fluorobenzyloxy)-N-(4-(4-fluorophenoxy)phenyl)propanamide; Compound 165, (S)-benzyl 4-(2-(1H-1,2,4-triazol-1-yl)acetamido)-5-(4-(4-fluorophenoxy)phenylamino)-5-oxopentylcarbamate; Compound 166, (S)-3-(benzyloxy)-N-(4-(4-fluorophenoxy)phenyl)-2-(2-(3-methyl-1H-pyrazol-5-yl)acetamido)propanamide Compound 167, (2S)-2-(2-(1H-imidazol-4-yl)propanamido)-3-(benzyloxy)-N-(4-(4-fluorophenoxy)phenyl)propanamide; Compound 168, (S)-2-(2-(1H-imidazol-5-yl)acetamido)-N-(4-(4-bromophenoxy)phenyl)-3-(4-fluorobenzyloxy)propanamide; Compound 169, (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide; Compound 170, (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide; Compound 171, (2S,4R)-1-(2-(1H-1,2,4-triazol-1-yl)acetyl)-N-(4-(4-fluorophenoxy)phenyl)-4-(3-methylbenzyl)pyrrolidine-2-carboxamide; Compound 172, (S)-2-(3-(3,5-dimethylisoxazol-4-yl)ureido)-3-benzyloxy-N-(4-(4-fluorophenoxy)phenyl)propanamide; Compound 173, (2S,4R)-1-(2-(1H-imidazol-5-yl)acetyl)-4-(benzylamino)-N-(4-(4-fluorophenoxy)phenyl)pyrrolidine-2-carboxamide; Compound 174, (S)-2-(2-(1H-1,2,3-triazol-1-yl)acetamido)-3-(benzyloxy)-N-(4-(4-fluorophenoxy)phenyl)propanamide; Compound 175 (S)-1-(2-(1H-imidazol-4-yl)acetyl)-4-benzyl-N-(4-(4-fluorophenoxy)phenyl)piperazine-2-carboxamide; Compound 176, (2S,4R)-1-(2-(1H-benzo[d][1,2,3]triazol-1-yl)acetyl)-4-benzyl-N-(4-(4-fluorophenoxy)phenyl)pyrrolidine-2-carboxamide; Compound 177, (2S,4R)-4-benzyl-N-(4-(4-fluorophenoxy)phenyl)-1-(2-(5-methyl-1H-pyrazol-3-yl)acetyl)pyrrolidine-2-carboxamide; Compound 178, (S)-2-(2-(1H-1,2,4-triazol-1-yl)acetamido)-3-(benzyloxy)-N-(4-(4-fluorophenylthio)phenyl)propanamide; Compound 179, (2S,4R)-1-(2-(1H-1,2,4-triazol-1-yl)acetyl)-4-(benzylamino)-N-(4-(4-fluorophenoxy)phenyl)pyrrolidine-2-carboxamide; Compound 180, (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide; Compound 181, (S)-2-(2-(1H-1,2,4-triazol-1-yl)acetamido)-3-(2-chlorobenzyloxy)-N-(4-(4-fluorophenoxy)phenyl)propanamide; Compound 182, (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide; Compound 183, 3-(benzyloxy)-2-(2-(2-fluorophenyl)acetamido)-N-(4-phenoxyphenyl)propanamide; Compound 184, N-(3-(benzyloxy)-1-oxo-1-(4-phenoxyphenylamino)propan-2-yl)-1H-indole-4-carboxamide; Compound 185, 2-(2-(3-methylisoxazol-5-yl)acetamido)-3-benzyloxy-N-(4-phenoxyphenyl)propanamide; Compound 186, N-(3-(benzyloxy)-1-oxo-1-(4-phenoxyphenylamino)propan-2-yl)-4-cyclopropyl-4-oxobutanamide; Compound 187, N-(3-(benzyloxy)-1-oxo-1-(4-phenoxyphenylamino)propan-2-yl)-1H-indole-6-carboxamide; Compound 188, N-(3-(benzyloxy)-1-oxo-1-(4-phenoxyphenylamino)propan-2-yl)-2,3-dihydro-1H-indene-2-carboxamide; Compound 189, N-(3-(benzyloxy)-1-oxo-1-(4-phenoxyphenylamino)propan-2-yl)-3-methyl-2-nitrobenzamide; Compound 190, 3-(benzyloxy)-2-(2-(2,5-dichlorophenyl)acetamido)-N-(4-phenoxyphenyl)propanamide; Compound 191, 3-(benzyloxy)-2-(2-(3-chloro-2-fluorophenyl)acetamido)-N-(4-phenoxyphenyl)propanamide; Compound 192, 3-(benzyloxy)-2-(2-(5-chloro-2-fluorophenyl)acetamido)-N-(4-phenoxyphenyl)propanamide; Compound 193, 2-(2-(1- acetylpyrrolidin-2-yl)acetamido)-3-benzyloxy-N-(4-phenoxyphenyl)propanamide; Compound 194, (S)-2-{2-((benzoyl)(methyl)amino)acetamido}-3-benzyloxy-N-(4-phenoxyphenyl)propanamide; Compound 195, (S)-2-(2-(1-methyl-1H-imidazol-4-yl)acetamido)-3-benzyloxy-N-(4-phenoxyphenyl)propanamide; Compound 196, (S)-2-(2-(2-fluorophenyl)acetamido)-3-benzyloxy-N-(4-phenoxyphenyl)propanamide; Compound 197, (S)-2-(2-(1H-indol-4-yl)acetamido)-3-benzyloxy-N-(4-phenoxyphenyl)propanamide; Compound 198, (S)-2-(2-(thien-2-yl)acetamido)-3-benzyloxy-N-(4-phenoxyphenyl)propanamide; Compound 199, (S)-2-(2-(2,5-dichlorophenyl)acetamido)-3-benzyloxy-N-(4-phenoxyphenyl)propanamide; Compound 200, (S)-2-(2-(1H-imidazol-4-yl)acetamido)-3-(benzyloxy)-N-(4-benzylphenyl)propanamide; Compound 201, (S)-3-(benzyloxy)-2-(2-(2,4-dioxoimidazolidin-1-yl)acetamido)-N-(4-phenoxyphenyl)propanamide; Compound 202, (S)-2-(2-(1H-imidazol-4-yl)acetamido)-3-(benzyloxy)-N-(4-(4-methoxyphenoxy)phenyl)propanamide; Compound 203, (S)-2-(2-(1H-imidazol-4-yl)-N-methylacetamido)-3-(benzyloxy)-N-(4-phenoxyphenyl)propanamide; Compound 204, (S)-2-(2-(1H-imidazol-5-yl)acetamido)-N-(4-(4-chlorophenoxy)phenyl)-3-phenylpropanamide; Compound 205, (S)-3-(benzyloxy)-N-(4-(4-fluorophenoxy)phenyl)-2-(2-(piperazin-1-yl)acetamido)propanamide; Compound 206, (S)-2-(2-(1H-imidazol-4-yl)acetamido)-3-(benzyloxy)-N-(4-(thiazol-2-yloxy)phenyl)propanamide; Compound 207, (S)-2-(3-(1H-imidazol-5-yl)propanamido)-3-(benzyloxy)-N-(4-(4-fluorophenoxy)phenyl)propanamide; Compound 208, (S)-2-(2-(1H-imidazol-5-yl)acetamido)-3-(benzyloxy)-N-(4-(cyclohexyloxy)phenyl)propanamide; Compound 209, (S)-3-(benzyloxy)-N-(4-(4-chlorophenoxy)phenyl)-2-(3-(dimethylamino)propanamido)propanamide; Compound 210, (S)-3-(4-fluorobenzyloxy)-N-(4-(4-fluorophenoxy)phenyl)-2-(2-morpholinoacetamido)propanamide; Compound 211, (S)-2-(2-(1H-imidazol-4-yl)acetamido)-3-(benzyloxy)-N-(4-(benzyloxy)phenyl)propanamide; Compound 212, (S)-3-(benzyloxy)-2-(2-(5-fluoro-1H-indol-3-yl)acetamido)-N-(4-(4-fluorophenoxy)phenyl)propanamide; Compound 213, (S)-2-(2-(1H-imidazol-4-yl)-2-methylpropanamido)-3-(benzyloxy)-N-(4-(4-fluorophenoxy)phenyl)propanamide; Compound 214, (S)-3-(benzyloxy)-2-(2-(2,5-dihydro-1H-pyrrol-1-yl)acetamido)-N-(4-(4-fluorophenoxy)phenyl)propanamide; Compound 215, (S)-3-(benzyloxy)-N-(4-(4-fluorophenoxy)phenyl)-2-(2-(pyrrolidin-1-yl)acetamido)propanamide; Compound 216, (S)-2-(2-(2-(1H-imidazol-4-yl)ethylamino)acetamido)-3-(benzyloxy)-N-(4-(4-fluorophenoxy)phenyl)propanamide; Compound 217, (S)-3-(benzyloxy)-N-(4-(4-fluorophenoxy)phenyl)-2-(2-(4-(2-methoxyphenyl)piperazin-1-yl)acetamido)propanamide; Compound 218, (S)-3-(benzyloxy)-N-(4-(4-fluorophenoxy)phenyl)-2-(2-(4-(4-fluorophenyl)piperazin-1-yl)acetamido)propanamide; Compound 219, (S)-2-(2-(2,3-dioxa-8-azaspiro[4.5]decan-8-yl)acetamido)-3-(benzyloxy)-N-(4-(4-fluorophenoxy)phenyl)propanamide; Compound 220, (S)-3-(benzyloxy)-2-(2-(4-benzylpiperidin-1-yl)acetamido)-N-(4-(4-fluorophenoxy)phenyl)propanamide; Compound 221, (S)-3-(benzyloxy)-2-(2-(3,4-dihydroisoquinolin-2(1H)-yl)acetamido)-N-(4-(4-fluorophenoxy)phenyl)propanamide; Compound 222, (2S)-3-(benzyloxy)-N-(4-(4-fluorophenoxy)phenyl)-2-(2-(octahydroisoquinolin-2(1H)-yl)acetamido)propanamide; Compound 223, (S)-3-(benzyloxy)-N-(4-(4-fluorophenoxy)phenyl)-2-(2-(4-(furan-2-carbonyl)piperazin-1-yl)acetamido)propanamide; Compound 224, (S)-3-(benzyloxy)-N-(4-(4-fluorophenoxy)phenyl)-2-(2-(4-(4-methoxyphenyl)piperazin-1-yl)acetamido)propanamide; Compound 225, (S)-3-(benzyloxy)-N-(4-(4-fluorophenoxy)phenyl)-2-(2-(4-phenylpiperazin-1-yl)acetamido)propanamide; Compound 226, (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide; Compound 227, (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide; Compound 228, (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide; Compound 229, (S)-2-(2-(4-(4-acetylphenyl)piperazin-1-yl)acetamido)-3-(benzyloxy)-N-(4-(4-fluorophenoxy)phenyl)propanamide; Compound 230, (S)-2-(2-(4-acetylpiperazin-1-yl)acetamido)-3-(benzyloxy)-N-(4-(4-fluorophenoxy)phenyl)propanamide; Compound 231, 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide; Compound 232, (S,E)-N-(3-(benzyloxy)-1-(4-(4-fluorophenoxy)phenylamino)-1-oxopropan-2-yl)hex-3-enamide; Compound 233, (S)-N-(3-(benzyloxy)-1-(4-(4-fluorophenoxy)phenylamino)-1-oxopropan-2-y)-3-methylbutanamide; Compound 234, (S)-3-(benzyloxy)-2-(2-((2R,6S)-2,6-dimethylmorpholino)acetamido)-N-(4-(4-fluorophenoxy)phenyl)propanamide; Compound 235, (S)-3-(benzyloxy)-N-(4-(4-fluorophenoxy)phenyl)-2-(2-(thiazolidin-3-yl)acetamido)propanamide; Compound 236, (S)-2-(2-(4-acetylpiperazin-1-yl)acetamido)-3-(benzyloxy)-N-(4-(4-fluorophenoxy)phenyl)propanamide; Compound 237, (2S)-3-(benzyloxy)-N-(4-(4-fluorophenoxy)phenyl)-2-(2-(4-(tetrahydrofuran-2-carbonyl)piperazin-1-yl)acetamido)propanamide; Compound 238, (S)-methyl 1-(2-(3-(benzyloxy)-1-(4-(4-fluorophenoxy)phenylamino)-1-oxopropan-2-ylamino)-2-oxoethyl)piperidine-4-carboxylate; Compound 239, (S)-3-(benzyloxy)-2-(2-(4-(2-chloro-6-fluorobenzyl)piperazin-1-yl)acetamido)-N-(4-(4-fluorophenoxy)phenyl)propanamide; Compound 240, (S)-3-(benzyloxy)-N-(4-(4-fluorophenoxy)phenyl)-2-(2-(isoindolin-2-yl)acetamido)propanamide; Compound 241, (S)-3-(benzyloxy)-N-(4-(4-fluorophenoxy)phenyl)-2-(2-(4-(2-methoxyethyl)piperazin-1-yl)acetamido)propanamide; Compound 242, (S)-3-(benzyloxy)-N-(4-(4-fluorophenoxy)phenyl)-2-(2-(4-(2-ethoxyethyl)piperazin-1-yl)acetamido)propanamide; Compound 243, (S)-2-(2-(1H-imidazol-4-yl)acetamido)-3-(benzyloxy)-N-(3-phenoxyphenyl)propanamide; Compound 244, (S)-3-(benzyloxy)-2-(2-(3-bromophenyl)acetamido)-N-(4-(4-fluorophenoxy)phenyl)propanamide; Compound 245, (S)-3-(benzyloxy)-N-(4-(4-fluorophenoxy)phenyl)-2-(3-nitropropanamido)propanamide; Compound 246, (S)-3-(benzyloxy)-N-(4-(4-fluorophenoxy)phenyl)-2-(2-(pyridin-2-yl)acetamido)propanamide; Compound 247, (S)-3-(benzyloxy)-N-(4-(4-fluorophenoxy)phenyl)-2-(2-(pyridin-3-yl)acetamido)propanamide; Compound 248, (S)-N-((S)-3-(benzyloxy)-1-(4-(4-fluorophenoxy)phenylamino)-1-oxopropan-2-yl)-3,7-dimethyloct-6-enamide; Compound 249, (S)-3-(benzyloxy)-N-(4-(4-fluorophenoxy)phenyl)-2-(2-phenylacetamido)propanamide; Compound 250, (S)-3-(benzyloxy)-N-(4-(4-fluorophenoxy)phenyl)-2-(2-(pyrimidin-5-yl)acetamido)propanamide; Compound 251, (2S,4S)-1-(2-(1H-imidazol-5-yl)acetyl)-N-(4-(4-fluorophenoxy)phenyl)-4-phenylpyrrolidine-2-carboxamide; Compound 252, (2S,4R)-1-(2-(1H-1,2,4-triazol-1-yl)acetyl)-4-(benzyloxy)-N-(4-(4-fluorophenoxy)phenyl)pyrrolidine-2-carboxamide; Compound 253, benzyl (3R,5S)-1-(2-(1H-imidazol-5-yl)acetyl)-5-(4-(4-fluorophenoxy)phenylcarbamoyl)pyrrolidin-3-ylcarbamate; Compound 254, (S)-2-(2-(1H-1,2,4-triazol-1-yl)acetamido)-5-acetamido-N-(4-(4- fluorophenoxy)phenyl)pentanamide; Compound 255, (S)-3-(benzyloxy)-N-(4-(4-fluorophenoxy)phenyl)-2-(2-methyl-2-(1H-1,2,4-triazol-1-yl)propanamido)propanamide; Compound 256, (S)-3-(benzyloxy)-2-(2-(3,5-dimethyl-1H-1,2,4-triazol-1-yl)acetamido)-N-(4-(4-fluorophenoxy)phenyl)propanamide; Compound 257, (S)-benzyl 4-(2-(1H-imidazol-4-yl)acetyl)-3-(4-(4-fluorophenoxy)phenylcarbamoyl)piperazine-1-carboxylate; Compound 258, (S)-2-(2-(3,5-dimethyl-1H-pyrazol-4-yl)acetamido)-3-(4-fluorobenzyloxy)-N-(4-(4-fluorophenoxy)phenyl)propanamide; Compound 259, (2S,4R)-1-(2-(1H-1,2,4-triazol-1-yl)acetyl)-N-(4-(4-fluorophenoxy)phenyl)-4-phenoxypyrrolidine-2-carboxamide; Compound 260, (2S,4R)-1-(2-(1H-1,2,4-triazol-1-yl)acetyl)-N-(4-(4-fluorophenoxy)phenyl)-4-(isoindolin-2-yl)pyrrolidine-2-carboxamide; Compound 261, (S)-1-(2-(1H-1,2,4-triazol-1-yl)acetyl)-4-benzyl-N-(4-(4-fluorophenoxy)phenyl)piperazine-2-carboxamide; Compound 262, (2S,4S)-1-(2-(1H-1,2,4-triazol-1-yl)acetyl)-4-((benzylamino)methyl)-N-(4-(4-fluorophenoxy)phenyl)pyrrolidine-2-carboxamide; Compound 263, (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide; Compound 264, (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide; Compound 265, (2S)-3-(benzyloxy)-2-(2-(2,6-dimethylmorpholino)acetamido)-N-(4-(4-fluorophenoxy)phenyl)propanamide; Compound 266, (S)-3-(benzyloxy)-N-(4-(4-fluorophenoxy)phenyl)-2-(2-thiomorpholinoacetamido)propanamide; Compound 267, (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide; Compound 268, (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide; Compound 269, N-(2-oxo-1-{[(phenylmethyl)oxy]methyl}-2-{[4-(phenyloxy)phenyl]amino}ethyl)acetamide; Compound 270, 4-(methyloxy)-N-(2-oxo-1-{[(phenylmethyl)oxy]methyl}-2-{[4-(phenyloxy)phenyl]amino}ethyl)benzamide; 4-benzyloxy-N-(2-oxo-1-{[(phenylmethyl)oxy]methyl}-2-{[4-(phenyloxy)phenyl]amino}ethyl)phenylacetamide; Compound 272, 2-bromo-5-(methyloxy)-N-(2-oxo-1-{[(phenylmethyl)oxy]methyl}-2-{[4-(phenyloxy)phenyl]amino}ethyl)benzamide; Compound 273, N-(2-oxo-1-{[(phenylmethyl)oxy]methyl}-2-{[4-(phenyloxy)phenyl]amino}ethyl)butanamide; Compound 274, 2-chloro-N-(2-oxo-1-{[(phenylmethyl)oxy]methyl}-2-{[4-(phenyloxy)phenyl]amino}ethyl)benzamide; Compound 275, 3-chloro-N-(2-oxo-1-{[(phenylmethyl)oxy]methyl}-2-{[4-(phenyloxy)phenyl]amino}ethyl)benzamide; Compound 276, 4-chloro-N-(2-oxo-1-{[(phenylmethyl)oxy]methyl}-2-{[4-(phenyloxy)phenyl]amino}ethyl)benzamide; Compound 277, N-(2-oxo-1-{[(phenylmethyl)oxy]methyl}-2-{[4-(phenyloxy)phenyl]amino}ethyl)cyclopropylamide; Compound 278, N-(2-oxo-1-{[(phenylmethyl)oxy]methyl}-2-{[4-(phenyloxy)phenyl]amino}ethyl)-3-cyclopentylpropanamide; Compound 279, 3,4-dimethyl-N-(2-oxo-1-{[(phenylmethyl)oxy]methyl}-2-{[4-(phenyloxy)phenyl]amino}ethyl)benzamide; Compound 280, N-(2-oxo-1-{[(phenylmethyl)oxy]methyl}-2-{[4-(phenyloxy)phenyl]amino}ethyl)-2,5-dimethoxyphenylacetamide; Compound 281, 4-(ethyloxy)-N-(2-oxo-1-{[(phenylmethyl)oxy]methyl}-2-{[4-(phenyloxy)phenyl]amino}ethyl)benzamide; Compound 282, N-(3-(benzyloxy)-1-oxo-1-(4-phenoxyphenylamino)propan-2-yl)-2-ethylhexanamide; Compound 283, N-(2-oxo-1-{[(phenylmethyl)oxy]methyl}-2-{[4-(phenyloxy)phenyl]amino}ethyl)furan-2-carboxamide; Compound 284, N-(2-oxo-1-{[(phenylmethyl)oxy]methyl}-2-{[4-(phenyloxy)phenyl]amino}ethyl)-2-methoxyacetamide; Compound 285, N-(2-oxo-1-{[(phenylmethyl)oxy]methyl}-2-{[4-(phenyloxy)phenyl]amino}ethyl)-3-methoxyphenylacetamide; Compound 286, 2-methyl-N-(2-oxo-1-{[(phenylmethyl)oxy]methyl}-2-{[4-(phenyloxy)phenyl]amino}ethyl)pentanamide; Compound 287, 4-methyl-N-(2-oxo-1-{[(phenylmethyl)oxy]methyl}-2-{[4-(phenyloxy)phenyl]amino}ethyl)pentanamide; Compound 288, N-(2-oxo-1-{[(phenylmethyl)oxy]methyl}-2-{[4-(phenyloxy)phenyl]amino}ethyl)naphthalene-2-carboxamide; Compound 289, N-(2-oxo-1-{[(phenylmethyl)oxy]methyl}-2-{[4-(phenyloxy)phenyl]amino}ethyl)phenoxyacetamide; Compound 290, N-(2-oxo-1-{[(phenylmethyl)oxy]methyl}-2-{[4-(phenyloxy)phenyl]amino}ethyl)-2-(phenyloxy)pyridine-3-carboxamide; Compound 291, 3,4,5-tris(methyloxy)-N-(2-oxo-1-{[(phenylmethyl)oxy]methyl}-2-{[4-(phenyloxy)phenyl]amino}ethyl)benzamide; Compound 292, N-(2-oxo-1-{[(phenylmethyl)oxy]methyl}-2-{[4-(phenyloxy)phenyl]amino}ethyl)thiophene-2-carboxamide; Compound 293, N-(2-oxo-1-{[(phenylmethyl)oxy]methyl}-2-{[4-(phenyloxy)phenyl]amino}ethyl)thien-2-ylacetamide; Compound 294, 4-(dimethylamino)-N-(2-oxo-1-{[(phenylmethyl)oxy]methyl}-2-{[4-(phenyloxy)phenyl]amino}ethyl)benzamide; Compound 295, N-(2-oxo-1-{[(phenylmethyl)oxy]methyl}-2-{[4-(phenyloxy)phenyl]amino}ethyl)hexanamide; Compound 296, 2-chloro-N-(2-oxo-1-{[(phenylmethyl)oxy]methyl}-2-{[4-(phenyloxy)phenyl]amino}ethyl)pyridine-3-carboxamide; Compound 297, 3-chloro-N-(2-oxo-1-{[(phenylmethyl)oxy]methyl}-2-{[4-(phenyloxy)phenyl]amino}ethyl)-1-benzothiophene-2-carboxamide; Compound 298, N-(2-oxo-1-{[(phenylmethyl)oxy]methyl}-2-{[4-(phenyloxy)phenyl]amino}ethyl)pent-4-enamide; Compound 299, 3-chloro-2-fluoro-N-(2-oxo-1-{[(phenylmethyl)oxy]methyl}-2-{[4-(phenyloxy)phenyl]amino}ethyl)benzamide Compound 300, N-(2-oxo-1-{[(phenylmethyl)oxy]methyl}-2-{[4-(phenyloxy)phenyl]amino}ethyl)-4-phenylbutanamide; Compound 301, N-(2-oxo-1-{[(phenylmethyl)oxy]methyl}-2-{[4-(phenyloxy)phenyl]amino}ethyl)-2-bromophenylacetamide; Compound 302, N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide; Compound 303, N-(2-oxo-1-{[(phenylmethyl)oxy]methyl}-2-{[4-(phenyloxy)phenyl]amino}ethyl)-2-methoxyethoxyacetamide; Compound 304, N-(2-oxo-1-{[(phenylmethyl)oxy]methyl}-2-{[4-(phenyloxy)phenyl]amino}ethyl)-3-(4-methoxyphenyl)propanamide; Compound 305, N-(2-oxo-1-{[(phenylmethyl)oxy]methyl}-2-{[4-(phenyloxy)phenyl]amino}ethyl)-2-acetylamino-4-methylthiazol-5-ylsulfonamide; Compound 306, 4-(methylthio)-N-(2-oxo-1-{[(phenylmethyl)oxy]methyl}-2-{[4-(phenyloxy)phenyl]amino}ethyl)benzamide; Compound 307, N-(2-oxo-1-{[(phenylmethyl)oxy]methyl}-2-{[4-(phenyloxy)phenyl]amino}ethyl)-2-(methylthio)acetamide; Compound 308, 5-fluoro-2-(methyloxy)-N-(2-oxo-1-{[(phenylmethyl)oxy]methyl}-2-{[4-(phenyloxy)phenyl]amino}ethyl)benzamide; Compound 309, 2-methyl-4-(methyloxy)-N-(2-oxo-1-{[(phenylmethyl)oxy]methyl}-2-{[4-(phenyloxy)phenyl]amino}ethyl)benzamide; Compound 310, 5-oxo-N-(2-oxo-1-{[(phenylmethyl)oxy]methyl}-2-{[4-(phenyloxy)phenyl]amino}ethyl)hexanamide; Compound 311, 4-bromo-2-methyl-N-(2-oxo-1-{[(phenylmethyl)oxy]methyl}-2-{[4-(phenyloxy)phenyl]amino}ethyl)benzamide; Compound 312, 4-oxo-N-(2-oxo-1-{[(phenylmethyl)oxy]methyl}-2-{[4-(phenyloxy)phenyl]amino}ethyl)-4-(2-thienyl)butanamide; Compound 313, N-(2-oxo-1-{[(phenylmethyl)oxy]methyl}-2-{[4-(phenyloxy)phenyl]amino}ethyl)-2-(phenylthio)acetamide; Compound 314, N-(2-oxo-1-{[(phenylmethyl)oxy]methyl}-2-{[4-(phenyloxy)phenyl]amino}ethyl)-2-(1H-pyrrol-1-yl)benzamide; Compound 315, N-(2-oxo-1-{[(phenylmethyl)oxy]methyl}-2-{[4-(phenyloxy)phenyl]amino}ethyl)-2-[2-(methoxy)ethoxy]ethoxyacetamide; Compound 316, 3,5-bis(methyloxy)-N-(2-oxo-1-{[(phenylmethyl)oxy]methyl}-2-[4-(phenyloxy)phenyl]amino}ethyl)benzamide; Compound 317, N-(2-oxo-1-{[(phenylmethyl)oxy]methyl}-2-{[4-(phenyloxy)phenyl]amino}ethyl)-3-cyclohexylpropanamide; Compound 318, 5-oxo-N-(2-oxo-1-{[(phenylmethyl)oxy]methyl}-2-{[4-(phenyloxy)phenyl]amino}ethyl)-5-phenylpentanamide; Compound 319, N-(2-oxo-1-{[(phenylmethyl)oxy]methyl}-2-{[4-(phenyloxy)phenyl]amino}ethyl)-4-acetylphenoxyacetamide; Compound 320, 4-[3,4-bis(methyloxy)phenyl]-N-(2-oxo-1-{[(phenylmethyl)oxy]methyl}-2-{[4-(phenyloxy)phenyl]amino}ethyl)butanamide; Compound 321, N-(2-oxo-1-{[(phenylmethyl)oxy]methyl}-2-{[4-(phenyloxy)phenyl]amino}ethyl)-5-[3-(trifluoromethyl)phenyl]furan-2-carboxamide; Compound 322, N-(2-oxo-1-{[(phenylmethyl)oxy]methyl}-2-{[4-(phenyloxy)phenyl]amino}ethyl)-3-(1,3-dioxoisoindolin-2-yl)propanamide; Compound 323, 5-oxo-N-(2-oxo-1-{[(phenylmethyl)oxy]methyl}-2-{[4-(phenyloxy)phenyl]amino}ethyl)-5-(2-thienyl)pentanamide; Compound 324, N-(2-oxo-1-{[(phenylmethyl)oxy]methyl}-2-{[4-(phenyloxy)phenyl]amino}ethyl)-2-oxo-2-phenylacetamide; Compound 325, N-(2-oxo-1-{[(phenylmethyl)oxy]methyl}-2-{[4-(phenyloxy)phenyl]amino}ethyl)-4-(2-thienyl)butanamide; Compound 326, 5-nitro-N-(2-oxo-1-{[(phenylmethyl)oxy]methyl}-2-{[4-(phenyloxy)phenyl]amino}ethyl)furan-2-carboxamide; Compound 328, N-(2-oxo-1-{[(phenylmethyl)oxy]methyl}-2-{[4-(phenyloxy)phenyl]amino}ethyl)-1,3-benzodioxol-5-ylacetamide; Compound 329, 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide; Compound 330, 4-fluoro-N-(2-oxo-1-{[(phenylmethyl)oxy]methyl}-2-{[4-(phenyloxy)phenyl]amino}ethyl)-2-(trifluoromethyl)benzamide; Compound 331, N-(2-oxo-1-{[(phenylmethyl)oxy]methyl}-2-{[4-(phenyloxy)phenyl]amino}ethyl)-2-(pyrimidin-2-ylthio)acetamide; Compound 332, 2,5-bis(methyloxy)-N-(2-oxo-1-{[(phenylmethyl)oxy]methyl}-2-{[4-(phenyloxy)phenyl]amino}ethyl)benzamide; Compound 333, 4-(methylsulfonyl)-N-(2-oxo-1-{[(phenylmethyl)oxy]methyl}-2-{[4-(phenyloxy)phenyl]amino}ethyl)benzamide; Compound 334, 2-chloro-4-(methylsulfonyl)-N-(2-oxo-1-{[(phenylmethyl)oxy]methyl}-2-{[4-(phenyloxy)phenyl]amino}ethyl)benzamide; Compound 335, N-(2-oxo-1-{[(phenylmethyl)oxy]methyl}-2-{[4-(phenyloxy)phenyl]amino}ethyl)2-(4-oxo-2-thioxothiazolidin-3-yl)acetamide; Compound 336, N-(2-oxo-1-{[(phenylmethyl)oxy]methyl}-2-{[4-(phenyloxy)phenyl]amino}ethyl)tetrahydrofuran-3-carboxamide; Compound 337, N-(2-oxo-1-{[(phenylmethyl)oxy]methyl}-2-{[4-(phenyloxy)phenyl]amino}ethyl)-3-methoxypropanamide; Compound 338, N-(2-oxo-1-{[(phenylmethyl)oxy]methyl}-2-{[4-(phenyloxy)phenyl]amino}ethyl)-2-ethoxyacetamide; Compound 339, N,N-dimethyl-N'-(2-oxo-1-{[(phenylmethyl)oxy]methyl}-2-{[4-(phenyloxy)phenyl]amino}ethyl)butanediamide; Compound 340, N-(2-oxo-1-{[(phenylmethyl)oxy]methyl}-2-{[4-(phenyloxy)phenyl]amino}ethyl)-N-benzoyl-N-methylaminoacetamide; Compound 341, N-(2-oxo-1-{[(phenylmethyl)oxy]methyl}-2-{[4-(phenyloxy)phenyl]amino}ethyl)-1H-indole-3-carboxamide; Compound 342, N-(2-oxo-1-{[(phenylmethyl)oxy]methyl}-2-{[4-(phenyloxy)phenyl]amino}ethyl)-1H-benzimidazole-5-carboxamide; Compound 343, N-(2-oxo-1-{[(phenylmethyl)oxy]methyl}-2-{[4-(phenyloxy)phenyl]amino}ethyl)-2-(4-ethoxyphenyl)acetamide; Compound 344, N-(2-oxo-1-{[(phenylmethyl)oxy]methyl}-2-{[4-(phenyloxy)phenyl]amino}ethyl)pent-4-ynamide; Compound 345, N-(2-oxo-1-{[(phenylmethyl)oxy]methyl}-2-{[4-(phenyloxy)phenyl]amino}ethyl)-4-(propyloxy)benzamide; Compound 346, 2-methyl-N-(2-oxo-1-{[(phenylmethyl)oxy]methyl}-2-{[4-(phenyloxy)phenyl]amino}ethyl)hexanamide; Compound 347, 4-oxo-N-(2-oxo-1-{[(phenylmethyl)oxy]methyl}-2-{[4-(phenyloxy)phenyl]amino}ethyl)pentanamide; Compound 348, N-(2-oxo-1-{[(phenylmethyl)oxy]methyl}-2-{[4-(phenyloxy)phenyl]amino}ethyl)-3-(3,4-dimethoxyphenyl)propanamide; Compound 349, 4-oxo-N-(2-oxo-1-{[(phenylmethyl)oxy]methyl}-2-{[4-(phenyloxy)phenyl]amino}ethyl)-4-phenylbutanamide; Compound 350, N-(2-oxo-1-{[(phenylmethyl)oxy]methyl}-2-{[4-(phenyloxy)phenyl]amino}ethyl)quinoline-3-carboxamide; Compound 351, N-(2-oxo-1-{[(phenylmethyl)oxy]methyl}-2-{[4-(phenyloxy)phenyl]amino}ethyl)pyrazine-2-carboxamide; Compound 352, N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide; Compound 353, N-(2-oxo-1-{[(phenylmethyl)oxy]methyl}-2-{[4-(phenyloxy)phenyl]amino}ethyl)-2-methoxy-2-phenylacetamide; Compound 354, N-(2-oxo-1-{[(phenylmethyl)oxy]methyl}-2-{[4-(phenyloxy)phenyl]amino}ethyl)-2R-phenylpropanamide; Compound 355, N-(2-oxo-1-{[(phenylmethyl)oxy]methyl}-2-{[4-(phenyloxy)phenyl]amino}ethyl)-1H-pyrazole-4-carboxamide; Compound 356, N-(2-oxo-1-{[(phenylmethyl)oxy]methyl}-2-{[4-(phenyloxy)phenyl]amino}ethyl)cinnoline-4-carboxamide; Compound 357, N-(2-oxo-1-{[(phenylmethyl)oxy]methyl}-2-{[4-(phenyloxy)phenyl]amino}ethyl)quinoline-8-carboxamide; Compound 358, 6-hydroxy-N-(2-oxo-1-{[(phenylmethyl)oxy]methyl}-2-{[4-(phenyloxy)phenyl]amino}ethyl)pyridine-2-carboxamide; Compound 359, N-(2-oxo-1-{[(phenylmethyl)oxy]methyl}-2-{[4-(phenyloxy)phenyl]amino}ethyl)-2-phenylpropanamide; Compound 360, N-(2-oxo-1-{[(phenylmethyl)oxy]methyl}-2-{[4-(phenyloxy)phenyl]amino}ethyl)-1-(4-methoxyphenyl)cyclopropanecarboxamide; Compound 361, N-(2-oxo-1-{[(phenylmethyl)oxy]methyl}-2-{[4-(phenyloxy)phenyl]amino}ethyl)-2-(2,3,6-trifluorophenyl)acetamide; Compound 362, N-(2-oxo-1-{[(phenylmethyl)oxy]methyl}-2-{[4-(phenyloxy)phenyl]amino}ethyl)-2,4-bis(trifluoromethyl)benzamide; Compound 363, N-(2-oxo-1-{[(phenylmethyl)oxy]methyl}-2-{[4-(phenyloxy)phenyl]amino}ethyl)-2-(2,4-difluorophenyl)acetamide; Compound 364, N-(2-oxo-1-{[(phenylmethyl)oxy]methyl}-2-{[4-(phenyloxy)phenyl]amino}ethyl)-2-(1-methyl-1H-indol-3-yl)acetamide; Compound 365, N-(2-oxo-1-{[(phenylmethyl)oxy]methyl}-2-{[4-(phenyloxy)phenyl]amino}ethyl)quinoline-4-carboxamide; Compound 366, N-(2-oxo-1-{[(phenylmethyl)oxy]methyl}-2-{[4-(phenyloxy)phenyl]amino}ethyl-1-benzofuran-2-carboxamide; Compound 367, 7-(methyloxy)-N-(2-oxo-1-{[(phenylmethyl)oxy]methyl}-2-{[4-(phenyloxy)phenyl]amino}ethyl)-1-benzofuran-2-carboxamide; Compound 368, N-(2-oxo-1-{[(phenylmethyl)oxy]methyl}-2-{[4-(phenyloxy)phenyl]amino}ethyl)-2-(4-fluorophenoxy)acetamide; Compound 369, N-(2-oxo-1-{[(phenylmethyl)oxy]methyl}-2-{[4-(phenyloxy)phenyl]amino}ethyl)-3-(pyridin-3-yl)propanamide; Compound 370, N-(2-oxo-1-{[(phenylmethyl)oxy]methyl}-2-{[4-(phenyloxy)phenyl]amino}ethyl)-2-(3,4-dichlorophenoxy)acetamide; Compound 371, N-(2-oxo-1-{[(phenylmethyl)oxy]methyl}-2-{[4-(phenyloxy)phenyl]amino}ethyl)-2-(naphthalen-1-yloxy)acetamide; Compound 372, N-(2-oxo- 1-{[(phenylmethyl)oxy]methyl}-2-{[4-(phenyloxy)phenyl]amino}ethyl)-2-p-tolylacetamide; Compound 373, N-(2-oxo-1-{[(phenylmethyl)oxy]methyl}-2-{[4-(phenyloxy)phenyl]amino}ethyl)-2-(2,5-dimethylphenyl)acetamide; Compound 374, N-(2-oxo-1-{[(phenylmethyl)oxy]methyl}-2-{[4-(phenyloxy)phenyl]amino}ethyl)-2-(benzylthio)acetamide; Compound 375, N-(2-oxo-1-{[(phenylmethyl)oxy]methyl}-2-{[4-(phenyloxy)phenyl]amino}ethyl)-2-(naphthalen-1-yl)acetamide; Compound 376, N-(2-oxo-1-{[(phenylmethyl)oxy]methyl}-2-{[4-(phenyloxy)phenyl]amino}ethyl)-3-ethoxypropanamide; Compound 377, N-(2-oxo-1-{[(phenylmethyl)oxy]methyl}-2-{[4-(phenyloxy)phenyl]amino}ethyl)-2-(3-chlorophenyl)acetamide; Compound 378, 5-butyl-N-(2-oxo-1-{[(phenylmethyl)oxy]methyl}-2-{[4-(phenyloxy)phenyl]amino}ethyl)pyridine-2carboxamide; Compound 379, 4-chloro-3-methyl-N-(2-oxo-1-{[(phenylmethyl)oxy]methyl}-2-{[4-(phenyloxy)phenyl]amino}ethyl)benzamide; Compound 380, 4-cyano-N-(2-oxo-1-{[(phenylmethyl)oxy]methyl}-2-{[4-(phenyloxy)phenyl]amino}ethyl)benzamide; Compound 381, N-(2-oxo-1-{[(phenylmethyl)oxy]methyl}-2-{[4-(phenyloxy)phenyl]amino}ethyl)-2S-methoxy-2-phenylacetamide; Compound 382, N-(2-oxo-1-{[(phenylmethyl)oxy]methyl}-2-{[4-(phenyloxy)phenyl]amino}ethyl)-3-(2,5-dimethoxyphenyl)propanamide; Compound 383, N-(2-oxo-1-{[(phenylmethyl)oxy]methyl}-2-{[4-(phenyloxy)phenyl]amino}ethyl)-3-(1H-indol-3-yl)propanamide; Compound 384, N-(2-oxo-1-{[(phenylmethyl)oxy]methyl}-2-{[4-(phenyloxy)phenyl]amino}ethyl)-2-(3-bromophenyl)acetamide; Compound 385, 3-methyl-N-(2-oxo-1-{[(phenylmethyl)oxy]methyl}-2-{[4-(phenyloxy)phenyl]amino}ethyl)pentanamide; Compound 386, N-(2-oxo-1-{[(phenylmethyl)oxy]methyl}-2-{[4-(phenyloxy)phenyl]amino}ethyl)-1H-indole-2-carboxamide; Compound 387, 4-chloro-2-fluoro-N-(2-oxo-1-{[(phenylmethyl)oxy]methyl}-2-{[4-(phenyloxy)phenyl]amino}ethyl)benzamide; Compound 388, 2-oxo-2-[(2-oxo-1-{[(phenylmethyl)oxy]methyl}-2-{[4-(phenyloxy)phenyl]amino}ethyl)amino]ethyl acetate; Compound 389, N-(2-oxo-1-{[(phenylmethyl)oxy]methyl}-2-{[4-(phenyloxy)phenyl]amino}ethyl)thiophene-3-carboxamide; Compound 390, N-(2-oxo-1-{[(phenylmethyl)oxy]methyl}-2-{[4-(phenyloxy)phenyl]amino}ethyl)-2-(4-bromophenyl)acetamide; Compound 391, N-(2-oxo-1-{[(phenylmethyl)oxy]methyl}-2-{[4-(phenyloxy)phenyl]amino}ethyl)-2-(2-chlorophenyl)acetamide; Compound 392, N-(2-oxo-1-{[(phenylmethyl)oxy]methyl}-2-{[4-(phenyloxy)phenyl]amino}ethyl)-2-(3,4,5-trimethoxyphenyl)acetamide; Compound 393, N-(2-oxo-1-{[(phenylmethyl)oxy]methyl}-2-{[4-(phenyloxy)phenyl]amino}ethyl)-2-(p-tolyloxy)acetamide; Compound 394, N-(2-oxo-1-{[(phenylmethyl)oxy]methyl}-2-{[4-(phenyloxy)phenyl]amino}ethyl)-3-(2-methoxyphenyl)propanamide; Compound 395, 3-hydroxy-N-(2-oxo-1-{[(phenylmethyl)oxy]methyl}-2-{[4-(phenyloxy)phenyl]amino}ethyl)quinoxaline-2-carboxamide; Compound 396, 4-acetyl-N-(2-oxo-1-{[(phenylmethyl)oxy]methyl}-2-{[4-(phenyloxy)phenyl]amino}ethyl)benzamide; Compound 397, methyl 4-{[(2-oxo-1-{[(phenylmethyl)oxy]methyl}-2-{[4-(phenyloxy)phenyl]amino}ethyl)amino]carbonyl}benzoate; Compound 398, 3-fluoro-N-(2-oxo-1-{[(phenylmethyl)oxy]methyl}-2-{[4-(phenyloxy)phenyl]amino}ethyl)-5-(trifluoromethyl)benzamide; Compound 399, 4-[(difluoromethyl)oxy]-N-(2-oxo-1-{[(phenylmethyl)oxy]methyl}-2-{[4-(phenyloxy)phenyl]amino}ethyl)benzamide; Compound 400, 3-fluoro-4-methyl-N-(2-oxo-1-{[(phenylmethyl)oxy]methyl}-2-{[4-(phenyloxy)phenyl]amino}ethyl)benzamide; Compound 401, 3-methyl-N-(2-oxo-1-{[(phenylmethyl)oxy]methyl}-2-{[4-(phenyloxy)phenyl]amino}ethyl)furan-2-carboxamide. Compound 402, N-(2-oxo-1-{[(phenylmethyl)oxy]methyl}-2-{[4-(phenyloxy)phenyl]amino}ethyl)cyclobutanecarboxamide; and Compound 403, N-(2-oxo-1-{[(phenylmethyl)oxy]methyl}-2-{[4-(phenyloxy)phenyl]amino}ethyl)-3-(thiophen-2-yl)propanamide.

Taxane compounds prevent the growth of cancer cells by affecting cell structures called microtubules, which play an important role in cell functions. In normal cell growth, microtubules are formed when a cell starts dividing. Once the cell stops dividing, the microtubules are broken down or destroyed. Taxane compounds stop the microtubules from breaking down, such that the cancer cells become clogged with microtubules so that they cannot grow and divide.

Taxane compounds are known in the art and include, for example, paclitaxel (available as TAXOL® from Bristol-Myers Squibb, Princeton, N.J.), docetaxel (available as TAXOTERE® from Sanofi-aventis, Bridgewater, N.J.), and the like. Other taxane compounds that become approved by the U.S. Food and Drug Administration (FDA) or foreign counterparts thereof are also preferred for use in the methods and compositions of the present invention. Other taxane compounds that can be used in the present invention include those described, for example, in 10th NCI-EORTC Symposium on New Drugs in Cancer Therapy, Amsterdam, page 100, Nos. 382 and 383 (Jun. 16-19, 1998); and U.S. Pat. Nos. 4,814,470, 5,721,268, 5,714,513, 5,739,362, 5,728,850, 5,728,725, 5,710,287, 5,637,484, 5,629,433, 5,580,899, 5,549,830, 5,523,219, 5,281,727, 5,939,567, 5,703,117, 5,480,639, 5,250,683, 5,700,669, 5,665,576, 5,618,538, 5,279,953, 5,243,045, 5,654,447, 5,527,702, 5,415,869, 5,279,949, 5,739,016, 5,698,582, 5,478,736, 5,227,400, 5,516,676, 5,489,601, 5,908,759, 5,760,251, 5,578,739, 5,547,981, 5,547,866, 5,344,775, 5,338,872, 5,717,115, 5,620,875, 5,284,865, 5,284,864, 5,254,703, 5,202,448, 5,723,634, 5,654,448, 5,466,834, 5,430,160, 5,407,816, 5,283,253, 5,719,177, 5,670,663, 5,616,330, 5,561,055, 5,449,790, 5,405,972, 5,380,916, 5,912,263, 8,808,113, 5,703,247, 5,618,952, 5,367,086, 5,200,534, 5,763,628, 5,705,508, 5,622,986, 5,476,954, 5,475,120, 5,412,116, 5,916,783, 5,879,929, 5,861,515, 5,795,909, 5,760,252, 5,637,732, 5,614,645, 5,599,820, 5,310,672, RE 34,277, U.S. Pat. Nos. 5,877,205, 5,808,102, 5,766,635, 5,760,219, 5,750,561, 5,637,723, 5,475,011, 5,256,801, 5,900,367, 5,869,680, 5,728,687, 5,565,478, 5,411,984, 5,334,732, 5,919,815, 5,912,264, 5,773,464, 5,670,673, 5,635,531, 5,508,447, 5,919,816, 5,908,835, 5,902,822, 5,880,131, 5,861,302, 5,850,032, 5,824,701, 5,817,867, 5,811,292, 5,763,477, 5,756,776, 5,686,623, 5,646,176, 5,621,121, 5,616,739, 5,602,272, 5,587,489, 5,567,614, 5,498,738, 5,438,072, 5,403,858, 5,356,928, 5,274,137, 5,019,504, 5,917,062, 5,892,063, 5,840,930, 5,840,900, 5,821,263, 5,756,301, 5,750,738, 5,750,562, 5,726,318, 5,714,512, 5,686,298, 5,684,168, 5,681,970, 5,679,807, 5,648,505, 5,641,803, 5,606,083, 5,599,942, 5,420,337, 5,407,674, 5,399,726, 5,322,779, 4,924,011, 5,939,566, 5,939,561, 5,935,955, 5,919,455, 5,854,278, 5,854,178, 5,840,929, 5,840,748, 5,821,363, 5,817,321, 5,814,658, 5,807,888, 5,792,877, 5,780,653, 5,770,745, 5,767,282, 5,739,359, 5,726,346, 5,717,103, 5,710,099, 5,698,712, 5,683,715, 5,677,462, 5,670,653, 5,665,761, 5,654,328, 5,643,575, 5,621,001, 5,608,102, 5,606,068, 5,587,493, 5,580,998, 5,580,997, 5,576,450, 5,574,156, 5,571,917, 5,556,878, 5,550,261, 5,539,103, 5,532,388, 5,470,866, 5,453,520, 5,384,399, 5,364,947, 5,350,866, 5,336,684, 5,296,506, 5,290,957, 5,274,124, 5,264,591, 5,250,722, 5,229,526, 5,175,315, 5,136,060, 5,015,744, 4,924,012, 6,118,011, 6,114,365, 6,107,332, 6,072,060, 6,066,749, 6,066,747, 6,051,724, 6,051,600, 6,048,990, 6,040,330, 6,030,818, 6,028,205, 6,025,516, 6,025,385, 6,018,073, 6,017,935, 6,011,056, 6,005,138, 6,005,138, 6,005,120, 6,002,023, 5,998,656, 5,994,576, 5,981,564, 5,977,386, 5,977,163, 5,965,739, 5,955,489, 5,939,567, 5,939,566, 5,919,815, 5,912,264, 5,912,263, 5,908,835, and 5,902,822, the disclosures of which are incorporated by reference herein in their entirety.

Other compounds that act as antimicrotubule agents, are the vinca alkaloids, such as Vincristine (available as ONCOVIN® from Eli Lilly and Company, Indianapolis, Ind., VINCASAR PFS®, VCR), Vinblastin (available as VELBAN® from Eli Lilly and Company, Indianapolis, Ind., VELSAR®) and Vinorelbine, and similar compounds are also known in the art. Compounds of this class act as microtubule destabilizing agents, causing microtubule depolymerization and ultimately cessation of cell growth and division resulting in apoptotic cell death.

Other compounds that can be used in the invention are those that act through a taxane mechanism. Compounds that act through a taxane mechanism include compounds that have the ability to exert microtubule-stabilizing effects and cytotoxic activity against rapidly proliferating cells, such as tumor cells or other hyperproliferative cellular diseases. Such compounds include, for example, epothilone compounds, such as, for example, epothilone A, B, C, D, E and F, and derivatives thereof. Other compounds that act through a taxane mechanism (e.g., epothilone compounds) that become approved by the FDA or foreign counterparts thereof are also preferred for use in the methods and compositions of the present invention. Epothilone compounds and derivatives thereof are known in the art and are described, for example, in U.S. Pat. Nos. 6,121,029, 6,117,659, 6,096,757, 6,043,372, 5,969,145, and 5,886,026; and WO 97/19086, WO 98/08849, WO 98/22461, WO 98/25929, WO 98/38192, WO 99/01124, WO 99/02514, WO 99/03848, WO 99/07692, WO 99/27890, and WO 99/28324, the disclosures of which are incorporated herein by reference in their entirety.

As described herein, the present invention is based on the unexpected discovery that the use of at least one S1P1R Receptor antagonist and at least one antimicrotubule agent, preferably a taxane or a vinca alkaloid, produces superior results in treating cancer. In one embodiment, the present invention provides methods of treating cancer and/or modulating the growth of selected cell populations (e.g., cancer cells) by administering at least one S1P1R Receptor antagonist and at least one antimicrotubule agent, preferably a taxane or a *vinca* alkaloid. In another embodiment, the present invention provides methods of treating cancer and/or modulating the growth of selected cell populations (e.g., cancer cells) by administering at least one S1P1R Receptor antagonist and at least one compound that acts via a taxane mechanism. One skilled in the art will appreciate that the methods described in the present invention encompass administering at least one S1P1R Receptor antagonist with taxane compounds, or compounds that act through a taxane mechanism. In the methods of the present invention, the S1P1R Receptor antagonist and the antimicrotubule agent, preferably a taxane compound or a vinca alkaloid compound, can be administered simultaneously, about the same time, or at different times, or can be components of a single composition.

Compositions and Administration:

A compound of the invention can be administered to a patient by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention or the compound of the invention may be formulated along with conventional excipients, pharmaceutical carriers, adjuvants and/or other medicinal or pharmaceutical agents. Acceptable exipients include, but are not limited to, (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac and zein; (d) disintegrants, such as cellulose, crosslinked polyvinyl pyrrolidone, sodium carboxymethyl cellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Pharmaceutical carriers include soluble polymers, microparticles made of insoluble or biodegradable natural and synthetic polymers, microcapsules, lipoproteins, liposomes and micelles.

A pharmaceutical composition of the invention will contain a therapeutically effective amount of a compound of the invention, or an individual stereoisomer or mixture of stereoisomers thereof, or a pharmaceutically acceptable salt thereof, with the remainder of the pharmaceutical composition comprised of one or more pharmaceutically acceptable excipients. Generally, a compound of the invention, or an individual stereoisomer or mixture of stereoisomers thereof, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, or an individual stereoisomer or mixture of stereoisomers thereof, or a pharmaceutically acceptable salt thereof will comprise from 5% to 75% by weight of a pharmaceutically acceptable composition, with the remainder of the composition comprised of one or more pharmaceutically acceptable excipients. Methods for preparing the dosage forms of the invention are known, or will be apparent, to those skilled in this art; for example, see Remington's Pharmaceutical Sciences, 18th Ed., (Mack Publishing Company, Easton, Pa., 1990).

A therapeutically effective amount of a compound of the invention will vary depending upon a sundry of factors including the activity, metabolic stability, rate of excretion and duration of action of the compound, the age, weight, general health, sex, diet and species of the patient, the mode and time of administration of the compound, the presence of adjuvants or additional therapeutically active ingredients in a composition and the severity of the disease for which the therapeutic effect is sought.

The compounds of the invention can be administered to human patients at dosage levels in the range of about 0.1 to about 10,000 mg per day. Thus, a normal human adult having a body weight of about 70 kilograms can be administered a dosage in the range of from about 0.15 µg to about 150 mg per kilogram of body weight per day. Typically, a normal adult human will be administered from about 3 mg to about 100 mg per kilogram of body weight per day. The optimum dose of a compound of the invention for a particular patient can be determined by one of ordinary skill in the art.

Other agents suitable for use in combination with a compound of the invention are disclosed in "Cancer Chemotherapy and Biotherapy: Principles and Practice," Third edition, B. A. Chabner and D. L. Longo, eds., 2001, Lippincott Williams and Wilkins, Philadelphia, U.S.A.; P. Calabresi and B. A. Chabner, "Chemotherapy of Neoplastic Diseases" in "Goodman and gilman's The Pharmacological Basis of Therapeutics," Tenth edition, J. g. Hardman and L. E. Limbird, eds., 2001, McGraw-Hill, New York, USA, pp. 1381-1388; and B. A. Chabner, D. P. Ryan, L. Paz-Ares, R. garcia-Carbonero, and P. Calabresi, "Antineoplastic Agents" in "Goodman and gilman's The Pharmacological Basis of Therapeutics," Tenth edition, J. g. Hardman and L. E. Limbird, eds., 2001, McGraw-Hill, New York, USA, pp. 1389-1459.

EXAMPLE 1

S1P1R Antagonist Assay

The S1P1R antagonist assay used to identify or analyze the compounds in Table 1 and list 1 is a fluorescent membrane potential dye measurement assay, indicative of intracellular cAMP changes due to G protein-coupled receptor activation. HEK293 cells engineered to express human S1P1 receptors and a cyclic nucleotide-gated (CNG) channel are obtained from BD Biosciences, 80300-250. The CNG channels are activated by elevated levels of cAMP, resulting in ion flux and cell membrane depolarization. Membrane depolarization is detected with a membrane potential dye. Stimulation of the cells with 5'-(N-ethylcarboxamido)adenosine (NECA), an A2b receptor agonist (Sigma, E2387), elicits an A2bR-dependent increase in cAMP.

Subsequent exposure of the cells to a S1P1R agonist suppresses the NECA induced increase in cAMP through S1P1R-specific signaling by inhibiting adenylyl cyclase and the formation of cAMP from ATP. The degree to which a test compound overcomes the S1P1R agonist suppression of the NECA induced increase in cAMP is a measure of S1P1R antagonist activity. Antagonist activity is quantified as the $IC_{50}$ (i.e., the concentration needed to elicited one-half of the maxium response of the test compound) and/or as the $EC_{50}$ (i.e., the concentration needed to elicited one-half of the NECA induced stimulation).

Day 1: Freshly thawed cells were plated into 384-well plates (Corning, 3683) at a density of 14,000 cells/well in 20 µL complete media and incubated for 16 hours at 37° C., 5% $CO_2$ and 99% relative humidity. Complete media included Dulbecco's modified Eagle's medium (Invitrogen, 11965-092), 10% Fetal bovine serum (Hyclone, SH30071.03), 250 µg/mL geneticin (Invitrogen, 10131-027), and 1 µg/mL Puromycin (Fluka, 82595).

Day 2: Membrane potential dye (20 µL, BD Biosciences, 341833) was added to each well and the plates were incubated for 2.5 hours at ambient temperature. Test compounds (20 µL) were added to the wells at various concentrations (≤10 µM, 1 to 3 dilutions) in a NECA base solution and incubated for 90 minutes in the presence of the S1P1R agonist {4-((4-phenyl-5-trifluoromethyl-2-thienyl)methoxy)benzyl}-3-azetidinecarboxylic acid (10 nM). The NECA-base solution contained Dulbecco's phosphate-buffered saline (Invitrogen, 14190-136), 2.5% DMSO (Fluka, 41648), 25 µM Ro 20-1724 (Sigma, B8279), and 500 nM NECA).

A HEK293 cell line that expresses the human CB1 receptor and a CNG channel (BD Biosciences, 80500-211) were used as the counterscreen. CB1R cells were stimulated with 500 nM NECA and with CB1R agonist CP-55940 (10 nM) causing a CB1R-specific decrease of NECA-induced elevated levels of cAMP. Specific S1P1R antagonists will have no effect on CB1R activation.

Assay plates were read with a PerkinElmer EnVision reader (Excitation 350 nm, Emission 590 nm) at time T=0 minutes, before compound addition and at time T=90 minutes. The signal was calculated as the ratio T90/T0. Data was analyzed in ActivityBase XE and graphs showing log of compound concentration (X-axis) vs. % activity (Y-axis) were generated for $IC_{50}$ determinations. Percent activity was calculated with the following formula: (Signal−Agonist Control Signal)/(NECA Control Signal−Agonist Control Signal)× 100.

Suitable S1P1R and CB agonists for use in the S1P1R antagonist assay are known in the art. For example, fingolimod or 2-amino-2-(4-nonylphenethyl)propane-1,3-diol, is a known S1P1R agonist. Methods for making and using fingolimod are found in European Patent Appliation EP0627406. 1-{4-((4-Phenyl-5-trifluoromethyl-2-thienyl)methoxy)benzyl}-3-azetidinecarboxylic acid is a known S1P1R agonist and methods for making and using it are found in WO 03/062252. Suitable CB1R agonists are known in the art, for example, WIN55,212-2 and CP-55940 are commerically available (Sigma, W102 and C1112, respectively).

The S1P1R antagonists of this invention were assayed by the methods described in Example 1 and were found to inhibit the S1P1R agonist elicited effects at $IC_{50}$ and/or $EC_{50}$ values ranging from about 1 nM to about 2 ηM concentrations. In contrast, the S1P1R antagonists of this invention were found not to inhibit CB1 R elicited effects. The activities the S1P1R antagonists of this invention are indicated in Table 2, wherein the letters A, B and C denote, respectively, that a compound has an $EC_{50}$ or $IC_{50}$ value of (i) less than or equal to 0.3 µM, (ii) greater than 0.3 µM but less than or equal to 1 µM, and (iii) greater than 1 µM.

TABLE 2

| | | | | | | | | | | | | | | |
|---|---|---|---|---|---|---|---|---|---|---|---|---|---|---|
| 1 | A | 2 | A | 3 | A | 4 | A | 5 | A | 6 | A | 7 | A | 8 A |
| 9 | A | 10 | A | 11 | A | 12 | B | 13 | C | 14 | C | 15 | C | 16 C |
| 17 | C | 18 | C | 19 | C | 20 | C | 21 | C | 22 | B | 23 | C | 24 C |
| 25 | C | 26 | C | 27 | C | 28 | C | 29 | C | 30 | A | 31 | A | 32 A |
| 33 | A | 34 | A | 35 | A | 36 | A | 37 | A | 38 | A | 39 | A | 40 A |
| 41 | C | 42 | C | 43 | C | 44 | C | 45 | C | 46 | C | 47 | C | 48 A |
| 49 | A | 50 | A | 51 | A | 52 | A | 53 | A | 54 | A | 55 | A | 56 A |
| 57 | A | 58 | A | 59 | B | 60 | C | 61 | A | 62 | A | 63 | C | 64 A |
| 65 | A | 66 | A | 67 | A | 68 | A | 69 | A | 70 | A | 71 | A | 72 A |
| 73 | A | 74 | A | 75 | A | 76 | A | 77 | B | 78 | B | 79 | A | 80 B |
| 81 | C | 82 | A | 83 | A | 84 | A | 85 | A | 86 | A | 87 | A | 88 A |
| 89 | A | 90 | A | 91 | A | 92 | A | 93 | A | 94 | A | 95 | A | 96 A |
| 97 | A | 98 | A | 99 | A | 100 | A | 101 | C | 102 | C | 103 | C | 104 C |
| 105 | C | 106 | A | 107 | A | 108 | A | 109 | C | 110 | C | 111 | C | 112 C |
| 113 | C | 114 | C | 115 | A | 116 | A | 117 | A | 118 | A | 119 | A | 120 A |
| 121 | A | 122 | A | 123 | A | 124 | A | 125 | A | 126 | C | 127 | C | 128 C |
| 129 | A | 130 | A | 131 | A | 132 | A | 133 | A | 134 | A | 135 | A | 136 A |
| 137 | A | 138 | A | 139 | A | 140 | A | 141 | A | 142 | A | 143 | A | 144 A |
| 145 | A | 146 | A | 147 | A | 148 | A | 149 | A | 150 | A | 151 | A | 152 A |
| 153 | A | 154 | A | 155 | A | 156 | A | 157 | A | 158 | A | 159 | A | 160 A |
| 161 | A | 162 | A | 163 | A | 164 | A | 165 | A | 166 | A | 167 | A | 168 A |
| 169 | A | 170 | A | 171 | A | 172 | A | 173 | A | 174 | A | 175 | A | 176 A |
| 177 | A | 178 | A | 179 | A | 180 | A | 181 | A | 182 | A | 183 | B | 184 B |
| 185 | A | 186 | B | 187 | B | 188 | B | 189 | B | 190 | B | 191 | B | 192 B |
| 193 | B | 194 | B | 195 | A | 196 | B | 197 | B | 198 | B | 199 | B | 200 A |
| 201 | A | 202 | A | 203 | A | 204 | B | 205 | A | 206 | B | 207 | A | 208 B |
| 209 | B | 210 | A | 211 | A | 212 | A | 213 | A | 214 | A | 215 | B | 216 B |
| 217 | B | 218 | B | 219 | B | 220 | B | 221 | B | 222 | B | 223 | B | 224 B |
| 225 | B | 226 | A | 227 | A | 228 | A | 229 | B | 230 | B | 231 | B | 232 C |
| 233 | B | 234 | B | 235 | B | 236 | B | 237 | B | 238 | B | 239 | A | 240 B |
| 241 | B | 242 | B | 243 | A | 244 | B | 245 | A | 246 | A | 247 | A | 248 B |
| 249 | B | 250 | A | 251 | A | 252 | A | 253 | A | 254 | A | 255 | B | 256 A |
| 257 | B | 258 | A | 259 | B | 260 | B | 261 | B | 262 | B | 263 | A | 264 A |
| 265 | A | 266 | B | 267 | A | 268 | A | 269 | C | 270 | C | 271 | C | 272 C |
| 273 | C | 274 | C | 275 | C | 276 | C | 277 | A | 278 | C | 279 | C | 280 C |
| 281 | C | 282 | C | 283 | C | 284 | C | 285 | C | 286 | C | 287 | C | 288 C |
| 289 | C | 290 | C | 291 | C | 292 | C | 293 | C | 294 | C | 295 | C | 296 C |
| 297 | C | 298 | C | 299 | C | 300 | B | 301 | B | 302 | C | 303 | B | 304 C |
| 305 | A | 306 | C | 307 | A | 308 | C | 309 | C | 310 | C | 311 | C | 312 C |
| 313 | B | 314 | C | 315 | C | 316 | C | 317 | C | 318 | C | 319 | C | 320 C |
| 321 | C | 322 | C | 323 | B | 324 | C | 325 | B | 326 | A | 327 | B | 328 C |
| 329 | C | 330 | C | 331 | C | 332 | B | 333 | C | 334 | C | 335 | C | 336 A |
| 337 | C | 338 | C | 339 | C | 340 | B | 341 | C | 342 | C | 343 | C | 344 C |
| 345 | C | 346 | B | 347 | C | 348 | B | 349 | B | 350 | C | 351 | C | 352 C |
| 353 | C | 354 | B | 355 | B | 356 | B | 357 | B | 358 | C | 359 | C | 360 C |
| 361 | C | 362 | B | 363 | C | 364 | C | 365 | C | 366 | C | 367 | C | 368 C |
| 369 | C | 370 | B | 371 | C | 372 | C | 373 | C | 374 | C | 375 | C | 376 C |
| 377 | B | 378 | B | 379 | C | 380 | C | 381 | C | 382 | C | 383 | C | 384 C |
| 385 | C | 386 | C | 387 | C | 388 | C | 389 | B | 390 | C | 391 | C | 392 B |
| 393 | C | 394 | C | 395 | C | 396 | C | 397 | B | 398 | C | 399 | C | 400 C |
| 401 | C | 402 | C | 403 | B | | | | | | | | | |

EXAMPLE 2

Figure 1B:
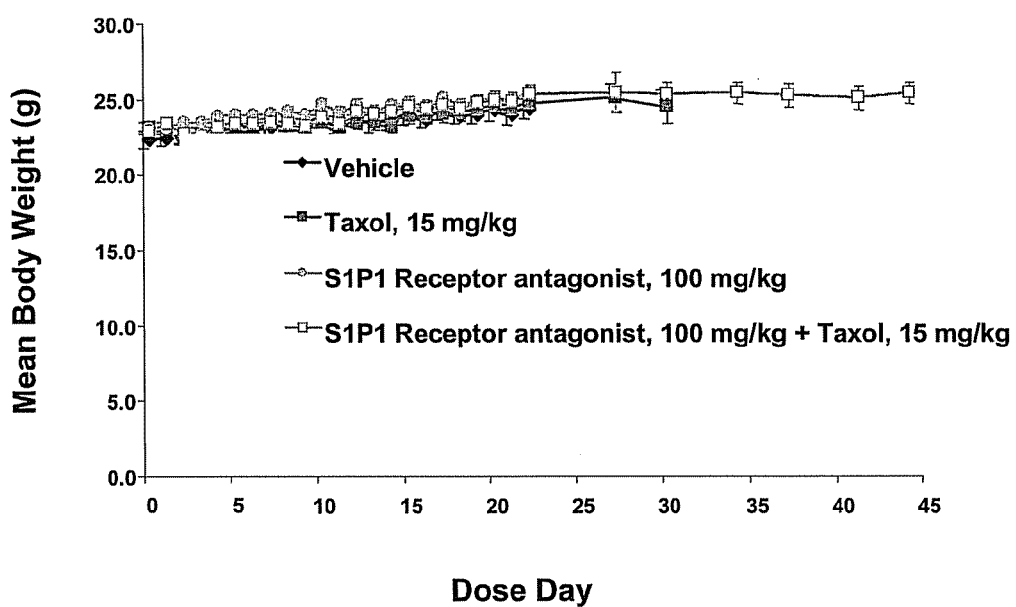
FIG. 1*b* demonstrates that all animals used in the study did not exhibit any toxic effects from the treatments.

Synergistic Effects of an S1P1R Receptor Antagonist and a Taxane Compound in an in Vivo Non-Small Cell Lung Carcinoma Animal Model In this experiment, a maximum efficacy dose of an S1P1R receptor antagonist was used with an optimal dose of paclitaxel (MP Biomedicals cat #193532). Compound #2, 50, 52 or 75 from Table 1 were used in these experiments and a representative result is shown in FIG. 1. Nude mice (athymic female mice, Taconic Farms, Inc., 10 animals per group) were inoculated subcutaneously with human non-small cell lung carcinoma cells (ATCC #HTB-56) ($1 \times 10^6$ cells per animal). After tumors were allowed to grow for 9 days, one group of animals was treated with a S1P1R receptor antagonist (100 mg/kg qd po). A second group of animals was treated with paclitaxel at a dose of 15 mg/kg q3d ip. A third group of animals was treated with a S1P1R receptor antagonist and paclitaxel using the same dose and schedule used for the individual agents. A fourth control group was treated with the vehicles used for each agent individually. Tumor dimensions were measured by calipers and then converted to weight using the formula: tumor weight (mg)=[tumor volume=length (mm)×width (mm$^2$)]/2. Animals were also monitored for weight loss as an indicator of signs of toxicity. The S1P1R receptor antagonist was formulated in a compostion containing 10% NMP (n-methyl pyrrolidone)+90% corn oil. The taxol was formulated in a composition containing 12.5% Cremophor/12.5% ethanol/50% water.

Results of an experiment with one of the S1P1R receptor antagonists are shown in FIG. 1. Cells were inoculated subcutaneously on day 0 and allowed to grow for 9 days. At time of first treatment, tumors averaged approximately 100 mgs. Dosing continued until day 31 and tumors from some animals in each of the four groups were measured and averaged. Some animals in the paclitaxel group and the combined treatment group were monitored after treatment stopped for a period of time. At the end of the treatment period, tumors in the control group of animals grew rapidly to an average size of about 1500 mgs. After treatment the tumors in animals dosed with an S1P1R receptor antagonist averaged about 1150 mgs and tumors in animals treated with paclitaxel averaged about 550 mgs. Tumors in animals treated with both agents exhibited a 52% regression after treatment, averaging approximately 40 mgs. There was no evidence of toxicity in these animals. These data indicate that treatment with 51P1R receptor antagonists and paclitaxel had an unexpectedly superior (e.g. synergistic) anti-tumor effect.

EXAMPLE 3

Figure 2A:
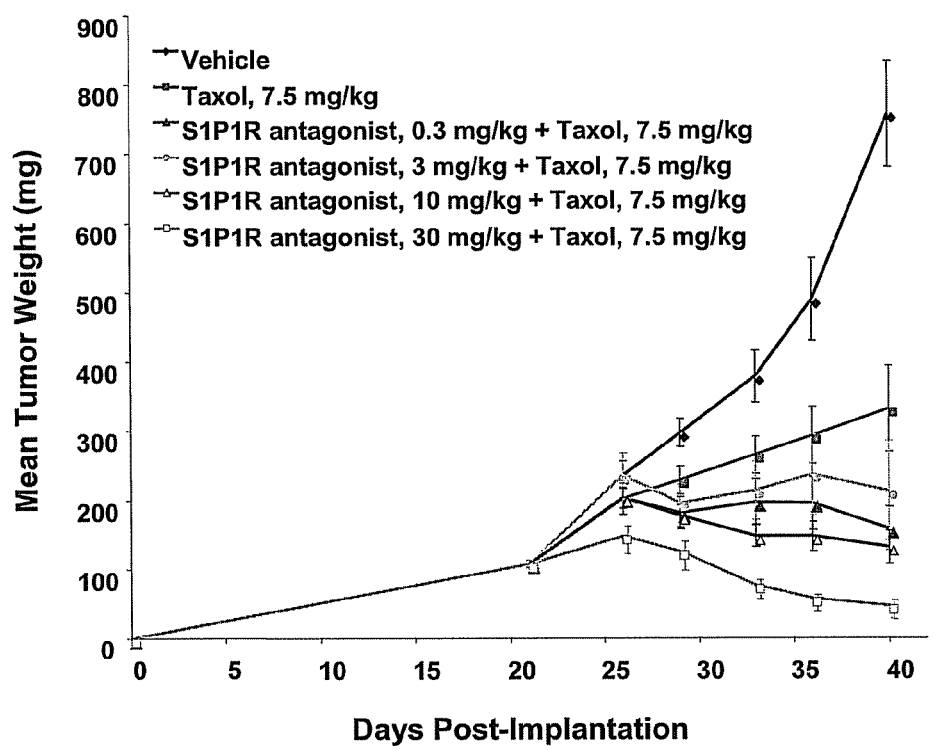
FIG. 2*a* is a graph comparing the anti-tumor activity of a control, and the combination of varying concetrations of an S1P1R receptor antagonist and paclitaxel, against human breast cancer xenographs in NUDE mice (S1P1R antagonist+taxol in MDA-MB-231 XN Model).
Figure 2B:
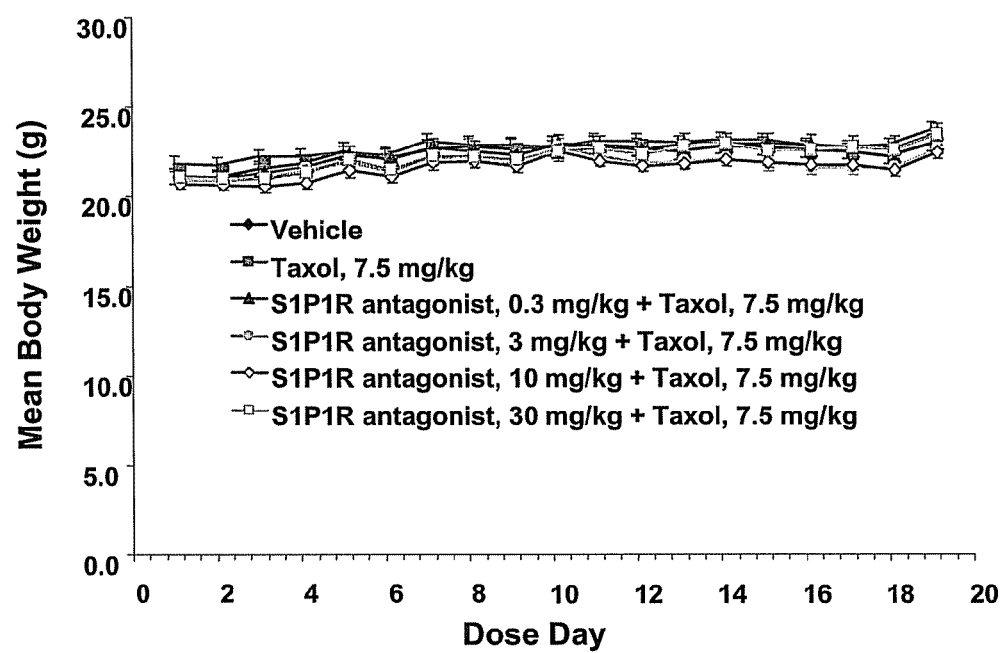
FIG. 2*b* demonstrates that all animals used in the study did not exhibit any toxic effects from the treatments

Synergistic Effects of an S1P1R Receptor Antagonist and a Taxane Compound in an in Vivo Breast Cancer Animal Model In this experiment, 4 different doses of an S1P1R receptor antagonist, 0.3 mgs/kg, 3 mgs/kg, 10 mgs/kg or 30 mgs/kg was used with an optimal dose of paclitaxel (MP Biomedicals cat #193532). Compound #2, 50, 52 or 75 were used in these experiments and a representative example is shown in FIG. 2. Nude mice (athymic female mice, Taconic Farms, Inc., 10 animals per group) were inoculated subcutaneously with human MDA-MB-231 cells breast cancer cells (ATCC #HTB-26) ($1 \times 10^6$ cells per animal). After tumors were allowed to grow for 21 days, one group of animals was treated with paclitaxel at a dose of 7.5 mg/kg q3d ip. Four groups of animals were treated with a specific concentration of S1P1R receptor antagonist and the same concentration of paclitaxel using the same schedule used for the individual paclitaxel group. Finally, a control group was treated with the vehicles used for each agent individually. Tumor dimensions were measured by calipers and then converted to weight using the formula: tumor weight (mg)=[tumor volume=length (mm)×width (mm$^2$)]/2. Animals were also monitored for weight loss as an indicator of signs of toxicity. The S1P1R Receptor antagonist was formulated in a compostion containing 10% NMP (n-methyl pyrrolidone)+90% corn oil. The taxol was formulated in a composition containing 12.5% Cremophor/12.5% ethanol/50% water.

Results of an experiment with one of the S1P1R receptor antagonists are shown in FIG. 2. Cells were inoculated subcutaneously on day 0 and allowed to grow for 21 days. At time of first treatment, tumors averaged 100 mgs. Dosing continued for 19 days and tumors in each of the four groups were measured and averaged. At the end of the 19 day treatment period, tumors in the control group of animals grew rapidly. After 19 days of treatment the tumors in animals dosed with paclitaxel averaged about 325 mgs. Tumors in animals treated with both agents exhibited a decreasing amount of tumor growth corresponding to the increasing amount of S1P1R receptor antagonist used in combination with paclitaxel. Animals treated with the highest dose of an S1P1R receptor antagonist exhibited tumor regression at the end of treatment, tumor weight less than 100 mgs. There was no evidence of toxicity in these animals. These data indicate that treatment with S1P1R receptor antagonists and paclitaxel had an unexpectedly superior (e.g. synergistic) anti-tumor effect.

EXAMPLE 4

Synergistic Effects of an 51P1R Receptor Antagonist and a Vinca Compound in an in Vivo Breast Cancer Animal Model In this experiment, a maximum efficacy dose of an S1P1R receptor antagonist was used with doses of vincristine (Yes Pharma, Ltd., CAS#2068-78-2, Lot#80702). Compound #2, 50, 52, or 75 were used in these experiments. Nude mice (athymic female mice, Taconic Farms, Inc., 10 animals per group) were inoculated subcutaneously with human MDA-MB-231 breast cancer cells (ATCC# HTB-26) ($1\times10^6$ cells per animal). After tumors were allowed to grow for 19 days, two groups of animals were treated with vincristine at doses of 0.1 or 1 mg/kg q3d iv. One group of animals was treated with a specific concentration of S1P1R receptor antagonist. Two groups of animals were treated with a specific dose of S1P1R receptor antagonist and the same dose of vincristine using the same schedule used for the individual vincristine groups. Finally, a control group was treated with the vehicles used for each agent individually. Tumor dimensions were measured by calipers and then converted to weight using the formula: tumor weight (mg)=[tumor volume=length (mm)×width$^2$(mm$^2$)]/2. Animals were also monitored for weight loss as an indicator of signs of toxicity. The S1P1R receptor antagonist was formulated in a composition containing 10%NMP (n-methyl pyrrolidone)+90% corn oil. The vincristine was formulated in normal saline (0.9% NaCl).

Results of an experiment with one of the S1P1R receptor antagonists and vincristine are as follows. Cells were inoculated subcutaneously on day 0 and allowed to grow for 19 days. At time of first treatment, tumors averaged 95 mgs. Dosing continued for 8 cycles (q3d) and tumors in each of the six groups were measured and averaged. After 8 cycles of treatment, the tumors in animals dosed with 0.1 mg/kg and 1 mg/kg vincristine averaged 659 and 26 mg, respectively. Tumors in animals treated with the S1P1R receptor antagonist and 0.1 mg/kg or 1 mg/kg vincristine averaged 260 and 5 mg, respectively, and represents 72% and 95% regression after treatment. There was no evidence of toxicity in these animals. These data indicate that treatment with S1P1R receptor antagonists and vincristine had an unexpectedly superior (eg, synergistic) anti-tumor effect.

EXPERIMENT 5

Synergistic Effects of an S1P1R Receptor Antagonist and a Taxane Compound in an in Vivo Breast Cancer Animal Model In this experiment, a maximum efficacy dose of an S1P1R receptor antagonist was used with an optimal dose of docetaxol (Haorui Pharma Chem, Inc; CAS#114977-28-5). Compound #2, 50, 52, or 75 were used in these experiments. Nude mice (athymic female mice, Taconic Farms, Inc., 10 animals per group) were inoculated subcutaneously with human MDA-MB-231 breast cancer cells (ATCC#HTB-26) ($1\times10^6$ cells per animal). After tumors were allowed to grow for 17 days, one group of animals was treated with docetaxel at a dose of 7 mg/kg q3d ip. One group of animals was treated with a specific dose of S1P1R receptor antagonist and the same dose of docetaxel using the same schedule used for the individual docetaxel group. Finally, a control group was treated with the vehicles used for each agent individually. Tumor dimensions were measured by calipers and then converted to weight using the formula: tumor weight (mg)=[tumor volume=length (mm)×width$^2$(mm$^2$)]/2. Animals were also monitored for weight loss as an indicator of signs of toxicity. The S1P1R receptor antagonist was formulated in a composition containing 10% NMP (n-methyl pyrrolidone)+90% corn oil. The docetaxel was formulated in a composition containing 12.5% Cremephor, 12.5% ethanol, and 75% saline.

Results of an experiment with one of the 51P1R receptor antagonists and doxetaxel are as follows. Cells were inoculated subcutaneously on day 0 and allowed to grow for 17 days. At time of first treatment, tumors averaged 96 mgs. Dosing continued for 7 cycles (q3d) and tumors in each of the three groups were measured and averaged. After 7 cycles of treatment, the tumors in animals dosed with docetaxel averaged about 310 mgs. Tumors in animals treated with both agents averaged 186 mgs. There was no evidence of toxicity in these animals. These data indicate that treatment with S1P1R receptor antagonists and docetaxel had an unexpectedly superior (eg, synergistic) anti-tumor effect.

What is claimed is:

1. A pharmaceutical composition comprising a synergistic combination of at least one S1P1R receptor antagonist and at least one antimicrotubule agent, wherein the S1P1R receptor antagonist is selected from the group of compounds consisting of
   1) (S)-2-(2-(1H-imidazol-5-yl)acetamido)-5-phenyl-N-(4-phenoxyphenyl)pentanamide;
   2) (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide;
   3) (2S,4R)-5-(2-(1H-1,2,3-triazol-1-yl)acetyl)-N-(4-(4-fluorophenoxy)phenyl)-4-(4-methylbenzyl)pyrrolidine-2-carboxamide;
   4) (2S,4R)-5-(2-(1H-1,2,4-triazol-1-yl)acetyl)-N-(4-(4-fluorophenoxy)phenyl)-4-(4-methylbenzyl)pyrrolidine-2-carboxamide;
   5) (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide;
   6) (2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide;
   7) (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide;
   8) (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide;
   9) (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide;
   10) (2S,4R)-1-(2-(1H-1,2,3-triazol-1-yl)acetyl)-4-benzyl-N-(4-(4-fluorophenoxy)phenyl)pyrrolidine-2-carboxamide;
   11) (2S,4R)-1-(2-(5-amino-3-(trifluoromethyl)-1H-1,2,4-triazol-1-yl)acetyl)-4-benzyl-N-(4-(4-fluorophenoxy)phenyl)pyrrolidine-2-carboxamide;

12) 1-((2S,4R)-4-benzyl-2-(5-(4-fluorophenoxy)-1H-benzo[d]imidazol-2-yl)pyrrolidin-1-yl)-2-(1H-1,2,4-triazol-1-yl)ethanone;
13) 3-(benzyloxy)-2-((S)-3-hydroxy-3-phenylpropanamido)-N-(4-phenoxyphenyl)propanamide;
14) 3-(benzyloxy)-2-(2-(furan-2-yl)-2-oxoacetamido)-N-(4-phenoxyphenyl)propanamide;
15) N-(3-(benzyloxy)-1-oxo-1-(4-phenoxyphenylamino)propan-2-yl)-6-(2,5-dioxo-2,5-dihydro-1H-pyrrol-1-yl)hexanamide;
16) 3-(benzyloxy)-2-(2-hydroxy-2-(2-hydroxyphenyl)acetamido)-N-(4-phenoxyphenyl)propanamide;
17) 4-(3-(benzyloxy)-1-oxo-1-(4-phenoxyphenylamino)propan-2-ylcarbamoyl)phenyl acetate;
18) N-(3-(benzyloxy)-1-oxo-1-(4-phenoxyphenylamino)propan-2-yl)-5-methylnicotinamide;
19) 3-(benzyloxy)-2-(2-(methylsulfonyl)acetamido)-N-(4-phenoxyphenyl)propanamide;
20) N-(3-(benzyloxy)-1-oxo-1-(4-phenoxyphenylamino)propan-2-yl)-1H-indole-5-carboxamide;
21) N-(3-(benzyloxy)-1-oxo-1-(4-phenoxyphenylamino)propan-2-yl)-2-bromo-5-fluorobenzamide;
22) N-(3-(benzyloxy)-1-oxo-1-(4-phenoxyphenylamino)propan-2-yl)-3,3,3-trifluoropropanamide;
23) (2R)-N-(3-(benzyloxy)-1-oxo-1-(4-phenoxyphenylamino)propan-2-yl)tetrahydrofuran-2-carboxamide;
24) 3-(benzyloxy)-2-((R)-2-(2-chlorophenyl)-2-hydroxyacetamido)-N-(4-phenoxyphenyl)propanamide;
25) (2S)-1-(3-(benzyloxy)-1-oxo-1-(4-phenoxyphenylamino)propan-2-ylamino)-1-oxopropan-2-yl acetate;
26) 3-(benzyloxy)-2-(2-(2-hydroxyphenoxy)acetamido)-N-(4-phenoxyphenyl)propanamide;
27) 3-(benzyloxy)-2-((R)-2-hydroxy-3-phenylpropanamido)-N-(4-phenoxyphenyl)propanamide;
28) N-(3-(benzyloxy)-1-oxo-1-(4-phenoxyphenylamino)propan-2-yl)-2-(methylthio)nicotinamide;
29) N-(3-(benzyloxy)-1-oxo-1-(4-phenoxyphenylamino)propan-2-yl)-1-(4-chlorobenzyl)-5-oxopyrrolidine-3-carboxamide;
30) (2S,4R)-4-benzyl-N-(4-(4-fluorophenoxy)phenyl)-1-(2-((1-methyl-1H-indol-2-yl)methylamino)acetyl)pyrrolidine-2-carboxamide;
31) (2S,4R)-4-benzyl-N-(4-(4-fluorophenoxy)phenyl)-1-(2-phenylacetyl)pyrrolidine-2-carboxamide;
32) (2S,4R)-4-benzyl-N-(4-(4-fluorophenoxy)phenyl)-1-(2-(3-methylisoxazol-5-yl)acetyl)pyrrolidine-2-carboxamide;
33) (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide;
34) 34,(2S,4R)-4-benzyl-N-(4-(4-fluorophenoxy)phenyl)-1-(3,3,3-trifluoropropanoyl)pyrrolidine-2-carboxamide;
35) (2S,4R)-4-benzyl-1-(2-(4-(dimethylamino)phenyl)acetyl)-N-(4-(4-fluorophenoxy)phenyl)pyrrolidine-2-carboxamide;
36) (2S,4R)-4-benzyl-N-(4-(4-fluorophenoxy)phenyl)-1-(tetrahydrofuran-3-carbonyl)pyrrolidine-2-carboxamide;
37) (2S,4R)-4-benzyl-N-(4-(4-fluorophenoxy)phenyl)-1-(2-(2-methyl-1H-indol-3-yl )acetyl)pyrrolidine-2-carboxamide;
38) (2S,4R)-4-benzyl-1-(2-butoxyacetyl)-N-(4-(4-fluorophenoxy)phenyl)pyrrolidine-2-carboxamide;
39) (2S,4R)-4-benzyl-N-(4-(4-fluorophenoxy)phenyl)-1-((S)-5-oxotetrahydrofuran-2-carbonyl)pyrrolidine-2-carboxamide;
40) (2S,4R)-4-benzyl-N-(4-(4-fluorophenoxy)phenyl)-1-((R)-2-hydroxy-2-phenylacetyl)pyrrolidine-2-carboxamide;
41) (S)-3-(benzyloxy)-N-(4-(4-fluorophenoxy)phenyl)-2-(2-(4-(pyrimidin-2-yl)piperazin-1-yl)acetamido)propanamide;
42) (S)-3-(benzyloxy)-N-(4-(4-fluorophenoxy)phenyl)-2-(2-(4-(3-methoxyphenyl)piperazin-1-yl)acetamido) propanamide;
43) (S)-3-(benzyloxy)-N-(4-(4-fluorophenoxy)phenyl)-2-(2-(4-(pyrrolidin-1-yl)piperidin-1-yl)acetamido)propanamide;
44) (S)-3-(4-fluorobenzyloxy)-N-(4-(4-fluorophenoxy)phenyl)-2-(2-(2-phenyloxazol-4-yl)acetamido)propanamide;
45) (2S)-3-(benzyloxy)-N-(4-(4-fluorophenoxy)phenyl)-2-(2-(octahydroquinolin-1(2H)-yl)acetamido)propanamide;
46) (2S)-3-(benzyloxy)-N-(4-(4-fluorophenoxy)phenyl)-2-(2-(3-methylpiperidin-1-yl)acetamido)propanamide;
47) (S)-2-(2-(1H-imidazol-5-yl)acetamido)-3-(benzyloxy)-N-(4-(4-fluorophenoxy)-2-methylphenyl)propanamide;
48) (2S,4R)-1-(2-(2H-1,2,3-triazol-2-yl)acetyl)-N-(4-(4-fluorophenoxy)phenyl)-4-(2-methylbenzyl)pyrrolidine-2-carboxamide;
49) (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide;
50) (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide;
51) (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide;
52) (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide;
53) (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide;
54) (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide;
55) (2S,4R)-1-(2-(1H-1,2,4-triazol-1-yl)acetyl)-N-(4-(4-fluorophenoxy)phenyl)-4-(2-methylbenzyl)pyrrolidine-2-carboxamide;
56) (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide;
57) (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide;
58) (2S,4R)-1-(2-(2H-1,2,3-triazol-2-yl)acetyl)-4-benzyl-N-(4-(4-fluorophenoxy)phenyl)pyrrolidine-2-carboxamide;
59) (R)-N-(2-(benzyloxy)-1-(5-(4-fluorophenoxy)-1H-benzo[d]imidazol-2-yl)ethyl)-2-(1H-imidazol-4-yl)acetamide;
60) (R)-N-(2-(benzyloxy)-1-(5-(4-fluorophenoxy)-1H-benzo[d]imidazol-2-yl)ethyl)acetamide;
61) (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide;
62) (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide;

63) (2S)-3-(benzyloxy)-N-(4-(4-fluorophenoxy)phenyl)-2-(2-(2-methylpyrrolidin-1-yl)acetamido)propanamide;
64) (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide;
65) (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide;
66) (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide;
67) (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide;
68) (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide;
69) (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide;
70) (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide;
71) (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide;
72) (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide;
73) (2S,4R)-1-(2-(1H-1,2,4-triazol-1-yl)acetyl)-N-(4-(4-fluoro-3-methylphenoxy)phenyl)-4-(4-fluorobenzyl)pyrrolidine-2-carboxamide;
74) (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide;
75) (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide;
76) (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide;
77) (2S,4S)-1-(2-(2H-1,2,3-triazol-2-yl)acetyl)-N-(4-(4-fluorophenoxy)phenyl)-4-phenylpyrrolidine-2-carboxamide;
78) (2S,4S)-1-(2-(1H-1,2,4-triazol-1-yl)acetyl)-N-(4-(4-fluorophenoxy)phenyl)-4-phenylpyrrolidine-2-carboxamide;
79) (2S,4R)-1-(2-(1H-1,2,4-triazol-1-yl)acetyl)-4-benzyl-N-(4-(4-chlorophenoxy)phenyl)pyrrolidine-2-carboxamide;
80) (2S,4S)-1-(2-(1H-1,2,4-triazol-1-yl)acetyl)-4-(benzylamino)-N-(4-(4-fluorophenoxy)phenyl)pyrrolidine-2-carboxamide;
81) (S)-3-(benzyloxy)-2-(3-(3-chloro-4-methoxyphenyl)propanamido)-N-(4-(4-fluorophenoxy)phenyl)propanamide;
82) (2S,4R)-4-benzyl-1-(2-(3,4-dihydroisoquinolin-2(1H)-yl)acetyl)-N-(4-(4-fluorophenoxy)phenyl)pyrrolidine-2-carboxamide;
83) (2S,4R)-4-benzyl-N-(4-(4-fluorophenoxy)phenyl)-1-(2-thiomorpholinoacetyl)pyrrolidine-2-carboxamide;
84) (2S,4R)-4-benzyl-N-(4-(4-fluorophenoxy)phenyl)-1-(2-(2,3,6-trifluorophenyl)acetyl)pyrrolidine-2-carboxamide;
85) (2S,4R)-4-benzyl-N-(4-(4-fluorophenoxy)phenyl)-1-(3-(methylthio)propanoyl)pyrrolidine-2-carboxamide;
86) (2S,4R)-4-benzyl-1-(3-ethoxypropanoyl)-N-(4-(4-fluorophenoxy)phenyl)pyrrolidine-2-carboxamide;
87) (2S,4R)-4-benzyl-N-(4-(4-fluorophenoxy)phenyl)-1-(2-(methylsulfonyl)acetyl)pyrrolidine-2-carboxamide;
88) (2S,4R)-4-benzyl-N-(4-(4-fluorophenoxy)phenyl)-1-(2-(2-methoxyethoxy)acetyl)pyrrolidine-2-carboxamide;
89) (2S,4R)-4-benzyl-1-(4-(dimethylamino)-4-oxobutanoyl)-N-(4-(4-fluorophenoxy)phenyl)pyrrolidine-2-carboxamide;
90) (2S,4R)-4-benzyl-N-(4-(4-fluorophenoxy)phenyl)-1-(3-methoxypropanoyl)pyrrolidine-2-carboxamide;
91) (2S,4R)-4-benzyl-N-(4-(4-fluorophenoxy)phenyl)-1-(4-oxo-4-(thien-2-yl)butanoyl)pyrrolidine-2-carboxamide;
92) (2S,4R)-4-benzyl-N-(4-(4-fluorophenoxy)phenyl)-1-(tetrahydrofuran-2-carbonyl)pyrrolidine-2-carboxamide;
93) (2S,4R)-1-((S)-1-acetylpyrrolidine-2-carbonyl)-4-benzyl-N-(4-(4-fluorophenoxy)phenyl)pyrrolidine-2-carboxamide;
94) (2S,4R)-4-benzyl-N-(4-(4-fluorophenoxy)phenyl)-1-(2-(pyrimidin-2-ylthio)acetyl)pyrrolidine-2-carboxamide;
95) (2S,4R)-4-benzyl-1-(2-(2,6-difluorophenyl)acetyl)-N-(4-(4-fluorophenoxy)phenyl)pyrrolidine-2-carboxamide;
96) (2S,4R)-4-benzyl-N-(4-(4-fluorophenoxy)phenyl)-1-(2-(pyridin-4-ylthio)acetyl)pyrrolidine-2-carboxamide;
97) (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide;
98) (2S,4R)-1-(2-(1H-indol-3-yl)acetyl)-4-benzyl-N-(4-(4-fluorophenoxy)phenyl)pyrrolidine-2-carboxamide;
99) (2S,4R)-4-benzyl-N-(4-(4-fluorophenoxy)phenyl)-1-(2-(4-oxo-2-thioxothiazolidin-3-yl)acetyl)pyrrolidine-2-carboxamide;
100) (2S,4R)-4-benzyl-N-(4-(4-fluorophenoxy)phenyl)-1-(2-(4-(2-methoxyethyl)piperazin-1-yl)acetyl)pyrrolidine-2-carboxamide;
101) (S)-3-(benzyloxy)-2-(2-(3-fluoro-4-(trifluoromethyl)phenyl)acetamido)-N-(4-(4-fluorophenoxy)phenyl)propanamide;
102) (S)-3-(benzyloxy)-N-(4-(4-fluorophenoxy)phenyl)-2-(2-(3-(trifluoromethoxy)phenyl)acetamido)propanamide;
103) (S)-tert-butyl 1-(2-((S)-3-(benzyloxy)-1-(4-(4-fluorophenoxy)phenylamino)-1-oxopropan-2-ylamino)-2-oxoethyl)pyrrolidine-2-carboxylate;
104) (S)-N-(3-(benzyloxy)-1-(4-(4-fluorophenoxy)phenylamino)-1-oxopropan-2-yl)-5-phenylpentanamide;
105) (S)-3-(benzyloxy)-N-(4-(4-fluorophenoxy)phenyl)-2-(2-(4-morpholinopiperidin-1-yl)acetamido)propanamide;
106) (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide;
107) (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide;
108) (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide;
109) (2S)-3-(benzyloxy)-2-(2-(3-(diethylamino)pyrrolidin-1-yl)acetamido)-N-(4-(4-fluorophenoxy)phenyl)propanamide;

110) (2S)-3-(benzyloxy)-N-(4-(4-fluorophenoxy)phenyl)-2-(2-(4-((tetrahydrofuran-2-yl)methyl)piperazin-1-yl)acetamido)propanamide;
111) (S)-3-(benzyloxy)-N-(4-(4-fluorophenoxy)phenyl)-2-(2-(4-isopropylpiperazin-1-yl)acetamido)propanamide;
112) (S)-3-(benzyloxy)-N-(4-(4-fluorophenoxy)phenyl)-2-(2-(4-(3-(trifluoromethyl)pyridin-2-yl)piperazin-1-yl)acetamido)propanamide;
113) (2S)-3-(benzyloxy)-N-(4-(4-fluorophenoxy)phenyl)-2-(2-(2(((S)-1-methylpyrrolidin-2-yl)methyl)piperidin-1-yl)acetamido)propanamide,
114) (S)-3-(benzyloxy)-2-(2-(4-ethylpiperazin-1-yl)acetamido)-N-(4-(4-fluorophenoxy)phenyl)propanamide;
115) (2S,4R)-1-(2-(4-acetylpiperazin-1-yl)acetyl)-4-benzyl-N-(4-(4-fluorophenoxy)phenyl)pyrrolidine-2-carboxamide;
116) (2S,4R)-4-benzyl-N-(4-(4-fluorophenoxy)phenyl)-1-(2-morpholinoacetyl)pyrrolidine-2-carboxamide;
117) (2S,4R)-4-benzyl-N-(4-(4-fluorophenoxy)phenyl)-1-(2-(thien-2-yl)acetyl)pyrrolidine-2-carboxamide;
118) (2S,4R)-4-benzyl-N-(4-(4-fluorophenoxy)phenyl)-1-(3-hydroxybutanoyl)pyrrolidine-2-carboxamide;
119) (2S,4R)-4-benzyl-1-(2-(2,6-dichlorophenyl)acetyl)-N-(4-(4-fluorophenoxy)phenyl)pyrrolidine-2-carboxamide;
120) (2S,4R)-4-benzyl-N-(4-(4-fluorophenoxy)phenyl)-1-(2-hydroxyacetyl)pyrrolidine-2-carboxamide;
121) (2S,4R)-4-benzyl-1-(2-ethoxyacetyl)-N-(4-(4-fluorophenoxy)phenyl)pyrrolidine-2-carboxamide;
122) (2S,4R)-4-benzyl-N-(4-(4-fluorophenoxy)phenyl)-1-(2-methoxyacetyl)pyrrolidine-2-carboxamide;
123) (2S,4R)-4-benzyl-N-(4-(4-fluorophenoxy)phenyl)-1-(4-oxopentanoyl)pyrrolidine-2-carboxamide;
124) (2S,4R)-4-benzyl-N-(4-(4-fluorophenoxy)phenyl)-1-(4-oxo-4-phenylbutanoyl)pyrrolidine-2-carboxamide;
125) methyl 4-((2S,4R)-4-benzyl-2-(4-(4-fluorophenoxy)phenylcarbamoyl)pyrrolidin-1-yl)-4-oxobutanoate;
126) (S)-3-(benzyloxy)-N-(4-(4-fluorophenoxy)phenyl)-2-(2-(4-(pyridin-2-yl)piperazin-1-yl)acetamido)propanamide;
127) (S)-3-(benzyloxy)-N-(4-(4-fluorophenoxy)phenyl)-2-(2-(4-(2-fluorophenyl)piperazin-1-yl)acetamido)propanamide;
128) (S)-2-2-(azepan-1-yl)acetamido)-3-(benzyloxy)-N-(4-(4-fluorophenoxy)phenyl)propanamide;
129) (2S,4R)-4-benzyl-1-(2-cyanoacetyl)-N-(4-(4-fluorophenoxy)phenyl)pyrrolidine-2-carboxamide;
130) (S)-3-(benzyloxy)-N-(4-(4-fluorophenoxy)phenyl)-2-(2-(4-methylpiperidin-1-yl)acetamido))propanamide;
131) (S)-2-(2-(1H-imidazol-5-yl)acetamido)-3-benzyloxy-N-(4-(4-fluorophenoxy)phenyl)propanamide;
132) (S)-2-(2-(1H-imidazol-5-yl)acetamido)-3-(4-fluorobenzyloxy)-N-(4-(4-chlorophenoxy)phenyl)propanamide;
133) (S)-2-(2-(1H-imidazol-5-yl)acetamido)-3-(4-fluorobenzyloxy)-N-(4-(4-fluorophenoxy)phenyl)propanamide;
134) (S)-2-(2-(1H-imidazol-1-yl)acetamido)-3-benzyloxy-N-(4-(4-fluorophenoxy)phenyl)propanamide;
135) (S)-2-(2-(1H-1,2,4-triazol-1-yl)acetamido)-3-(4-fluorobenzyloxy)-N-(4-(4-fluorophenoxy)phenyl)propanamide;
136) (S)-3-(benzyloxy)-2-(2-chloroacetamido)-N-(4-(4-fluorophenoxy)phenyl)propanamide;
137) (S)-2-(2-(1H-imidazol-5-yl)acetamido)-5-phenyl-N-(4-(4-fluorophenoxy)phenyl)pentanamide;
138) (S)-2-(2-(2H-1,2,3-triazol-2-yl)acetamido)-3-(benzyloxy)-N-(4-(4-fluorophenoxy)phenyl)propanamide;
139) (S)-2-(2-(1H-1,2,4-triazol-1-yl)acetamido)-N-(4-(4-fluorophenoxy)phenyl)-3-(2-(trifluoromethoxy)benzyloxy)propanamide;
140) (2S,4R)-1-(2-(1H-1,2,4-triazol-1-yl)acetyl)-4-benzyl-N-(4-(4-fluorophenoxy)phenyl)pyrrolidine-2-carboxamide;
141) (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide;
142) 2-(2-(1H-imidazol-5-yl)acetamido)-3-benzyloxy-N-(4-phenoxyphenyl)propanamide;
143) (S)-2-(2-(1H-imidazol-5-yl)acetamido)-3-benzyloxy-N-(4-phenoxyphenyl)propanamide;
144) (S)-2-(2-(1H-tetrazol-1-yl)acetamido)-3-benzyloxy-N-(4-phenoxyphenyl)propanamide;
145) (S)-2-(2-(1H-imidazol-5-yl)acetamido)-3-benzyloxy-N-(4-(4-chlorophenoxy)phenyl)propanamide;
146) (S)-2-(2-(1H-1,2,4-triazol-1-yl)acetamido)-3-(benzyloxy)-N-(4-phenoxyphenyl)propanamide;
147) (S)-2-(2-(1H-imidazol-4-yl)acetamido)-3-(benzyloxy)-N-(3-chloro-4-phenoxyphenyl)propanamide;
148) (S)-2-(2-(1H-imidazol-4-yl)acetamido)-3-(benzyloxy)-N-(4-(3-chlorophenoxy)phenyl)propanamide;
149) (S)-2-(2-(1H-1,2,4-triazol-1-yl)acetamido)-3-benzyloxy-N-(4-(4-fluorophenoxy)phenyl)propanamide;
150) (S)-3-(benzyloxy)-2-(2-(3,5-dimethylisoxazol-4-yl)acetamido)-N-(4-(4-fluorophenoxy)phenyl)propanamide;
151) (S)-2-(2-(1H-benzo [d][1,2,3]triazol-1-yl)acetamido)-3-(benzyloxy)-N-(4-(4-fluorophenoxy)phenyl) propanamide;
152) (S)-3-(benzyloxy)-2-(2-(3,5-dimethyl-1H-pyrazol-4-yl)acetamido)-N-(4-(4-fluorophenoxy)phenyl)propanamide;
153) (S)-3-(benzyloxy)-N-(4-(4-fluorophenoxy)phenyl)-2-(2-(4-methyl-1H-1,2,3-triazol-1-yl)acetamido)propanamide;
154) (S)-2-(2-(1H-imidazol-4-yl)acetamido)-3-(benzyloxy)-N-(3-chloro-4-(4-chlorophenoxy)phenyl)propanamide;
155) (S)-3-(benzyloxy)-N-(4-(4-fluorophenoxy)phenyl)-2-(2-morpholinoacetamido)propanamide;
156) (S)-2-(2-(1H-imidazol-4-yl)acetamido)-3-(benzyloxy)-N-(4-(5-bromothiazol-2-yloxy)phenyl)propanamide;
157) (S)-2-(2-(1H-imidazol-5-yl)acetamido)-N-(4-(4-chlorophenoxy)phenyl)-4-phenylbutanamide;
158) (S)-2-(2-(1H-imidazol-5-yl)acetamido)-3-(benzyloxy)-N-(4-(p-tolyloxy)phenyl)propanamide;
159) (S)-3-(benzyloxy)-N-(4-(4-fluorophenoxy)phenyl)-2-(2-(pyrazin-2-yl)acetamido)propanamide;
160) (S)-3-(benzyloxy)-N-(4-(4-fluorophenoxy)phenyl)-2-(2-(2-methyl-1H-imidazol-1-yl)acetamido)propanamide;
161) (S)-2-(2-(1H-imidazol-4-yl)-2-methylpropanamido)-3-(4-fluorobenzyloxy)-N-(4-(4-fluorophenoxy)phenyl)propanamide;
162) (S)-3-(benzyloxy)-N-(4-(4-fluorophenoxy)phenyl)-2-(2-(2-methyl-1H-imidazol-4-yl)acetamido)propanamide;
163) (2S,3S)-1-(2-(1H-imidazol-4-yl)acetyl)-3-benzyl-N-(4-(4-fluorophenoxy)phenyl)pyrrolidine-2-carboxamide;

164) (S)-2-acetamido-3-(4-fluorobenzyloxy)-N-(4-(4-fluorophenoxy)phenyl)propanamide;
165) (S)-benzyl 4-(2-(1H-1,2,4-triazol-1-yl)acetamido)-5-(4-(4-fluorophenoxy)phenylamino)-5-oxopentylcarbamate;
166) (S)-3-(benzyloxy)-N-(4-(4-fluorophenoxy)phenyl)-2-(2-(3-methyl-1H-pyrazol-5-yl)acetamido)propanamide
167) (2S)-2-(2-(1H-imidazol-4-yl)propanamido)-3-(benzyloxy)-N-(4-(4-fluorophenoxy)phenyl)propanamide;
168) (S)-2-(2-(1H-imidazol-5-yl)acetamido)-N-(4-(4-bromophenoxy)phenyl)-3-(4-fluorobenzyloxy)propanamide;
169) (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide;
170) (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide;
171) (2S,4R)-1-(2-(1H-1,2,4-triazol-1-yl)acetyl)-N-(4-(4-fluorophenoxy)phenyl)-4-(3-methylbenzyl)pyrrolidine-2-carboxamide;
172) (S)-2-(3-(3,5-dimethylisoxazol-4-yl)ureido)-3-benzyloxy-N-(4-(4-fluorophenoxy)phenyl)propanamide;
173) (2S,4R)-1-(2-(1H-imidazol-5-yl)acetyl)-4-(benzylamino)-N-(4-(4-fluorophenoxy)phenyl)pyrrolidine-2-carboxamide;
174) (S)-2-(2-(1H-1,2,3-triazol-1-yl)acetamido)-3-(benzyloxy)-N-(4-(4-fluorophenoxy)phenyl)propanamide;
175) 175 (S)-1-(2-(1H-imidazol-4-yl)acetyl)-4-benzyl-N-(4-(4-fluorophenoxy)phenyl)piperazine-2-carboxamide;
176) (2S,4R)-1-(2-(1H-benzo[d][1,2,3]triazol-1-yl)acetyl)-4-benzyl-N-(4-(4-fluorophenoxy)phenyl)pyrrolidine-2-carboxamide;
177) (2S,4R)-4-benzyl-N-(4-(4-fluorophenoxy)phenyl)-1-(2-(5-methyl-1H-pyrazol-3-yl)acetyl)pyrrolidine-2-carboxamide;
178) (S)-2-(2-(1H-1,2,4-triazol-1-yl)acetamido)-3-(benzyloxy)-N-(4-(4-fluorophenylthio)phenyl)propanamide;
179) (2S,4R)-1-(2-(1H-1,2,4-triazol-1-yl)acetyl)-4-(benzylamino)-N-(4-(4-fluorophenoxy)phenyl)pyrrolidine-2-carboxamide;
180) (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide;
181) (S)-2-(2-(1H-1,2,4-triazol-1-yl)acetamido)-3-(2-chlorobenzyloxy)-N-(4-(4-fluorophenoxy)phenyl)propanamide;
182) (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide;
183) 3-(benzyloxy)-2-(2-(2-fluorophenyl)acetamido)-N-(4-phenoxyphenyl)propanamide;
184) N-(3-(benzyloxy)-1-oxo-1-(4-phenoxyphenylamino)propan-2-yl)-1H-indole-4-carboxamide;
185) 2-(2-(3-methylisoxazol-5-yl)acetamido)-3-benzyloxy-N-(4-phenoxyphenyl)propanamide;
186) N-(3-(benzyloxy)-1-oxo-1-(4-phenoxyphenylamino)propan-2-yl)-4-cyclopropyl-4-oxobutanamide;
187) N-(3-(benzyloxy)-1-oxo-1-(4-phenoxyphenylamino)propan-2-yl)-1H-indole-6-carboxamide;
188) N-(3-(benzyloxy)-1-oxo-1-(4-phenoxyphenylamino)propan-2-yl)-2,3-dihydro-1H-indene-2-carboxamide;
189) N-(3-(benzyloxy)-1-oxo-1-(4-phenoxyphenylamino)propan-2-yl)-3-methyl-2-nitrobenzamide;
190) 3-(benzyloxy)-2-(2-(2,5-dichlorophenyl)acetamido)-N-(4-phenoxyphenyl)propanamide;
191) 3-(benzyloxy)-2-(2-(3-chloro-2-fluorophenyl)acetamido)-N-(4-phenoxyphenyl)propanamide;
192) 3-(benzyloxy)-2-(2-(5-chloro-2-fluorophenyl)acetamido)-N-(4-phenoxyphenyl)propanamide;
193) 2-(2-(1-acetylpyrrolidin-2-yl)acetamido)-3-benzyloxy-N-(4-phenoxyphenyl)propanamide;
194) (S)-2-{2-((benzoyl)(methyl)amino)acetamido}-3-benzyloxy-N-(4-phenoxyphenyl)propanamide;
195) (S)-2-(2-(1-methyl-1H-imidazol-4-yl)acetamido)-3-benzyloxy-N-(4-phenoxyphenyl)propanamide;
196) (S)-2-(2-(2-fluorophenyl)acetamido)-3-benzyloxy-N-(4-phenoxyphenyl)propanamide;
197) (S)-2-(2-(1H-indol-4-yl)acetamido)-3-benzyloxy-N-(4-phenoxyphenyl)propanamide;
198) (S)-2-(2-(thien-2-yl)acetamido)-3-benzyloxy-N-(4-phenoxyphenyl)propanamide;
199) (S)-2-(2-(2,5-dichlorophenyl)acetamido)-3-benzyloxy-N-(4-phenoxyphenyl)propanamide;
200) (S)-2-(2-(1H-imidazol-4-yl)acetamido)-3-(benzyloxy)-N-(4-benzylphenyl)propanamide;
201) (S)-3-(benzyloxy)-2-(2-(2,4-dioxoimidazolidin-1-yl)acetamido)-N-(4-phenoxyphenyl)propanamide;
202) (S)-2-(2-(1H-imidazol-4-yl)acetamido)-3-(benzyloxy)-N-(4-(4-methoxyphenoxy)phenyl)propanamide;
203) (S)-2-(2-(1H-imidazol-4-yl)-N-methylacetamido)-3-(benzyloxy)-N-(4-phenoxyphenyl)propanamide;
204) (S)-2-(2-(1H-imidazol-5-yl)acetamido)-N-(4-(4-chlorophenoxy)phenyl)-3-phenylpropanamide;
205) (S)-3-(benzyloxy)-N-(4-(4-fluorophenoxy)phenyl)-2-(2-(piperazin-1-yl)acetamido)propanamide;
206) (S)-2-(2-(1H-imidazol-4-yl)acetamido)-3-(benzyloxy)-N-(4-(thiazol-2-yloxy)phenyl)propanamide;
207) (S)-2-(3-(1H-imidazol-5-yl)propanamido)-3-(benzyloxy)-N-(4-(4-fluorophenoxy)phenyl)propanamide;
208) (S)-2-(2-(1H-imidazol-5-yl)acetamido)-3-(benzyloxy)-N-(4-(cyclohexyloxy)phenyl)propanamide;
209) (S)-3-(benzyloxy)-N-(4-(4-chlorophenoxy)phenyl)-2-(3-(dimethylamino)propanamido)propanamide;
210) (S)-3-(4-fluorobenzyloxy)-N-(4-(4-fluorophenoxy)phenyl)-2-(2-morpholinoacetamido)propanamide;
211) (S)-2-(2-(1H-imidazol-4-yl)acetamido)-3-(benzyloxy)-N-(4-(benzyloxy)phenyl)propanamide;
212) (S)-3-(benzyloxy)-2-(2-(5-fluoro-1H-indol-3-yl)acetamido)-N-(4-(4-fluorophenoxy)phenyl)propanamide;
213) (S)-2-(2-(1H-imidazol-4-yl)-2-methylpropanamido)-3-(benzyloxy)-N-(4-(4-fluorophenoxy)phenyl)propanamide;
214) (S)-3-(benzyloxy)-2-(2-(2,5-dihydro-1H-pyrrol-1-yl)acetamido)-N-(4-(4-fluorophenoxy)phenyl)propanamide;
215) (S)-3-(benzyloxy)-N-(4-(4-fluorophenoxy)phenyl)-2-(2-(pyrrolidin-1-yl)acetamido)propanamide;
216) (S)-2-(2-(2-(1H-imidazol-4-yl)ethylamino)acetamido)-3-(benzyloxy)-N-(4-(4-fluorophenoxy)phenyl)propanamide;
217) (S)-3-(benzyloxy)-N-(4-(4-fluorophenoxy)phenyl)-2-(2-(4-(2-methoxyphenyl)piperazin-1-yl)acetamido)propanamide;
218) (S)-3-(benzyloxy)-N-(4-(4-fluorophenoxy)phenyl)-2-(2-(4-(4-fluorophenyl)piperazin-1-yl)acetamido)propanamide;

219) (2S)-2-(2-(2,3-dioxa-8-azaspiro[4.5]decan-8-yl)acetamido)-3-(benzyloxy)-N-(4-(4-fluorophenoxy)phenyl)propanamide;
220) (S)-3-(benzyloxy)-2-(2-(4-benzylpiperidin-1-yl)acetamido)-N-(4-(4-fluorophenoxy)phenyl)propanamide;
221) (S)-3-(benzyloxy)-2-(2-(3,4-dihydroisoquinolin-2(1H)-yl)acetamido)-N-(4-(4-fluorophenoxy)phenyl)propanamide;
222) (2S)-3-(benzyloxy)-N-(4-(4-fluorophenoxy)phenyl)-2-(2-(octahydroisoquinolin-2(1H)-yl)acetamido)propanamide;
223) (S)-3-(benzyloxy)-N-(4-(4-fluorophenoxy)phenyl)-2-(2-(4-(furan-2-carbonyl)piperazin-1-yl)acetamido)propanamide;
224) (S)-3-(benzyloxy)-N-(4-(4-fluorophenoxy)phenyl)-2-(2-(4-(4-methoxyphenyl)piperazin-1-yl)acetamido)propanamide;
225) (S)-3-(benzyloxy)-N-(4-(4-fluorophenoxy)phenyl)-2-(2-(4-phenylpiperazin-1-yl)acetamido)propanamide;
226) (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide;
227) (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide;
228) (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide;
229) (S)-2-(2-(4-(4-acetylphenyl)piperazin-1-yl)acetamido)-3-(benzyloxy)-N-(4-(4-fluorophenoxy)phenyl)propanamide;
230) (S)-2-(2-(4-acetylpiperazin-1-yl)acetamido)-3-(benzyloxy)-N-(4-(4-fluorophenoxy)phenyl)propanamide;
231) 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide;
232) (S,E)-N-(3-(benzyloxy)-1-(4-(4-fluorophenoxy)phenylamino)-1-oxopropan-2-yl)hex-3-enamide;
233) (S)-N-(3-(benzyloxy)-1-(4-(4-fluorophenoxy)phenylamino)-1-oxopropan-2-yl)-3-methylbutanamide;
234) (S)-3-(benzyloxy)-2-(2-((2R,6S)-2,6-dimethylmorpholino)acetamido)-N-(4-(4-fluorophenoxy)phenyl)propanamide;
235) (S)-3-(benzyloxy)-N-(4-(4-fluorophenoxy)phenyl)-2-(2-(thiazolidin-3-yl)acetamido)propanamide;
236) (S)-2-(2-(4-acetylpiperazin-1-yl)acetamido)-3-(benzyloxy)-N-(4-(4-fluorophenoxy)phenyl)propanamide;
237) (2S)-3-(benzyloxy)-N-(4-(4-fluorophenoxy)phenyl)-2-(2-(4-(tetrahydrofuran-2-carbonyl)piperazin-1-yl)acetamido)propanamide;
238) (S)-methyl 1-(2-(3-(benzyloxy)-1-(4-(4-fluorophenoxy)phenylamino)-1-oxopropan-2-ylamino)-2-oxoethyl)piperidine-4-carboxylate;
239) (S)-3-(benzyloxy)-2-(2-(4-(2-chloro-6-fluorobenzyl)piperazin-1-yl)acetamido)-N-(4-(4-fluorophenoxy)phenyl)propanamide;
240) (S)-3-(benzyloxy)-N-(4-(4-fluorophenoxy)phenyl)-2-(2-(isoindolin-2-yl)acetamido)propanamide;
241) (S)-3-(benzyloxy)-N-(4-(4-fluorophenoxy)phenyl)-2-(2-(4-(2-methoxyethyl)piperazin-1-yl)acetamido)propanamide;
242) (S)-3-(benzyloxy)-N-(4-(4-fluorophenoxy)phenyl)-2-(2-(4-(2-ethoxyethyl)piperazin-1-yl)acetamido)propanamide;
243) (S)-2-(2-(1H-imidazol-4-yl)acetamido)-3-(benzyloxy)-N-(3-phenoxyphenyl)propanamide;
244) (S)-3-(benzyloxy)-2-(2-(3-bromophenyl)acetamido)-N-(4-(4-fluorophenoxy)phenyl)propanamide;
245) (S)-3-(benzyloxy)-N-(4-(4-fluorophenoxy)phenyl)-2-(3-nitropropanamido)propanamide;
246) (S)-3-(benzyloxy)-N-(4-(4-fluorophenoxy)phenyl)-2-(2-(pyridin-2-yl)acetamido)propanamide;
247) (S)-3-(benzyloxy)-N-(4-(4-fluorophenoxy)phenyl)-2-(2-(pyridin-3-yl)acetamido)propanamide;
248) (S)-N-((S)-3-(benzyloxy)-1-(4-(4-fluorophenoxy)phenylamino)-1-oxopropan-2-yl)-3,7-dimethyloct-6-enamide;
249) (S)-3-(benzyloxy)-N-(4-(4-fluorophenoxy)phenyl)-2-(2-phenylacetamido)propanamide;
250) (S)-3-(benzyloxy)-N-(4-(4-fluorophenoxy)phenyl)-2-(2-(pyrimidin-5-yl)acetamido)propanamide;
251) (2S,4S)-1-(2-(1H-imidazol-5-yl)acetyl)-N-(4-(4-fluorophenoxy)phenyl)-4-phenylpyrrolidine-2-carboxamide;
252) (2S,4R)-1-(2-(1H-1,2,4-triazol-1-yl)acetyl)-4-(benzyloxy)-N-(4-(4-fluorohenoxy)phenyl)pyrrolidine-2-carboxamide;
253) benzyl (3R,5S)-1-(2-(1H-imidazol-5-yl)acetyl)-5-(4-(4-fluorophenoxy)phenylcarbamoyl)pyrrolidin-3-ylcarbamate;
254) (S)-2-(2-(1H-1,2,4-triazol-1-yl)acetamido)-5-acetamido-N-(4-(4-fluorophenoxy)phenyl)pentanamide;
255) (S)-3-(benzyloxy)-N-(4-(4-fluorophenoxy)phenyl)-2-(2-methyl-2-(1H-1,2,4-triazol-1-yl)propanamido)propanamide;
256) (S)-3-(benzyloxy)-2-(2-(3,5-dimethyl-1H-1,2,4-triazol-1-yl)acetamido)-N-(4-(4-fluorophenoxy)phenyl)propanamide;
257) (S)-benzyl 4-(2-(1H-imidazol-4-yl)acetyl)-3-(4-(4-fluorophenoxy)phenylcarbamoyl)piperazine-1-carboxylate;
258) (S)-2-(2-(3,5-dimethyl-1H-pyrazol-4-yl)acetamido)-3-(4-fluorobenzyloxy)-N-(4-(4-fluorophenoxy)phenyl)propanamide;
259) (2S,4R)-1-(2-(1H-1,2,4-triazol-1-yl)acetyl)-N-(4-(4-fluorophenoxy)phenyl)-4-phenoxypyrrolidine-2-carboxamide;
260) (2S,4R)-1-(2-(1H-1,2,4-triazol-1-yl)acetyl)-N-(4-(4-fluorophenoxy)phenyl)-4-(isoindolin-2-pyrrolidine-2-carboxamide;
261) (S)-1-(2-(1H-1,2,4-triazol-1-yl)acetyl)-4-benzyl-N-(4-(4-fluorophenoxy)phenyl)piperazine-2-carboxamide;
262) (2S,4S)-1-(2-(1H-1,2,4-triazol-1-yl)acetyl)-4-((benzylamino)methyl)-N-(4-(4-fluorophenoxy)phenyl)pyrrolidine-2-carboxamide;
263) (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide;
264) (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide;
265) (2S)-3-(benzyloxy)-2-(2-(2,6-dimethylmorpholino)acetamido)-N-(4-(4-fluorophenoxy)phenyl)propanamide;
266) (S)-3-(benzyloxy)-N-(4-(4-fluorophenoxy)phenyl)-2-(2-thiomorpholinoacetamido)propanamide;
267) (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide;
268) (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide;

269) N-(2-oxo-1-{[(phenylmethyl)oxy]methyl}-2-{[4-(phenyloxy)phenyl]amino}ethyl)acetamide;
270) 4-(methyloxy)-N-(2-oxo-1-{[(phenylmethyl)oxy]methyl}-2-{[4-(phenyloxy)phenyl]amino}ethyl)benzamide;
271) 4-benzyloxy-N-(2-oxo-1-{[(phenylmethyl)oxy]methyl}-2-{[4-(phenyloxy)phenyl]amino}ethyl)phenylacetamide;
272) 2-bromo-5-(methyloxy)-N-(2-oxo-1-{[(phenylmethyl)oxy]methyl}-2-{[4-(phenyloxy)phenyl]amino}ethyl)benzamide;
273) N-(2-oxo-1-{[(phenylmethyl)oxy]methyl}-2-{[4-(phenyloxy)phenyl]amino}ethyl)butanamide;
274) 2-chloro-N-(2-oxo-1-{[(phenylmethyl)oxy]methyl}-2-{[4-(phenyloxy)phenyl]amino}ethyl)benzamide;
275) 3-chloro-N-(2-oxo-1-{[(phenylmethyl)oxy]methyl}-2-{[4-(phenyloxy)phenyl]amino}ethyl)benzamide;
276) 4-chloro-N-(2-oxo-1-{[(phenylmethyl)oxy]methyl}-2-{[4-(phenyloxy)phenyl]amino}ethyl)benzamide;
277) N-(2-oxo-1-{[(phenylmethyl)oxy]methyl}-2-{[4-(phenyloxy)phenyl]amino}ethyl)cyclopropylamide;
278) N-(2-oxo-1-{[(phenylmethyl)oxy]methyl}-2-{[4-(phenyloxy)phenyl]amino}ethyl)-3-cyclopentylpropanamide;
279) 3,4-dimethyl-N-(2-oxo-1-{[(phenylmethyl)oxy]methyl}-2-{[4-(phenyloxy)phenyl]amino}ethyl)benzamide;
280) N-(2-oxo-1-{[(phenylmethyl)oxy]methyl}-2-{[4-(phenyloxy)phenyl]amino}ethyl)-2,5-dimethoxyphenylacetamide;
281) 4-(ethyloxy)-N-(2-oxo-1-{[(phenylmethyl)oxy]methyl}-2-{[4-(phenyloxy)phenyl]amino}ethyl)benzamide;
282) N-(3-(benzyloxy)-1-oxo-1-(4-phenoxyphenylamino)propan-2-yl)-2-ethylhexanamide;
283) N-(2-oxo-1-{[(phenylmethyl)oxy]methyl}-2-{[4-(phenyloxy)phenyl]amino}ethyl)furan-2-carboxamide;
284) N-(2-oxo-1-{[(phenylmethyl)oxy]methyl}-2-{[4-(phenyloxy)phenyl]amino}ethyl)-2-methoxyacetamide;
285) N-(2-oxo-1-{[(phenylmethyl)oxy]methyl}-2-{[4-(phenyloxy)phenyl]amino}ethyl)-3-methoxyphenylacetamide;
286) 2-methyl-N-(2-oxo-1-{[(phenylmethyl)oxy]methyl}-2-{[4-(phenyloxy)phenyl]amino}ethyl)pentanamide;
287) 4-methyl-N-(2-oxo-1-{[(phenylmethyl)oxy]methyl}-2-{[4-(phenyloxy)phenyl]amino}ethyl)pentanamide;
288) N-(2-oxo-1-{[(phenylmethyl)oxy]methyl}-2-{[4-(phenyloxy)phenyl]amino}ethyl)naphthalene-2-carboxamide;
289) N-(2-oxo-1-{[(phenylmethyl)oxy]methyl}-2-{[4-(phenyloxy)phenyl]amino}ethyl)phenoxyacetamide;
290) N-(2-oxo-1-{[(phenylmethyl)oxy]methyl}-2-{[4-(phenyloxy)phenyl]amino}ethyl)-2-(phenyloxy)pyridine-3-carboxamide;
291) 3,4,5-tris(methyloxy)-N-(2-oxo-1-{[(phenylmethyl)oxy]methyl}-2-{[4-(phenyloxy)phenyl]amino}ethyl)benzamide;
292) N-(2-oxo-1-{[(phenylmethyl)oxy]methyl}-2-{[4-(phenyloxy)phenyl]amino}ethyl)thiophene-2-carboxamide;
293) N-(2-oxo-1-{[(phenylmethyl)oxy]methyl}-2-{[4-(phenyloxy)phenyl]amino}ethyl)thien-2-ylacetamide;
294) 4-(dimethylamino)-N-(2-oxo-1-{[(phenylmethyl)oxy]methyl}-2-{[4-(phenyloxy)phenyl]amino}ethyl)benzamide;
295) N-(2-oxo-1-{[(phenylmethyl)oxy]methyl}-2-{[4-(phenyloxy)phenyl]amino}ethyl)hexanamide;
296) 2-chloro-N-(2-oxo-1-{[(phenylmethyl)oxy]methyl}-2-{[4-(phenyloxy)phenyl]amino}ethyl)pyridine-3-carboxamide;
297) 3-chloro-N-(2-oxo-1-{[(phenylmethyl)oxy]methyl}-2-{[4-(phenyloxy)phenyl]amino}ethyl)-1-benzothiophene-2-carboxamide;
298) N-(2-oxo-1-{[(phenylmethyl)oxy]methyl}-2-{[4-(phenyloxy)phenyl]amino}ethyl)pent-4-enamide;
299) 3-chloro-2-fluoro-N-(2-oxo-1-{[(phenylmethyl)oxy]methyl}-2-{[4-(phenyloxy)phenyl]amino}ethyl)benzamide;
300) N-(2-oxo-1-{[(phenylmethyl)oxy]methyl}-2-{[4-(phenyloxy)phenyl]amino}ethyl)-4-phenylbutanamide;
301) N-(2-oxo-1-{[(phenylmethyl)oxy]methyl}-2-{[4-(phenyloxy)phenyl]amino}ethyl)-2-bromophenylacetamide;
302) N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide;
303) N-(2-oxo-1-{[(phenylmethyl)oxy]methyl}-2-{[4-(phenyloxy)phenyl]amino}ethyl)-2-methoxyethoxyacetamide;
304) N-(2-oxo-1-{[(phenylmethyl)oxy]methyl}-2-{[4-(phenyloxy)phenyl]amino}ethyl)-3-(4-methoxyphenyl)propanamide;
305) N-(2-oxo-1-{[(phenylmethyl)oxy]methyl}-2-{[4-(phenyloxy)phenyl]amino}ethyl)-2-acetylamino-4-methylthiazol-5-ylsulfonamide;
306) 4-(methylthio)-N-(2-oxo-1-{[(phenylmethyl)oxy]methyl}-2-{[4-(phenyloxy)phenyl]amino}ethyl)benzamide;
307) N-(2-oxo-1-{[(phenylmethyl)oxy]methyl}-2-{[4-(phenyloxy)phenyl]amino}ethyl)-2-(methylthio)acetamide;
308) 5-fluoro-2-(methyloxy)-N-(2-oxo-1-{[(phenylmethyl)oxy]methyl}-2-{[4-(phenyloxy)phenyl]amino}ethyl)benzamide;
309) 2-methyl-4-(methyloxy)-N-(2-oxo-1-{[(phenylmethyl)oxy]methyl}-2-{[4-(phenyloxy)phenyl]amino}ethyl)benzamide;
310) 5-oxo-N-(2-oxo-1-{[(phenylmethyl)oxy]methyl}-2-{[4-(phenyloxy)phenyl]amino}ethyl)hexanamide;
311) 4-bromo-2-methyl-N-(2-oxo-1-{[(phenylmethyl)oxy]methyl}-2-{[4-(phenyloxy)phenyl]amino}ethyl)benzamide;
312) 4-oxo-N-(2-oxo-1-{[(phenylmethyl)oxy]methyl}-2-{[4-(phenyloxy)phenyl]amino}ethyl)-4-(2-thienyl)butanamide;
313) N-(2-oxo-1-{[(phenylmethyl)oxy]methyl}-2-{[4-(phenyloxy)phenyl]amino}ethyl)-2-(phenylthio)acetamide;
314) N-(2-oxo-1-{[(phenylmethyl)oxy]methyl}-2-{[4-(phenyloxy)phenyl]amino}ethyl)-2-(1H-pyrrol-1-yl)benzamide;
315) N-(2-oxo-1-{[(phenylmethyl)oxy]methyl}-2-{[4-(phenyloxy)phenyl]amino}ethyl)-2-[2-(methoxy)ethoxy]ethoxyacetamide;
316) 3,5-bis(methyloxy)-N-(2-oxo-1-{[(phenylmethyl)oxy]methyl}-2-{[4-(phenyloxy)phenyl]amino}ethyl)benzamide;

317) N-(2-oxo-1-{[(phenylmethyl)oxy]methyl}-2-{[4-(phenyloxy)phenyl]amino}ethyl)-3-cyclohexylpropanamide;
318) 5-oxo-N-(2-oxo-1-{[(phenylmethyl)oxy]methyl}-2-{[4-(phenyloxy)phenyl]amino}ethyl)-5-phenylpentanamide;
319) N-(2-oxo-1-{[(phenylmethyl)oxy]methyl}-2-{[4-(phenyloxy)phenyl]amino}ethyl)-4-acetylphenoxyacetamide;
320) 4-[3,4-bis(methyloxy)phenyl]-N-(2-oxo-1-{[(phenylmethyl)oxy]methyl}-2-{[4-(phenyloxy)phenyl]amino}ethyl)butanamide;
321) N-(2-oxo-1-{[(phenylmethyl)oxy]methyl}-2-{[4-(phenyloxy)phenyl]amino}ethyl)-5-[3-(trifluoromethyl)phenyl]furan-2-carboxamide;
322) N-(2-oxo-1-{[(phenylmethyl)oxy]methyl}-2-{[4-(phenyloxy)phenyl]amino}ethyl)-3-(1,3-dioxoisoindolin-2-yl)propanamide;
323) 5-oxo-N-(2-oxo-1-{[(phenylmethyl)oxy]methyl}-2-{[4-(phenyloxy)phenyl]amino}ethyl)-5-(2-thienyl)pentanamide;
324) N-(2-oxo-1-{[(phenylmethyl)oxy]methyl}-2-{[4-(phenyloxy)phenyl]amino}ethyl)-2-oxo-2-phenylacetamide;
325) N-(2-oxo-1-{[(phenylmethyl)oxy]methyl}-2-{[4-(phenyloxy)phenyl]amino}ethyl)-4-(2-thienyl)butanamide;
326) 5-nitro-N-(2-oxo-1-{[(phenylmethyl)oxy]methyl}-2-{[4-(phenyloxy)phenyl]amino}ethyl)furan-2-carboxamide;
327) (E)-N-(3-(benzyloxy)-1-oxo-1-(4-phenoxyphenylamino)propan-2-yl)hex-3-enamide
328) N-(2-oxo-1-{[(phenylmethyl)oxy]methyl}-2-{[4-(phenyloxy)phenyl]amino}ethyl)-1,3-benzodioxol-5-ylacetamide;
329) 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide;
330) 4-fluoro-N-(2-oxo-1-{[(phenylmethyl)oxy]methyl}-2-{[4-(phenyloxy)phenyl]amino}ethyl)-2-(trifluoromethyl)benzamide;
331) N-(2-oxo-1-{[(phenylmethyl)oxy]methyl}-2-{[4-(phenyloxy)phenyl]amino}ethyl)-2-(pyrimidin-2-ylthio)acetamide;
332) 2,5-bis(methyloxy)-N-(2-oxo-1-{[(phenylmethyl)oxy]methyl}-2-{[4-(phenyloxy)phenyl]amino}ethyl)benzamide;
333) 4-(methylsulfonyl)-N-(2-oxo-1-{[(phenylmethyl)oxy]methyl}-2-{[4-(phenyloxy)phenyl]amino}ethyl)benzamide;
334) 2-chloro-4-(methylsulfonyl)-N-(2-oxo-1-{[(phenylmethyl)oxy]methyl}-2-{[4-(phenyloxy)phenyl]amino}ethyl)benzamide;
335) N-(2-oxo-1-{[(phenylmethyl)oxy]methyl}-2-{[4-(phenyloxy)phenyl]amino}ethyl)2-(4-oxo-2-thioxothiazolidin-3-yl)acetamide;
336) N-(2-oxo-1-{[(phenylmethyl)oxy]methyl}-2-{[4-(phenyloxy)phenyl]amino}ethyl)tetrahydrofuran-3-carboxamide;
337) N-(2-oxo-1-{[(phenylmethyl)oxy]methyl}-2-{[4-(phenyloxy)phenyl]amino}ethyl)-3-methoxypropanamide;
338) N-(2-oxo-1-{[(phenylmethyl)oxy]methyl}-2-{[4-(phenyloxy)phenyl]amino}ethyl)-2-ethoxyacetamide;
339) N,N-dimethyl-N'-(2-oxo-1-{[(phenylmethyl)oxy]methyl}-2-{[4-(phenyloxy)phenyl]amino}ethyl)butanediamide;
340) N-(2-oxo-1-{[(phenylmethyl)oxy]methyl}-2-{[4-(phenyloxy)phenyl]amino}ethyl)-N-benzoyl-N-methylaminoacetamide;
341) N-(2-oxo-1-{[(phenylmethyl)oxy]methyl}-2-{[4-(phenyloxy)phenyl]amino}ethyl)-1H-indole-3-carboxamide;
342) N-(2-oxo-1-{[(phenylmethyl)oxy]methyl}-2-{[4-(phenyloxy)phenyl]amino}ethyl)-1H-benzimidazole-5-carboxamide;
343) N-(2-oxo-1-{[(phenylmethyl)oxy]methyl}-2-{[4-(phenyloxy)phenyl]amino}ethyl)-2-(4-ethoxyphenyl)acetamide;
344) N-(2-oxo-1-{[(phenylmethyl)oxy]methyl}-2-{[4-(phenyloxy)phenyl]amino}ethyl)pent-4-ynamide;
345) N-(2-oxo-1-{[(phenylmethyl)oxy]methyl}-2-{[4-(phenyloxy)phenyl]amino}ethyl)-4-(propyloxy)benzamide;
346) 2-methyl-N-(2-oxo-1-{[(phenylmethyl)oxy]methyl}-2-{[4-(phenyloxy)phenyl]amino}ethyl)hexanamide;
347) 4-oxo-N-(2-oxo-1-{[(phenylmethyl)oxy]methyl}-2-{[4-(phenyloxy)phenyl]amino}ethyl)pentanamide;
348) N-(2-oxo-1-{[(phenylmethyl)oxy]methyl}-2-{[4-(phenyloxy)phenyl]amino}ethyl)-3-(3,4-dimethoxyphenyl)propanamide;
349) 4-oxo-N-(2-oxo-1-{[(phenylmethyl)oxy]methyl}-2-{[4-(phenyloxy)phenyl]amino}ethyl)-4-phenylbutanamide;
350) N-(2-oxo-1-{[(phenylmethyl)oxy]methyl}-2-{[4-(phenyloxy)phenyl]amino}ethyl)quinoline-3-carboxamide;
351) N-(2-oxo-1-{[(phenylmethyl)oxy]methyl}-2-{[4-(phenyloxy)phenyl]amino}ethyl)pyrazine-2-carboxamide;
352) N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide;
353) N-(2-oxo-1-{[(phenylmethyl)oxy]methyl}-2-{[4-(phenyloxy)phenyl]amino}ethyl)-2-methoxy-2-phenylacetamide;
354) N-(2-oxo-1-{[(phenylmethyl)oxy]methyl}-2-{[4-(phenyloxy)phenyl]amino}ethyl)-2R-phenylpropanamide;
355) N-(2-oxo-1-{[(phenylmethyl)oxy]methyl}-2-{[4-(phenyloxy)phenyl]amino}ethyl)-1H-pyrazole-4-carboxamide;
356) N-(2-oxo-1-{[(phenylmethyl)oxy]methyl}-2-{[4-(phenyloxy)phenyl]amino}ethyl)cinnoline-4-carboxamide;
357) N-(2-oxo-1-{[(phenylmethyl)oxy]methyl}-2-{[4-(phenyloxy)phenyl]amino}ethyl)quinoline-8-carboxamide;
358) 6-hydroxy-N-(2-oxo-1-{[(phenylmethyl)oxy]methyl}-2-{[4-(phenyloxy)phenyl]amino}ethyl)pyridine-2-carboxamide;
359) N-(2-oxo-1-{[(phenylmethyl)oxy]methyl}-2-{[4-(phenyloxy)phenyl]amino}ethyl)-2-phenylpropanamide;
360) N-(2-oxo-1-{[(phenylmethyl)oxy]methyl}-2-{[4-(phenyloxy)phenyl]amino}ethyl)-1-(4-methoxyphenyl)cyclopropanecarboxamide;
361) N-(2-oxo-1-{[(phenylmethyl)oxy]methyl}-2-{[4-(phenyloxy)phenyl]amino}ethyl)-2-(2,3,6-trifluorophenyl)acetamide;
362) N-(2-oxo-1-{[(phenylmethyl)oxy]methyl}-2-{[4-(phenyloxy)phenyl]amino}ethyl)-2,4-bis(trifluoromethyl)benzamide;

363) N-(2-oxo-1-{[(phenylmethyl)oxy]methyl}-2-{[4-(phenyloxy)phenyl]amino}ethyl)-2-(2,4-difluorophenyl)acetamide;
364) N-(2-oxo-1-{[(phenylmethyl)oxy]methyl}-2-{[4-(phenyloxy)phenyl]amino}ethyl)-2-(1-methyl-1H-indol-3-yl)acetamide;
365) N-(2-oxo-1-{[(phenylmethyl)oxy]methyl}-2-{[4-(phenyloxy)phenyl]amino}ethyl)quinoline-4-carboxamide;
366) N-(2-oxo-1-{[(phenylmethyl)oxy]methyl}-2-{[4-(phenyloxy)phenyl]amino}ethyl)-1-benzofuran-2-carboxamide;
367) 7-(methyloxy)-N-(2-oxo-1-{[(phenylmethyl)oxy]methyl}-2-{[4-(phenyloxy)phenyl]amino}ethyl)-1-benzofuran-2-carboxamide;
368) N-(2-oxo-1-{[(phenylmethyl)oxy]methyl}-2-{[4-(phenyloxy)phenyl]amino}ethyl)-2-(4-fluorophenoxy)acetamide;
369) N-(2-oxo-1-{[(phenylmethyl)oxy]methyl}-2-{[4-(phenyloxy)phenyl]amino}ethyl)-3-(pyridin-3-yl)propanamide;
370) N-(2-oxo-1-{[(phenylmethyl)oxy]methyl}-2-{[4-(phenyloxy)phenyl]amino}ethyl)-2-(3,4-dichlorophenoxy)acetamide;
371) N-(2-oxo-1-{[(phenylmethyl)oxy]methyl}-2-{[4-(phenyloxy)phenyl]amino}ethyl)-2-(naphthalen-1-yloxy)acetamide;
372) N-(2-oxo-1-{[(phenylmethyl)oxy]methyl}-2-{[4-(phenyloxy)phenyl]amino}ethyl)-2-p-tolylacetamide;
373) N-(2-oxo-1-{[(phenylmethyl)oxy]methyl}-2-{[4-(phenyloxy)phenyl]amino}ethyl)-2-(2,5-dimethylphenyl)acetamide;
374) N-(2-oxo-1-{[(phenylmethyl)oxy]methyl}-2-{[4-(phenyloxy)phenyl]amino}ethyl)-2-(benzylthio)acetamide;
375) N-(2-oxo-1-{[(phenylmethyl)oxy]methyl}-2-{[4-(phenyloxy)phenyl]amino}ethyl)-2-(naphthalen-1-yl)acetamide;
376) N-(2-oxo-1-{[(phenylmethyl)oxy]methyl}-2-{[4-(phenyloxy)phenyl]amino}ethyl)-3-ethoxypropanamide;
377) N-(2-oxo-1-{[(phenylmethyl)oxy]methyl}-2-{[4-(phenyloxy)phenyl]amino}ethyl)-2-(3-chlorophenyl)acetamide;
378) 5-butyl-N-(2-oxo-1-{[(phenylmethyl)oxy]methyl}-2-{[4-(phenyloxy)phenyl]amino}ethyl)pyridine-2-carboxamide;
379) 4-chloro-3-methyl-N-(2-oxo-1-{[(phenylmethyl)oxy]methyl}-2-{[4-(phenyloxy)phenyl]amino}ethyl)benzamide;
380) 4-cyano-N-(2-oxo-1-{[(phenylmethyl)oxy]methyl}-2-{[4-(phenyloxy)phenyl]amino}ethyl)benzamide;
381) N-(2-oxo-1-{[(phenylmethyl)oxy]methyl}-2-{[4-(phenyloxy)phenyl]amino}ethyl)-2S-methoxy-2-phenylacetamide;
382) N-(2-oxo-1-{[(phenylmethyl)oxy]methyl}-2-{[4-(phenyloxy)phenyl]amino}ethyl)-3-(2,5-dimethoxyphenyl)propanamide;
383) N-(2-oxo-1-{[(phenylmethyl)oxy]methyl}-2-{[4-(phenyloxy)phenyl]amino}ethyl)-3-(1H-indol-3-yl)propanamide;
384) N-(2-oxo-1-{[(phenylmethyl)oxy]methyl}-2-{[4-(phenyloxy)phenyl]amino}ethyl)-2-(3-bromophenyl)acetamide;
385) 3-methyl-N-(2-oxo-1-{[(phenylmethyl)oxy]methyl}-2-{[4-(phenyloxy)phenyl]amino}ethyl)pentanamide;
386) N-(2-oxo-1-{[(phenylmethyl)oxy]methyl}-2-{[4-(phenyloxy)phenyl]amino}ethyl)-1H-indole-2-carboxamide;
387) 4-chloro-2-fluoro-N-(2-oxo-1-{[(phenylmethyl)oxy]methyl}-2-{[4-(phenyloxy)phenyl]amino}ethyl)benzamide;
388) 2-oxo-2-[(2-oxo-1-{[(phenylmethyl)oxy]methyl}-2-{[4-(phenyloxy)phenyl]amino}ethyl)amino]ethyl acetate;
389) N-(2-oxo-1-{[(phenylmethyl)oxy]methyl}-2-{[4-(phenyloxy)phenyl]amino}ethyl)thiophene-3-carboxamide;
390) N-(2-oxo-1-{[(phenylmethyl)oxy]methyl}-2-{[4-(phenyloxy)phenyl]amino}ethyl)-2-(4-bromophenyl)acetamide;
391) N-(2-oxo-1-{[(phenylmethyl)oxy]methyl}-2-{[4-(phenyloxy)phenyl]amino}ethyl)-2-(2-chlorophenyl)acetamide;
392) N-(2-oxo-1-{[(phenylmethyl)oxy]methyl}-2-{[4-(phenyloxy)phenyl]amino}ethyl)-2-(3,4,5-trimethoxyphenyl)acetamide;
393) N-(2-oxo-1-{[(phenylmethyl)oxy]methyl}-2-{[4-(phenyloxy)phenyl]amino}ethyl)-2-(p-tolyloxy)acetamide;
394) N-(2-oxo-1-{[(phenylmethyl)oxy]methyl}-2-{[4-(phenyloxy)phenyl]amino}ethyl)-3-(2-methoxyphenyl)propanamide;
395) 3-hydroxy-N-(2-oxo-1-{[(phenylmethyl)oxy]methyl}-2-{[4-(phenyloxy)phenyl]amino}ethyl)quinoxaline-2-carboxamide;
396) 4-acetyl-N-(2-oxo-1-{[(phenylmethyl)oxy]methyl}-2-{[4-(phenyloxy)phenyl]amino}ethyl)benzamide;
397) methyl 4-{[(2-oxo-1-{[(phenylmethyl)oxy]methyl}-2-{[4-(phenyloxy)phenyl]amino}ethyl)amino]carbonyl}benzoate;
398) 3-fluoro-N-(2-oxo-1-{[(phenylmethyl)oxy]methyl}-2-{[4-(phenyloxy)phenyl]amino}ethyl)-5-(trifluoromethyl)benzamide;
399) 4-[(difluoromethyl)oxy]-N-(2-oxo-1-{[(phenylmethyl)oxy]methyl}-2-{[4-(phenyloxy)phenyl]amino}ethyl)benzamide;
400) 3-fluoro-4-methyl-N-(2-oxo-1-{[(phenylmethyl)oxy]methyl}-2-{[4-(phenyloxy)phenyl]amino}ethyl)benzamide;
401) 3-methyl-N-(2-oxo-1-{[(phenylmethyl)oxy]methyl}-2-{[4-(phenyloxy)phenyl]amino}ethyl)furan-2-carboxamide.
402) N-(2-oxo-1-{[(phenylmethyl)oxy]methyl}-2-{[4-(phenyloxy)phenyl]amino}ethyl)cyclobutanecarboxamide; and
403) N-(2-oxo-1-{[(phenylmethyl)oxy]methyl}-2-{[4-(phenyloxy)phenyl]amino}ethyl)-3-(thiophen-2-yl)propanamide.

2. The pharmaceutical composition of claim 1, wherein the antimicrotubule agent is selected from the group consisting of a taxane or a vinca alkaloid.

3. The pharmaceutical composition of claim 2, wherein the taxane is paclitaxel or docetaxel.

4. The pharmaceutical composition of claim 1, wherein the S1P1R receptor antagonist is selected from the group consisting of
(2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide,
(2S,4R)-1-(2-(2H-1,2,3-triazol-2-yl)acetyl)-4-(4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

5. The pharmaceutical composition of claim 2, wherein the S1P1R receptor antagonist is selected from the group consisting of
- (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and
- (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

6. The pharmaceutical composition of claim 3, wherein the S1P1R receptor antagonist is selected from the group consisting of
- (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and
- (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

7. The pharmaceutical composition of claim 6, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide, and the taxane is paclitaxel or docetaxel.

8. The pharmaceutical composition of claim 6, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide and the taxane is paclitaxel or docetaxel.

9. The pharmaceutical composition of claim 6, wherein the S1P1R receptor antagonist is (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide and the taxane is paclitaxel or docetaxel.

10. The pharmaceutical composition of claim 6, wherein the S1P1R receptor antagonist is 2S,4R)-1-(2-(1H-1,2,3-triazol-1-yl)acetyl)-4-(4-fluorobenzyl)-N-(4-(4-fluorophenoxy)phenyl)pyrrolidine-2-carboxamide and the taxane is paclitaxel or docetaxel.

11. The pharmaceutical composition of claim 2, wherein the vinca alkaloid is vincristine, vinblastine, or vinorelbine.

12. The pharmaceutical composition of claim 11, wherein the S1P1R receptor antagonist is selected from the group consisting of
- (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide,
- (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and
- (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

13. The pharmaceutical composition of claim 12, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide and the vinca alkaloid is selected from the group consisting of vincristine, vinblastine or vinorelbine.

14. The pharmaceutical composition of claim 12, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide and the vinca alkaloid is selected from the group consisting of vincristine, vinblastine or vinorelbine.

15. The pharmaceutical composition of claim 12, wherein the S1P1R receptor antagonist is (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide and the vinca alkaloid is selected from the group consisting of vincristine, vinblastine or vinorelbine.

16. The pharmaceutical composition of claim 12, wherein the S1P1R receptor antagonist is (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide and the vinca alkaloid is selected from the group consisting of vincristine, vinblastine or vinorelbine.

17. A method of inhibiting or relieving cancer in a subject, comprising administering a therapeutically effective amount of at least one S1P1R receptor antagonist and at least one antimicrotubule agent, wherein the cancer is breast or lung cancer and the S1P1R receptor antagonist is selected from the group of compounds consisting of
1) (S)-2-(2-(1H-imidazol-5-yl)acetamido)-5-phenyl-N-(4-phenoxyphenyl)pentanamide;
2) (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide;
3) (2S,4R)-5-(2-(1H-1,2,3-triazol-1-yl)acetyl)-N-(4-(4-fluorophenoxy)phenyl)-4-(4-methylbenzyl)pyrrolidine-2-carboxamide;
4) (2S,4R)-5-(2-(1H-1,2,4-triazol-1-yl)acetyl)-N-(4-(4-fluorophenoxy)phenyl)-4-(4-methylbenzyl)pyrrolidine-2-carboxamide;
5) (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide;
6) (2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide;
7) (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide;
8) (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide;
9) (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide;
10) (2S,4R)-1-(2-(1H-1,2,3-triazol-1-yl)acetyl)-4-benzyl-N-(4-(4-fluorophenoxy)phenyl)pyrrolidine-2-carboxamide;

11) (2S,4R)-1-(2-(5-amino-3-(trifluoromethyl)-1H-1,2,4-triazol-1-yl)acetyl)-4-benzyl-N-(4-(4-fluorophenoxy)phenyl)pyrrolidine-2-carboxamide;
12) 1-((2S,4R)-4-benzyl-2-(5-(4-fluorophenoxy)-1H-benzo[d]imidazol-2-yl)pyrrolidin-1-yl)-2-(1H-1,2,4-triazol-1-yl)ethanone;
13) 3-(benzyloxy)-2-((S)-3-hydroxy-3-phenylpropanamido)-N-(4-phenoxyphenyl)propanamide;
14) 3-(benzyloxy)-2-(2-(furan-2-yl)-2-oxoacetamido)-N-(4-phenoxyphenyl)propanamide;
15) N-(3-(benzyloxy)-1-oxo-1-(4-phenoxyphenylamino)propan-2-yl)-6-(2,5-dioxo-2,5-dihydro-1H-pyrrol-1-yl)hexanamide;
16) 3-(benzyloxy)-2-(2-hydroxy-2-(2-hydroxyphenyl)acetamido)-N-(4-phenoxyphenyl)propanamide;
17) 4-(3-(benzyloxy)-1-oxo-1-(4-phenoxyphenylamino)propan-2-ylcarbamoyl)phenyl acetate;
18) N-(3-(benzyloxy)-1-oxo-1-(4-phenoxyphenylamino)propan-2-yl)-5-methylnicotinamide;
19) 3-(benzyloxy)-2-(2-(methylsulfonyl)acetamido)-N-(4-phenoxyphenyl)propanamide;
20) N-(3-(benzyloxy)-1-oxo-1-(4-phenoxyphenylamino)propan-2-yl)-1H-indole-5-carboxamide;
21) N-(3-(benzyloxy)-1-oxo-1-(4-phenoxyphenylamino)propan-2-yl)-2-bromo-5-fluorobenzamide;
22) N-(3-(benzyloxy)-1-oxo-1-(4-phenoxyphenylamino)propan-2-yl)-3,3,3-trifluoropropanamide;
23) (2R)-N-3-(benzyloxy)-1-oxo-1-(4-phenoxyphenylamino)propan-2-yl)tetrahydrofuran-2-carboxamide;
24) 3-(benzyloxy)-24-((R)-2-(2-chlorophenyl)-2-hydroxyacetamido)-N-(4-phenoxyphenyl)propanamide;
25) (2S)-1-(3-(benzyloxy)-1-oxo-1-(4-phenoxyphenylamino)propan-2-ylamino)-1-oxopropan-2-yl acetate;
26) 3-(benzyloxy)-2-(2-(2-hydroxyphenoxy)acetamido)-N-(4-phenoxyphenyl)propanamide;
27) 3-(benzyloxy)-2-((R)-2-hydroxy-3-phenylpropanamido)-N-(4-phenoxyphenyl)propanamide;
28) N-(3-(benzyloxy)-1-oxo-1-(4-phenoxyphenylamino)propan-2-yl)-2-(methylthio)nicotinamide;
29) N-(3-(benzyloxy)-1-oxo-1-(4-phenoxyphenylamino)propan-2-yl)-1-(4-chlorobenzyl)-5-oxopyrrolidine-3-carboxamide;
30) (2S,4R)-4-benzyl-N-(4-(4-fluorophenoxy)phenyl)-1-(2-((1-methyl-1H-indol-2-yl)methylamino)acetyl)pyrrolidine-2-carboxamide;
31) (2S,4R)-4-benzyl-N-(4-(4-fluorophenoxy)phenyl)-1-(2-phenylacetyl)pyrrolidine-2-carboxamide;
32) (2S,4R)-4-benzyl-N-(4-(4-fluorophenoxy)phenyl)-1-(2-(3-methylisoxazol-5-yl)acetyl)pyrrolidine-2-carboxamide;
33) (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide;
34) 34,(2S,4R)-4-benzyl-N-(4-(4-fluorophenoxy)phenyl)-1-(3,3,3-trifluoropropanoyl)pyrrolidine-2-carboxamide;
35) (2S,4R)-4-benzyl-1-(2-(4-(dimethylamino)phenyl)acetyl)-N-(4-(4-fluorophenoxy)phenyl)pyrrolidine-2-carboxamide;
36) (2S,4R)-4-benzyl-N-(4-(4-fluorophenoxy)phenyl)-1-(tetrahydrofuran-3-carbonyl)pyrrolidine-2-carboxamide;
37) (2S,4R)-4-benzyl-N-(4-(4-fluorophenoxy)phenyl)-1-(2-(2-methyl-1H-indol-3-yl)acetyl)pyrrolidine-2-carboxamide;
38) (2S,4R)-4-benzyl-1-(2-butoxyacetyl)-N-(4-(4-fluorophenoxy)phenyl)pyrrolidine-2-carboxamide;
39) (2S,4R)-4-benzyl-N-(4-(4-fluorophenoxy)phenyl)-1-((S)-5-oxotetrahydrofuran-2-carbonyl)pyrrolidine-2-carboxamide;
40) (2S,4R)-4-benzyl-N-(4-(4-fluorophenoxy)phenyl)-1-((R)-2-hydroxy-2-phenylacetyl)pyrrolidine-2-carboxamide;
41) (S)-3-(benzyloxy)-N-(4-(4-fluorophenoxy)phenyl)-2-(2-(4-(pyrimidin-2-yl)piperazin-1-yl)acetamido)propanamide;
42) (S)-3-(benzyloxy)-N-(4-(4-fluorophenoxy)phenyl)-2-(2-(4-(3-methoxyphenyl)piperazin-1-yl)acetamido)propanamide;
43) (S)-3-(benzyloxy)-N-(4-(4-fluorophenoxy)phenyl)-2-(2-(4-(pyrrolidin-1-yl)piperidin-1-yl)acetamido)propanamide;
44) (S)-3-(4-fluorobenzyloxy)-N-(4-(4-fluorophenoxy)phenyl)-2-(2-(2-phenyloxazol-4-yl)acetamido)propanamide;
45) (2S)-3-(benzyloxy)-N-(4-(4-fluorophenoxy)phenyl)-2-(2-(octahydroquinolin-1(2H)-yl)acetamido)propanamide;
46) (2S)-3-(benzyloxy)-N-(4-(4-fluorophenoxy)phenyl)-2-(2-(3-methylpiperidin-1-yl)acetamido)propanamide;
47) (S)-2-(2-(1H-imidazol-5-yl)acetamido)-3-(benzyloxy)-N-(4-(4-fluorophenoxy)-2-methylphenyl)propanamide;
48) (2S,4R)-1-(2-(2H-1,2,3-triazol-2-yl)acetyl)-N-(4-(4-fluorophenoxy)phenyl)-4-(2-methylbenzyl)pyrrolidine-2-carboxamide;
49) (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide;
50) (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide;
51) (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide;
52) (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide;
53) (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide;
54) (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide;
55) (2S,4R)-1-(2-(1H-1,2,4-triazol-1-yl)acetyl)-N-(4-(4-fluorophenoxy)phenyl)-4-(2-methylbenzyl)pyrrolidine-2-carboxamide;
56) (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide;
57) (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide;
58) (2S,4R)-1-(2-(2H-1,2,3-triazol-2-yl)acetyl)-4-benzyl-N-(4-(4-fluorophenoxy)phenyl)pyrrolidine-2-carboxamide;
59) (R)-N-(2-(benzyloxy)-1-(5-(4-fluorophenoxy)-1H-benzo[d]imidazol-2-yl)ethyl)-2-(1H-imidazol-4-yl)acetamide;
60) (R)-N-(2-(benzyloxy)-1-(5-(4-fluorophenoxy)-1H-benzo[d]imidazol-2-yl)ethyl)acetamide;
61) (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide;

62) (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide;
63) (2S)-3-(benzyloxy)-N-(4-(4-fluorophenoxy)phenyl)-2-(2-(2-methylpyrrolidin-1-yl)acetamido)propanamide;
64) (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide;
65) (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide;
66) (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide;
67) (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide;
68) (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide;
69) (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide;
70) (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide;
71) (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide;
72) (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide;
73) (2S,4R)-1-(2-(1H-1,2,4-triazol-1-yl)acetyl)-N-(4-(4-fluoro-3-methylphenoxy)phenyl)-4-(4-fluorobenzyl)pyrrolidine-2-carboxamide;
74) (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide;
75) (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide;
76) (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide;
77) (2S,4S)-1-(2-(2H-1,2,3-triazol-2-yl)acetyl)-N-(4-(4-fluorophenoxy)phenyl)-4-phenylpyrrolidine-2-carboxamide;
78) (2S,4S)-1-(2-(1H-1,2,4-triazol-1-yl)acetyl)-N-(4-(4-fluorophenoxy)phenyl)-4-phenylpyrrolidine-2-carboxamide;
79) (2S,4R)-1-(2-(1H-1,2,4-triazol-1-yl)acetyl)-4-benzyl-N-(4-(4-chlorophenoxy)phenyl)pyrrolidine-2-carboxamide;
80) (2S,4S)-1-(2-(1H-1,2,4-triazol-1-yl)acetyl)-4-(benzylamino)-N-(4-(4-fluorophenoxy)phenyl)pyrrolidine-2-carboxamide;
81) (S)-3-(benzyloxy)-2-(3-(3-chloro-4-methoxyphenyl)propanamido)-N-(4-(4-fluorophenoxy)phenyl)propanamide;
82) (2S,4R)-4-benzyl-1-(2-(3,4-dihydroisoquinolin-2(1H)-yl)acetyl)-N-(4-(4-fluorophenoxy)phenyl)pyrrolidine-2-carboxamide;
83) (2S,4R)-4-benzyl-N-(4-(4-fluorophenoxy)phenyl)-1-(2-thiomorpholinoacetyl)pyrrolidine-2-carboxamide;
84) (2S,4R)-4-benzyl-N-(4-(4-fluorophenoxy)phenyl)-1-(2-(2,3,6-trifluorophenyl)acetyl)pyrrolidine-2-carboxamide;
85) (2S,4R)-4-benzyl-N-(4-(4-fluorophenoxy)phenyl)-1-(3-(methylthio)propanoyl)pyrrolidine-2-carboxamide;
86) (2S,4R)-4-benzyl-1-(3-ethoxypropanoyl)-N-(4-(4-fluorophenoxy)phenyl)pyrrolidine-2-carboxamide;
87) (2S,4R)-4-benzyl-N-(4-(4-fluorophenoxy)phenyl)-1-(2-(methylsulfonyl)acetyl)pyrrolidine-2-carboxamide;
88) (2S,4R)-4-benzyl-N-(4-(4-fluorophenoxy)phenyl)-1-(2-(2-methoxyethoxy)acetyl)pyrrolidine-2-carboxamide;
89) (2S,4R)-4-benzyl-1-(4-(dimethylamino)-4-oxobutanoyl)-N-(4-(4-fluorophenoxy)phenyl)pyrrolidine-2-carboxamide;
90) (2S,4R)-4-benzyl-N-(4-(4-fluorophenoxy)phenyl)-1-(3-methoxypropanoyl)pyrrolidine-2-carboxamide;
91) (2S,4R)-4-benzyl-N-(4-(4-fluorophenoxy)phenyl)-1-(4-oxo-4-(thien-2-yl)butanoyl)pyrrolidine-2-carboxamide;
92) (2S,4R)-4-benzyl-N-(4-(4-fluorophenoxy)phenyl)-1-(tetrahydrofuran-2-carbonyl)pyrrolidine-2-carboxamide;
93) (2S,4R)-1-((S)-1-acetylpyrrolidine-2-carbonyl)-4-benzyl-N-(4-(4-fluorophenoxy)phenyl)pyrrolidine-2-carboxamide;
94) (2S,4R)-4-benzyl-N-(4-(4-fluorophenoxy)phenyl)-1-(2-(pyrimidin-2-ylthio)acetyl)pyrrolidine-2-carboxamide;
95) (2S,4R)-4-benzyl-1-(2-(2,6-difluorophenyl)acetyl)-N-(4-(4-fluorophenoxy)phenyl)pyrrolidine-2-carboxamide;
96) (2S,4R)-4-benzyl-N-(4-(4-fluorophenoxy)phenyl)-1-(2-(pyridin-4-ylthio)acetyl)pyrrolidine-2-carboxamide;
97) (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide;
98) (2S,4R)-1-(2-(1H-indol-3-yl)acetyl)-4-benzyl-N-(4-(4-fluorophenoxy)phenyl)pyrrolidine-2-carboxamide;
99) (2S,4R)-4-benzyl-N-(4-(4-fluorophenoxy)phenyl)-1-(2-(4-oxo-2-thioxothiazolidin-3-yl)acetyl)pyrrolidine-2-carboxamide;
100) (2S,4R)-4-benzyl-N-(4-(4-fluorophenoxy)phenyl)-1-(2-(4-(2-methoxyethyl)piperazin-1-yl)acetyl)pyrrolidine-2-carboxamide;
101) (S)-3-(benzyloxy)-2-(2-(3-fluoro-4-(trifluoromethyl)phenyl)acetamido)-N-(4-(4-fluorophenoxy)phenyl)propanamide;
102) (S)-3-(benzyloxy)-N-(4-(4-fluorophenoxy)phenyl)-2-(2-(3-(trifluoromethoxy)phenyl)acetamido)propanamide;
103) (S)-tert-butyl 1-(2-((S)-3-(benzyloxy)-1-(4-(4-fluorophenoxy)phenylamino)-1-oxopropan-2-ylamino)-2-oxoethyl)pyrrolidine-2-carboxylate;
104) (S)-N-(3-(benzyloxy)-1-(4-(4-fluorophenoxy)phenylamino)-1-oxopropan-2-yl)-5-phenylpentanamide;
105) (S)-3-(benzyloxy)-N-(4-(4-fluorophenoxy)phenyl)-2-(2-(4-morpholinopiperidin-1-yl)acetamido)propanamide;
106) (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide;
107) (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide;

108) (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide;
109) (2S)-3-(benzyloxy)-2-(2-(3-(diethylamino)pyrrolidin-1-yl)acetamido)-N-(4-(4-fluorophenoxy)phenyl)propanamide;
110) (2S)-3-(benzyloxy)-N-(4-(4-fluorophenoxy)phenyl)-2-(2-(4-((tetrahydrofuran-2-yl)methyl)piperazin-1-yl)acetamido)propanamide;
111) (S)-3-(benzyloxy)-N-(4-(4-fluorophenoxy)phenyl)-2-(2-(4-isopropylpiperazin-1-yl)acetamido)propanamide;
112) (S)-3-(benzyloxy)-N-(4-(4-fluorophenoxy)phenyl)-2-(2-(4-(3-(trifluoromethyl)pyridin-2-yl)piperazin-1-yl)acetamido)propanamide;
113) (2S)-3-(benzyloxy)-N-(4-(4-fluorophenoxy)phenyl)-2-(2-(2-(((S)-1-methylpyrrolidin-2-yl)methyl)piperidin-1-yl)acetamido)propanamide,
114) (S)-3-(benzyloxy)-2-(2-(4-ethylpiperazin-1-yl)acetamido)-N-(4-(4-fluorophenoxy)phenyl)propanamide;
115) (2S,4R)-1-(2-(4-acetylpiperazin-1-yl)acetyl)-4-benzyl-N-(4-(4-fluorophenoxy)phenyl)pyrrolidine-2-carboxamide;
116) (2S,4R)-4-benzyl-N-(4-(4-fluorophenoxy)phenyl)-1-(2-morpholinoacetyl)pyrrolidine-2-carboxamide;
117) (2S,4R)-4-benzyl-N-(4-(4-fluorophenoxy)phenyl)-1-(2-(thien-2-yl)acetyl)pyrrolidine-2-carboxamide;
118) (2S,4R)-4-benzyl-N-(4-(4-fluorophenoxy)phenyl)-1-(3-hydroxybutanoyl)pyrrolidine-2-carboxamide;
119) (2S,4R)-4-benzyl-1-(2-(2,6-dichlorophenyl)acetyl)-N-(4-(4-fluorophenoxy)phenyl)pyrrolidine-2-carboxamide;
120) (2S,4R)-4-benzyl-N-(4-(4-fluorophenoxy)phenyl)-1-(2-hydroxyacetyl)pyrrolidine-2-carboxamide;
121) (2S,4R)-4-benzyl-1-(2-ethoxyacetyl)-N-(4-(4-fluorophenoxy)phenyl)pyrrolidine-2-carboxamide;
122) (2S,4R)-4-benzyl-N-(4-(4-fluorophenoxy)phenyl)-1-(2-methoxyacetyl)pyrrolidine-2-carboxamide;
123) (2S,4R)-4-benzyl-N-(4-(4-fluorophenoxy)phenyl)-1-(4-oxopentanoyl)pyrrolidine-2-carboxamide;
124) (2S,4R)-4-benzyl-N-(4-(4-fluorophenoxy)phenyl)-1-(4-oxo-4-phenylbutanoyl)pyrrolidine-2-carboxamide;
125) methyl 4-((2S,4R)-4-benzyl-2-(4-(4-fluorophenoxy)phenylcarbamoyl)pyrrolidin-1-yl)-4-oxobutanoate;
126) (S)-3-(benzyloxy)-N-(4-(4-fluorophenoxy)phenyl)-2-(2-(4-(pyridin-2-yl)piperazin-1-yl)acetamido)propanamide;
127) (S)-3-(benzyloxy)-N-(4-(4-fluorophenoxy)phenyl)-2-(2-(4-(2-fluorophenyl)piperazin-1-yl)acetamido)propanamide;
128) (S)-2-(2-(azepan-1-yl)acetamido)-3-(benzyloxy)-N-(4-(4-fluorophenoxy)phenyl)propanamide;
129) (2S,4R)-4-benzyl-1-(2-cyanoacetyl)-N-(4-(4-fluorophenoxy)phenyl)pyrrolidine-2-carboxamide;
130) (S)-3-(benzyloxy)-N-(4-(4-fluorophenoxy)phenyl)-2-(2-(4-methylpiperidin-1-yl)acetamido)propanamide;
131) (S)-2-(2-(1H-imidazol-5-yl)acetamido)-3-benzyloxy-N-(4-(4-fluorophenoxy)phenyl)propanamide;
132) (S)-2-(2-(1H-imidazol-5-yl)acetamido)-3-(4-fluorobenzyloxy)-N-(4-(4-chlorophenoxy)phenyl)propanamide;
133) (S)-2-(2-(1H-imidazol-5-yl)acetamido)-3-(4-fluorobenzyloxy)-N-(4-(4-fluorophenoxy)phenyl)propanamide;
134) (S)-2-(2-(1H-imidazol-1-yl)acetamido)-3-benzyloxy-N-(4-(4-fluorophenoxy)phenyl)propanamide;
135) (S)-2-(2-(1H-1,2,4-triazol-1-yl)acetamido)-3-(4-fluorobenzyloxy)-N-(4-(4-fluorophenoxy)phenyl)propanamide;
136) (S)-3-(benzyloxy)-2-(2-chloroacetamido)-N-(4-(4-fluorophenoxy)phenyl)propanamide;
137) (S)-2-(2-(1H-imidazol-5-yl)acetamido)-5-phenyl-N-(4-(4-fluorophenoxy)phenyl)pentanamide;
138) (S)-2-(2-(2H-1,2,3-triazol-2-yl)acetamido)-3-(benzyloxy)-N-(4-(4-fluorophenoxy)phenyl)propanamide;
139) (S)-2-(2-(1H-1,2,4-triazol-1-yl)acetamido)-N-(4-(4-fluorophenoxy)phenyl)-3-(2-(trifluoromethoxy)benzyloxy)propanamide;
140) (2S,4R)-1-(2-(1H-1,2,4-triazol-1-yl)acetyl)-4-benzyl-N-(4-(4-fluorophenoxy)phenyl)pyrrolidine-2-carboxamide;
141) (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide;
142) 2-(2-(1H-imidazol-5-yl)acetamido)-3-benzyloxy-N-(4-phenoxyphenyl)propanamide;
143) (S)-2-(2-(1H-imidazol-5-yl)acetamido)-3-benzyloxy-N-(4-phenoxyphenyl)propanamide;
144) (S)-2-(2-(1H-tetrazol-1-yl)acetamido)-3-benzyloxy-N-(4-phenoxyphenyl)propanamide;
145) (S)-2-(2-(1H-imidazol-5-yl)acetamido)-3-benzyloxy-N-(4-(4-chlorophenoxy)phenyl)propanamide;
146) (S)-2-(2-(1H-1,2,4-triazol-1-yl)acetamido)-3-(benzyloxy)-N-(4-phenoxyphenyl)propanamide;
147) (S)-2-(2-(1H-imidazol-4-yl)acetamido)-3-(benzyloxy)-N-(3-chloro-4-phenoxyphenyl)propanamide;
148) (S)-2-(2-(1H-imidazol-4-yl)acetamido)-3-(benzyloxy)-N-(4-(3-chlorophenoxy)phenyl)propanamide;
149) (S)-2-(2-(1H-1,2,4-triazol-1-yl)acetamido)-3-benzyloxy-N-(4-(4-fluorophenoxy)phenyl)propanamide;
150) (S)-3-(benzyloxy)-2-(2-(3,5-dimethylisoxazol-4-yl)acetamido)-N-(4-(4-fluorophenoxy)phenyl)propanamide;
151) (S)-2-(2-(1H-benzo [d][1,2,3]triazol-1-yl)acetamido)-3-(benzyloxy)-N-(4-(4-fluorophenoxy)phenyl)propanamide;
152) (S)-3-(benzyloxy)-2-(2-(3,5-dimethyl-1H-pyrazol-4-yl)acetamido)-N-(4-(4-fluorophenoxy)phenyl)propanamide;
153) (S)-3-(benzyloxy)-N-(4-(4-fluorophenoxy)phenyl)-2-(2-(4-methyl-1H-1,2,3-triazol-1-yl)acetamido)propanamide;
154) (S)-2-(2-(1H-imidazol-4-yl)acetamido)-3-(benzyloxy)-N-(3-chloro-4-(4-chlorophenoxy)phenyl)propanamide;
155) (S)-3-(benzyloxy)-N-(4-(4-fluorophenoxy)phenyl)-2-(2-morpholinoacetamido)propanamide;
156) (S)-2-(2-(1H-imidazol-4-yl)acetamido)-3-(benzyloxy)-N-(4-(5-bromothiazol-2-yloxy)phenyl)propanamide;
157) (S)-2-(2-(1H-imidazol-5-yl)acetamido)-N-(4-(4-chlorophenoxy)phenyl)-4-phenylbutanamide;
158) (S)-2-(2-(1H-imidazol-5-yl)acetamido)-3-(benzyloxy)-N-(4-(p-tolyloxy)phenyl)propanamide;
159) (S)-3-(benzyloxy)-N-(4-(4-fluorophenoxy)phenyl)-2-(2-(pyrazin-2-yl)acetamido)propanamide;
160) (S)-3-(benzyloxy)-N-(4-(4-fluorophenoxy)phenyl)-2-(2-(2-methyl-1H-imidazol-1-yl)acetamido)propanamide;
161) (S)-2-(2-(1H-imidazol-4-yl)-2-methylpropanamido)-3-(4-fluorobenzyloxy)-N-(4-(4-fluorophenoxy)phenyl)propanamide;

162) (S)-3-(benzyloxy)-N-(4-(4-fluorophenoxy)phenyl)-2-(2-(2-methyl-1H-imidazol-4-yl)acetamido)propanamide;
163) (2S,3S)-1-(2-(1H-imidazol-4-yl)acetyl)-3-benzyl-N-(4-(4-fluorophenoxy)phenyl)pyrrolidine-2-carboxamide;
164) (S)-2-acetamido-3-(4-fluorobenzyloxy)-N-(4-(4-fluorophenoxy)phenyl)propanamide;
165) (S)-benzyl 4-(2-(1H-1,2,4-triazol-1-yl)acetamido)-5-(4-(4-fluorophenoxy)phenylamino)-5-oxopentylcarbamate;
166) (S)-3-(benzyloxy)-N-(4-(4-fluorophenoxy)phenyl)-2-(2-(3-methyl-1H-pyrazol-5-yl)acetamido)propanamide
167) (2S)-2-(2-(1H-imidazol-4-yl)propanamido)-3-(benzyloxy)-N-(4-(4-fluorophenoxy)phenyl)propanamide;
168) (S)-2-(2-(1H-imidazol-5-yl)acetamido)-N-(4-(4-bromophenoxy)phenyl)-3-(4-fluorobenzyloxy)propanamide;
169) (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide;
170) (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide;
171) (2S,4R)-1-(2-(1H-1,2,4-triazol-1-yl)acetyl)-N-(4-(4-fluorophenoxy)phenyl)-4-(3-methylbenzyl)pyrrolidine-2-carboxamide;
172) (S)-2-(3-(3,5-dimethylisoxazol-4-yl)ureido)-3-benzyloxy-N-(4-(4-fluorophenoxy)phenyl)propanamide;
173) (2S,4R)-1-(2-(1H-imidazol-5-yl)acetyl)-4-(benzylamino)-N-(4-(4-fluorophenoxy)phenyl)pyrrolidine-2-carboxamide;
174) (S)-2-(2-(1H-1,2,3-triazol-1-yl)acetamido)-3-(benzyloxy)-N-(4-(4-fluorophenoxy)phenyl)propanamide;
175) 175 (S)-1-(2-(1H-imidazol-4-yl)acetyl)-4-benzyl-N-(4-(4-fluorophenoxy)phenyl)piperazine-2-carboxamide;
176) (2S,4R)-1-(2-(1H-benzo [d][1,2,3]triazol-1-yl)acetyl)-4-benzyl-N-(4-(4-fluorophenoxy)phenyl)pyrrolidine-2-carboxamide;
177) (2S,4R)-4-benzyl-N-(4-(4-fluorophenoxy)phenyl)-1-(2-(5-methyl-1H-pyrazol-3-yl)acetyl)pyrrolidine-2-carboxamide;
178) (S)-2-(2-(1H-1,2,4-triazol-1-yl)acetamido)-3-(benzyloxy)-N-(4-(4-fluorophenylthio)phenyl)propanamide;
179) (2S,4R)-1-(2-(1H-1,2,4-triazol-1-yl)acetyl)-4-(benzylamino)-N-(4-(4-fluorophenoxy)phenyl)pyrrolidine-2-carboxamide;
180) (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide;
181) (S)-2-(2-(1H-1,2,4-triazol-1-yl)acetamido)-3-(2-chlorobenzyloxy)-N-(4-(4-fluorophenoxy)phenyl)propanamide;
182) (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide;
183) 3-(benzyloxy)-2-(2-(2-fluorophenyl)acetamido)-N-(4-phenoxyphenyl)propanamide;
184) N-(3-(benzyloxy)-1-oxo-1-(4-phenoxyphenylamino)propan-2-yl)-1H-indole-4-carboxamide;
185) 2-(2-(3-methylisoxazol-5-yl)acetamido)-3-benzyloxy-N-(4-phenoxyphenyl)propanamide;
186) N-(3-(benzyloxy)-1-oxo-1-(4-phenoxyphenylamino)propan-2-yl)-4-cyclopropyl-4-oxobutanamide;
187) N-(3-(benzyloxy)-1-oxo-1-(4-phenoxyphenylamino)propan-2-yl)-1H-indole-6-carboxamide;
188) N-(3-(benzyloxy)-1-oxo-1-(4-phenoxyphenylamino)propan-2-yl)-2,3-dihydro-1H-indene-2-carboxamide;
189) N-(3-(benzyloxy)-1-oxo-1-(4-phenoxyphenylamino)propan-2-yl)-3-methyl-2-nitrobenzamide;
190) 3-(benzyloxy)-2-(2-(2,5-dichlorophenyl)acetamido)-N-(4-phenoxyphenyl)propanamide;
191) 3-(benzyloxy)-2-(2-(3-chloro-2-fluorophenyl)acetamido)-N-(4-phenoxyphenyl)propanamide;
192) 3-(benzyloxy)-2-(2-(5-chloro-2-fluorophenyl)acetamido)-N-(4-phenoxyphenyl)propanamide;
193) 2-(2-(1-acetylpyrrolidin-2-yl)acetamido)-3-benzyloxy-N-(4-phenoxyphenyl)propanamide;
194) (S)-2-{2-((benzoyl)(methyl)amino)acetamido}-3-benzyloxy-N-(4-phenoxyphenyl)propanamide;
195) (S)-2-(2-(1-methyl-1H-imidazol-4-yl)acetamido)-3-benzyloxy-N-(4-phenoxyphenyl)propanamide;
196) (S)-2-(2-(2-fluorophenyl)acetamido)-3-benzyloxy-N-(4-phenoxyphenyl)propanamide;
197) (S)-2-(2-(1H-indol-4-yl)acetamido)-3-benzyloxy-N-(4-phenoxyphenyl)propanamide;
198) (S)-2-(2-(thien-2-yl)acetamido)-3-benzyloxy-N-(4-phenoxyphenyl)propanamide;
199) (S)-2-(2-(2,5-dichlorophenyl)acetamido)-3-benzyloxy-N-(4-phenoxyphenyl)propanamide;
200) (S)-2-(2-(1H-imidazol-4-yl)acetamido)-3-(benzyloxy)-N-(4-benzylphenyl)propanamide;
201) (S)-3-(benzyloxy)-2-(2-(2,4-dioxoimidazolidin-1-yl)acetamido)-N-(4-phenoxyphenyl)propanamide;
202) (S)-2-(2-(1H-imidazol-4-yl)acetamido)-3-(benzyloxy)-N-(4-(4-methoxyphenoxy)phenyl)propanamide;
203) (S)-2-(2-(1H-imidazol-4-yl)-N-methylacetamido)-3-(benzyloxy)-N-(4-phenoxyphenyl)propanamide;
204) (S)-2-(2-(1H-imidazol-5-yl)acetamido)-N-(4-(4-chlorophenoxy)phenyl)-3-phenylpropanamide;
205) (S)-3-(benzyloxy)-N-(4-(4-fluorophenoxy)phenyl)-2-(2-(piperazin-1-yl)acetamido)propanamide;
206) (S)-2-(2-(1H-imidazol-4-yl)acetamido)-3-(benzyloxy)-N-(4-(thiazol-2-yloxy)phenyl)propanamide;
207) (S)-2-(3-(1H-imidazol-5-yl)propanamido)-3-(benzyloxy)-N-(4-(4-fluorophenoxy)phenyl)propanamide;
208) (S)-2-(2-(1H-imidazol-5-yl)acetamido)-3-(benzyloxy)-N-(4-(cyclohexyloxy)phenyl)propanamide;
209) (S)-3-(benzyloxy)-N-(4-(4-chlorophenoxy)phenyl)-2-(3-(dimethylamino)propanamido)propanamide;
210) (S)-3-(4-fluorobenzyloxy)-N-(4-(4-fluorophenoxy)phenyl)-2-(2-morpholinoacetamido)propanamide;
211) (S)-2-(2-(1H-imidazol-4-yl)acetamido)-3-(benzyloxy)-N-(4-(benzyloxy)phenyl)propanamide;
212) (S)-3-(benzyloxy)-2-(2-(5-fluoro-1H-indol-3-yl)acetamido)-N-(4-(4-fluorophenoxy)phenyl)propanamide;
213) (S)-2-(2-(1H-imidazol-4-yl)-2-methylpropanamido)-3-(benzyloxy)-N-(4-(4-fluorophenoxy)phenyl)propanamide;
214) (S)-3-(benzyloxy)-2-(2-(2,5-dihydro-1H-pyrrol-1-yl)acetamido)-N-(4-(4-fluorophenoxy)phenyl)propanamide;
215) (S)-3-(benzyloxy)-N-(4-(4-fluorophenoxy)phenyl)-2-(2-(pyrrolidin-1-yl)acetamido)propanamide;
216) (S)-2-(2-(2-(1H-imidazol-4-yl)ethylamino)acetamido)-3-(benzyloxy)-N-(4-(4-fluorophenoxy)phenyl)propanamide;
217) (S)-3-(benzyloxy)-N-(4-(4-fluorophenoxy)phenyl)-2-(2-(4-(2-methoxyphenyl)piperazin-1-yl)acetamido)propanamide;

218) (S)-3-(benzyloxy)-N-(4-(4-fluorophenoxy)phenyl)-2-(2-(4-(4-fluorophenyl)piperazin-1-yl)acetamido)propanamide;
219) (2S)-2-(2-(2,3-dioxa-8-azaspiro[4.5]decan-8-yl)acetamido)-3-(benzyloxy)-N-(4-(4-fluorophenoxy)phenyl)propanamide;
220) (S)-3-(benzyloxy)-2-(2-(4-benzylpiperidin-1-yl)acetamido)-N-(4-(4-fluorophenoxy)phenyl)propanamide;
221) (S)-3-(benzyloxy)-2-(2-(3,4-dihydroisoquinolin-2(1H)-yl)acetamido)-N-(4-(4-fluorophenoxy)phenyl)propanamide;
222) (2S)-3-(benzyloxy)-N-(4-(4-fluorophenoxy)phenyl)-2-(2-(octahydroisoquinolin-2(1H)-yl)acetamido)propanamide;
223) (S)-3-(benzyloxy)-N-(4-(4-fluorophenoxy)phenyl)-2-(2-(4-(furan-2-carbonyl)piperazin-1-yl)acetamido)propanamide;
224) (S)-3-(benzyloxy)-N-(4-(4-fluorophenoxy)phenyl)-2-(2-(4-(4-methoxyphenyl)piperazin-1-yl)acetamido)propanamide;
225) (S)-3-(benzyloxy)-N-(4-(4-fluorophenoxy)phenyl)-2-(2-(4-phenylpiperazin-1-yl)acetamido)propanamide;
226) (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide;
227) (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide;
228) (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide;
229) (S)-2-(2-(4-(4-acetylphenyl)piperazin-1-yl)acetamido)-3-(benzyloxy)-N-(4-(4-fluorophenoxy)phenyl)propanamide;
230) (S)-2-(2-(4-acetylpiperazin-1-yl)acetamido)-3-(benzyloxy)-N-(4-(4-fluorophenoxy)phenyl)propanamide;
231) 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide;
232) (S,E)-N-(3-(benzyloxy)-1-(4-(4-fluorophenoxy)phenylamino)-1-oxopropan-2-yl)hex-3-enamide;
233) (S)-N-(3-(benzyloxy)-1-(4-(4-fluorophenoxy)phenylamino)-1-oxopropan-2-yl)-3-methylbutanamide;
234) (S)-3-(benzyloxy)-2-(2-((2R,6S)-2,6-dimethylmorpholino)acetamido)-N-(4-(4-fluorophenoxy)phenyl)propanamide;
235) (S)-3-(benzyloxy)-N-(4-(4-fluorophenoxy)phenyl)-2-(2-(thiazolidin-3-yl)acetamido)propanamide;
236) (S)-2-(2-(4-acetylpiperazin-1-yl)acetamido)-3-(benzyloxy)-N-(4-(4-fluorophenoxy)phenyl)propanamide;
237) (2S)-3-(benzyloxy)-N-(4-(4-fluorophenoxy)phenyl)-2-(2-(4-(tetrahydrofuran-2-carbonyl)piperazin-1-yl)acetamido)propanamide;
238) (S)-methyl 1-(2-(3-(benzyloxy)-1-(4-(4-fluorophenoxy)phenylamino)-1-oxopropan-2-ylamino)-2-oxoethyl)piperidine-4-carboxylate;
239) (S)-3-(benzyloxy)-2-(2-(4-(2-chloro-6-fluorobenzyl)piperazin-1-yl)acetamido)-N-(4-(4-fluorophenoxy)phenyl)propanamide;
240) (S)-3-(benzyloxy)-N-(4-(4-fluorophenoxy)phenyl)-2-(2-(isoindolin-2-yl)acetamido)propanamide;
241) (S)-3-(benzyloxy)-N-(4-(4-fluorophenoxy)phenyl)-2-(2-(4-(2-methoxyethyl)piperazin-1-yl)acetamido)propanamide;
242) (S)-3-(benzyloxy)-N-(4-(4-fluorophenoxy)phenyl)-2-(2-(4-(2-ethoxyethyl)piperazin-1-yl)acetamido)propanamide;
243) (S)-2-(2-(1H-imidazol-4-yl)acetamido)-3-(benzyloxy)-N-(3-phenoxyphenyl)propanamide;
244) (S)-3-(benzyloxy)-2-(2-(3-bromophenyl)acetamido)-N-(4-(4-fluorophenoxy)phenyl)propanamide;
245) (S)-3-(benzyloxy)-N-(4-(4-fluorophenoxy)phenyl)-2-(3-nitropropanamido)propanamide;
246) (S)-3-(benzyloxy)-N-(4-(4-fluorophenoxy)phenyl)-2-(2-(pyridin-2-yl)acetamido)propanamide;
247) (S)-3-(benzyloxy)-N-(4-(4-fluorophenoxy)phenyl)-2-(2-(pyridin-3-yl)acetamido)propanamide;
248) (S)-N-((S)-3-(benzyloxy)-1-(4-(4-fluorophenoxy)phenylamino)-1-oxopropan-2-yl)-3,7-dimethyloct-6-enamide;
249) (S)-3-(benzyloxy)-N-(4-(4-fluorophenoxy)phenyl)-2-(2-phenylacetamido)propanamide;
250) (S)-3-(benzyloxy)-N-(4-(4-fluorophenoxy)phenyl)-2-(2-(pyrimidin-5-yl)acetamido)propanamide;
251) (2S,4S)-1-(2-(1H-imidazol-5-yl)acetyl)-N-(4-(4-fluorophenoxy)phenyl)-4-phenylpyrrolidine-2-carboxamide;
252) (2S,4R)-1-(2-(1H-1,2,4-triazol-1-yl)acetyl)-4-(benzyloxy)-N-(4-(4-fluorophenoxy)phenyl)pyrrolidine-2-carboxamide;
253) benzyl (3R,5S)-1-(2-(1H-imidazol-5-yl)acetyl)-5-(4-(4-fluorophenoxy)phenylcarbamoyl)pyrrolidin-3-ylcarbamate;
254) (S)-2-(2-(1H-1,2,4-triazol-1-yl)acetamido)-5-acetamido-N-(4-(4-fluorophenoxy)phenyl)pentanamide;
255) (S)-3-(benzyloxy)-N-(4-(4-fluorophenoxy)phenyl)-2-(2-methyl-2-(1H-1,2,4-triazol-1-yl)propanamido)propanamide;
256) (S)-3-(benzyloxy)-2-(2-(3,5-dimethyl-1H-1,2,4-triazol-1-yl)acetamido)-N-(4-(4-fluorophenoxy)phenyl)propanamide;
257) (S)-benzyl 4-(2-(1H-imidazol-4-yl)acetyl)-3-(4-(4-fluorophenoxy)phenylcarbamoyl)piperazine-1-carboxylate;
258) (S)-2-(2-(3,5-dimethyl-1H-pyrazol-4-yl)acetamido)-3-(4-fluorobenzyloxy)-N-(4-(4-fluorophenoxy)phenyl)propanamide;
259) (2S,4R)-1-(2-(1H-1,2,4-triazol-1-yl)acetyl)-N-(4-(4-fluorophenoxy)phenyl)-4-phenoxypyrrolidine-2-carboxamide;
260) (2S,4R)-1-(2-(1H-1,2,4-triazol-1-yl)acetyl)-N-(4-(4-fluorophenoxy)phenyl)-4-(isoindolin-2-pyrrolidine-2-carboxamide;
261) (S)-1-(2-(1H-1,2,4-triazol-1-yl)acetyl)-4-benzyl-N-(4-(4-fluorophenoxy)phenyl)piperazine-2-carboxamide;
262) (2S,4S)-1-(2-(1H-1,2,4-triazol-1-yl)acetyl)-4-((benzylamino)methyl)-N-(4-(4-fluorophenoxy)phenyl)pyrrolidine-2-carboxamide;
263) (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide;
264) (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide;
265) (2S)-3-(benzyloxy)-2-(2-(2,6-dimethylmorpholino)acetamido)-N-(4-(4-fluorophenoxy)phenyl)propanamide;
266) (S)-3-(benzyloxy)-N-(4-(4-fluorophenoxy)phenyl)-2-(2-thiomorpholinoacetamido)propanamide;
267) (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide;

268) (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide;
269) N-(2-oxo-1-{[(phenylmethyl)oxy]methyl}-2-{[4-(phenyloxy)phenyl]amino}ethyl)acetamide;
270) 4-(methyloxy)-N-(2-oxo-1-{[(phenylmethyl)oxy]methyl}-2-{[4-(phenyloxy)phenyl]amino}ethyl)benzamide;
271) 4-benzyloxy-N-(2-oxo-1-{[(phenylmethyl)oxy]methyl}-2-{[4-(phenyloxy)phenyl]amino}ethyl)phenylacetamide;
272) 2-bromo-5-(methyloxy)-N-(2-oxo-1-{[(phenylmethyl)oxy]methyl}-2-{[4-(phenyloxy)phenyl]amino}ethyl)benzamide;
273) N-(2-oxo-1-{[(phenylmethyl)oxy]methyl}-2-{[4-(phenyloxy)phenyl]amino}ethyl)butanamide;
274) 2-chloro-N-(2-oxo-1-{[(phenylmethyl)oxy]methyl}-2-{[4-(phenyloxy)phenyl]amino}ethyl)benzamide;
275) 3-chloro-N-(2-oxo-1-{[(phenylmethyl)oxy]methyl}-2-{[4-(phenyloxy)phenyl]amino}ethyl)benzamide;
276) 4-chloro-N-(2-oxo-1-{[(phenylmethyl)oxy]methyl}-2-{[4-(phenyloxy)phenyl]amino}ethyl)benzamide;
277) N-(2-oxo-1-{[(phenylmethyl)oxy]methyl}-2-{[4-(phenyloxy)phenyl]amino}ethyl)cyclopropylamide;
278) N-(2-oxo-1-{[(phenylmethyl)oxy]methyl}-2-{[4-(phenyloxy)phenyl]amino}ethyl)-3-cyclopentylpropanamide;
279) 3,4-dimethyl-N-(2-oxo-1-{[(phenylmethyl)oxy]methyl}-2-{[4-(phenyloxy)phenyl]amino}ethyl)benzamide;
280) N-(2-oxo-1-{[(phenylmethyl)oxy]methyl}-2-{[4-(phenyloxy)phenyl]amino}ethyl)-2,5-dimethoxyphenylacetamide;
281) 4-(ethyloxy)-N-(2-oxo-1-{[(phenylmethyl)oxy]methyl}-2-{[4-(phenyloxy)phenyl]amino}ethyl)benzamide;
282) N-(3-(benzyloxy)-1-oxo-1-(4-phenoxyphenylamino)propan-2-yl)-2-ethylhexanamide;
283) N-(2-oxo-1-{[(phenylmethyl)oxy]methyl}-2-{[4-(phenyloxy)phenyl]amino}ethyl)furan-2-carboxamide;
284) N-(2-oxo-1-{[(phenylmethyl)oxy]methyl}-2-{[4-(phenyloxy)phenyl]amino}ethyl)-2-methoxyacetamide;
285) N-(2-oxo-1-{[(phenylmethyl)oxy]methyl}-2-{[4-(phenyloxy)phenyl]amino}ethyl)-3-methoxyphenylacetamide;
286) 2-methyl-N-(2-oxo-1-{[(phenylmethyl)oxy]methyl}-2-{[4-(phenyloxy)phenyl]amino}ethyl)pentanamide;
287) 4-methyl-N-(2-oxo-1-{[(phenylmethyl)oxy]methyl}-2-{[4-(phenyloxy)phenyl]amino}ethyl)pentanamide;
288) N-(2-oxo-1-{[(phenylmethyl)oxy]methyl}-2-{[4-(phenyloxy)phenyl]amino}ethyl)naphthalene-2-carboxamide;
289) N-(2-oxo-1-{[(phenylmethyl)oxy]methyl}-2-{[4-(phenyloxy)phenyl]amino}ethyl)phenoxyacetamide;
290) N-(2-oxo-1-{[(phenylmethyl)oxy]methyl}-2-{[4-(phenyloxy)phenyl]amino}ethyl)-2-(phenyloxy)pyridine-3-carboxamide;
291) 3,4,5-tris(methyloxy)-N-(2-oxo-1-{[(phenylmethyl)oxy]methyl}-2-{[4-(phenyloxy)phenyl]amino}ethyl)benzamide;
292) N-(2-oxo-1-{[(phenylmethyl)oxy]methyl}-2-{[4-(phenyloxy)phenyl]amino}ethyl)thiophene-2-carboxamide;
293) N-(2-oxo-1-{[(phenylmethyl)oxy]methyl}-2-{[4-(phenyloxy)phenyl]amino}ethyl)thien-2-ylacetamide;
294) 4-(dimethylamino)-N-(2-oxo-1-{[(phenylmethyl)oxy]methyl}-2-{[4-(phenyloxy)phenyl]amino}ethyl)benzamide;
295) N-(2-oxo-1-{[(phenylmethyl)oxy]methyl}-2-{[4-(phenyloxy)phenyl]amino}ethyl)hexanamide;
296) 2-chloro-N-(2-oxo-1-{[(phenylmethyl)oxy]methyl}-2-{[4-(phenyloxy)phenyl]amino}ethyl)pyridine-3-carboxamide;
297) 3-chloro-N-(2-oxo-1-{[(phenylmethyl)oxy]methyl}-2-{[4-(phenyloxy)phenyl]amino}ethyl)-1-benzothiophene-2-carboxamide;
298) N-(2-oxo-1-{[(phenylmethyl)oxy]methyl}-2-{[4-(phenyloxy)phenyl]amino}ethyl)pent-4-enamide;
299) 3-chloro-2-fluoro-N-(2-oxo-1-{[(phenylmethyl)oxy]methyl}-2-{[4-(phenyloxy)phenyl]amino}ethyl)benzamide;
300) N-(2-oxo-1-{[(phenylmethyl)oxy]methyl}-2-{[4-(phenyloxy)phenyl]amino}ethyl)-4-phenylbutanamide;
301) N-(2-oxo-1-{[(phenylmethyl)oxy]methyl}-2-{[4-(phenyloxy)phenyl]amino}ethyl)-2-bromophenylacetamide;
302) N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide;
303) N-(2-oxo-1-{[(phenylmethyl)oxy]methyl}-2-{[4-(phenyloxy)phenyl]amino}ethyl)-2-methoxyethoxyacetamide;
304) N-(2-oxo-1-{[(phenylmethyl)oxy]methyl}-2-{[4-(phenyloxy)phenyl]amino}ethyl)-3-(4-methoxyphenyl)propanamide;
305) N-(2-oxo-1-{[(phenylmethyl)oxy]methyl}-2-{[4-(phenyloxy)phenyl]amino}ethyl)-2-acetylamino-4-methylthiazol-5-ylsulfonamide;
306) 4-(methylthio)-N-(2-oxo-1-{[(phenylmethyl)oxy]methyl}-2-{[4-(phenyloxy)phenyl]amino}ethyl)benzamide;
307) N-(2-oxo-1-{[(phenylmethyl)oxy]methyl}-2-{[4-(phenyloxy)phenyl]amino}ethyl)-2-(methylthio)acetamide;
308) 5-fluoro-2-(methyloxy)-N-(2-oxo-1-{[(phenylmethyl)oxy]methyl}-2-{[4-(phenyloxy)phenyl]amino}ethyl)benzamide;
309) 2-methyl-4-(methyloxy)-N-(2-oxo-1-{[(phenylmethyl)oxy]methyl}-2-{[4-(phenyloxy)phenyl]amino}ethyl)benzamide;
310) 5-oxo-N-(2-oxo-1-{[(phenylmethyl)oxy]methyl}-2-{[4-(phenyloxy)phenyl]amino}ethyl)hexanamide;
311) 4-bromo-2-methyl-N-(2-oxo-1-{[(phenylmethyl)oxy]methyl}-2-{[4-(phenyloxy)phenyl]amino}ethyl)benzamide;
312) 4-oxo-N-(2-oxo-1-{[(phenylmethyl)oxy]methyl}-2-{[4-(phenyloxy)phenyl]amino}ethyl)-4-(2-thienyl)butanamide;
313) N-(2-oxo-1-{[(phenylmethyl)oxy]methyl}-2-{[4-(phenyloxy)phenyl]amino}ethyl)-2-(phenylthio)acetamide;
314) N-(2-oxo-1-{[(phenylmethyl)oxy]methyl}-2-{[4-(phenyloxy)phenyl]amino}ethyl)-2-(1H-pyrrol-1-yl)benzamide;
315) N-(2-oxo-1-{[(phenylmethyl)oxy]methyl}-2-{[4-phenyloxy)phenyl]amino}ethyl)-2-[2-(methoxy)ethoxy]ethoxyacetamide;

316) 3,5-bis(methyloxy)-N-(2-oxo-1-{[(phenylmethyl)oxy]methyl}-2-{[4-(phenyloxy)phenyl]amino}ethyl)benzamide;
317) N-(2-oxo-1-{[(phenylmethyl)oxy]methyl}-2-{[4-(phenyloxy)phenyl]amino}ethyl)-3-cyclohexylpropanamide;
318) 5-oxo-N-(2-oxo-1-{[(phenylmethyl)oxy]methyl}-2-{[4-(phenyloxy)phenyl]amino}ethyl)-5-phenylpentanamide;
319) N-(2-oxo-1-{[(phenylmethyl)oxy]methyl}-2-{[4-(phenyloxy)phenyl]amino}ethyl)-4-acetylphenoxyacetamide;
320) 4-[3,4-bis(methyloxy)phenyl]-N-(2-oxo-1-{[(phenylmethyl)oxy]methyl}-2-{[4-(phenyloxy)phenyl]amino}ethyl)butanamide;
321) N-(2-oxo-1-{[(phenylmethyl)oxy]methyl}-2-{[4-(phenyloxy)phenyl]amino}ethyl)-5-[3-(trifluoromethyl)phenyl]furan-2-carboxamide;
322) N-(2-oxo-1-{[(phenylmethyl)oxy]methyl}-2-{[4-(phenyloxy)phenyl]amino}ethyl)-3-(1,3-dioxoisoindolin-2-yl)propanamide;
323) 5-oxo-N-(2-oxo-1-{[(phenylmethyl)oxy]methyl}-2-{[4-(phenyloxy)phenyl]amino}ethyl)-5-(2-thienyl)pentanamide;
324) N-(2-oxo-1-{[(phenylmethyl)oxy]methyl}-2-{[4-(phenyloxy)phenyl]amino}ethyl)-2-oxo-2-phenylacetamide;
325) N-(2-oxo-1-{[(phenylmethyl)oxy]methyl}-2-{[4-(phenyloxy)phenyl]amino}ethyl)-4-(2-thienyl)butanamide;
326) 5-nitro-N-(2-oxo-1-{[(phenylmethyl)oxy]methyl}-2-{[4-(phenyloxy)phenyl]amino}ethyl)furan-2-carboxamide;
327) (E)-N-(3-(benzyloxy)-1-oxo-1-(4-phenoxyphenylamino)propan-2-yl)hex-3-enamide
328) N-(2-oxo-1-{[(phenylmethyl)oxy]methyl}-2-{[4-(phenyloxy)phenyl]amino}ethyl)-1,3-benzodioxol-5-ylacetamide;
329) 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide;
330) 4-fluoro-N-(2-oxo-1-{[(phenylmethyl)oxy]methyl}-2-{[4-(phenyloxy)phenyl]amino}ethyl)-2-(trifluoromethyl)benzamide;
331) N-(2-oxo-1-{[(phenylmethyl)oxy]methyl}-2-{[4-(phenyloxy)phenyl]amino}ethyl)-2-(pyrimidin-2-ylthio)acetamide;
332) 2,5-bis(methyloxy)-N-(2-oxo-1-{[(phenylmethyl)oxy]methyl}-2-{[4-(phenyloxy)phenyl]amino}ethyl)benzamide;
333) 4-(methylsulfonyl)-N-(2-oxo-1-{[(phenylmethyl)oxy]methyl}-2-{[4-(phenyloxy)phenyl]amino}ethyl)benzamide;
334) 2-chloro-4-(methylsulfonyl)-N-(2-oxo-1-{[(phenylmethyl)oxy]methyl}-2-{[4-(phenyloxy)phenyl]amino}ethyl)benzamide;
335) N-(2-oxo-1-{[(phenylmethyl)oxy]methyl}-2-{[4-(phenyloxy)phenyl]amino}ethyl)2-(4-oxo-2-thioxothiazolidin-3-yl)acetamide;
336) N-(2-oxo-1-{[(phenylmethyl)oxy]methyl}-2-{[4-(phenyloxy)phenyl]amino}ethyl)tetrahydrofuran-3-carboxamide;
337) N-(2-oxo-1-{[(phenylmethyl)oxy]methyl}-2-{[4-(phenyloxy)phenyl]amino}ethyl)-3-methoxypropanamide;
338) N-(2-oxo-1-{[(phenylmethyl)oxy]methyl}-2-{[4-(phenyloxy)phenyl]amino}ethyl)-2-ethoxyacetamide;
339) N,N-dimethyl-N'-(2-oxo-1-{[(phenylmethyl)oxy]methyl}-2-{[4-(phenyloxy)phenyl]amino}ethyl)butanediamide;
340) N-(2-oxo-1-{[(phenylmethyl)oxy]methyl}-2-{[4-(phenyloxy)phenyl]amino}ethyl)-N-benzoyl-N-methylaminoacetamide;
341) N-(2-oxo-1-{[(phenylmethyl)oxy]methyl}-2-{[4-(phenyloxy)phenyl]amino}ethyl)-1H-indole-3-carboxamide;
342) N-(2-oxo-1-{[(phenylmethyl)oxy]methyl}-2-{[4-(phenyloxy)phenyl]amino}ethyl)-1H-benzimidazole-5-carboxamide;
343) N-(2-oxo-1-{[(phenylmethyl)oxy]methyl}-2-{[4-(phenyloxy)phenyl]amino}ethyl)-2-(4-ethoxyphenyl)acetamide;
344) N-(2-oxo-1-{[(phenylmethyl)oxy]methyl}-2-{[4-(phenyloxy)phenyl]amino}ethyl)pent-4-ynamide;
345) N-(2-oxo-1-{[(phenylmethyl)oxy]methyl}-2-{[4-(phenyloxy)phenyl]amino}ethyl)-4-(propyloxy)benzamide;
346) 2-methyl-N-(2-oxo-1-{[(phenylmethyl)oxy]methyl}-2-{[4-(phenyloxy)phenyl]amino}ethyl)hexanamide;
347) 4-oxo-N-(2-oxo-1-{[(phenylmethyl)oxy]methyl}-2-{[4-(phenyloxy)phenyl]amino}ethyl)pentanamide;
348) N-(2-oxo-1-{[(phenylmethyl)oxy]methyl}-2-{[4-(phenyloxy)phenyl]amino}ethyl)-3-(3,4-dimethoxyphenyl)propanamide;
349) 4-oxo-N-(2-oxo-1-{[(phenylmethyl)oxy]methyl}-2-{[4-(phenyloxy)phenyl]amino}ethyl)-4-phenylbutanamide;
350) N-(2-oxo-1-{[(phenylmethyl)oxy]methyl}-2-{[4-(phenyloxy)phenyl]amino}ethyl)quinoline-3-carboxamide;
351) N-(2-oxo-1-{[(phenylmethyl)oxy]methyl}-2-{[4-(phenyloxy)phenyl]amino}ethyl)pyrazine-2-carboxamide;
352) N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide;
353) N-(2-oxo-1-{[(phenylmethyl)oxy]methyl}-2-{[4-(phenyloxy)phenyl]amino}ethyl)-2-methoxy-2-phenylacetamide;
354) N-(2-oxo-1-{[(phenylmethyl)oxy]methyl}-2-{[4-(phenyloxy)phenyl]amino}ethyl)-2R-phenylpropanamide;
355) N-(2-oxo-1-{[(phenylmethyl)oxy]methyl}-2-{[4-(phenyloxy)phenyl]amino}ethyl)-1H-pyrazole-4-carboxamide;
356) N-(2-oxo-1-{[(phenylmethyl)oxy]methyl}-2-{[4-(phenyloxy)phenyl]amino}ethyl cinnoline-4-carboxamide;
357) N-(2-oxo-1-{[(phenylmethyl)oxy]methyl}-2-{[4-(phenyloxy)phenyl]amino}ethyl)quinoline-8-carboxamide;
358) 6-hydroxy-N-(2-oxo-1-{[(phenylmethyl)oxy]methyl}-2-{[4-(phenyloxy)phenyl]amino}ethyl)pyridine-2-carboxamide;
359) N-(2-oxo-1-{[(phenylmethyl)oxy]methyl}-2-{[4-(phenyloxy)phenyl]amino}ethyl)-2-phenylpropanamide;
360) N-(2-oxo-1-{[(phenylmethyl)oxy]methyl}-2-{[4-(phenyloxy)phenyl]amino}ethyl)-1-(4-methoxyphenyl)cyclopropanecarboxamide;
361) N-(2-oxo-1-{[(phenylmethyl)oxy]methyl}-2-{[4-(phenyloxy)phenyl]amino}ethyl)-2-(2,3,6-trifluorophenyl)acetamide;

362) N-(2-oxo-1-{[(phenylmethyl)oxy]methyl}-2-{[4-(phenyloxy)phenyl]amino}ethyl)-2,4-bis(trifluoromethyl)benzamide;
363) N-(2-oxo-1-{[(phenylmethyl)oxy]methyl}-2-{[4-(phenyloxy)phenyl]amino}ethyl)-2-(2,4-difluorophenyl)acetamide;
364) N-(2-oxo-1-{[(phenylmethyl)oxy]methyl}-2-{[4-(phenyloxy)phenyl]amino}ethyl)-2-(1-methyl-1H-indol-3-yl)acetamide;
365) N-(2-oxo-1-{[(phenylmethyl)oxy]methyl}-2-{[4-(phenyloxy)phenyl]amino}ethyl)quinoline-4-carboxamide;
366) N-(2-oxo-1-{[(phenylmethyl)oxy]methyl}-2-{[4-(phenyloxy)phenyl]amino}ethyl)-1-benzofuran-2-carboxamide;
367) 7-(methyloxy)-N-(2-oxo-1-{[(phenylmethyl)oxy]methyl}-2-{[4-(phenyloxy)phenyl]amino}ethyl)-1-benzofuran-2-carboxamide;
368) N-(2-oxo-1-{[(phenylmethyl)oxy]methyl}-2-{[4-(phenyloxy)phenyl]amino}ethyl)-2-(4-fluorophenoxy)acetamide;
369) N-(2-oxo-1-{[(phenylmethyl)oxy]methyl}-2-{[4-(phenyloxy)phenyl]amino}ethyl)-3-(pyridin-3-yl)propanamide;
370) N-(2-oxo-1-{[(phenylmethyl)oxy]methyl}-2-{[4-(phenyloxy)phenyl]amino}ethyl)-2-(3,4-dichlorophenoxy)acetamide;
371) N-(2-oxo-1-{[(phenylmethyl)oxy]methyl}-2-{[4-(phenyloxy)phenyl]amino}ethyl)-2-(naphthalen-1-yloxy)acetamide;
372) N-(2-oxo-1-{[(phenylmethyl)oxy]methyl}-2-{[4-(phenyloxy)phenyl]amino}ethyl)-2-p-tolylacetamide;
373) N-(2-oxo-1-{[(phenylmethyl)oxy]methyl}-2-{[4-(phenyloxy)phenyl]amino}ethyl)-2-(2,5-dimethylphenyl)acetamide;
374) N-(2-oxo-1-{[(phenylmethyl)oxy]methyl}-2-{[4-(phenyloxy)phenyl]amino}ethyl)-2-(benzylthio)acetamide;
375) N-(2-oxo-1-{[(phenylmethyl)oxy]methyl}-2-{[4-(phenyloxy)phenyl]amino}ethyl)-2-(naphthalen-1-yl)acetamide;
376) N-(2-oxo-1-{[(phenylmethyl)oxy]methyl}-2-{[4-(phenyloxy)phenyl]amino}ethyl)-3-ethoxypropanamide;
377) N-(2-oxo-1-{[(phenylmethyl)oxy]methyl}-2-{[4-(phenyloxy)phenyl]amino}ethyl)-2-(3-chlorophenyl)acetamide;
378) 5-butyl-N-(2-oxo-1-{[(phenylmethyl)oxy]methyl}-2-{[4-(phenyloxy)phenyl]amino}ethyl)pyridine-2-carboxamide;
379) 4-chloro-3-methyl-N-(2-oxo-1-{[(phenylmethyl)oxy]methyl}-2-{[4-(phenyloxy)phenyl]amino}ethyl)benzamide;
380) 4-cyano-N-(2-oxo-1-{[(phenylmethyl)oxy]methyl}-2-{[4-(phenyloxy)phenyl]amino}ethyl)benzamide;
381) N-(2-oxo-1-{[(phenylmethyl)oxy]methyl}-2-{[4-(phenyloxy)phenyl]amino}ethyl)-2S-methoxy-2-phenylacetamide;
382) N-(2-oxo-1-{[(phenylmethyl)oxy]methyl}-2-{[4-(phenyloxy)phenyl]amino}ethyl)-3-(2,5-dimethoxyphenyl)propanamide;
383) N-(2-oxo-1-{[(phenylmethyl)oxy]methyl}-2-{[4-(phenyloxy)phenyl]amino}ethyl)-3-(1H-indol-3-yl)propanamide;
384) N-(2-oxo-1-{[(phenylmethyl)oxy]methyl}-2-{[4-(phenyloxy)phenyl]amino}ethyl)-2-(3-bromophenyl)acetamide;
385) 3-methyl-N-(2-oxo-1-{[(phenylmethyl)oxy]methyl}-2-{[4-(phenyloxy)phenyl]amino}ethyl)pentanamide;
386) N-(2-oxo-1-{[(phenylmethyl)oxy]methyl}-2-{[4-(phenyloxy)phenyl]amino}ethyl)-1H-indole-2-carboxamide;
387) 4-chloro-2-fluoro-N-(2-oxo-1-{[(phenylmethyl)oxy]methyl}-2-{[4-(phenyloxy)phenyl]amino}ethyl)benzamide;
388) 2-oxo-2-[(2-oxo-1-{[(phenylmethyl)oxy]methyl}-2-{[4-(phenyloxy)phenyl]amino}ethyl)amino]ethyl acetate;
389) N-(2-oxo-1-{[(phenylmethyl)oxy]methyl}-2-{[4-(phenyloxy)phenyl]amino}ethyl)thiophene-3-carboxamide;
390) N-(2-oxo-1-{[(phenylmethyl)oxy]methyl}-2-{[4-(phenyloxy)phenyl]amino}ethyl)-2-(4-bromophenyl)acetamide;
391) N-(2-oxo-1-{[(phenylmethyl)oxy]methyl}-2-{[4-(phenyloxy)phenyl]amino}ethyl)-2-(2-chlorophenyl)acetamide;
392) N-(2-oxo-1-{[(phenylmethyl)oxy]methyl}-2-{[4-(phenyloxy)phenyl]amino}ethyl)-2-(3,4,5-trimethoxyphenyl)acetamide;
393) N-(2-oxo-1-{[(phenylmethyl)oxy]methyl}-2-{[4-(phenyloxy)phenyl]amino}ethyl)-2-(p-tolyloxy)acetamide;
394) N-(2-oxo-1-{[(phenylmethyl)oxy]methyl}-2-{[4-(phenyloxy)phenyl]amino}ethyl)-3-(2-methoxyphenyl)propanamide;
395) 3-hydroxy-N-(2-oxo-1-{[(phenylmethyl)oxy]methyl}-2-{[4-(phenyloxy)phenyl]amino}ethyl)quinoxaline-2-carboxamide;
396) 4-acetyl-N-(2-oxo-1-{[(phenylmethyl)oxy]methyl}-2-{[4-(phenyloxy)phenyl]amino}ethyl)benzamide;
397) methyl 4-{[(2-oxo-1-{[(phenylmethyl)oxy]methyl}-2-{[4-(phenyloxy)phenyl]amino}ethyl)amino]carbonyl}benzoate;
398) 3-fluoro-N-(2-oxo-1-{[(phenylmethyl)oxy]methyl}-2-{[4-(phenyloxy)phenyl]amino}ethyl)-5-(trifluoromethyl)benzamide;
399) 4-[(difluoromethyl)oxy]-N-(2-oxo-1-{[(phenylmethyl)oxy]methyl}-2-{[4-(phenyloxy)phenyl]amino}ethyl)benzamide;
400) 3-fluoro-4-methyl-N-(2-oxo-1-{[(phenylmethyl)oxy]methyl}-2-{[4-(phenyloxy)phenyl]amino}ethyl)benzamide;
401) 3-methyl-N-(2-oxo-1-{[(phenylmethyl)oxy]methyl}-2-{[4-(phenyloxy)phenyl]amino}ethyl)furan-2-carboxamide.
402) N-(2-oxo-1-{[(phenylmethyl)oxy]methyl}-2-{[4-(phenyloxy)phenyl]amino}ethyl)cyclobutanecarboxamide; and
403) N-(2-oxo-1-{[(phenylmethyl)oxy]methyl}-2-{[4-(phenyloxy)phenyl]amino}ethyl)-3-(thiophen-2-yl)propanamide.

18. The method according to claim 17, wherein the antimicrotubule agent is selected from the group consisting of a taxane or a vinca alkaloid.

19. The method of claim 18, wherein the taxane compound is paclitaxel or docetaxel.

20. The method of claim 17, wherein the S1P1R receptor antagonist is selected from the group consisting of
(2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(4-fluo-robenzyl)-N-(4-(4-fluorophenoxy)phenyl)pyrrolidine-2-carboxamide, (2S,4R)-1-(2-(2H-1,2,3-triazol-2-yl)acetyl)-4-(2,4-dif-luorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluo-robenzyl)-N-(4-(4-fluorophenoxy)phenyl)pyrrolidine-2-carboxamide.

21. The method of claim 18, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrro-lidine-2-carboxamide, (2S,4R)-1-(2-(2H-1,2,3-triazol-2-yl)acetyl)-4-(4-fluo-robenzyl)-N-(4-(4-fluorophenoxy)phenyl)pyrrolidine-2-carboxamide, (2S,4R)-1-(2-(2H-1,2,3-triazol-2-yl)acetyl)-4-(2,4-dif-luorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluo-robenzyl)-N-(4-(4-fluorophenoxy)phenyl)pyrrolidine-2-carboxamide.

22. The method of claim 19, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrro-lidine-2-carboxamide, (2S,4R)-1-(2-(2H-1,2,3-triazol-2-yl)acetyl)-4-(4-fluo-robenzyl)-N-(4-(4-fluorophenoxy)phenyl)pyrrolidine-2-carboxamide, (2S,4R)-1-(2-(2H-1,2,3-triazol-2-yl)acetyl)-4-(2,4-dif-luorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluo-robenzyl)-N-(4-(4-fluorophenoxy)phenyl)pyrrolidine-2-carboxamide.

23. The method of claim 22, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide and the taxane is paclitaxel or docetaxel.

24. The method of claim 22, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide and the taxane is paclitaxel or docetaxel.

25. The method of claim 22, wherein the S1P1R receptor antagonist is (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide and the taxane is paclitaxel or docetaxel.

26. The method of claim 22, wherein the S1P1R receptor antagonist is (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide and the taxane is paclitaxel or docetaxel.

27. The method of claim 18, wherein the vinca alkaloid is vincristine, vinblastine, or vinorelbine.

28. The method of claim 27, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrro-lidine-2-carboxamide, (2S,4R)-1-(2-(2H-1,2,3-triazol-2-yl)acetyl)-4-(4-fluo-robenzyl)-N-(4-(4-fluorophenoxy)phenyl)pyrrolidine-2-carboxamide, (2S,4R)-1-(2-(2H-1,2,3-triazol-2-yl)acetyl)-4-(2,4-dif-luorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluo-robenzyl)-N-(4-(4-fluorophenoxy)phenyl)pyrrolidine-2-carboxamide.

29. The method of claim 28, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl) pyrrolidine-2-carboxamide and the vinca alkaloid is selected from the group consisting of vincristine, vinblastine or vinorelbine.

30. The method of claim 28, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrroli-dine-2-carboxamide and the vinca alkaloid is selected from the group consisting of vincristine, vinblastine or vinorelbine.

31. The method of claim 28, wherein the S1P1R receptor antagonist is (2S,4R)-1-(2-(2H-1,2,3-triazol-2-yl)acetyl)-4-(2,4-difluorobenzyl)-N-(4-(4-fluorophenoxy)phenyl)pyrro-lidine-2-carboxamide and the vinca alkaloid is selected from the group consisting of vincristine, vinblastine or vinorelbine.

32. The method of claim 28, wherein the S1P1R receptor antagonist is (2S,4R)-1-(2-(1H-1,2,3-triazol-1-yl)acetyl)-4-(4-fluorobenzyl)-N-(4-(4-fluorophenoxy)phenyl)pyrroli-dine-2-carboxamide and the vinca alkaloid is selected from the group consisting of vincristine, vinblastine or vinorelbine.

33. A combination comprising at least one S1P1R receptor antagonist and at least one antimicrotubule agent, wherin the S1P1R receptor antagonist is selected from the group of compounds consisting of 1) (S)-2-(2-(1H-imidazol-5-yl)acetamido)-5-phenyl-N-(4-phenoxyphenyl)pentanamide;

2) (2S,4R)-1-(2-(1H-1,2,3-triazol-1-yl)acetyl)-4-(2-chloro-4-fluorobenzyl)-N-(4-(4-fluorophenoxy)phe-nyl)pyrrolidine-2-carboxamide;

3) (2S,4R)-5-(2-(1H-1,2,3-triazol-1-yl)acetyl)-N-(4-(4-fluorophenoxy)phenyl)-4-(4-methylbenzyl)pyrroli-dine-2-carboxamide;

4) (2S,4R)-5-(2-(1H-1,2,4-triazol-1-yl)acetyl)-N-(4-(4-fluorophenoxy)phenyl)-4-(4-methylbenzyl)pyrroli-dine-2-carboxamide;

5) (2S,4R)-1-(2-(2H-1,2,3-triazol-2-yl)acetyl)-4-(2-chloro-4-fluorobenzyl)-N-(4-(4-fluorophenoxy)phe-nyl)pyrrolidine-2-carboxamide;

6) (2S,4R)-1-(2-(1H-1,2,3-triazol-1-yl)acetyl)-4-(4-fluoro-2-methylbenzyl)-N-(4-(4-fluorophenoxy)phe-nyl)pyrrolidine-2-carboxamide;

7) (2S,4R)-1-(2-(2H-1,2,3-triazol-2-yl)acetyl)-4-(4-fluoro-2-methylbenzyl)-N-(4-(4-fluorophenoxy)phe-nyl)pyrrolidine-2-carboxamide;

8) (2S,4R)-1-(2-(1H-1,2,4-triazol-1-yl)acetyl)-4-(4-fluoro-2-methylbenzyl)-N-(4-(4-fluorophenoxy)phe-nyl)pyrrolidine-2-carboxamide;

9) (2S,4R)-1-(2-(1H-1,2,4-triazol-1-yl)acetyl)-4-(2-chloro-4-fluorobenzyl)-N-(4-(4-fluorophenoxy)phe-nyl)pyrrolidine-2-carboxamide;

10) (2S,4R)-1-(2-(1H-1,2,3-triazol-1-yl)acetyl)-4-benzyl-N-(4-(4-fluorophenoxy)phenyl)pyrrolidine-2-carboxa-mide;

11) (2S,4R)-1-(2-(5-amino-3-(trifluoromethyl)-1H-1,2,4-triazol-1-yl)acetyl)-4-benzyl-N-(4-(4-fluorophenoxy) phenyl)pyrrolidine-2-carboxamide;

12) 1-((2S,4R)-4-benzyl-2-(5-(4-fluorophenoxy)-1H-benzo [d]imidazol-2-yl)pyrrolidin-1-yl)-2-(1H-1,2,4-triazol-1-yl)ethanone;

13) 3-(benzyloxy)-2-((S)-3-hydroxy-3-phenylpropanamido)-N-(4-phenoxyphenyl)propanamide;
14) 3-(benzyloxy)-2-(2-(furan-2-yl)-2-oxoacetamido)-N-(4-phenoxyphenyl)propanamide;
15) N-(3-(benzyloxy)-1-oxo-1-(4-phenoxyphenylamino)propan-2-yl)-6-(2,5-dioxo-2,5-dihydro-1H-pyrrol-1-yl)hexanamide;
16) 3-(benzyloxy)-2-(2-hydroxy-2-(2-hydroxyphenyl)acetamido)-N-(4-phenoxyphenyl)propanamide;
17) 4-(3-(benzyloxy)-1-oxo-1-(4-phenoxyphenylamino)propan-2-ylcarbamoyl)phenyl acetate;
18) N-(3-(benzyloxy)-1-oxo-1-(4-phenoxyphenylamino)propan-2-yl)-5-methylnicotinamide;
19) 3-(benzyloxy)-2-(2-(methylsulfonyl)acetamido)-N-(4-phenoxyphenyl)propanamide;
20) N-(3-(benzyloxy)-1-oxo-1-(4-phenoxyphenylamino)propan-2-yl)-1H-indole-5-carboxamide;
21) N-(3-(benzyloxy)-1-oxo-1-(4-phenoxyphenylamino)propan-2-yl)-2-bromo-5-fluorobenzamide;
22) N-(3-(benzyloxy)-1-oxo-1-(4-phenoxyphenylamino)propan-2-yl)-3,3,3-trifluoropropanamide;
23) (2R)-N-(3-(benzyloxy)-1-oxo-1-(4-phenoxyphenylamino)propan-2-yl)tetrahydrofuran-2-carboxamide;
24) 3-(benzyloxy)-24-((R)-2-(2-chlorophenyl)-2-hydroxyacetamido)-N-(4-phenoxyphenyl)propanamide;
25) (2S)-1-(3-(benzyloxy)-1-oxo-1-(4-phenoxyphenylamino)propan-2-ylamino)-1-oxopropan-2-yl acetate;
26) 3-(benzyloxy)-2-(2-(2-hydroxyphenoxy)acetamido)-N-(4-phenoxyphenyl)propanamide;
27) 3-(benzyloxy)-24-((R)-2-hydroxy-3-phenylpropanamido)-N-(4-phenoxyphenyl)propanamide;
28) N-(3-(benzyloxy)-1-oxo-1-(4-phenoxyphenylamino)propan-2-yl)-2-(methylthio)nicotinamide;
29) N-(3-(benzyloxy)-1-oxo-1-(4-phenoxyphenylamino)propan-2-yl)-1-(4-chlorobenzyl)-5-oxopyrrolidine-3-carboxamide;
30) (2S,4R)-4-benzyl-N-(4-(4-fluorophenoxy)phenyl)-1-(2-((1-methyl-1H-indol-2-yl)methylamino)acetyl)pyrrolidine-2-carboxamide;
31) (2S,4R)-4-benzyl-N-(4-(4-fluorophenoxy)phenyl)-1-(2-phenylacetyl)pyrrolidine-2-carboxamide;
32) (2S,4R)-4-benzyl-N-(4-(4-fluorophenoxy)phenyl)-1-(2-(3-methylisoxazol-5-yl)acetyl)pyrrolidine-2-carboxamide;
33) (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide;
34) 34,(2S,4R)-4-benzyl-N-(4-(4-fluorophenoxy)phenyl)-1-(3,3,3-trifluoropropanoyl)pyrrolidine-2-carboxamide;
35) (2S,4R)-4-benzyl-1-(2-(4-(dimethylamino)phenyl)acetyl)-N-(4-(4-fluorophenoxy)phenyl)pyrrolidine-2-carboxamide;
36) (2S,4R)-4-benzyl-N-(4-(4-fluorophenoxy)phenyl)-1-(tetrahydrofuran-3-carbonyl)pyrrolidine-2-carboxamide;
37) (2S,4R)-4-benzyl-N-(4-(4-fluorophenoxy)phenyl)-1-(2-(2-methyl-1H-indol-3-yl)acetyl)pyrrolidine-2-carboxamide;
38) (2S,4R)-4-benzyl-1-(2-butoxyacetyl)-N-(4-(4-fluorophenoxy)phenyl)pyrrolidine-2-carboxamide;
39) (2S,4R)-4-benzyl-N-(4-(4-fluorophenoxy)phenyl)-1-((S)-5-oxotetrahydrofuran-2-carbonyl)pyrrolidine-2-carboxamide;
40) (2S,4R)-4-benzyl-N-(4-(4-fluorophenoxy)phenyl)-1-((R)-2-hydroxy-2-phenylacetyl)pyrrolidine-2-carboxamide;
41) (S)-3-(benzyloxy)-N-(4-(4-fluorophenoxy)phenyl)-2-(2-(4-(pyrimidin-2-yl)piperazin-1-yl)acetamido)propanamide;
42) (S)-3-(benzyloxy)-N-(4-(4-fluorophenoxy)phenyl)-2-(2-(4-(3-methoxyphenyl)piperazin-1-yl)acetamido)propanamide;
43) (S)-3-(benzyloxy)-N-(4-(4-fluorophenoxy)phenyl)-2-(2-(4-(pyrrolidin-1-yl)piperidin-1-yl)acetamido)propanamide;
44) (S)-3-(4-fluorobenzyloxy)-N-(4-(4-fluorophenoxy)phenyl)-2-(2-(2-phenyloxazol-4-yl)acetamido)propanamide;
45) (2S)-3-(benzyloxy)-N-(4-(4-fluorophenoxy)phenyl)-2-(2-(octahydroquinolin-1(2H)-yl)acetamido)propanamide;
46) (2S)-3-(benzyloxy)-N-(4-(4-fluorophenoxy)phenyl)-2-(2-(3-methylpiperidin-1-yl)acetamido)propanamide;
47) (S)-2-(2-(1H-imidazol-5-yl)acetamido)-3-(benzyloxy)-N-(4-(4-fluorophenoxy)-2-methylphenyl)propanamide;
48) (2S,4R)-1-(2-(2H-1,2,3-triazol-2-yl)acetyl)-N-(4-(4-fluorophenoxy)phenyl)-4-(2-methylbenzyl)pyrrolidine-2-carboxamide;
49) (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide;
50) (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide;
51) (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide;
52) (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide;
53) (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide;
54) (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide;
55) (2S,4R)-1-(2-(1H-1,2,4-triazol-1-yl)acetyl)-N-(4-(4-fluorophenoxy)phenyl)-4-(2-methylbenzyl)pyrrolidine-2-carboxamide;
56) (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide;
57) (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide;
58) (2S,4R)-1-(2-(2H-1,2,3-triazol-2-yl)acetyl)-4-benzyl-N-(4-(4-fluorophenoxy)phenyl)pyrrolidine-2-carboxamide;
59) (R)-N-(2-(benzyloxy)-1-(5-(4-fluorophenoxy)-1H-benzo[d]imidazol-2-yl)ethyl)-2-(1H-imidazol-4-yl)acetamide;
60) (R)-N-(2-(benzyloxy)-1-(5-(4-fluorophenoxy)-1H-benzo[d]imidazol-2-yl)ethyl)acetamide;
61) (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide;
62) (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide;
63) (2S)-3-(benzyloxy)-N-(4-(4-fluorophenoxy)phenyl)-2-(2-(2-methylpyrrolidin-1-yl)acetamido)propanamide;

64) (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide;
65) (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide;
66) (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide;
67) (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide;
68) (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide;
69) (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide;
70) (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide;
71) (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide;
72) (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide;
73) (2S,4R)-1-(2-(1H-1,2,4-triazol-1-yl)acetyl)-N-(4-(4-fluoro-3-methylphenoxy)phenyl)-4-(4-fluorobenzyl)pyrrolidine-2-carboxamide;
74) (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide;
75) (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide;
76) (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide;
77) (2S,4S)-1-(2-(2H-1,2,3-triazol-2-yl)acetyl)-N-(4-(4-fluorophenoxy)phenyl)-4-phenylpyrrolidine-2-carboxamide;
78) (2S,4S)-1-(2-(1H-1,2,4-triazol-1-yl)acetyl)-N-(4-(4-fluorophenoxy)phenyl)-4-phenylpyrrolidine-2-carboxamide;
79) (2S,4R)-1-(2-(1H-1,2,4-triazol-1-yl)acetyl)-4-benzyl-N-(4-(4-chlorophenoxy)phenyl)pyrrolidine-2-carboxamide;
80) (2S,4S)-1-(2-(1H-1,2,4-triazol-1-yl)acetyl)-4-(benzylamino)-N-(4-(4-fluorophenoxy)phenyl)pyrrolidine-2-carboxamide;
81) (S)-3-(benzyloxy)-2-(3-(3-chloro-4-methoxyphenyl)propanamido)-N-(4-(4-fluorophenoxy)phenyl)propanamide;
82) (2S,4R)-4-benzyl-1-(2-(3,4-dihydroisoquinolin-2(1H)-yl)acetyl)-N-(4-(4-fluorophenoxy)phenyl)pyrrolidine-2-carboxamide;
83) (2S,4R)-4-benzyl-N-(4-(4-fluorophenoxy)phenyl)-1-(2-thiomorpholinoacetyl)pyrrolidine-2-carboxamide;
84) (2S,4R)-4-benzyl-N-(4-(4-fluorophenoxy)phenyl)-1-(2-(2,3,6-trifluorophenyl)acetyl)pyrrolidine-2-carboxamide;
85) (2S,4R)-4-benzyl-N-(4-(4-fluorophenoxy)phenyl)-1-(3-(methylthio)propanoyl)pyrrolidine-2-carboxamide;
86) (2S,4R)-4-benzyl-1-(3-ethoxypropanoyl)-N-(4-(4-fluorophenoxy)phenyl)pyrrolidine-2-carboxamide;
87) (2S,4R)-4-benzyl-N-(4-(4-fluorophenoxy)phenyl)-1-(2-(methylsulfonyl)acetyl)pyrrolidine-2-carboxamide;
88) (2S,4R)-4-benzyl-N-(4-(4-fluorophenoxy)phenyl)-1-(2-(2-methoxyethoxy)acetyl)pyrrolidine-2-carboxamide;
89) (2S,4R)-4-benzyl-1-(4-(dimethylamino)-4-oxobutanoyl)-N-(4-(4-fluorophenoxy)phenyl)pyrrolidine-2-carboxamide;
90) (2S,4R)-4-benzyl-N-(4-(4-fluorophenoxy)phenyl)-1-(3-methoxypropanoyl)pyrrolidine-2-carboxamide;
91) (2S,4R)-4-benzyl-N-(4-(4-fluorophenoxy)phenyl)-1-(4-oxo-4-(thien-2-yl)butanoyl)pyrrolidine-2-carboxamide;
92) (2S,4R)-4-benzyl-N-(4-(4-fluorophenoxy)phenyl)-1-(tetrahydrofuran-2-carbonyl)pyrrolidine-2-carboxamide;
93) (2S,4R)-1-((S)-1-acetylpyrrolidine-2-carbonyl)-4-benzyl-N-(4-(4-fluorophenoxy)phenyl)pyrrolidine-2-carboxamide;
94) (2S,4R)-4-benzyl-N-(4-(4-fluorophenoxy)phenyl)-1-(2-(pyrimidin-2-ylthio)acetyl)pyrrolidine-2-carboxamide;
95) (2S,4R)-4-benzyl-1-(2-(2,6-difluorophenyl)acetyl)-N-(4-(4-fluorophenoxy)phenyl)pyrrolidine-2-carboxamide;
96) (2S,4R)-4-benzyl-N-(4-(4-fluorophenoxy)phenyl)-1-(2-(pyridin-4-ylthio)acetyl)pyrrolidine-2-carboxamide;
97) (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide;
98) (2S,4R)-1-(2-(1H-indol-3-yl)acetyl)-4-benzyl-N-(4-(4-fluorophenoxy)phenyl)pyrrolidine-2-carboxamide;
99) (2S,4R)-4-benzyl-N-(4-(4-fluorophenoxy)phenyl)-1-(2-(4-oxo-2-thioxothiazolidin-3-yl)acetyl)pyrrolidine-2-carboxamide;
100) (2S,4R)-4-benzyl-N-(4-(4-fluorophenoxy)phenyl)-1-(2-(4-(2-methoxyethyl)piperazin-1-yl)acetyl)pyrrolidine-2-carboxamide;
101) (S)-3-(benzyloxy)-2-(2-(3-fluoro-4-(trifluoromethyl)phenyl)acetamido)-N-(4-(4-fluorophenoxy)phenyl)propanamide;
102) (S)-3-(benzyloxy)-N-(4-(4-fluorophenoxy)phenyl)-2-(2-(3-(trifluoromethoxy)phenyl)acetamido)propanamide;
103) (S)-tert-butyl 1-(2-((S)-3-(benzyloxy)-1-(4-(4-fluorophenoxy)phenylamino)-1-oxopropan-2-ylamino)-2-oxoethyl)pyrrolidine-2-carboxylate;
104) (S)-N-(3-(benzyloxy)-1-(4-(4-fluorophenoxy)phenylamino)-1-oxopropan-2-yl)-5-phenylpentanamide;
105) (S)-3-(benzyloxy)-N-(4-(4-fluorophenoxy)phenyl)-2-(2-(4-morpholinopiperidin-1-yl)acetamido)propanamide;
106) (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide;
107) (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide;
108) (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide;
109) (2S)-3-(benzyloxy)-2-(2-(3-(diethylamino)pyrrolidin-1-yl)acetamido)-N-(4-(4-fluorophenoxy)phenyl)propanamide;
110) (2S)-3-(benzyloxy)-N-(4-(4-fluorophenoxy)phenyl)-2-(2-(4-((tetrahydrofuran-2-yl)methyl)piperazin-1-yl)acetamido)propanamide;

111) (S)-3-(benzyloxy)-N-(4-(4-fluorophenoxy)phenyl)-2-(2-(4-isopropylpiperazin-1-yl)acetamido)propanamide;
112) (S)-3-(benzyloxy)-N-(4-(4-fluorophenoxy)phenyl)-2-(2-(4-(3-(trifluoromethyl)pyridin-2-yl)piperazin-1-yl)acetamido)propanamide;
113) (2S)-3-(benzyloxy)-N-(4-(4-fluorophenoxy)phenyl)-2-(2-(2-(((S)-1-methylpyrrolidin-2-yl)methyl)piperidin-1-yl)acetamido)propanamide,
114) (S)-3-(benzyloxy)-2-(2-(4-ethylpiperazin-1-yl)acetamido)-N-(4-(4-fluorophenoxy)phenyl)propanamide;
115) (2S,4R)-1-(2-(4-acetylpiperazin-1-yl)acetyl)-4-benzyl-N-(4-(4-fluorophenoxy)phenyl)pyrrolidine-2-carboxamide;
116) (2S,4R)-4-benzyl-N-(4-(4-fluorophenoxy)phenyl)-1-(2-morpholinoacetyl)pyrrolidine-2-carboxamide;
117) (2S,4R)-4-benzyl-N-(4-(4-fluorophenoxy)phenyl)-1-(2-(thien-2-yl)acetyl)pyrrolidine-2-carboxamide;
118) (2S,4R)-4-benzyl-N-(4-(4-fluorophenoxy)phenyl)-1-(3-hydroxybutanoyl)pyrrolidine-2-carboxamide;
119) (2S,4R)-4-benzyl-1-(2-(2,6-dichlorophenyl)acetyl)-N-(4-(4-fluorophenoxy)phenyl)pyrrolidine-2-carboxamide;
120) (2S,4R)-4-benzyl-N-(4-(4-fluorophenoxy)phenyl)-1-(2-hydroxyacetyl)pyrrolidine-2-carboxamide;
121) (2S,4R)-4-benzyl-1-(2-ethoxyacetyl)-N-(4-(4-fluorophenoxy)phenyl)pyrrolidine-2-carboxamide;
122) (2S,4R)-4-benzyl-N-(4-(4-fluorophenoxy)phenyl)-1-(2-methoxyacetyl)pyrrolidine-2-carboxamide;
123) (2S,4R)-4-benzyl-N-(4-(4-fluorophenoxy)phenyl)-1-(4-oxopentanoyl)pyrrolidine-2-carboxamide;
124) (2S,4R)-4-benzyl-N-(4-(4-fluorophenoxy)phenyl)-1-(4-oxo-4-phenylbutanoyl)pyrrolidine-2-carboxamide;
125) methyl 4-((2S,4R)-4-benzyl-2-(4-(4-fluorophenoxy)phenylcarbamoyl)pyrrolidin-1-yl)-4-oxobutanoate;
126) (S)-3-(benzyloxy)-N-(4-(4-fluorophenoxy)phenyl)-2-(2-(4-(pyridin-2-yl)piperazin-1-yl)acetamido)propanamide;
127) (S)-3-(benzyloxy)-N-(4-(4-fluorophenoxy)phenyl)-2-(2-(4-(2-fluorophenyl)piperazin-1-yl)acetamido)propanamide;
128) (S)-2-(2-(azepan-1-yl)acetamido)-3-(benzyloxy)-N-(4-(4-fluorophenoxy)phenyl)propanamide;
129) (2S,4R)-4-benzyl-1-(2-cyanoacetyl)-N-(4-(4-fluorophenoxy)phenyl)pyrrolidine-2-carboxamide;
130) (S)-3-(benzyloxy)-N-(4-(4-fluorophenoxy)phenyl)-2-(2-(4-methylpiperidin-1-yl)acetamido)propanamide;
131) (S)-2-(2-(1H-imidazol-5-yl)acetamido)-3-benzyloxy-N-(4-(4-fluorophenoxy)phenyl)propanamide;
132) (S)-2-(2-(1H-imidazol-5-yl)acetamido)-3-(4-fluorobenzyloxy)-N-(4-(4-chlorophenoxy)phenyl)propanamide;
133) (S)-2-(2-(1H-imidazol-5-yl)acetamido)-3-(4-fluorobenzyloxy)-N-(4-(4-fluorophenoxy)phenyl)propanamide;
134) (S)-2-(2-(1H-imidazol-1-yl)acetamido)-3-benzyloxy-N-(4-(4-fluorophenoxy)phenyl)propanamide;
135) (S)-2-(2-(1H-1,2,4-triazol-1-yl)acetamido)-3-(4-fluorobenzyloxy)-N-(4-(4-fluorophenoxy)phenyl)propanamide;
136) (S)-3-(benzyloxy)-2-2-chloroacetamido)-N-(4-(4-fluorophenoxy)phenyl)propanamide;
137) (S)-2-(2-(1H-imidazol-5-yl)acetamido)-5-phenyl-N-(4-(4-fluorophenoxy)phenyl)pentanamide;
138) (S)-2-(2-(2H-1,2,3-triazol-2-yl)acetamido)-3-(benzyloxy)-N-(4-(4-fluorophenoxy)phenyl)propanamide;
139) (S)-2-(2-(1H-1,2,4-triazol-1-yl)acetamido)-N-(4-(4-fluorophenoxy)phenyl)-3-(2-(trifluoromethoxy)benzyloxy)propanamide;
140) (2S,4R)-1-(2-(1H-1,2,4-triazol-1-yl)acetyl)-4-benzyl-N-(4-(4-fluorophenoxy)phenyl)pyrrolidine-2-carboxamide;
141) (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide;
142) 2-(2-(1H-imidazol-5-yl)acetamido)-3-benzyloxy-N-(4-phenoxyphenyl)propanamide;
143) (S)-2-(2-(1H-imidazol-5-yl)acetamido)-3-benzyloxy-N-(4-phenoxyphenyl)propanamide;
144) (S)-2-(2-(1H-tetrazol-1-yl)acetamido)-3-benzyloxy-N-(4-phenoxyphenyl)propanamide;
145) (S)-2-(2-(1H-imidazol-5-yl)acetamido)-3-benzyloxy-N-(4-(4-chlorophenoxy)phenyl)propanamide;
146) (S)-2-(2-(1H-1,2,4-triazol-1-yl)acetamido)-3-(benzyloxy)-N-(4-phenoxyphenyl)propanamide;
147) (S)-2-(2-(1H-imidazol-4-yl)acetamido)-3-(benzyloxy)-N-(3-chloro-4-phenoxyphenyl)propanamide;
148) (S)-2-(2-(1H-imidazol-4-yl)acetamido)-3-(benzyloxy)-N-(4-(3-chlorophenoxy)phenyl)propanamide;
149) (S)-2-(2-(1H-1,2,4-triazol-1-yl)acetamido)-3-benzyloxy-N-(4-(4-fluorophenoxy)phenyl)propanamide;
150) (S)-3-(benzyloxy)-2-(2-(3,5-dimethylisoxazol-4-yl)acetamido)-N-(4-(4-fluorophenoxy)phenyl)propanamide;
151) (S)-2-(2-(1H-benzo [d][1,2,3]triazol-1-yl)acetamido)-3-(benzyloxy)-N-(4-(4-fluorophenoxy)phenyl) propanamide;
152) (S)-3-(benzyloxy)-2-(2-(3,5-dimethyl-1H-pyrazol-4-yl)acetamido)-N-(4-(4-fluorophenoxy)phenyl)propanamide;
153) (S)-3-(benzyloxy)-N-(4-(4-fluorophenoxy)phenyl)-2-(2-(4-methyl-1H-1,2,3-triazol-1-yl)acetamido)propanamide;
154) (S)-2-(2-(1H-imidazol-4-yl)acetamido)-3-(benzyloxy)-N-(3-chloro-4-(4-chlorophenoxy)phenyl)propanamide;
155) (S)-3-(benzyloxy)-N-(4-(4-fluorophenoxy)phenyl)-2-(2-morpholinoacetamido)propanamide;
156) (S)-2-(2-(1H-imidazol-4-yl)acetamido)-3-(benzyloxy)-N-(4-(5-bromothiazol-2-yloxy)phenyl)propanamide;
157) (S)-2-(2-(1H-imidazol-5-yl)acetamido)-N-(4-(4-chlorophenoxy)phenyl)-4-phenylbutanamide;
158) (S)-2-(2-(1H-imidazol-5-yl)acetamido)-3-(benzyloxy)-N-(4-(p-tolyloxy)phenyl)propanamide;
159) (S)-3-(benzyloxy)-N-(4-(4-fluorophenoxy)phenyl)-2-(2-(pyrazin-2-yl)acetamido)propanamide;
160) (S)-3-(benzyloxy)-N-(4-(4-fluorophenoxy)phenyl)-2-(2-(2-methyl-1H-imidazol-1-yl)acetamido)propanamide;
161) (S)-2-(2-(1H-imidazol-4-yl)-2-methylpropanamido)-3-(4-fluorobenzyloxy)-N-(4-(4-fluorophenoxy)phenyl)propanamide;
162) (S)-3-(benzyloxy)-N-(4-(4-fluorophenoxy)phenyl)-2-(2-(2-methyl-1H-imidazol-4-yl)acetamido)propanamide;
163) (2S,3S)-1-(2-(1H-imidazol-4-yl)acetyl)-3-benzyl-N-(4-(4-fluorophenoxy)phenyl)pyrrolidine-2-carboxamide;
164) (S)-2-acetamido-3-(4-fluorobenzyloxy)-N-(4-(4-fluorophenoxy)phenyl)propanamide;

165) (S)-benzyl 4-(2-(1H-1,2,4-triazol-1-yl)acetamido)-5-(4-(4-fluorophenoxy)phenylamino)-5-oxopentylcarbamate;
166) (S)-3-(benzyloxy)-N-(4-(4-fluorophenoxy)phenyl)-2-(2-(3-methyl-1H-pyrazol-5-yl)acetamido)propanamide
167) (2S)-2-(2-(1H-imidazol-4-yl)propanamido)-3-(benzyloxy)-N-(4-(4-fluorophenoxy)phenyl)propanamide;
168) (S)-2-(2-(1H-imidazol-5-yl)acetamido)-N-(4-(4-bromophenoxy)phenyl)-3-(4-fluorobenzyloxy)propanamide;
169) (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide;
170) (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide;
171) (2S,4R)-1-(2-(1H-1,2,4-triazol-1-yl)acetyl)-N-(4-(4-fluorophenoxy)phenyl)-4-(3-methylbenzyl)pyrrolidine-2-carboxamide;
172) (S)-2-(3-(3,5-dimethylisoxazol-4-yl)ureido)-3-benzyloxy-N-(4-(4-fluorophenoxy)phenyl)propanamide;
173) (2S,4R)-1-(2-(1H-imidazol-5-yl)acetyl)-4-(benzylamino)-N-(4-(4-fluorophenoxy)phenyl)pyrrolidine-2-carboxamide;
174) (S)-2-(2-(1H-1,2,3-triazol-1-yl)acetamido)-3-(benzyloxy)-N-(4-(4-fluorophenoxy)phenyl)propanamide;
175) 175 (S)-1-(2-(1H-imidazol-4-yl)acetyl)-4-benzyl-N-(4-(4-fluorophenoxy)phenyl)piperazine-2-carboxamide;
176) (2S,4R)-1-(2-(1H-benzo [d][1,2,3]triazol-1-yl)acetyl)-4-benzyl-N-(4-(4-fluorophenoxy)phenyl)pyrrolidine-2-carboxamide;
177) (2S,4R)-4-benzyl-N-(4-(4-fluorophenoxy)phenyl)-1-(2-(5-methyl-1H-pyrazol-3-yl)acetyl)pyrrolidine-2-carboxamide;
178) (S)-2-(2-(1H-1,2,4-triazol-1-yl)acetamido)-3-(benzyloxy)-N-(4-(4-fluorophenylthio)phenyl)propanamide;
179) (2S,4R)-1-(2-(1H-1,2,4-triazol-1-yl)acetyl)-4-(benzylamino)-N-(4-(4-fluorophenoxy)phenyl)pyrrolidine-2-carboxamide;
180) (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide;
181) (S)-2-(2-(1H-1,2,4-triazol-1-yl)acetamido)-3-(2-chlorobenzyloxy)-N-(4-(4-fluorophenoxy)phenyl)propanamide;
182) (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide;
183) 3-(benzyloxy)-2-(2-(2-fluorophenyl)acetamido)-N-(4-phenoxyphenyl)propanamide;
184) N-(3-(benzyloxy)-1-oxo-1-(4-phenoxyphenylamino)propan-2-yl)-1H-indole-4-carboxamide;
185) 2-(2-(3-methylisoxazol-5-yl)acetamido)-3-benzyloxy-N-(4-phenoxyphenyl)propanamide;
186) N-(3-(benzyloxy)-1-oxo-1-(4-phenoxyphenylamino)propan-2-yl)-4-cyclopropyl-4-oxobutanamide;
187) N-(3-(benzyloxy)-1-oxo-1-(4-phenoxyphenylamino)propan-2-yl)-1H-indole-6-carboxamide;
188) N-(3-(benzyloxy)-1-oxo-1-(4-phenoxyphenylamino)propan-2-yl)-2,3-dihydro-1H-indene-2-carboxamide;
189) N-(3-(benzyloxy)-1-oxo-1-(4-phenoxyphenylamino)propan-2-yl)-3-methyl-2-nitrobenzamide;
190) 3-(benzyloxy)-2-(2-(2,5-dichlorophenyl)acetamido)-N-(4-phenoxyphenyl)propanamide;
191) 3-(benzyloxy)-2-(2-(3-chloro-2-fluorophenyl)acetamido)-N-(4-phenoxyphenyl)propanamide;
192) 3-(benzyloxy)-2-(2-(5-chloro-2-fluorophenyl)acetamido)-N-(4-phenoxyphenyl)propanamide;
193) 2-(2-(1-acetylpyrrolidin-2-yl)acetamido)-3-benzyloxy-N-(4-phenoxyphenyl)propanamide;
194) (S)-2-{2-((benzoyl)(methyl)amino)acetamido}-3-benzyloxy-N-(4-phenoxyphenyl)propanamide;
195) (S)-2-(2-(1-methyl-1H-imidazol-4-yl)acetamido)-3-benzyloxy-N-(4-phenoxyphenyl)propanamide;
196) (S)-2-(2-(2-fluorophenyl)acetamido)-3-benzyloxy-N-(4-phenoxyphenyl)propanamide;
197) (S)-2-(2-(1H-indol-4-yl)acetamido)-3-benzyloxy-N-(4-phenoxyphenyl)propanamide;
198) (S)-2-(2-(thien-2-yl)acetamido)-3-benzyloxy-N-(4-phenoxyphenyl)propanamide;
199) (S)-2-(2-(2,5-dichlorophenyl)acetamido)-3-benzyloxy-N-(4-phenoxyphenyl)propanamide;
200) (S)-2-(2-(1H-imidazol-4-yl)acetamido)-3-(benzyloxy)-N-(4-benzylphenyl)propanamide;
201) (S)-3-(benzyloxy)-2-(2-(2,4-dioxoimidazolidin-1-yl)acetamido)-N-(4-phenoxyphenyl)propanamide;
202) (S)-2-(2-(1H-imidazol-4-yl)acetamido)-3-(benzyloxy)-N-(4-(4-methoxyphenoxy)phenyl)propanamide;
203) (S)-2-(2-(1H-imidazol-4-yl)-N-methylacetamido)-3-(benzyloxy)-N-(4-phenoxyphenyl)propanamide;
204) (S)-2-(2-(1H-imidazol-5-yl)acetamido)-N-(4-(4-chlorophenoxy)phenyl)-3-phenylpropanamide;
205) (S)-3-(benzyloxy)-N-(4-(4-fluorophenoxy)phenyl)-2-(2-(piperazin-1-yl)acetamido)propanamide;
206) (S)-2-(2-(1H-imidazol-4-yl)acetamido)-3-(benzyloxy)-N-(4-(thiazol-2-yloxy)phenyl)propanamide;
207) (S)-2-(3-(1H-imidazol-5-yl)propanamido)-3-(benzyloxy)-N-(4-(4-fluorophenoxy)phenyl)propanamide;
208) (S)-2-(2-(1H-imidazol-5-yl)acetamido)-3-(benzyloxy)-N-(4-(cyclohexyloxy)phenyl)propanamide;
209) (S)-3-(benzyloxy)-N-(4-(4-chlorophenoxy)phenyl)-2-(3-(dimethylamino)propanamido)propanamide;
210) (S)-3-(4-fluorobenzyloxy)-N-(4-(4-fluorophenoxy)phenyl)-2-(2-morpholinoacetamido)propanamide;
211) (S)-2-(2-(1H-imidazol-4-yl)acetamido)-3-(benzyloxy)-N-(4-(benzyloxy)phenyl)propanamide;
212) (S)-3-(benzyloxy)-2-(2-(5-fluoro-1H-indol-3-yl)acetamido)-N-(4-(4-fluorophenoxy)phenyl)propanamide;
213) (S)-2-(2-(1H-imidazol-4-yl)-2-methylpropanamido)-3-(benzyloxy)-N-(4-(4-fluorophenoxy)phenyl)propanamide;
214) (S)-3-(benzyloxy)-2-(2-(2,5-dihydro-1H-pyrrol-1-yl)acetamido)-N-(4-(4-fluorophenoxy)phenyl)propanamide;
215) (S)-3-(benzyloxy)-N-(4-(4-fluorophenoxy)phenyl)-2-(2-(pyrrolidin-1-yl)acetamido)propanamide;
216) (S)-2-(2-(2-(1H-imidazol-4-yl)ethylamino)acetamido)-3-(benzyloxy)-N-(4-(4-fluorophenoxy)phenyl)propanamide;
217) (S)-3-(benzyloxy)-N-(4-(4-fluorophenoxy)phenyl)-2-(2-(4-(2-methoxyphenyl)piperazin-1-yl)acetamido)propanamide;
218) (S)-3-(benzyloxy)-N-(4-(4-fluorophenoxy)phenyl)-2-(2-(4-(4-fluorophenyl)piperazin-1-yl)acetamido)propanamide;
219) (2S)-2-(2-(2,3-dioxa-8-azaspiro[4.5]decan-8-yl)acetamido)-3-(benzyloxy)-N-(4-(4-fluorophenoxy)phenyl)propanamide;

220) (S)-3-(benzyloxy)-2-(2-(4-benzylpiperidin-1-yl)acetamido)-N-(4-(4-fluorophenoxy)phenyl)propanamide;
221) (S)-3-(benzyloxy)-2-(2-(3,4-dihydroisoquinolin-2(1H)-yl)acetamido)-N-(4-(4-fluorophenoxy)phenyl)propanamide;
222) (2S)-3-(benzyloxy)-N-(4-(4-fluorophenoxy)phenyl)-2-(2-(octahydroisoquinolin-2(1H)-yl)acetamido)propanamide;
223) (S)-3-(benzyloxy)-N-(4-(4-fluorophenoxy)phenyl)-2-(2-(4-(furan-2-carbonyl)piperazin-1-yl)acetamido)propanamide;
224) (S)-3-(benzyloxy)-N-(4-(4-fluorophenoxy)phenyl)-2-(2-(4-(4-methoxyphenyl)piperazin-1-yl)acetamido)propanamide;
225) (S)-3-(benzyloxy)-N-(4-(4-fluorophenoxy)phenyl)-2-(2-(4-phenylpiperazin-1-yl)acetamido)propanamide;
226) (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide;
227) (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide;
228) (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide;
229) (S)-2-(2-(4-(4-acetylphenyl)piperazin-1-yl)acetamido)-3-(benzyloxy)-N-(4-(4-fluorophenoxy)phenyl)propanamide;
230) (S)-2-(2-(4-acetylpiperazin-1-yl)acetamido)-3-(benzyloxy)-N-(4-(4-fluorophenoxy)phenyl)propanamide;
231) 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide;
232) (S,E)-N-(3-(benzyloxy)-1-(4-(4-fluorophenoxy)phenylamino)-1-oxopropan-2-yl)hex-3-enamide;
233) (S)-N-(3-(benzyloxy)-1-(4-(4-fluorophenoxy)phenylamino)-1-oxopropan-2-yl)-3-methylbutanamide;
234) (S)-3-(benzyloxy)-2-(2-((2R,6S)-2,6-dimethylmorpholino)acetamido)-N-(4-(4-fluorophenoxy)phenyl)propanamide;
235) (S)-3-(benzyloxy)-N-(4-(4-fluorophenoxy)phenyl)-2-(2-(thiazolidin-3-yl)acetamido)propanamide;
236) (S)-2-(2-(4-acetylpiperazin-1-yl)acetamido)-3-(benzyloxy)-N-(4-(4-fluorophenoxy)phenyl)propanamide;
237) (2S)-3-(benzyloxy)-N-(4-(4-fluorophenoxy)phenyl)-2-(2-(4-(tetrahydrofuran-2-carbonyl)piperazin-1-yl)acetamido)propanamide;
238) (S)-methyl 1-(2-(3-(benzyloxy)-1-(4-(4-fluorophenoxy)phenylamino)-1-oxopropan-2-ylamino)-2-oxoethyl)piperidine-4-carboxylate;
239) (S)-3-(benzyloxy)-2-(2-(4-(2-chloro-6-fluorobenzyl)piperazin-1-yl)acetamido)-N-(4-(4-fluorophenoxy)phenyl)propanamide;
240) (S)-3-(benzyloxy)-N-(4-(4-fluorophenoxy)phenyl)-2-(2-(isoindolin-2-yl)acetamido)propanamide;
241) (S)-3-(benzyloxy)-N-(4-(4-fluorophenoxy)phenyl)-2-(2-(4-(2-methoxyethyl)piperazin-1-yl)acetamido)propanamide;
242) (S)-3-(benzyloxy)-N-(4-(4-fluorophenoxy)phenyl)-2-(2-(4-(2-ethoxyethyl)piperazin-1-yl)acetamido)propanamide;
243) (S)-2-(2-(1H-imidazol-4-yl)acetamido)-3-(benzyloxy)-N-(3-phenoxyphenyl)propanamide;
244) (S)-3-(benzyloxy)-2-(2-(3-bromophenyl)acetamido)-N-(4-(4-fluorophenoxy)phenyl)propanamide;
245) (S)-3-(benzyloxy)-N-(4-(4-fluorophenoxy)phenyl)-2-(3-nitropropanamido)propanamide;
246) (S)-3-(benzyloxy)-N-(4-(4-fluorophenoxy)phenyl)-2-(2-(pyridin-2-yl)acetamido)propanamide;
247) (S)-3-(benzyloxy)-N-(4-(4-fluorophenoxy)phenyl)-2-(2-(pyridin-3-yl)acetamido)propanamide;
248) (S)-N-((S)-3-(benzyloxy)-1-(4-(4-fluorophenoxy)phenylamino)-1-oxopropan-2-yl)-3,7-dimethyloct-6-enamide;
249) (S)-3-(benzyloxy)-N-(4-(4-fluorophenoxy)phenyl)-2-(2-phenylacetamido)propanamide;
250) (S)-3-(benzyloxy)-N-(4-(4-fluorophenoxy)phenyl)-2-(2-(pyrimidin-5-yl)acetamido)propanamide;
251) (2S,4S)-1-(2-(1H-imidazol-5-yl)acetyl)-N-(4-(4-fluorophenoxy)phenyl)-4-phenylpyrrolidine-2-carboxamide;
252) (2S,4R)-1-(2-(1H-1,2,4-triazol-1-yl)acetyl)-4-(benzyloxy)-N-(4-(4-fluorophenoxy)phenyl)pyrrolidine-2-carboxamide;
253) benzyl (3R,5S)-1-(2-(1H-imidazol-5-yl)acetyl)-5-(4-(4-fluorophenoxy)phenylcarbamoyl)pyrrolidin-3-ylcarbamate;
254) (S)-2-(2-(1H-1,2,4-triazol-1-yl)acetamido)-5-acetamido-N-(4-(4-fluorophenoxy)phenyl)pentanamide;
255) (S)-3-(benzyloxy)-N-(4-(4-fluorophenoxy)phenyl)-2-(2-methyl-2-(1H-1,2,4-triazol-1-yl)propanamido)propanamide;
256) (S)-3-(benzyloxy)-2-(2-(3,5-dimethyl-1H-1,2,4-triazol-1-yl)acetamido)-N-(4-(4-fluorophenoxy)phenyl)propanamide;
257) (S)-benzyl 4-(2-(1H-imidazol-4-yl)acetyl)-3-(4-(4-fluorophenoxy)phenylcarbamoyl)piperazine-1-carboxylate;
258) (S)-2-(2-(3,5-dimethyl-1H-pyrazol-4-yl)acetamido)-3-(4-fluorobenzyloxy)-N-(4-(4-fluorophenoxy)phenyl)propanamide;
259) (2S,4R)-1-(2-(1H-1,2,4-triazol-1-yl)acetyl)-N-(4-(4-fluorophenoxy)phenyl)-4-phenoxypyrrolidine-2-carboxamide;
260) (2S,4R)-1-(2-(1H-1,2,4-triazol-1-yl)acetyl)-N-(4-(4-fluorophenoxy)phenyl)-4-(isoindolin-2-pyrrolidine-2-carboxamide;
261) (S)-1-(2-(1H-1,2,4-triazol-1-yl)acetyl)-4-benzyl-N-(4-(4-fluorophenoxy)phenyl)piperazine-2-carboxamide;
262) (2S,4S)-1-(2-(1H-1,2,4-triazol-1-yl)acetyl)-4-((benzylamino)methyl)-N-(4-(4-fluorophenoxy)phenyl)pyrrolidine-2-carboxamide;
263) (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide;
264) (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide;
265) (2S)-3-(benzyloxy)-2-(2-(2,6-dimethylmorpholino)acetamido)-N-(4-(4-fluorophenoxy)phenyl)propanamide;
266) (S)-3-(benzyloxy)-N-(4-(4-fluorophenoxy)phenyl)-2-(2-thiomorpholinoacetamido)propanamide;
267) (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide;
268) (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide;
269) N-(2-oxo-1-{[(phenylmethyl)oxy]methyl}-2-{[4-(phenyloxy)phenyl]amino}ethyl)acetamide;

270) 4-(methyloxy)-N-(2-oxo-1-{[(phenylmethyl)oxy]methyl}-2-{[4-(phenyloxy)phenyl]amino}ethyl)benzamide;
271) 4-benzyloxy-N-(2-oxo-1-{[(phenylmethyl)oxy]methyl}-2-{[4-(phenyloxy)phenyl]amino}ethyl)phenylacetamide;
272) 2-bromo-5-(methyloxy)-N-(2-oxo-1-{[(phenylmethyl)oxy]methyl}-2-{[4-(phenyloxy)phenyl]amino}ethyl)benzamide;
273) N-(2-oxo-1-{[(phenylmethyl)oxy]methyl}-2-{[4-(phenyloxy)phenyl]amino}ethyl)butanamide;
274) 2-chloro-N-(2-oxo-1-{[(phenylmethyl)oxy]methyl}-2-{[4-(phenyloxy)phenyl]amino}ethyl)benzamide;
275) 3-chloro-N-(2-oxo-1-{[(phenylmethyl)oxy]methyl}-2-{[4-(phenyloxy)phenyl]amino}ethyl)benzamide;
276) 4-chloro-N-(2-oxo-1-{[(phenylmethyl)oxy]methyl}-2-{[4-(phenyloxy)phenyl]amino}ethyl)benzamide;
277) N-(2-oxo-1-{[(phenylmethyl)oxy]methyl}-2-{[4-(phenyloxy)phenyl]amino}ethyl)cyclopropylamide;
278) N-(2-oxo-1-{[(phenylmethyl)oxy]methyl}-2-{[4-(phenyloxy)phenyl]amino}ethyl)-3-cyclopentylpropanamide;
279) 3,4-dimethyl-N-(2-oxo-1-{[(phenylmethyl)oxy]methyl}-2-{[4-(phenyloxy)phenyl]amino}ethyl)benzamide;
280) N-(2-oxo-1-{[(phenylmethyl)oxy]methyl}-2-{[4-(phenyloxy)phenyl]amino}ethyl)-2,5-dimethoxyphenylacetamide;
281) 4-(ethyloxy)-N-(2-oxo-1-{[(phenylmethyl)oxy]methyl}-2-{[4-(phenyloxy)phenyl]amino}ethyl)benzamide;
282) N-(3-(benzyloxy)-1-oxo-1-(4-phenoxyphenylamino)propan-2-yl)-2-ethylhexanamide;
283) N-(2-oxo-1-{[(phenylmethyl)oxy]methyl}-2-{[4-(phenyloxy)phenyl]amino}ethyl)furan-2-carboxamide;
284) N-(2-oxo-1-{[(phenylmethyl)oxy]methyl}-2-{[4-(phenyloxy)phenyl]amino}ethyl)-2-methoxyacetamide;
285) N-(2-oxo-1-{[(phenylmethyl)oxy]methyl}-2-{[4-(phenyloxy)phenyl]amino}ethyl)-3-methoxyphenylacetamide;
286) 2-methyl-N-(2-oxo-1-{[(phenylmethyl)oxy]methyl}-2-{[4-(phenyloxy)phenyl]amino}ethyl)pentanamide;
287) 4-methyl-N-(2-oxo-1-{[(phenylmethyl)oxy]methyl}-2-{[4-(phenyloxy)phenyl]amino}ethyl)pentanamide;
288) N-(2-oxo-1-{[(phenylmethyl)oxy]methyl}-2-{[4-(phenyloxy)phenyl]amino}ethyl)naphthalene-2-carboxamide;
289) N-(2-oxo-1-{[(phenylmethyl)oxy]methyl}-2-{[4-(phenyloxy)phenyl]amino}ethyl)phenoxyacetamide;
290) N-(2-oxo-1-{[(phenylmethyl)oxy]methyl}-2-{[4-(phenyloxy)phenyl]amino}ethyl)-2-(phenyloxy)pyridine-3-carboxamide;
291) 3,4,5-tris(methyloxy)-N-(2-oxo-1-{[(phenylmethyl)oxy]methyl}-2-{[4-(phenyloxy)phenyl]amino}ethyl)benzamide;
292) N-(2-oxo-1-{[(phenylmethyl)oxy]methyl}-2-{[4-(phenyloxy)phenyl]amino}ethyl)thiophene-2-carboxamide;
293) N-(2-oxo-1-{[(phenylmethyl)oxy]methyl}-2-{[4-(phenyloxy)phenyl]amino}ethyl)thien-2-ylacetamide;
294) 4-(dimethylamino)-N-(2-oxo-1-{[(phenylmethyl)oxy]methyl}-2-{[4-(phenyloxy)phenyl]amino}ethyl)benzamide;
295) N-(2-oxo-1-{[(phenylmethyl)oxy]methyl}-2-{[4-(phenyloxy)phenyl]amino}ethyl)hexanamide;
296) 2-chloro-N-(2-oxo-1-{[(phenylmethyl)oxy]methyl}-2-{[4-(phenyloxy)phenyl]amino}ethyl)pyridine-3-carboxamide;
297) 3-chloro-N-(2-oxo-1-{[(phenylmethyl)oxy]methyl}-2-{[4-(phenyloxy)phenyl]amino}ethyl)-1-benzothiophene-2-carboxamide;
298) N-(2-oxo-1-{[(phenylmethyl)oxy]methyl}-2-{[4-(phenyloxy)phenyl]amino}ethyl)pent-4-enamide;
299) 3-chloro-2-fluoro-N-(2-oxo-1-{[(phenylmethyl)oxy]methyl}-2-{[4-(phenyloxy)phenyl]amino}ethyl)benzamide;
300) N-(2-oxo-1-{[(phenylmethyl)oxy]methyl}-2-{[4-(phenyloxy)phenyl]amino}ethyl)-4-phenylbutanamide;
301) N-(2-oxo-1-{[(phenylmethyl)oxy]methyl}-2-{[4-(phenyloxy)phenyl]amino}ethyl)-2-bromophenylacetamide;
302) N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide;
303) N-(2-oxo-1-{[(phenylmethyl)oxy]methyl}-2-{[4-(phenyloxy)phenyl]amino}ethyl)-2-methoxyethoxyacetamide;
304) N-(2-oxo-1-{[(phenylmethyl)oxy]methyl}-2-{[4-(phenyloxy)phenyl]amino}ethyl)-3-(4-methoxyphenyl)propanamide;
305) N-(2-oxo-1-{[(phenylmethyl)oxy]methyl}-2-{[4-(phenyloxy)phenyl]amino}ethyl)-2-acetylamino-4-methylthiazol-5-ylsulfonamide;
306) 4-(methylthio)-N-(2-oxo-1-{[(phenylmethyl)oxy]methyl}-2-{[4-(phenyloxy)phenyl]amino}ethyl)benzamide;
307) N-(2-oxo-1-{[(phenylmethyl)oxy]methyl}-2-{[4-(phenyloxy)phenyl]amino}ethyl)-2-(methylthio)acetamide;
308) 5-fluoro-2-(methyloxy)-N-(2-oxo-1-{[(phenylmethyl)oxy]methyl}-2-{[4-(phenyloxy)phenyl]amino}ethyl)benzamide;
309) 2-methyl-4-(methyloxy)-N-(2-oxo-1-{[(phenylmethyl)oxy]methyl}-2-{[4-(phenyloxy)phenyl]amino}ethyl)benzamide;
310) 5-oxo-N-(2-oxo-1-{[(phenylmethyl)oxy]methyl}-2-{[4-(phenyloxy)phenyl]amino}ethyl)hexanamide;
311) 4-bromo-2-methyl-N-(2-oxo-1-{[(phenylmethyl)oxy]methyl}-2-{[4-(phenyloxy)phenyl]amino}ethyl)benzamide;
312) 4-oxo-N-(2-oxo-1-{[(phenylmethyl)oxy]methyl}-2-{[4-(phenyloxy)phenyl]amino}ethyl)-4-(2-thienyl)butanamide;
313) N-(2-oxo-1-{[(phenylmethyl)oxy]methyl}-2-{[4-(phenyloxy)phenyl]amino}ethyl)-2-(phenylthio)acetamide;
314) N-(2-oxo-1-{[(phenylmethyl)oxy]methyl}-2-{[4-(phenyloxy)phenyl]amino}ethyl)-2-(1H-pyrrol-1-yl)benzamide;
315) N-(2-oxo-1-{[(phenylmethyl)oxy]methyl}-2-{[4-(phenyloxy)phenyl]amino}ethyl)-2-[2-(methoxy)ethoxy]ethoxyacetamide;
316) 3,5-bis(methyloxy)-N-(2-oxo-1-{[(phenylmethyl)oxy]methyl}-2-{[4-(phenyloxy)phenyl]amino}ethyl)benzamide;
317) N-(2-oxo-1-{[(phenylmethyl)oxy]methyl}-2-{[4-(phenyloxy)phenyl]amino}ethyl)-3-cyclohexylpropanamide;

318) 5-oxo-N-(2-oxo-1-{[(phenylmethyl)oxy]methyl}-2-{[4-(phenyloxy)phenyl]amino}ethyl)-5-phenylpentanamide;
319) N-(2-oxo-1-{[(phenylmethyl)oxy]methyl}-2-{[4-(phenyloxy)phenyl]amino}ethyl)-4-acetylphenoxyacetamide;
320) 4-[3,4-bis(methyloxy)phenyl]-N-(2-oxo-1-{[(phenylmethyl)oxy]methyl}-2-{[4-(phenyloxy)phenyl]amino}ethyl)butanamide;
321) N-(2-oxo-1-{[(phenylmethyl)oxy]methyl}-2-{[4-(phenyloxy)phenyl]amino}ethyl)-5-[3-(trifluoromethyl)phenyl]furan-2-carboxamide;
322) N-(2-oxo-1-{[(phenylmethyl)oxy]methyl}-2-{[4-(phenyloxy)phenyl]amino}ethyl)-3-(1,3-dioxoisoindolin-2-yl)propanamide;
323) 5-oxo-N-(2-oxo-1-{[(phenylmethyl)oxy]methyl}-2-{[4-(phenyloxy)phenyl]amino}ethyl)-5-(2-thienyl)pentanamide;
324) N-(2-oxo-1-{[(phenylmethyl)oxy]methyl}-2-{[4-(phenyloxy)phenyl]amino}ethyl)-2-oxo-2-phenylacetamide;
325) N-(2-oxo-1-{[(phenylmethyl)oxy]methyl}-2-{[4-(phenyloxy)phenyl]amino}ethyl)-4-(2-thienyl)butanamide;
326) 5-nitro-N-(2-oxo-1-{[(phenylmethyl)oxy]methyl}-2-{[4-(phenyloxy)phenyl]amino}ethyl)furan-2-caroxamide;
327) (E)-N-(3-(benzyloxy)-1-oxo-1-(4-phenoxyphenylamino)propan-2-yl)hex-3-enamide
328) N-(2-oxo-1-{[(phenylmethyl)oxy]methyl}-2-{[4-(phenyloxy)phenyl]amino}ethyl)-1,3-benzodioxol-5-ylacetamide;
329) 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide;
330) 4-fluoro-N-(2-oxo-1-{[(phenylmethyl)oxy]methyl}-2-{[4-(phenyloxy)phenyl]amino}ethyl)-2-(trifluoromethyl)benzamide;
331) N-(2-oxo-1-{[(phenylmethyl)oxy]methyl}-2-{[4-(phenyloxy)phenyl]amino}ethyl)-2-(pyrimidin-2-ylthio)acetamide;
332) 2,5-bis(methyloxy)-N-(2-oxo-1-{[(phenylmethyl)oxy]methyl}-2-{[4-(phenyloxy)phenyl]amino}ethyl)benzamide;
333) 4-(methylsulfonyl)-N-(2-oxo-1-{[(phenylmethyl)oxy]methyl}-2-{[4-(phenyloxy)phenyl]amino}ethyl)benzamide;
334) 2-chloro-4-(methylsulfonyl)-N-(2-oxo-1-{[(phenylmethyl)oxy]methyl}-2-{[4-(phenyloxy)phenyl]amino}ethyl)benzamide;
335) N-(2-oxo-1-{[(phenylmethyl)oxy]methyl}-2-{[4-(phenyloxy)phenyl]amino}ethyl)2-(4-oxo-2-thioxothiazolidin-3-yl)acetamide;
336) N-(2-oxo-1-{[(phenylmethyl)oxy]methyl}-2-{[4-(phenyloxy)phenyl]amino}ethyl)tetrahydrofuran-3-carboxamide;
337) N-(2-oxo-1-{[(phenylmethyl)oxy]methyl}-2-{[4-(phenyloxy)phenyl]amino}ethyl)-3-methoxypropanamide;
338) N-(2-oxo-1-{[(phenylmethyl)oxy]methyl}-2-{[4-(phenyloxy)phenyl]amino}ethyl)-2-ethoxyacetamide;
339) N,N-dimethyl-N'-(2-oxo-1-{[(phenylmethyl)oxy]methyl}-2-{[4-(phenyloxy)phenyl]amino}ethyl)butanediamide;
340) N-(2-oxo-1-{[(phenylmethyl)oxy]methyl}-2-{[4-(phenyloxy)phenyl]amino}ethyl)-N-benzoyl-N-methylaminoacetamide;
341) N-(2-oxo-1-{[(phenylmethyl)oxy]methyl}-2-{[4-(phenyloxy)phenyl]amino}ethyl)-1H-indole-3-carboxamide;
342) N-(2-oxo-1-{[(phenylmethyl)oxy]methyl}-2-{[4-(phenyloxy)phenyl]amino}ethyl)-1H-benzimidazole-5-carboxamide;
343) N-(2-oxo-1-{[(phenylmethyl)oxy]methyl}-2-{[4-(phenyloxy)phenyl]amino}ethyl)-2-(4-ethoxyphenyl)acetamide;
344) N-(2-oxo-1-{[(phenylmethyl)oxy]methyl}-2-{[4-(phenyloxy)phenyl]amino}ethyl)pent-4-ynamide;
345) N-(2-oxo-1-{[(phenylmethyl)oxy]methyl}-2-{[4-(phenyloxy)phenyl]amino}ethyl)-4-(propyloxy)benzamide;
346) 2-methyl-N-(2-oxo-1-{[(phenylmethyl)oxy]methyl}-2-{[4-(phenyloxy)phenyl]amino}ethyl)hexanamide;
347) 4-oxo-N-(2-oxo-1-{[(phenylmethyl)oxy]methyl}-2-{[4-(phenyloxy)phenyl]amino}ethyl)pentanamide;
348) N-(2-oxo-1-{[(phenylmethyl)oxy]methyl}-2-{[4-(phenyloxy)phenyl]amino}ethyl)-3-(3,4-dimethoxyphenyl)propanamide;
349) 4-oxo-N-(2-oxo-1-{[(phenylmethyl)oxy]methyl}-2-{[4-(phenyloxy)phenyl]amino}ethyl)-4-phenylbutanamide;
350) N-(2-oxo-1-{[(phenylmethyl)oxy]methyl}-2-{[4-(phenyloxy)phenyl]amino}ethyl)quinoline-3-carboxamide;
351) N-(2-oxo-1-{[(phenylmethyl)oxy]methyl}-2-{[4-(phenyloxy)phenyl]amino}ethyl)pyrazine-2-carboxamide;
352) N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide;
353) N-(2-oxo-1-{[(phenylmethyl)oxy]methyl}-2-{[4-(phenyloxy)phenyl]amino}ethyl)-2-methoxy-2-phenylacetamide;
354) N-(2-oxo-1-{[(phenylmethyl)oxy]methyl}-2-{[4-(phenyloxy)phenyl]amino}ethyl)-2R-phenylpropanamide;
355) N-(2-oxo-1-{[(phenylmethyl)oxy]methyl}-2-{[4-(phenyloxy)phenyl]amino}ethyl)-1H-pyrazole-4-carboxamide;
356) N-(2-oxo-1-{[(phenylmethyl)oxy]methyl}-2-{[4-(phenyloxy)phenyl]amino}ethyl cinnoline-4-carboxamide;
357) N-(2-oxo-1-{[(phenylmethyl)oxy]methyl}-2-{[4-(phenyloxy)phenyl]amino}ethyl)quinoline-8-carboxamide;
358) 6-hydroxy-N-(2-oxo-1-{[(phenylmethyl)oxy]methyl}-2-{[4-(phenyloxy)phenyl]amino}ethyl)pyridine-2-carboxamide;
359) N-(2-oxo-1-{[(phenylmethyl)oxy]methyl}-2-{[4-(phenyloxy)phenyl]amino}ethyl)-2-phenylpropanamide;
360) N-(2-oxo-1-{[(phenylmethyl)oxy]methyl}-2-{[4-(phenyloxy)phenyl]amino}ethyl)-1-(4-methoxyphenyl)cyclopropanecarboxamide;
361) N-(2-oxo-1-{[(phenylmethyl)oxy]methyl}-2-{[4-(phenyloxy)phenyl]amino}ethyl)-2-(2,3,6-trifluorophenyl)acetamide;
362) N-(2-oxo-1-{[(phenylmethyl)oxy]methyl}-2-{[4-(phenyloxy)phenyl]amino}ethyl)-2,4-bis(trifluoromethyl)benzamide;
363) N-(2-oxo-1-{[(phenylmethyl)oxy]methyl}-2-{[4-(phenyloxy)phenyl]amino}ethyl)-2-(2,4-difluorophenyl)acetamide;

364) N-(2-oxo-1-{[(phenylmethyl)oxy]methyl}-2-{[4-(phenyloxy)phenyl]amino}ethyl)-2-(1-methyl-1H-indol-3-yl)acetamide;
365) N-(2-oxo-1-{[(phenylmethyl)oxy]methyl}-2-{[4-(phenyloxy)phenyl]amino}ethyl)quinoline-4-carboxamide;
366) N-(2-oxo-1-{[(phenylmethyl)oxy]methyl}-2-{[4-(phenyloxy)phenyl]amino}ethyl)-1-benzofuran-2-carboxamide;
367) 7-(methyloxy)-N-(2-oxo-1-{[(phenylmethyl)oxy]methyl}-2-{[4-(phenyloxy)phenyl]amino}ethyl)-1-benzofuran-2-carboxamide;
368) N-(2-oxo-1-{[(phenylmethyl)oxy]methyl}-2-{[4-(phenyloxy)phenyl]amino}ethyl)-2-(4-fluorophenoxy)acetamide;
369) N-(2-oxo-1-{[(phenylmethyl)oxy]methyl}-2-{[4-(phenyloxy)phenyl]amino}ethyl)-3-(pyridin-3-yl)propanamide;
370) N-(2-oxo-1-{[(phenylmethyl)oxy]methyl}-2-{[4-(phenyloxy)phenyl]amino}ethyl)-2-(3,4-dichlorophenoxy)acetamide;
371) N-(2-oxo-1-{[(phenylmethyl)oxy]methyl}-2-{[4-(phenyloxy)phenyl]amino}ethyl)-2-(naphthalen-1-yloxy)acetamide;
372) N-(2-oxo-1-{[(phenylmethyl)oxy]methyl}-2-{[4-(phenyloxy)phenyl]amino}ethyl)-2-p-tolylacetamide;
373) N-(2-oxo-1-{[(phenylmethyl)oxy]methyl}-2-{[4-(phenyloxy)phenyl]amino}ethyl)-2-(2,5-dimethylphenyl)acetamide;
374) N-(2-oxo-1-{[(phenylmethyl)oxy]methyl}-2-{[4-(phenyloxy)phenyl]amino}ethyl)-2-(benzylthio)acetamide;
375) N-(2-oxo-1-{[(phenylmethyl)oxy]methyl}-2-{[4-(phenyloxy)phenyl]amino}ethyl)-2-(naphthalen-1-yl)acetamide;
376) N-(2-oxo-1-{[(phenylmethyl)oxy]methyl}-2-{[4-(phenyloxy)phenyl]amino}ethyl)-3-ethoxypropanamide;
377) N-(2-oxo-1-{[(phenylmethyl)oxy]methyl}-2-{[4-(phenyloxy)phenyl]amino}ethyl)-2-(3-chlorophenyl)acetamide;
378) 5-butyl-N-(2-oxo-1-{[(phenylmethyl)oxy]methyl}-2-{[4-(phenyloxy)phenyl]amino}ethyl)pyridine-2-carboxamide;
379) 4-chloro-3-methyl-N-(2-oxo-1-{[(phenylmethyl)oxy]methyl}-2-{[4-(phenyloxy)phenyl]amino}ethyl)benzamide;
380) 4-cyano-N-(2-oxo-1-{[(phenylmethyl)oxy]methyl}-2-{[4-(phenyloxy)phenyl]amino}ethyl)benzamide;
381) N-(2-oxo-1-{[(phenylmethyl)oxy]methyl}-2-{[4-(phenyloxy)phenyl]amino}ethyl)-2S-methoxy-2-phenylacetamide;
382) N-(2-oxo-1-{[(phenylmethyl)oxy]methyl}-2-{[4-(phenyloxy)phenyl]amino}ethyl)-3-(2,5-dimethoxyphenyl)propanamide;
383) N-(2-oxo-1-{[(phenylmethyl)oxy]methyl}-2-{[4-(phenyloxy)phenyl]amino}ethyl)-3-(1H-indol-3-yl)propanamide;
384) N-(2-oxo-1-{[(phenylmethyl)oxy]methyl}-2-{[4-(phenyloxy)phenyl]amino}ethyl)-2-(3-bromophenyl)acetamide;
385) 3-methyl-N-(2-oxo-1-{[(phenylmethyl)oxy]methyl}-2-{[4-(phenyloxy)phenyl]amino}ethyl)pentanamide;
386) N-(2-oxo-1-{[(phenylmethyl)oxy]methyl}-2-{[4-(phenyloxy)phenyl]amino}ethyl)-1H-indole-2-carboxamide;
387) 4-chloro-2-fluoro-N-(2-oxo-1-{[(phenylmethyl)oxy]methyl}-2-{[4-(phenyloxy)phenyl]amino}ethyl)benzamide;
388) 2-oxo-2-[(2-oxo-1-{[(phenylmethyl)oxy]methyl}-2-{[4-(phenyloxy)phenyl]amino}ethyl)amino]ethyl acetate;
389) N-(2-oxo-1-{[(phenylmethyl)oxy]methyl}-2-{[4-(phenyloxy)phenyl]amino}ethyl)thiophene-3-carboxamide;
390) N-(2-oxo-1-{[(phenylmethyl)oxy]methyl}-2-{[4-(phenyloxy)phenyl]amino}ethyl)-2-(4-bromophenyl)acetamide;
391) N-(2-oxo-1-{[(phenylmethyl)oxy]methyl}-2-{[4-(phenyloxy)phenyl]amino}ethyl)-2-(2-chlorophenyl)acetamide;
392) N-(2-oxo-1-{[(phenylmethyl)oxy]methyl}-2-{[4-(phenyloxy)phenyl]amino}ethyl)-2-(3,4,5-trimethoxyphenyl)acetamide;
393) N-(2-oxo-1-{[(phenylmethyl)oxy]methyl}-2-{[4-(phenyloxy)phenyl]amino}ethyl)-2-(p-tolyloxy)acetamide;
394) N-(2-oxo-1-{[(phenylmethyl)oxy]methyl}-2-{[4-(phenyloxy)phenyl]amino}ethyl)-3-(2-methoxyphenyl)propanamide;
395) 3-hydroxy-N-(2-oxo-1-{[(phenylmethyl)oxy]methyl}-2-{[4-(phenyloxy)phenyl]amino}ethyl)quinoxaline-2-carboxamide;
396) 4-acetyl-N-(2-oxo-1-{[(phenylmethyl)oxy]methyl}-2-{[4-(phenyloxy)phenyl]amino}ethyl)benzamide;
397) methyl 4-{[(2-oxo-1-{[(phenylmethyl)oxy]methyl}-2-{[4-(phenyloxy)phenyl]amino}ethyl)amino]carbonyl}benzoate;
398) 3-fluoro-N-(2-oxo-1-{[(phenylmethyl)oxy]methyl}-2-{[4-(phenyloxy)phenyl]amino}ethyl)-5-(trifluoromethyl)benzamide;
399) 4-[(difluoromethyl)oxy]-N-(2-oxo-1-{[(phenylmethyl)oxy]methyl}-2-{[4-(phenyloxy)phenyl]amino}ethyl)benzamide;
400) 3-fluoro-4-methyl-N-(2-oxo-1-{[(phenylmethyl)oxy]methyl}-2-{[4-(phenyloxy)phenyl]amino}ethyl)benzamide;
401) 3-methyl-N-(2-oxo-1-{[(phenylmethyl)oxy]methyl}-2-{[4-(phenyloxy)phenyl]amino}ethyl)furan-2-carboxamide.
402) N-(2-oxo-1-{[(phenylmethyl)oxy]methyl}-2-{[4-(phenyloxy)phenyl]amino}ethyl)cyclobutanecarboxamide; and
403) N-(2-oxo-1-{[(phenylmethyl)oxy]methyl}-2-{[4-(phenyloxy)phenyl]amino}ethyl)-3-(thiophen-2-yl)propanamide, and wherein the combination has therapeutic synergy in inhibiting or relieving breast or lung cancer.

34. The combination of claim 33, wherein the antimicrotubule agent is selected from the group consisting of a taxane or a vinca alkaloid.

35. The combination of claim 34, wherein the taxane compound is paclitaxel, or docetaxel.

36. The combination of claim 33, wherein the S1P1R receptor antagonist is selected from the group consisting of
(2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide,
(2S,4R)-1-(2-(2H-1,2,3-triazol-2-yl)acetyl)-4-(4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

37. The combination of claim 34, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

38. The combination of claim 35, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

39. The combination of claim 38, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide and the taxane is paclitaxel or doxetaxel.

40. The combination of claim 38, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide and the taxane is paclitaxel or doxetaxel.

41. The combination of claim 38, wherein the S1P1R receptor antagonist is (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide and the taxane is paclitaxel or doxetaxel.

42. The combination of claim 38, wherein the S1P1R receptor antagonist is (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide and the taxane is paclitaxel or doxetaxel.

43. The combination of claim 34, wherein the vinca alkaloid is vincristine, vinblastine, or vinorelbine.

44. The combination of claim 43, wherein the S1P1R receptor antagonist is selected from the group consisting of (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide, and (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide.

45. The combination of claim 44, wherein the S1P1R receptor antagonist is (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide and the vinca alkaloid is selected from the group consisting of vincristine, vinblastine, or vinorelbine.

46. The combination of claim 44, wherein the S1P1R receptor antagonist is (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide and the vinca alkaloid is selected from the group consisting of vincristine, vinblastine, or vinorelbine.

47. The combination of claim 44, wherein the S1P1R receptor antagonist is (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide and the vinca alkaloid is selected from the group consisting of vincristine, vinblastine, or vinorelbine.

48. The combination of claim 44, wherein the S1P1R receptor antagonist is and the vinca alkaloid is selected from the group consisting of vincristine, vinblastine, or vinorelbine.

49. A kit comprising one or more containers filled with one or more of ingredients comprising at least one S1P1R receptor antagonist and at least one antimicrotubule agent, wherin the S1P1R receptor antagonist is selected from the group of compounds consisting of 1) (S)-2-(2-(1H-imidazol-5-yl)acetamido)-5-phenyl-N-(4-phenoxyphenyl)pentanamide;

2) (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide;

3) (2S,4R)-5-(2-(1H-1,2,3-triazol-1-yl)acetyl)-N-(4-(4-fluorophenoxy)phenyl)-4-(4-methylbenzyl)pyrrolidine-2-carboxamide;

4) (2S,4R)-5-(2-(1H-1,2,4-triazol-1-yl)acetyl)-N-(4-(4-fluorophenoxy)phenyl)-4-(4-methylbenzyl)pyrrolidine-2-carboxamide;

5) (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide;

6) (2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide;

7) (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide;

8) (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide;

9) (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide;

10) (2S,4R)-1-(2-(1H-1,2,3-triazol-1-yl)acetyl)-4-benzyl-N-(4-(4-fluorophenoxy)phenyl)pyrrolidine-2-carboxamide;

11) (2S,4R)-1-(2-(5-amino-3-(trifluoromethyl)-1H-1,2,4-triazol-1-yl)acetyl)-4-benzyl-N-(4-(4-fluorophenoxy)phenyl)pyrrolidine-2-carboxamide;

12) 1-((2S,4R)-4-benzyl-2-(5-(4-fluorophenoxy)-1H-benzo[d]imidazol-2-yl)pyrrolidin-1-yl)-2-(1H-1,2,4-triazol-1-yl)ethanone;

13) 3-(benzyloxy)-2-((S)-3-hydroxy-3-phenylpropanamido)-N-(4-phenoxyphenyl)propanamide;

14) 3-(benzyloxy)-2-(2-(furan-2-yl)-2-oxoacetamido)-N-(4-phenoxyphenyl)propanamide;
15) N-(3-(benzyloxy)-1-oxo-1-(4-phenoxyphenylamino)propan-2-yl)-6-(2,5-dioxo-2,5-dihydro-1H-pyrrol-1-yl)hexanamide;
16) 3-(benzyloxy)-2-(2-hydroxy-2-(2-hydroxyphenyl)acetamido)-N-(4-phenoxyphenyl)propanamide;
17) 4-(3-(benzyloxy)-1-oxo-1-(4-phenoxyphenylamino)propan-2-ylcarbamoyl)phenyl acetate;
18) N-(3-(benzyloxy)-1-oxo-1-(4-phenoxyphenylamino)propan-2-yl)-5-methylnicotinamide;
19) 3-(benzyloxy)-2-(2-(methylsulfonyl)acetamido)-N-(4-phenoxyphenyl)propanamide;
20) N-(3-(benzyloxy)-1-oxo-1-(4-phenoxyphenylamino)propan-2-yl)-1H-indole-5-carboxamide;
21) N-(3-(benzyloxy)-1-oxo-1-(4-phenoxyphenylamino)propan-2-yl)-2-bromo-5-fluorobenzamide;
22) N-(3-(benzyloxy)-1-oxo-1-(4-phenoxyphenylamino)propan-2-yl)-3,3,3-trifluoropropanamide;
23) (2R)-N-(3-(benzyloxy)-1-oxo-1-(4-phenoxyphenylamino)propan-2-yl)tetrahydrofuran-2-carboxamide;
24) 3-(benzyloxy)-24-((R)-2-(2-chlorophenyl)-2-hydroxyacetamido)-N-(4-phenoxyphenyl)propanamide;
25) (2S)-1-(3-(benzyloxy)-1-oxo-1-(4-phenoxyphenylamino)propan-2-ylamino)-1-oxopropan-2-yl acetate;
26) 3-(benzyloxy)-2-(2-(2-hydroxyphenoxy)acetamido)-N-(4-phenoxyphenyl)propanamide;
27) 3-(benzyloxy)-24-((R)-2-hydroxy-3-phenylpropanamido)-N-(4-phenoxyphenyl)propanamide;
28) N-(3-(benzyloxy)-1-oxo-1-(4-phenoxyphenylamino)propan-2-yl)-2-(methylthio)nicotinamide;
29) N-(3-(benzyloxy)-1-oxo-1-(4-phenoxyphenylamino)propan-2-yl)-1-(4-chlorobenzyl)-5-oxopyrrolidine-3-carboxamide;
30) (2S,4R)-4-benzyl-N-(4-(4-fluorophenoxy)phenyl)-1-(2-((1-methyl-1H-indol-2-yl)methylamino)acetyl)pyrrolidine-2-carboxamide;
31) (2S,4R)-4-benzyl-N-(4-(4-fluorophenoxy)phenyl)-1-(2-phenylacetyl)pyrrolidine-2-carboxamide;
32) (2S,4R)-4-benzyl-N-(4-(4-fluorophenoxy)phenyl)-1-(2-(3-methylisoxazol-5-yl)acetyl)pyrrolidine-2-carboxamide;
33) (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide;
34) 34,(2S,4R)-4-benzyl-N-(4-(4-fluorophenoxy)phenyl)-1-(3,3,3-trifluoropropanoyl)pyrrolidine-2-carboxamide;
35) (2S,4R)-4-benzyl-1-(2-(4-(dimethylamino)phenyl)acetyl)-N-(4-(4-fluorophenoxy)phenyl)pyrrolidine-2-carboxamide;
36) (2S,4R)-4-benzyl-N-(4-(4-fluorophenoxy)phenyl)-1-(tetrahydrofuran-3-carbonyl)pyrrolidine-2-carboxamide;
37) (2S,4R)-4-benzyl-N-(4-(4-fluorophenoxy)phenyl)-1-(2-(2-methyl-1H-indol-3-yl)acetyl)pyrrolidine-2-carboxamide;
38) (2S,4R)-4-benzyl-1-(2-butoxyacetyl)-N-(4-(4-fluorophenoxy)phenyl)pyrrolidine-2-carboxamide;
39) (2S,4R)-4-benzyl-N-(4-(4-fluorophenoxy)phenyl)-1-((S)-5-oxotetrahydrofuran-2-carbonyl)pyrrolidine-2-carboxamide;
40) (2S,4R)-4-benzyl-N-(4-(4-fluorophenoxy)phenyl)-1-((R)-2-hydroxy-2-phenylacetyl)pyrrolidine-2-carboxamide;
41) (S)-3-(benzyloxy)-N-(4-(4-fluorophenoxy)phenyl)-2-(2-(4-(pyrimidin-2-yl)piperazin-1-yl)acetamido)propanamide;
42) (S)-3-(benzyloxy)-N-(4-(4-fluorophenoxy)phenyl)-2-(2-(4-(3-methoxyphenyl)piperazin-1-yl)acetamido)propanamide;
43) (S)-3-(benzyloxy)-N-(4-(4-fluorophenoxy)phenyl)-2-(2-(4-(pyrrolidin-1-yl)piperidin-1-yl)acetamido)propanamide;
44) (S)-3-(4-fluorobenzyloxy)-N-(4-(4-fluorophenoxy)phenyl)-2-(2-(2-phenyloxazol-4-yl)acetamido)propanamide;
45) (2S)-3-(benzyloxy)-N-(4-(4-fluorophenoxy)phenyl)-2-(2-(octahydroquinolin-1(2H)-yl)acetamido)propanamide;
46) (2S)-3-(benzyloxy)-N-(4-(4-fluorophenoxy)phenyl)-2-(2-(3-methylpiperidin-1-yl)acetamido)propanamide;
47) (S)-2-(2-(1H-imidazol-5-yl)acetamido)-3-(benzyloxy)-N-(4-(4-fluorophenoxy)-2-methylphenyl)propanamide;
48) (2S,4R)-1-(2-(2H-1,2,3-triazol-2-yl)acetyl)-N-(4-(4-fluorophenoxy)phenyl)-4-(2-methylbenzyl)pyrrolidine-2-carboxamide;
49) (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide;
50) (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide;
51) (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide;
52) (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide;
53) (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide;
54) (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide;
55) (2S,4R)-1-(2-(1H-1,2,4-triazol-1-yl)acetyl)-N-(4-(4-fluorophenoxy)phenyl)-4-(2-methylbenzyl)pyrrolidine-2-carboxamide;
56) (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide;
57) (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide;
58) (2S,4R)-1-(2-(2H-1,2,3-triazol-2-yl)acetyl)-4-benzyl-N-(4-(4-fluorophenoxy)phenyl)pyrrolidine-2-carboxamide;
59) (R)-N-(2-(benzyloxy)-1-(5-(4-fluorophenoxy)-1H-benzo[d]imidazol-2-yl)ethyl)-2-(1H-imidazol-4-yl)acetamide;
60) (R)-N-(2-(benzyloxy)-1-(5-(4-fluorophenoxy)-1H-benzo[d]imidazol-2-yl)ethyl)acetamide;
61) (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide;
62) (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide;
63) (2S)-3-(benzyloxy)-N-(4-(4-fluorophenoxy)phenyl)-2-(2-(2-methylpyrrolidin-1-yl)acetamido)propanamide;

64) (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide;
65) (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide;
66) (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide;
67) (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide;
68) (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide;
69) (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide;
70) (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide;
71) (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide;
72) (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide;
73) (2S,4R)-1-(2-(1H-1,2,4-triazol-1-yl)acetyl)-N-(4-(4-fluoro-3-methylphenoxy)phenyl)-4-(4-fluorobenzyl)pyrrolidine-2-carboxamide;
74) (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide;
75) (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide;
76) (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide;
77) (2S,4S)-1-(2-(2H-1,2,3-triazol-2-yl)acetyl)-N-(4-(4-fluorophenoxy)phenyl)-4-phenylpyrrolidine-2-carboxamide;
78) (2S,4S)-1-(2-(1H-1,2,4-triazol-1-yl)acetyl)-N-(4-(4-fluorophenoxy)phenyl)-4-phenylpyrrolidine-2-carboxamide;
79) (2S,4R)-1-(2-(1H-1,2,4-triazol-1-yl)acetyl)-4-benzyl-N-(4-(4-chlorophenoxy)phenyl)pyrrolidine-2-carboxamide;
80) (2S,4S)-1-(2-(1H-1,2,4-triazol-1-yl)acetyl)-4-(benzylamino)-N-(4-(4-fluorophenoxy)phenyl)pyrrolidine-2-carboxamide;
81) (S)-3-(benzyloxy)-2-(3-(3-chloro-4-methoxyphenyl)propanamido)-N-(4-(4-fluorophenoxy)phenyl)propanamide;
82) (2S,4R)-4-benzyl-1-(2-(3,4-dihydroisoquinolin-2(1H)-yl)acetyl)-N-(4-(4-fluorophenoxy)phenyl)pyrrolidine-2-carboxamide;
83) (2S,4R)-4-benzyl-N-(4-(4-fluorophenoxy)phenyl)-1-(2-thiomorpholinoacetyl)pyrrolidine-2-carboxamide;
84) (2S,4R)-4-benzyl-N-(4-(4-fluorophenoxy)phenyl)-1-(2-(2,3,6-trifluorophenyl)acetyl)pyrrolidine-2-carboxamide;
85) (2S,4R)-4-benzyl-N-(4-(4-fluorophenoxy)phenyl)-1-(3-(methylthio)propanoyl)pyrrolidine-2-carboxamide;
86) (2S,4R)-4-benzyl-1-(3-ethoxypropanoyl)-N-(4-(4-fluorophenoxy)phenyl)pyrrolidine-2-carboxamide;
87) (2S,4R)-4-benzyl-N-(4-(4-fluorophenoxy)phenyl)-1-(2-(methylsulfonyl)acetyl)pyrrolidine-2-carboxamide;
88) (2S,4R)-4-benzyl-N-(4-(4-fluorophenoxy)phenyl)-1-(2-(2-methoxyethoxy)acetyl)pyrrolidine-2-carboxamide;
89) (2S,4R)-4-benzyl-1-(4-(dimethylamino)-4-oxobutanoyl)-N-(4-(4-fluorophenoxy)phenyl)pyrrolidine-2-carboxamide;
90) (2S,4R)-4-benzyl-N-(4-(4-fluorophenoxy)phenyl)-1-(3-methoxypropanoyl)pyrrolidine-2-carboxamide;
91) (2S,4R)-4-benzyl-N-(4-(4-fluorophenoxy)phenyl)-1-(4-oxo-4-(thien-2-yl)butanoyl)pyrrolidine-2-carboxamide;
92) (2S,4R)-4-benzyl-N-(4-(4-fluorophenoxy)phenyl)-1-(tetrahydrofuran-2-carbonyl)pyrrolidine-2-carboxamide;
93) (2S,4R)-1-((S)-1-acetylpyrrolidine-2-carbonyl)-4-benzyl-N-(4-(4-fluorophenoxy)phenyl)pyrrolidine-2-carboxamide;
94) (2S,4R)-4-benzyl-N-(4-(4-fluorophenoxy)phenyl)-1-(2-(pyrimidin-2-ylthio)acetyl)pyrrolidine-2-carboxamide;
95) (2S,4R)-4-benzyl-1-(2-(2,6-difluorophenyl)acetyl)-N-(4-(4-fluorophenoxy)phenyl)pyrrolidine-2-carboxamide;
96) (2S,4R)-4-benzyl-N-(4-(4-fluorophenoxy)phenyl)-1-(2-(pyridin-4-ylthio)acetyl)pyrrolidine-2-carboxamide;
97) (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide;
98) (2S,4R)-1-(2-(1H-indol-3-yl)acetyl)-4-benzyl-N-(4-(4-fluorophenoxy)phenyl)pyrrolidine-2-carboxamide;
99) (2S,4R)-4-benzyl-N-(4-(4-fluorophenoxy)phenyl)-1-(2-(4-oxo-2-thioxothiazolidin-3-yl)acetyl)pyrrolidine-2-carboxamide;
100) (2S,4R)-4-benzyl-N-(4-(4-fluorophenoxy)phenyl)-1-(2-(4-(2-methoxyethyl)piperazin-1-yl)acetyl)pyrrolidine-2-carboxamide;
101) (S)-3-(benzyloxy)-2-(2-(3-fluoro-4-(trifluoromethyl)phenyl)acetamido)-N-(4-(4-fluorophenoxy)phenyl)propanamide;
102) (S)-3-(benzyloxy)-N-(4-(4-fluorophenoxy)phenyl)-2-(2-(3-(trifluoromethoxy)phenyl)acetamido)propanamide;
103) (S)-tert-butyl 1-(2-((S)-3-(benzyloxy)-1-(4-(4-fluorophenoxy)phenylamino)-1-oxopropan-2-ylamino)-2-oxoethyl)pyrrolidine-2-carboxylate;
104) (S)-N-(3-(benzyloxy)-1-(4-(4-fluorophenoxy)phenylamino)-1-oxopropan-2-yl)-5-phenylpentanamide;
105) (S)-3-(benzyloxy)-N-(4-(4-fluorophenoxy)phenyl)-2-(2-(4-morpholinopiperidin-1-yl)acetamido)propanamide;
106) (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide;
107) (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide;
108) (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide;
109) (2S)-3-(benzyloxy)-2-(2-(3-(diethylamino)pyrrolidin-1-yl)acetamido)-N-(4-(4-fluorophenoxy)phenyl)propanamide;
110) (2S)-3-(benzyloxy)-N-(4-(4-fluorophenoxy)phenyl)-2-(2-(4-((tetrahydrofuran-2-yl)methyl)piperazin-1-yl)acetamido)propanamide;

111) (S)-3-(benzyloxy)-N-(4-(4-fluorophenoxy)phenyl)-2-(2-(4-isopropylpiperazin-1-yl)acetamido)propanamide;
112) (S)-3-(benzyloxy)-N-(4-(4-fluorophenoxy)phenyl)-2-(2-(4-(3-(trifluoromethyl)pyridin-2-yl)piperazin-1-yl)acetamido)propanamide;
113) (2S)-3-(benzyloxy)-N-(4-(4-fluorophenoxy)phenyl)-2-(2-(2-(((S)-1-methylpyrrolidin-2-yl)methyl)piperidin-1-yl)acetamido)propanamide,
114) (S)-3-(benzyloxy)-2-(2-(4-ethylpiperazin-1-yl)acetamido)-N-(4-(4-fluorophenoxy)phenyl)propanamide;
115) (2S,4R)-1-(2-(4-acetylpiperazin-1-yl)acetyl)-4-benzyl-N-(4-(4-fluorophenoxy)phenyl)pyrrolidine-2-carboxamide;
116) (2S,4R)-4-benzyl-N-(4-(4-fluorophenoxy)phenyl)-1-(2-morpholinoacetyl)pyrrolidine-2-carboxamide;
117) (2S,4R)-4-benzyl-N-(4-(4-fluorophenoxy)phenyl)-1-(2-(thien-2-yl)acetyl)pyrrolidine-2-carboxamide;
118) (2S,4R)-4-benzyl-N-(4-(4-fluorophenoxy)phenyl)-1-(3-hydroxybutanoyl)pyrrolidine-2-carboxamide;
119) (2S,4R)-4-benzyl-1-(2-(2,6-dichlorophenyl)acetyl)-N-(4-(4-fluorophenoxy)phenyl)pyrrolidine-2-carboxamide;
120) (2S,4R)-4-benzyl-N-(4-(4-fluorophenoxy)phenyl)-1-(2-hydroxyacetyl)pyrrolidine-2-carboxamide;
121) (2S,4R)-4-benzyl-1-(2-ethoxyacetyl)-N-(4-(4-fluorophenoxy)phenyl)pyrrolidine-2-carboxamide;
122) (2S,4R)-4-benzyl-N-(4-(4-fluorophenoxy)phenyl)-1-(2-methoxyacetyl)pyrrolidine-2-carboxamide;
123) (2S,4R)-4-benzyl-N-(4-(4-fluorophenoxy)phenyl)-1-(4-oxopentanoyl)pyrrolidine-2-carboxamide;
124) (2S,4R)-4-benzyl-N-(4-(4-fluorophenoxy)phenyl)-1-(4-oxo-4-phenylbutanoyl)pyrrolidine-2-carboxamide;
125) methyl 4-((2S,4R)-4-benzyl-2-(4-(4-fluorophenoxy)phenylcarbamoyl)pyrrolidin-1-yl)-4-oxobutanoate;
126) (S)-3-(benzyloxy)-N-(4-(4-fluorophenoxy)phenyl)-2-(2-(4-(pyridin-2-yl)piperazin-1-yl)acetamido)propanamide;
127) (S)-3-(benzyloxy)-N-(4-(4-fluorophenoxy)phenyl)-2-(2-(4-(2-fluorophenyl)piperazin-1-yl)acetamido)propanamide;
128) (S)-2-(2-(azepan-1-yl)acetamido)-3-(benzyloxy)-N-(4-(4-fluorophenoxy)phenyl)propanamide;
129) (2S,4R)-4-benzyl-1-(2-cyanoacetyl)-N-(4-(4-fluorophenoxy)phenyl)pyrrolidine-2-carboxamide;
130) (S)-3-(benzyloxy)-N-(4-(4-fluorophenoxy)phenyl)-2-(2-(4-methylpiperidin-1-yl)acetamido)propanamide;
131) (S)-2-(2-(1H-imidazol-5-yl)acetamido)-3-benzyloxy-N-(4-(4-fluorophenoxy)phenyl)propanamide;
132) (S)-2-(2-(1H-imidazol-5-yl)acetamido)-3-(4-fluorobenzyloxy)-N-(4-(4-chlorophenoxy)phenyl)propanamide;
133) (S)-2-(2-(1H-imidazol-5-yl)acetamido)-3-(4-fluorobenzyloxy)-N-(4-(4-fluorophenoxy)phenyl)propanamide;
134) (S)-2-(2-(1H-imidazol-1-yl)acetamido)-3-benzyloxy-N-(4-(4-fluorophenoxy)phenyl)propanamide;
135) (S)-2-(2-(1H-1,2,4-triazol-1-yl)acetamido)-3-(4-fluorobenzyloxy)-N-(4-(4-fluorophenoxy)phenyl)propanamide;
136) (S)-3-(benzyloxy)-2-(2-chloroacetamido)-N-(4-(4-fluorophenoxy)phenyl)propanamide;
137) (S)-2-(2-(1H-imidazol-5-yl)acetamido)-5-phenyl-N-(4-(4-fluorophenoxy)phenyl)pentanamide;
138) (S)-2-(2-(2H-1,2,3-triazol-2-yl)acetamido)-3-(benzyloxy)-N-(4-(4-fluorophenoxy)phenyl)propanamide;
139) (S)-2-(2-(1H-1,2,4-triazol-1-yl)acetamido)-N-(4-(4-fluorophenoxy)phenyl)-3-(2-(trifluoromethoxy)benzyloxy)propanamide;
140) (2S,4R)-1-(2-(1H-1,2,4-triazol-1-yl)acetyl)-4-benzyl-N-(4-(4-fluorophenoxy)phenyl)pyrrolidine-2-carboxamide;
141) (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide;
142) 2-(2-(1H-imidazol-5-yl)acetamido)-3-benzyloxy-N-(4-phenoxyphenyl)propanamide;
143) (S)-2-(2-(1H-imidazol-5-yl)acetamido)-3-benzyloxy-N-(4-phenoxyphenyl)propanamide;
144) (S)-2-(2-(1H-tetrazol-1-yl)acetamido)-3-benzyloxy-N-(4-phenoxyphenyl)propanamide;
145) (S)-2-(2-(1H-imidazol-5-yl)acetamido)-3-benzyloxy-N-(4-(4-chlorophenoxy)phenyl)propanamide;
146) (S)-2-(2-(1H-1,2,4-triazol-1-yl)acetamido)-3-(benzyloxy)-N-(4-phenoxyphenyl)propanamide;
147) (S)-2-(2-(1H-imidazol-4-yl)acetamido)-3-(benzyloxy)-N-(3-chloro-4-phenoxyphenyl)propanamide;
148) (S)-2-(2-(1H-imidazol-4-yl)acetamido)-3-(benzyloxy)-N-(4-(3-chlorophenoxy)phenyl)propanamide;
149) (S)-2-(2-(1H-1,2,4-triazol-1-yl)acetamido)-3-benzyloxy-N-(4-(4-fluorophenoxy)phenyl)propanamide;
150) (S)-3-(benzyloxy)-2-(2-(3,5-dimethylisoxazol-4-yl)acetamido)-N-(4-(4-fluorophenoxy)phenyl)propanamide;
151) (S)-2-(2-(1H-benzo [d][1,2,3]triazol-1-yl)acetamido)-3-(benzyloxy)-N-(4-(4-fluorophenoxy)phenyl)propanamide;
152) (S)-3-(benzyloxy)-2-(2-(3,5-dimethyl-1H-pyrazol-4-yl)acetamido)-N-(4-(4-fluorophenoxy)phenyl)propanamide;
153) (S)-3-(benzyloxy)-N-(4-(4-fluorophenoxy)phenyl)-2-(2-(4-methyl-1H-1,2,3-triazol-1-yl)acetamido)propanamide;
154) (S)-2-(2-(1H-imidazol-4-yl)acetamido)-3-(benzyloxy)-N-(3-chloro-4-(4-chlorophenoxy)phenyl)propanamide;
155) (S)-3-(benzyloxy)-N-(4-(4-fluorophenoxy)phenyl)-2-(2-morpholinoacetamido)propanamide;
156) (S)-2-(2-(1H-imidazol-4-yl)acetamido)-3-(benzyloxy)-N-(4-(5-bromothiazol-2-yloxy)phenyl)propanamide;
157) (S)-2-(2-(1H-imidazol-5-yl)acetamido)-N-(4-(4-chlorophenoxy)phenyl)-4-phenylbutanamide;
158) (S)-2-(2-(1H-imidazol-5-yl)acetamido)-3-(benzyloxy)-N-(4-(p-tolyloxy)phenyl)propanamide;
159) (S)-3-(benzyloxy)-N-(4-(4-fluorophenoxy)phenyl)-2-(2-(pyrazin-2-yl)acetamido)propanamide;
160) (S)-3-(benzyloxy)-N-(4-(4-fluorophenoxy)phenyl)-2-(2-(2-methyl-1H-imidazol-1-yl)acetamido)propanamide;
161) (S)-2-(2-(1H-imidazol-4-yl)-2-methylpropanamido)-3-(4-fluorobenzyloxy)-N-(4-(4-fluorophenoxy)phenyl)propanamide;
162) (S)-3-(benzyloxy)-N-(4-(4-fluorophenoxy)phenyl)-2-(2-(2-methyl-1H-imidazol-4-yl)acetamido)propanamide;
163) (2S,3S)-1-(2-(1H-imidazol-4-yl)acetyl)-3-benzyl-N-(4-(4-fluorophenoxy)phenyl)pyrrolidine-2-carboxamide;
164) (S)-2-acetamido-3-(4-fluorobenzyloxy)-N-(4-(4-fluorophenoxy)phenyl)propanamide;

165) (S)-benzyl 4-(2-(1H-1,2,4-triazol-1-yl)acetamido)-5-(4-(4-fluorophenoxy)phenylamino)-5-oxopentylcarbamate;
166) (S)-3-(benzyloxy)-N-(4-(4-fluorophenoxy)phenyl)-2-(2-(3-methyl-1H-pyrazol-5-yl)acetamido)propanamide
167) (2S)-2-(2-(1H-imidazol-4-yl)propanamido)-3-(benzyloxy)-N-(4-(4-fluorophenoxy)phenyl)propanamide;
168) (S)-2-(2-(1H-imidazol-5-yl)acetamido)-N-(4-(4-bromophenoxy)phenyl)-3-(4-fluorobenzyloxy)propanamide;
169) (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide;
170) (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide;
171) (2S,4R)-1-(2-(1H-1,2,4-triazol-1-yl)acetyl)-N-(4-(4-fluorophenoxy)phenyl)-4-(3-methylbenzyl)pyrrolidine-2-carboxamide;
172) (S)-2-(3-(3,5-dimethylisoxazol-4-yl)ureido)-3-benzyloxy-N-(4-(4-fluorophenoxy)phenyl)propanamide;
173) (2S,4R)-1-(2-(1H-imidazol-5-yl)acetyl)-4-(benzylamino)-N-(4-(4-fluorophenoxy)phenyl)pyrrolidine-2-carboxamide;
174) (S)-2-(2-(1H-1,2,3-triazol-1-yl)acetamido)-3-(benzyloxy)-N-(4-(4-fluorophenoxy)phenyl)propanamide;
175) 175 (S)-1-(2-(1H-imidazol-4-yl)acetyl)-4-benzyl-N-(4-(4-fluorophenoxy)phenyl)piperazine-2-carboxamide;
176) (2S,4R)-1-(2-(1H-benzo[d][1,2,3]triazol-1-yl)acetyl)-4-benzyl-N-(4-(4-fluorophenoxy)phenyl)pyrrolidine-2-carboxamide;
177) (2S,4R)-4-benzyl-N-(4-(4-fluorophenoxy)phenyl)-1-(2-(5-methyl-1H-pyrazol-3-yl)acetyl)pyrrolidine-2-carboxamide;
178) (S)-2-(2-(1H-1,2,4-triazol-1-yl)acetamido)-3-(benzyloxy)-N-(4-(4-fluorophenylthio)phenyl)propanamide;
179) (2S,4R)-1-(2-(1H-1,2,4-triazol-1-yl)acetyl)-4-(benzylamino)-N-(4-(4-fluorophenoxy)phenyl)pyrrolidine-2-carboxamide;
180) (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide;
181) (S)-2-(2-(1H-1,2,4-triazol-1-yl)acetamido)-3-(2-chlorobenzyloxy)-N-(4-(4-fluorophenoxy)phenyl)propanamide;
182) (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide;
183) 3-(benzyloxy)-2-(2-(2-fluorophenyl)acetamido)-N-(4-phenoxyphenyl)propanamide;
184) N-(3-(benzyloxy)-1-oxo-1-(4-phenoxyphenylamino)propan-2-yl)-1H-indole-4-carboxamide;
185) 2-(2-(3-methylisoxazol-5-yl)acetamido)-3-benzyloxy-N-(4-phenoxyphenyl)propanamide;
186) N-(3-(benzyloxy)-1-oxo-1-(4-phenoxyphenylamino)propan-2-yl)-4-cyclopropyl -4-oxobutanamide;
187) N-(3-(benzyloxy)-1-oxo-1-(4-phenoxyphenylamino)propan-2-yl)-1H-indole-6-carboxamide;
188) N-(3-(benzyloxy)-1-oxo-1-(4-phenoxyphenylamino)propan-2-yl)-2,3-dihydro-1H-indene-2-carboxamide;
189) N-(3-(benzyloxy)-1-oxo-1-(4-phenoxyphenylamino)propan-2-yl)-3-methyl-2-nitrobenzamide;
190) 3-(benzyloxy)-2-(2-(2,5-dichlorophenyl)acetamido)-N-(4-phenoxyphenyl)propanamide;
191) 3-(benzyloxy)-2-(2-(3-chloro-2-fluorophenyl)acetamido)-N-(4-phenoxyphenyl)propanamide;
192) 3-(benzyloxy)-2-(2-(5-chloro-2-fluorophenyl)acetamido)-N-(4-phenoxyphenyl)propanamide;
193) 2-(2-(1-acetylpyrrolidin-2-yl)acetamido)-3-benzyloxy-N-(4-phenoxyphenyl)propanamide;
194) (S)-2-{2-((benzoyl)(methyl)amino)acetamido}-3-benzyloxy-N-(4-phenoxyphenyl)propanamide;
195) (S)-2-(2-(1-methyl-1H-imidazol-4-yl)acetamido)-3-benzyloxy-N-(4-phenoxyphenyl)propanamide;
196) (S)-2-(2-(2-fluorophenyl)acetamido)-3-benzyloxy-N-(4-phenoxyphenyl)propanamide;
197) (S)-2-(2-(1H-indol-4-yl)acetamido)-3-benzyloxy-N-(4-phenoxyphenyl)propanamide;
198) (S)-2-(2-(thien-2-yl)acetamido)-3-benzyloxy-N-(4-phenoxyphenyl)propanamide;
199) (S)-2-(2-(2,5-dichlorophenyl)acetamido)-3-benzyloxy-N-(4-phenoxyphenyl)propanamide;
200) (S)-2-(2-(1H-imidazol-4-yl)acetamido)-3-(benzyloxy)-N-(4-benzylphenyl)propanamide;
201) (S)-3-(benzyloxy)-2-(2-(2,4-dioxoimidazolidin-1-yl)acetamido)-N-(4-phenoxyphenyl)propanamide;
202) (S)-2-(2-(1H-imidazol-4-yl)acetamido)-3-(benzyloxy)-N-(4-(4-methoxyphenoxy)phenyl)propanamide;
203) (S)-2-(2-(1H-imidazol-4-yl)-N-methylacetamido)-3-(benzyloxy)-N-(4-phenoxyphenyl)propanamide;
204) (S)-2-(2-(1H-imidazol-5-yl)acetamido)-N-(4-(4-chlorophenoxy)phenyl)-3-phenylpropanamide;
205) (S)-3-(benzyloxy)-N-(4-(4-fluorophenoxy)phenyl)-2-(2-(piperazin-1-yl)acetamido)propanamide;
206) (S)-2-(2-(1H-imidazol-4-yl)acetamido)-3-(benzyloxy)-N-(4-(thiazol-2-yloxy)phenyl)propanamide;
207) (S)-2-(3-(1H-imidazol-5-yl)propanamido)-3-(benzyloxy)-N-(4-(4-fluorophenoxy)phenyl)propanamide;
208) (S)-2-(2-(1H-imidazol-5-yl)acetamido)-3-(benzyloxy)-N-(4-(cyclohexyloxy)phenyl)propanamide;
209) (S)-3-(benzyloxy)-N-(4-(4-chlorophenoxy)phenyl)-2-(3-(dimethylamino)propanamido)propanamide;
210) (S)-3-(4-fluorobenzyloxy)-N-(4-(4-fluorophenoxy)phenyl)-2-(2-morpholinoacetamido)propanamide;
211) (S)-2-(2-(1H-imidazol-4-yl)acetamido)-3-(benzyloxy)-N-(4-(benzyloxy)phenyl)propanamide;
212) (S)-3-(benzyloxy)-2-(2-(5-fluoro-1H-indol-3-yl)acetamido)-N-(4-(4-fluorophenoxy)phenyl)propanamide;
213) (S)-2-(2-(1H-imidazol-4-yl)-2-methylpropanamido)-3-(benzyloxy)-N-(4-(4-fluorophenoxy)phenyl)propanamide;
214) (S)-3-(benzyloxy)-2-(2-(2,5-dihydro-1H-pyrrol-1-yl)acetamido)-N-(4-(4-fluorophenoxy)phenyl)propanamide;
215) (S)-3-(benzyloxy)-N-(4-(4-fluorophenoxy)phenyl)-2-(2-(pyrrolidin-1-yl)acetamido)propanamide;
216) (S)-2-(2-(1H-imidazol-4-yl)ethylamino)acetamido)-3-(benzyloxy)-N-(4-(4-fluorophenoxy)phenyl)propanamide;
217) (S)-3-(benzyloxy)-N-(4-(4-fluorophenoxy)phenyl)-2-(2-(4-(2-methoxyphenyl)piperazin-1-yl)acetamido)propanamide;
218) (S)-3-(benzyloxy)-N-(4-(4-fluorophenoxy)phenyl)-2-(2-(4-(4-fluorophenyl)piperazin-1-yl)acetamido)propanamide;
219) (2S)-2-(2-(2,3-dioxa-8-azaspiro[4.5]decan-8-yl)acetamido)-3-(benzyloxy)-N-(4-(4-fluorophenoxy)phenyl)propanamide;

220) (S)-3-(benzyloxy)-2-(2-(4-benzylpiperidin-1-yl)acetamido)-N-(4-(4-fluorophenoxy)phenyl)propanamide;
221) (S)-3-(benzyloxy)-2-(2-(3,4-dihydroisoquinolin-2(1H)-yl)acetamido)-N-(4-(4-fluorophenoxy)phenyl)propanamide;
222) (2S)-3-(benzyloxy)-N-(4-(4-fluorophenoxy)phenyl)-2-(2-(octahydroisoquinolin-2(1H)-yl)acetamido)propanamide;
223) (S)-3-(benzyloxy)-N-(4-(4-fluorophenoxy)phenyl)-2-(2-(4-(furan-2-carbonyl)piperazin-1-yl)acetamido)propanamide;
224) (S)-3-(benzyloxy)-N-(4-(4-fluorophenoxy)phenyl)-2-(2-(4-(4-methoxyphenyl)piperazin-1-yl)acetamido)propanamide;
225) (S)-3-(benzyloxy)-N-(4-(4-fluorophenoxy)phenyl)-2-(2-(4-phenylpiperazin-1-yl)acetamido)propanamide;
226) (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide;
227) (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide;
228) (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide;
229) (S)-2-(2-(4-(4-acetylphenyl)piperazin-1-yl)acetamido)-3-(benzyloxy)-N-(4-(4-fluorophenoxy)phenyl)propanamide;
230) (S)-2-(2-(4-acetylpiperazin-1-yl)acetamido)-3-(benzyloxy)-N-(4-(4-fluorophenoxy)phenyl)propanamide;
231) 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide;
232) (S,E)-N-(3-(benzyloxy)-1-(4-(4-fluorophenoxy)phenylamino)-1-oxopropan-2-yl)hex-3-enamide;
233) (S)-N-(3-(benzyloxy)-1-(4-(4-fluorophenoxy)phenylamino)-1-oxopropan-2-yl)-3-methylbutanamide;
234) (S)-3-(benzyloxy)-2-(2-((2R,6S)-2,6-dimethylmorpholino)acetamido)-N-(4-(4-fluorophenoxy)phenyl)propanamide;
235) (S)-3-(benzyloxy)-N-(4-(4-fluorophenoxy)phenyl)-2-(2-(thiazolidin-3-yl)acetamido)propanamide;
236) (S)-2-(2-(4-acetylpiperazin-1-yl)acetamido)-3-(benzyloxy)-N-(4-(4-fluorophenoxy)phenyl)propanamide;
237) (2S)-3-(benzyloxy)-N-(4-(4-fluorophenoxy)phenyl)-2-(2-(4-(tetrahydrofuran-2-carbonyl)piperazin-1-yl)acetamido)propanamide;
238) (S)-methyl 1-(2-(3-(benzyloxy)-1-(4-(4-fluorophenoxy)phenylamino)-1-oxopropan-2-ylamino)-2-oxoethyl)piperidine-4-carboxylate;
239) (S)-3-(benzyloxy)-2-(2-(4-(2-chloro-6-fluorobenzyl)piperazin-1-yl)acetamido)-N-(4-(4-fluorophenoxy)phenyl)propanamide;
240) (S)-3-(benzyloxy)-N-(4-(4-fluorophenoxy)phenyl)-2-(2-(isoindolin-2-yl)acetamido)propanamide;
241) (S)-3-(benzyloxy)-N-(4-(4-fluorophenoxy)phenyl)-2-(2-(4-(2-methoxyethyl)piperazin-1-yl)acetamido)propanamide;
242) (S)-3-(benzyloxy)-N-(4-(4-fluorophenoxy)phenyl)-2-(2-(4-(2-ethoxyethyl)piperazin-1-yl)acetamido)propanamide;
243) (S)-2-(2-(1H-imidazol-4-yl)acetamido)-3-(benzyloxy)-N-(3-phenoxyphenyl)propanamide;
244) (S)-3-(benzyloxy)-2-(2-(3-bromophenyl)acetamido)-N-(4-(4-fluorophenoxy)phenyl)propanamide;
245) (S)-3-(benzyloxy)-N-(4-(4-fluorophenoxy)phenyl)-2-(3-nitropropanamido)propanamide;
246) (S)-3-(benzyloxy)-N-(4-(4-fluorophenoxy)phenyl)-2-(2-(pyridin-2-yl)acetamido)propanamide;
247) (S)-3-(benzyloxy)-N-(4-(4-fluorophenoxy)phenyl)-2-(2-(pyridin-3-yl)acetamido)propanamide;
248) (S)-N-((S)-3-(benzyloxy)-1-(4-(4-fluorophenoxy)phenylamino)-1-oxopropan-2-yl)-3,7-dimethyloct-6-enamide;
249) (S)-3-(benzyloxy)-N-(4-(4-fluorophenoxy)phenyl)-2-(2-phenylacetamido)propanamide;
250) (S)-3-(benzyloxy)-N-(4-(4-fluorophenoxy)phenyl)-2-(2-(pyrimidin-5-yl)acetamido)propanamide;
251) (2S,4S)-1-(2-(1H-imidazol-5-yl)acetyl)-N-(4-(4-fluorophenoxy)phenyl)-4-phenylpyrrolidine-2-carboxamide;
252) (2S,4R)-1-(2-(1H-1,2,4-triazol-1-yl)acetyl)-4-(benzyloxy)-N-(4-(4-fluorophenoxy)phenyl)pyrrolidine-2-carboxamide;
253) benzyl (3R,5S)-1-(2-(1H-imidazol-5-yl)acetyl)-5-(4-(4-fluorophenoxy)phenylcarbamoyl)pyrrolidin-3-ylcarbamate;
254) (S)-2-(2-(1H-1,2,4-triazol-1-yl)acetamido)-5-acetamido-N-(4-(4-fluorophenoxy)phenyl)pentanamide;
255) (S)-3-(benzyloxy)-N-(4-(4-fluorophenoxy)phenyl)-2-(2-methyl-2-(1H-1,2,4-triazol-1-yl)propanamido)propanamide;
256) (S)-3-(benzyloxy)-2-(2-(3,5-dimethyl-1H-1,2,4-triazol-1-yl)acetamido)-N-(4-(4-fluorophenoxy)phenyl)propanamide;
257) (S)-benzyl 4-(2-(1H-imidazol-4-yl)acetyl)-3-(4-(4-fluorophenoxy)phenylcarbamoyl)piperazine-1-carboxylate;
258) (S)-2-(2-(3,5-dimethyl-1H-pyrazol-4-yl)acetamido)-3-(4-fluorobenzyloxy)-N-(4-(4-fluorophenoxy)phenyl)propanamide;
259) (2S,4R)-1-(2-(1H-1,2,4-triazol-1-yl)acetyl)-N-(4-(4-fluorophenoxy)phenyl)-4-phenoxypyrrolidine-2-carboxamide;
260) (2S,4R)-1-(2-(1H-1,2,4-triazol-1-yl)acetyl)-N-(4-(4-fluorophenoxy)phenyl)-4-(isoindolin-2-pyrrolidine-2-carboxamide;
261) (S)-1-(2-(1H-1,2,4-triazol-1-yl)acetyl)-4-benzyl-N-(4-(4-fluorophenoxy)phenyl)piperazine-2-carboxamide;
262) (2S,4S)-1-(2-(1H-1,2,4-triazol-1-yl)acetyl)-4-((benzylamino)methyl)-N-(4-(4-fluorophenoxy)phenyl)pyrrolidine-2-carboxamide;
263) (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide;
264) (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide;
265) (2S)-3-(benzyloxy)-2-(2-(2,6-dimethylmorpholino)acetamido)-N-(4-(4-fluorophenoxy)phenyl)propanamide;
266) (S)-3-(benzyloxy)-N-(4-(4-fluorophenoxy)phenyl)-2-(2-thiomorpholinoacetamido)propanamide;
267) (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide;
268) (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide;
269) N-(2-oxo-1-{[(phenylmethyl)oxy]methyl}-2-{[4-(phenyloxy)phenyl]amino}ethyl)acetamide;

270) 4-(methyloxy)-N-(2-oxo-1-{[(phenylmethyl)oxy]methyl}-2-{[4-(phenyloxy)phenyl]amino}ethyl)benzamide;
271) 4-benzyloxy-N-(2-oxo-1-{[(phenylmethyl)oxy]methyl}-2-{[4-(phenyloxy)phenyl]amino}ethyl)phenylacetamide;
272) 2-bromo-5-(methyloxy)-N-(2-oxo-1-{[(phenylmethyl)oxy]methyl}-2-{[4-(phenyloxy)phenyl]amino}ethyl)benzamide;
273) N-(2-oxo-1-{[(phenylmethyl)oxy]methyl}-2-{[4-(phenyloxy)phenyl]amino}ethyl)butanamide;
274) 2-chloro-N-(2-oxo-1-{[(phenylmethyl)oxy]methyl}-2-{[4-(phenyloxy)phenyl]amino}ethyl)benzamide;
275) 3-chloro-N-(2-oxo-1-{[(phenylmethyl)oxy]methyl}-2-{[4-(phenyloxy)phenyl]amino}ethyl)benzamide;
276) 4-chloro-N-(2-oxo-1-{[(phenylmethyl)oxy]methyl}-2-{[4-(phenyloxy)phenyl]amino}ethyl)benzamide;
277) N-(2-oxo-1-{[(phenylmethyl)oxy]methyl}-2-{[4-(phenyloxy)phenyl]amino}ethyl)cyclopropylamide;
278) N-(2-oxo-1-{[(phenylmethyl)oxy]methyl}-2-{[4-(phenyloxy)phenyl]amino}ethyl)-3-cyclopentylpropanamide;
279) 3,4-dimethyl-N-(2-oxo-1-{[(phenylmethyl)oxy]methyl}-2-{[4-(phenyloxy)phenyl]amino}ethyl)benzamide;
280) N-(2-oxo-1-{[(phenylmethyl)oxy]methyl}-2-{[4-(phenyloxy)phenyl]amino}ethyl)-2,5-dimethoxyphenylacetamide;
281) 4-(ethyloxy)-N-(2-oxo-1-{[(phenylmethyl)oxy]methyl}-2-{[4-(phenyloxy)phenyl]amino}ethyl)benzamide;
282) N-(3-(benzyloxy)-1-oxo-1-(4-phenoxyphenylamino)propan-2-yl)-2-ethylhexanamide;
283) N-(2-oxo-1-{[(phenylmethyl)oxy]methyl}-2-{[4-(phenyloxy)phenyl]amino}ethyl furan-2-carboxamide;
284) N-(2-oxo-1-{[(phenylmethyl)oxy]methyl}-2-{[4-(phenyloxy)phenyl]amino}ethyl)-2-methoxyacetamide;
285) N-(2-oxo-1-{[(phenylmethyl)oxy]methyl}-2-{[4-(phenyloxy)phenyl]amino}ethyl)-3-methoxyphenylacetamide;
286) 2-methyl-N-(2-oxo-1-{[(phenylmethyl)oxy]methyl}-2-{[4-(phenyloxy)phenyl]amino}ethyl)pentanamide;
287) 4-methyl-N-(2-oxo-1-{[(phenylmethyl)oxy]methyl}-2-{[4-(phenyloxy)phenyl]amino}ethyl)pentanamide;
288) N-(2-oxo-1-{[(phenylmethyl)oxy]methyl}-2-{[4-(phenyloxy)phenyl]amino}ethyl)naphthalene-2-carboxamide;
289) N-(2-oxo-1-{[(phenylmethyl)oxy]methyl}-2-{[4-(phenyloxy)phenyl]amino}ethyl)phenoxyacetamide;
290) N-(2-oxo-1-{[(phenylmethyl)oxy]methyl}-2-{[4-(phenyloxy)phenyl]amino}ethyl)-2-(phenyloxy)pyridine-3-carboxamide;
291) 3,4,5-tris(methyloxy)-N-(2-oxo-1-{[(phenylmethyl)oxy]methyl}-2-{[4-(phenyloxy)phenyl]amino}ethyl)benzamide;
292) N-(2-oxo-1-{[(phenylmethyl)oxy]methyl}-2-{[4-(phenyloxy)phenyl]amino}ethyl)thiophene-2-carboxamide;
293) N-(2-oxo-1-{[(phenylmethyl)oxy]methyl}-2-{[4-(phenyloxy)phenyl]amino}ethyl)thien-2-ylacetamide;
294) 4-(dimethylamino)-N-(2-oxo-1-{[(phenylmethyl)oxy]methyl}-2-{[4-(phenyloxy)phenyl]amino}ethyl)benzamide;
295) N-(2-oxo-1-{[(phenylmethyl)oxy]methyl}-2-{[4-(phenyloxy)phenyl]amino}ethyl)hexanamide;
296) 2-chloro-N-(2-oxo-1-{[(phenylmethyl)oxy]methyl}-2-{[4-(phenyloxy)phenyl]amino}ethyl)pyridine-3-carboxamide;
297) 3-chloro-N-(2-oxo-1-{[(phenylmethyl)oxy]methyl}-2-{[4-(phenyloxy)phenyl]amino}ethyl)-1-benzothiophene-2-carboxamide;
298) N-(2-oxo-1-{[(phenylmethyl)oxy]methyl}-2-{[4-(phenyloxy)phenyl]amino}ethyl)pent-4-enamide;
299) 3-chloro-2-fluoro-N-(2-oxo-1-{[(phenylmethyl)oxy]methyl}-2-{[4-(phenyloxy)phenyl]amino}ethyl)benzamide;
300) N-(2-oxo-1-{[(phenylmethyl)oxy]methyl}-2-{[4-(phenyloxy)phenyl]amino}ethyl)-4-phenylbutanamide;
301) N-(2-oxo-1-{[(phenylmethyl)oxy]methyl}-2-{[4-(phenyloxy)phenyl]amino}ethyl)-2-bromophenylacetamide;
302) N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide;
303) N-(2-oxo-1-{[(phenylmethyl)oxy]methyl}-2-{[4-(phenyloxy)phenyl]amino}ethyl)-2-methoxyethoxyacetamide;
304) N-(2-oxo-1-{[(phenylmethyl)oxy]methyl}-2-{[4-(phenyloxy)phenyl]amino}ethyl)-3-(4-methoxyphenyl)propanamide;
305) N-(2-oxo-1-{[(phenylmethyl)oxy]methyl}-2-{[4-(phenyloxy)phenyl]amino}ethyl)-2-acetylamino-4-methylthiazol-5-ylsulfonamide;
306) 4-(methylthio)-N-(2-oxo-1-{[(phenylmethyl)oxy]methyl}-2-{[4-(phenyloxy)phenyl]amino}ethyl)benzamide;
307) N-(2-oxo-1-{[(phenylmethyl)oxy]methyl}-2-{[4-(phenyloxy)phenyl]amino}ethyl)-2-(methylthio)acetamide;
308) 5-fluoro-2-(methyloxy)-N-(2-oxo-1-{[(phenylmethyl)oxy]methyl}-2-{[4-(phenyloxy)phenyl]amino}ethyl)benzamide;
309) 2-methyl-4-(methyloxy)-N-(2-oxo-1-{[(phenylmethyl)oxy]methyl}-2-{[4-(phenyloxy)phenyl]amino}ethyl)benzamide;
310) 5-oxo-N-(2-oxo-1-{[(phenylmethyl)oxy]methyl}-2-{[4-(phenyloxy)phenyl]amino}ethyl)hexanamide;
311) 4-bromo-2-methyl-N-(2-oxo-1-{[(phenylmethyl)oxy]methyl}-2-{[4-(phenyloxy)phenyl]amino}ethyl)benzamide;
312) 4-oxo-N-(2-oxo-1-{[(phenylmethyl)oxy]methyl}-2-{[4-(phenyloxy)phenyl]amino}ethyl)-4-(2-thien butanamide;
313) N-(2-oxo-1-{[(phenylmethyl)oxy]methyl}-2-{[4-(phenyloxy)phenyl]amino}ethyl)-2-(phenylthio)acetamide;
314) N-(2-oxo-1-{[(phenylmethyl)oxy]methyl}-2-{[4-(phenyloxy)phenyl]amino}ethyl)-2-(1H-pyrrol-1-yl)benzamide;
315) N-(2-oxo-1-{[(phenylmethyl)oxy]methyl}-2-{[4-(phenyloxy)phenyl]amino}ethyl)-2-[2-(methoxy)ethoxy]ethoxyacetamide;
316) 3,5-bis(methyloxy)-N-(2-oxo-1-{[(phenylmethyl)oxy]methyl}-2-{[4-(phenyloxy)phenyl]amino}ethyl)benzamide;
317) N-(2-oxo-1-{[(phenylmethyl)oxy]methyl}-2-{[4-(phenyloxy)phenyl]amino}ethyl)-3-cyclohexylpropanamide;

318) 5-oxo-N-(2-oxo-1-{[(phenylmethyl)oxy]methyl}-2-{[4-(phenyloxy)phenyl]amino}ethyl)-5-phenylpentanamide;
319) N-(2-oxo-1-{[(phenylmethyl)oxy]methyl}-2-{[4-(phenyloxy)phenyl]amino}ethyl)-4-acetylphenoxyacetamide;
320) 4-[3,4-bis(methyloxy)phenyl]-N-(2-oxo-1-{[(phenylmethyl)oxy]methyl}-2-{[4-(phenyloxy)phenyl]amino}ethyl)butanamide;
321) N-(2-oxo-1-{[(phenylmethyl)oxy]methyl}-2-{[4-(phenyloxy)phenyl]amino}ethyl)-5-[3-(trifluoromethyl)phenyl]furan-2-carboxamide;
322) N-(2-oxo-1-{[(phenylmethyl)oxy]methyl}-2-{[4-(phenyloxy)phenyl]amino}ethyl)-3-(1,3-dioxoisoindolin-2-yl)propanamide;
323) 5-oxo-N-(2-oxo-1-{[(phenylmethyl)oxy]methyl}-2-{[4-(phenyloxy)phenyl]amino}ethyl)-5-(2-thienyl)pentanamide;
324) N-(2-oxo-1-{[(phenylmethyl)oxy]methyl}-2-{[4-(phenyloxy)phenyl]amino}ethyl)-2-oxo-2-phenylacetamide;
325) N-(2-oxo-1-{[(phenylmethyl)oxy]methyl}-2-{[4-(phenyloxy)phenyl]amino}ethyl)-4-(2-thienyl)butanamide;
326) 5-nitro-N-(2-oxo-1-{[(phenylmethyl)oxy]methyl}-2-{[4-(phenyloxy)phenyl]amino}ethyl)furan-2-carboxamide;
327) (E)-N-(3-(benzyloxy)-1-oxo-1-(4-phenoxyphenylamino)propan-2-yl)hex-3-enamide
328) N-(2-oxo-1-{[(phenylmethyl)oxy]methyl}-2-{[4-(phenyloxy)phenyl]amino}ethyl)-1,3-benzodioxol-5-ylacetamide;
329) 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide;
330) 4-fluoro-N-(2-oxo-1-{[(phenylmethyl)oxy]methyl}-2-{[4-(phenyloxy)phenyl]amino}ethyl)-2-(trifluoromethyl)benzamide;
331) N-(2-oxo-1-{[(phenylmethyl)oxy]methyl}-2-{[4-(phenyloxy)phenyl]amino}ethyl)-2-(pyrimidin-2-ylthio)acetamide;
332) 2,5-bis(methyloxy)-N-(2-oxo-1-{[(phenylmethyl)oxy]methyl}-2-{[4-(phenyloxy)phenyl]amino}ethyl)benzamide;
333) 4-(methylsulfonyl)-N-(2-oxo-1-{[(phenylmethyl)oxy]methyl}-2-{[4-(phenyloxy)phenyl]amino}ethyl)benzamide;
334) 2-chloro-4-(methylsulfonyl)-N-(2-oxo-1-{[(phenylmethyl)oxy]methyl}-2-{[4-(phenyloxy)phenyl]amino}ethyl)benzamide;
335) N-(2-oxo-1-{[(phenylmethyl)oxy]methyl}-2-{[4-(phenyloxy)phenyl]amino}ethyl)2-(4-oxo-2-thioxothiazolidin-3-yl)acetamide;
336) N-(2-oxo-1-{[(phenylmethyl)oxy]methyl}-2-{[4-(phenyloxy)phenyl]amino}ethyl)tetrahydrofuran-3-carboxamide;
337) N-(2-oxo-1-{[(phenylmethyl)oxy]methyl}-2-{[4-(phenyloxy)phenyl]amino}ethyl)-3-methoxypropanamide;
338) N-(2-oxo-1-{[(phenylmethyl)oxy]methyl}-2-{[4-(phenyloxy)phenyl]amino}ethyl)-2-ethoxyacetamide;
339) N,N-dimethyl-N'-(2-oxo-1-{[(phenylmethyl)oxy]methyl}-2-{[4-(phenyloxy)phenyl]amino}ethyl)butanediamide;
340) N-(2-oxo-1-{[(phenylmethyl)oxy]methyl}-2-{[4-(phenyloxy)phenyl]amino}ethyl)-N-benzoyl-N-methylaminoacetamide;
341) N-(2-oxo-1-{[(phenylmethyl)oxy]methyl}-2-{[4-(phenyloxy)phenyl]amino}ethyl)-1H-indole-3-carboxamide;
342) N-(2-oxo-1-{[(phenylmethyl)oxy]methyl}-2-{[4-(phenyloxy)phenyl]amino}ethyl)-1H-benzimidazole-5-carboxamide;
343) N-(2-oxo-1-{[(phenylmethyl)oxy]methyl}-2-{[4-(phenyloxy)phenyl]amino}ethyl)-2-(4-ethoxyphenyl)acetamide;
344) N-(2-oxo-1-{[(phenylmethyl)oxy]methyl}-2-{[4-(phenyloxy)phenyl]amino}ethyl)pent-4-ynamide;
345) N-(2-oxo-1-{[(phenylmethyl)oxy]methyl}-2-{[4-(phenyloxy)phenyl]amino}ethyl)-4-(propyloxy)benzamide;
346) 2-methyl-N-(2-oxo-1-{[(phenylmethyl)oxy]methyl}-2-{[4-(phenyloxy)phenyl]amino}ethyl)hexanamide;
347) 4-oxo-N-(2-oxo-1-{[(phenylmethyl)oxy]methyl}-2-{[4-(phenyloxy)phenyl]amino}ethyl)pentanamide;
348) N-(2-oxo-1-{[(phenylmethyl)oxy]methyl}-2-{[4-(phenyloxy)phenyl]amino}ethyl)-3-(3,4-dimethoxyphenyl)propanamide;
349) 4-oxo-N-(2-oxo-1-{[(phenylmethyl)oxy]methyl}-2-{[4-(phenyloxy)phenyl]amino}ethyl)-4-phenylbutanamide;
350) N-(2-oxo-1-{[(phenylmethyl)oxy]methyl}-2-{[4-(phenyloxy)phenyl]amino}ethyl)quinoline-3-carboxamide;
351) N-(2-oxo-1-{[(phenylmethyl)oxy]methyl}-2-{[4-(phenyloxy)phenyl]amino}ethyl)pyrazine-2-carboxamide;
352) N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide;
353) N-(2-oxo-1-{[(phenylmethyl)oxy]methyl}-2-{[4-(phenyloxy)phenyl]amino}ethyl)-2-methoxy-2-phenylacetamide;
354) N-(2-oxo-1-{[(phenylmethyl)oxy]methyl}-2-{[4-(phenyloxy)phenyl]amino}ethyl)-2R-phenylpropanamide;
355) N-(2-oxo-1-{[(phenylmethyl)oxy]methyl}-2-{[4-(phenyloxy)phenyl]amino}ethyl)-1H-pyrazole-4-carboxamide;
356) N-(2-oxo-1-{[(phenylmethyl)oxy]methyl}-2-{[4-(phenyloxy)phenyl]amino}ethyl)cinnoline-4-carboxamide;
357) N-(2-oxo-1-{[(phenylmethyl)oxy]methyl}-2-{[4-(phenyloxy)phenyl]amino}ethyl)quinoline-8-carboxamide;
358) 6-hydroxy-N-(2-oxo-1-{[(phenylmethyl)oxy]methyl}-2-{[4-(phenyloxy)phenyl]amino}ethyl)pyridine-2-carboxamide;
359) N-(2-oxo-1-{[(phenylmethyl)oxy]methyl}-2-{[4-(phenyloxy)phenyl]amino}ethyl)-2-phenylpropanamide;
360) N-(2-oxo-1-{[(phenylmethyl)oxy]methyl}-2-{[4-(phenyloxy)phenyl]amino}ethyl)-1-(4-methoxyphenyl)cyclopropanecarboxamide;
361) N-(2-oxo-1-{[(phenylmethyl)oxy]methyl}-2-{[4-(phenyloxy)phenyl]amino}ethyl)-2-(2,3,6-trifluorophenyl)acetamide;
362) N-(2-oxo-1-{[(phenylmethyl)oxy]methyl}-2-{[4-(phenyloxy)phenyl]amino}ethyl)-2,4-bis(trifluoromethyl)benzamide;
363) N-(2-oxo-1-{[(phenylmethyl)oxy]methyl}-2-{[4-(phenyloxy)phenyl]amino}ethyl)-2-(2,4-difluorophenyl)acetamide;

364) N-(2-oxo-1-{[(phenylmethyl)oxy]methyl}-2-{[4-(phenyloxy)phenyl]amino}ethyl)-2-(1-methyl-1H-indol-3-yl)acetamide;

365) N-(2-oxo-1-{[(phenylmethyl)oxy]methyl}-2-{[4-(phenyloxy)phenyl]amino}ethyl)quinoline-4-carboxamide;

366) N-(2-oxo-1-{[(phenylmethyl)oxy]methyl}-2-{[4-(phenyloxy)phenyl]amino}ethyl)-1-benzofuran-2-carboxamide;

367) 7-(methyloxy)-N-(2-oxo-1-{[(phenylmethyl)oxy]methyl}-2-{[4-(phenyloxy)phenyl]amino}ethyl)-1-benzofuran-2-carboxamide;

368) N-(2-oxo-1-{[(phenylmethyl)oxy]methyl}-2-{[4-(phenyloxy)phenyl]amino}ethyl)-2-(4-fluorophenoxy)acetamide;

369) N-(2-oxo-1-{[(phenylmethyl)oxy]methyl}-2-{[4-(phenyloxy)phenyl]amino}ethyl)-3-(pyridin-3-yl)propanamide;

370) N-(2-oxo-1-{[(phenylmethyl)oxy]methyl}-2-{[4-(phenyloxy)phenyl]amino}ethyl)-2-(3,4-dichlorophenoxy)acetamide;

371) N-(2-oxo-1-{[(phenylmethyl)oxy]methyl}-2-{[4-(phenyloxy)phenyl]amino}ethyl)-2-(naphthalen-1-yloxy)acetamide;

372) N-(2-oxo-1-{[(phenylmethyl)oxy]methyl}-2-{[4-(phenyloxy)phenyl]amino}ethyl)-2-p-tolylacetamide;

373) N-(2-oxo-1-{[(phenylmethyl)oxy]methyl}-2-{[4-(phenyloxy)phenyl]amino}ethyl)-2-(2,5-dimethylphenyl)acetamide;

374) N-(2-oxo-1-{[(phenylmethyl)oxy]methyl}-2-{[4-(phenyloxy)phenyl]amino}ethyl)-2-(benzylthio)acetamide;

375) N-(2-oxo-1-{[(phenylmethyl)oxy]methyl}-2-{[4-(phenyloxy)phenyl]amino}ethyl)-2-(naphthalen-1-yl)acetamide;

376) N-(2-oxo-1-{[(phenylmethyl)oxy]methyl}-2-{[4-(phenyloxy)phenyl]amino}ethyl)-3-ethoxypropanamide;

377) N-(2-oxo-1-{[(phenylmethyl)oxy]methyl}-2-{[4-(phenyloxy)phenyl]amino}ethyl)-2-(3-chlorophenyl)acetamide;

378) 5-butyl-N-(2-oxo-1-{[(phenylmethyl)oxy]methyl}-2-{[4-(phenyloxy)phenyl]amino}ethyl)pyridine-2-carboxamide;

379) 4-chloro-3-methyl-N-(2-oxo-1-{[(phenylmethyl)oxy]methyl}-2-{[4-(phenyloxy)phenyl]amino}ethyl)benzamide;

380) 4-cyano-N-(2-oxo-1-{[(phenylmethyl)oxy]methyl}-2-{[4-(phenyloxy)phenyl]amino}ethyl)benzamide;

381) N-(2-oxo-1-{[(phenylmethyl)oxy]methyl}-2-{[4-(phenyloxy)phenyl]amino}ethyl)-2S-methoxy-2-phenylacetamide;

382) N-(2-oxo-1-{[(phenylmethyl)oxy]methyl}-2-{[4-(phenyloxy)phenyl]amino}ethyl)-3-(2,5-dimethoxyphenyl)propanamide;

383) N-(2-oxo-1-{[(phenylmethyl)oxy]methyl}-2-{[4-(phenyloxy)phenyl]amino}ethyl)-3-(1H-indol-3-yl)propanamide;

384) N-(2-oxo-1-{[(phenylmethyl)oxy]methyl}-2-{[4-(phenyloxy)phenyl]amino}ethyl)-2-(3-bromophenyl)acetamide;

385) 3-methyl-N-(2-oxo-1-{[(phenylmethyl)oxy]methyl}-2-{[4-(phenyloxy)phenyl]amino}ethyl)pentanamide;

386) N-(2-oxo-1-{[(phenylmethyl)oxy]methyl}-2-{[4-(phenyloxy)phenyl]amino}ethyl)-1H-indole-2-carboxamide;

387) 4-chloro-2-fluoro-N-(2-oxo-1-{[(phenylmethyl)oxy]methyl}-2-{[4-(phenyloxy)phenyl]amino}ethyl)benzamide;

388) 2-oxo-2-[(2-oxo-1-{[(phenylmethyl)oxy]methyl}-2-{[4-(phenyloxy)phenyl]amino}ethyl)amino]ethyl acetate;

389) N-(2-oxo-1-{[(phenylmethyl)oxy]methyl}-2-{[4-(phenyloxy)phenyl]amino}ethyl)thiophene-3-carboxamide;

390) N-(2-oxo-1-{[(phenylmethyl)oxy]methyl}-2-{[4-(phenyloxy)phenyl]amino}ethyl)-2-(4-bromophenyl)acetamide;

391) N-(2-oxo-1-{[(phenylmethyl)oxy]methyl}-2-{[4-(phenyloxy)phenyl]amino}ethyl)-2-(2-chlorophenyl)acetamide;

392) N-(2-oxo-1-{[(phenylmethyl)oxy]methyl}-2-{[4-(phenyloxy)phenyl]amino}ethyl)-2-(3,4,5-trimethoxyphenyl)acetamide;

393) N-(2-oxo-1-{[(phenylmethyl)oxy]methyl}-2-{[4-(phenyloxy)phenyl]amino}ethyl)-2-(p-tolyloxy)acetamide;

394) N-(2-oxo-1-{[(phenylmethyl)oxy]methyl}-2-{[4-(phenyloxy)phenyl]amino}ethyl)-3-(2-methoxyphenyl)propanamide;

395) 3-hydroxy-N-(2-oxo-1-{[(phenylmethyl)oxy]methyl}-2-{[4-(phenyloxy)phenyl]amino}ethyl)quinoxaline-2-carboxamide;

396) 4-acetyl-N-(2-oxo-1-{[(phenylmethyl)oxy]methyl}-2-{[4-(phenyloxy)phenyl]amino}ethyl)benzamide;

397) methyl 4-{[(2-oxo-1-{[(phenylmethyl)oxy]methyl}-2-{[4-(phenyloxy)phenyl]amino}ethyl)amino]carbonyl}benzoate;

398) 3-fluoro-N-(2-oxo-1-{[(phenylmethyl)oxy]methyl}-2-{[4-(phenyloxy)phenyl]amino}ethyl)-5-(trifluoromethyl)benzamide;

399) 4-[(difluoromethyl)oxy]-N-(2-oxo-1-{[(phenylmethyl)oxy]methyl}-2-{[4-(phenyloxy)phenyl]amino}ethyl)benzamide;

400) 3-fluoro-4-methyl-N-(2-oxo-1-{[(phenylmethyl)oxy]methyl}-2-{[4-(phenyloxy)phenyl]amino}ethyl)benzamide;

401) 3-methyl-N-(2-oxo-1-{[(phenylmethyl)oxy]methyl}-2-{[4-(phenyloxy)phenyl]amino}ethyl)furan-2-carboxamide;

402) N-(2-oxo-1-{[(phenylmethyl)oxy]methyl}-2-{[4-(phenyloxy)phenyl]amino}ethyl)cyclobutanecarboxamide; and 403) N-(2-oxo-1-{[(phenylmethyl)oxy]methyl}-2-{[4-(phenyloxy)phenyl]amino}ethyl)-3-(thiophen-2-yl)propanamide.

50. The kit of claim 49, wherein the antimicrotubule agent is selected from the group consisting of a taxane or a vinca alkaloid.

51. The pharmaceutical composition of claim 1, wherein the composition is adapted for inhibiting or relieving breast or lung cancer.

\* \* \* \* \*